US011999934B2

(12) United States Patent
Thomas et al.

(10) Patent No.: US 11,999,934 B2
(45) Date of Patent: Jun. 4, 2024

(54) INTEGRATED MICROFLUIDIC SYSTEM FOR GENERATION OF MICROORGANOSPHERES (MOS)

(71) Applicant: Xilis, Inc., Durham, NC (US)

(72) Inventors: Bradley Scott Thomas, Cary, NC (US); Timothy A. Miller, Durham, NC (US); Daniel Nelson, Durham, NC (US); Raheel Samuel, Durham, NC (US); George Robinson, Durham, NC (US); Tyler Welder, Durham, NC (US)

(73) Assignee: Xilis, Inc., Durham, NC (US)

( * ) Notice: Subject to any disclaimer, the term of this patent is extended or adjusted under 35 U.S.C. 154(b) by 0 days.

(21) Appl. No.: 18/378,921

(22) Filed: Oct. 11, 2023

(65) Prior Publication Data

US 2024/0124820 A1 Apr. 18, 2024

Related U.S. Application Data

(60) Provisional application No. 63/415,235, filed on Oct. 11, 2022, provisional application No. 63/415,232, (Continued)

(51) Int. Cl.
*C12M 1/12* (2006.01)
*C12M 1/00* (2006.01)
(Continued)

(52) U.S. Cl.
CPC ............ *C12M 25/16* (2013.01); *C12M 23/16* (2013.01); *C12M 23/40* (2013.01); *C12M 41/12* (2013.01); *C12M 41/36* (2013.01); *C12M 41/40* (2013.01)

(58) Field of Classification Search
CPC ...... C12M 25/16; C12M 23/16; C12M 23/40; C12M 41/12; C12M 41/36; C12M 41/40
See application file for complete search history.

(56) References Cited

U.S. PATENT DOCUMENTS

| | | | |
|---|---|---|---|
| 2014/0170665 A1 | 6/2014 | Hiddessen et al. | |
| 2016/0045843 A1* | 2/2016 | Stone | B01L 3/502769 422/243 |

(Continued)

OTHER PUBLICATIONS

Invitation to Pay Additional Fees in International Appln. No. PCT/US2023/034886, mailed on Dec. 27, 2023, 2 pages.
(Continued)

*Primary Examiner* — Liban M Hassan
(74) *Attorney, Agent, or Firm* — Fish & Richardson P.C.

(57) ABSTRACT

A microfluidic apparatus includes a microfluidic chip for MicroOrganoSpheres (MOS) generation. A first channel is defined in a surface of the microfluidic chip and includes: a droplet generation portion including an inlet portion, a junction between the inlet portion and an emulsifying fluid channel, and a chamber downstream of the junction. A cross-sectional area of the chamber is larger than that of the inlet portion. The first channel includes a polymerization portion downstream of the droplet generation portion, the polymerization portion having a serpentine configuration. The apparatus includes a cartridge for MOS demulsification, including: a collection container; a substrate disposed on the collection container, and a membrane disposed between the collection container and the surface of the substrate. A second channel is defined in the surface of the substrate that faces the collection container and is fluidically connected to an output of the polymerization portion of the first channel.

29 Claims, 46 Drawing Sheets

Related U.S. Application Data filed on Oct. 11, 2022, provisional application No. 63/415,240, filed on Oct. 11, 2022, provisional application No. 63/415,228, filed on Oct. 11, 2022.

(51) Int. Cl.
  *C12M 1/34* (2006.01)
  *C12M 3/06* (2006.01)

(56) References Cited

U.S. PATENT DOCUMENTS

| | | | |
|---|---|---|---|
| 2018/0045634 A1 | 2/2018 | Bachalo et al. | |
| 2020/0377861 A1 | 12/2020 | Shen et al. | |
| 2021/0252516 A1* | 8/2021 | Kvist | B01L 3/502784 |
| 2022/0062791 A1 | 3/2022 | Wang et al. | |

OTHER PUBLICATIONS darwin-microfluidics.com [online], "Microfluidic Droplet Generators," available on or before Oct. 2022, via Internet Archive Wayback Machine URL <http://web.archive.org/web/20231115163039/https://darwin-microfluidics.com/collections/microfluidic-droplet-generators?page=2>, retreived on Nov. 15, 2023, URL<https://darwin-microfluidics.com/collections/microfluidic-droplet-generators?page=2, 3 pages.

dropletex.com [online], "Droplet Microfluidics," 2023, retreived on Nov. 15, 2023, retrieved from URL<https://dropletex.com/?gclid=Cj0KCQjwmPSSBhCNARIsAH3cYgZUarfyfALWYq0xQOoGVtWzVksg7hTrvxUJwo2ZmYqzAGCWsM0we68aAvRCEALw_wcB>, 4 pages.

fluigent.com [online], "Microfluidics for Droplet Generation, The science of flow control for emulsion and particle production," available on or before May 24, 2022, via Internet Archive: Wayback Machine URL<http://web.archive.org/web/20231115161806/https://www.fluigent.com/research/applications/droplet-particle-generation/>, retrieved on Nov. 15, 2023, URL<https://www.fluigent.com/research/applications/droplet-particle-generation/?gclid=Cj0KCQjwmPSSBhCNARIsAH3cYgYVDLY-qNhxVS6oCBdV6X3ykGj1ee8aPRo87Y9TYvTPgSztPYB76BAaAh0cEALw_wcB>, 25 pages.

Jiang et al., "An Automated Organoid Platform with Inter-organoid Homogeneity and Inter-patient Heterogeneity," Dec. 22, 2020, Cell Reports Medicine 1:100161, 18 pages.

Mohamed, et al., "An integrated microfluidic flow-focusing platform for on-chip fabrication and filtration of cell-laden microgels," Lab Chip, Mar. 2019, 19:1621-1632.

precigenome.com, [online], "iFlow™ Droplet Generation System w. Microfluidic Droplet Generator Chips," 2023, retrieved on Nov. 15, 2023, retrieved from URL< https://www.precigenome.com/microfluidic-droplet-generator?gclid=Cj0KCQjwmPSSBhCNARIsAH3cYgYItqWW45qWRKqflxPGPnfH-5A8AlJjzgwE4hQSlg6H3RGcyj9x2GYaAvBkEALw_wcB>.

store.micronit.com [online], Micronit, 2020, retrieved on Nov. 15, 2023, retrieved from URL< https://store.micronit.com>, 1 page.

Gong et al., "All-Electronic Droplet Generation On-Chip with Real-Time Feedback Control for Ewod Digitial Microfluidics," Lab on the Chip, Jun. 2008, 8(6):898-906.

Mudugamuwa et al., "Vision-Based Performance Analysis of an Active Microfluidic Droplet Generation System Using Droplet Images," Sensors, Sep. 2022, 22(18):1-16.

International Search Report and Written Opinion in International Appln. No. PCT/US2023/034886, mailed on Mar. 11, 2024, 22 pages.

\* cited by examiner

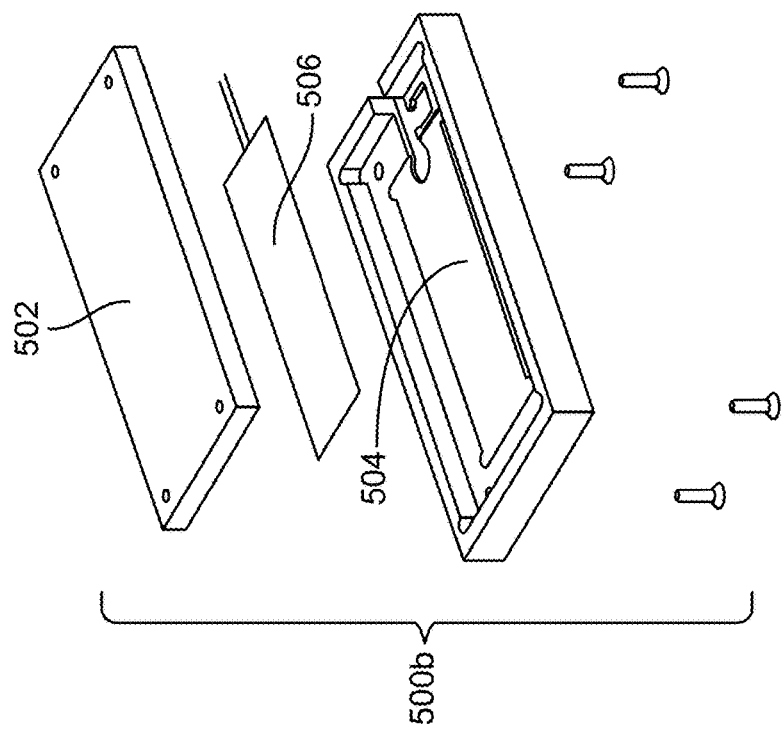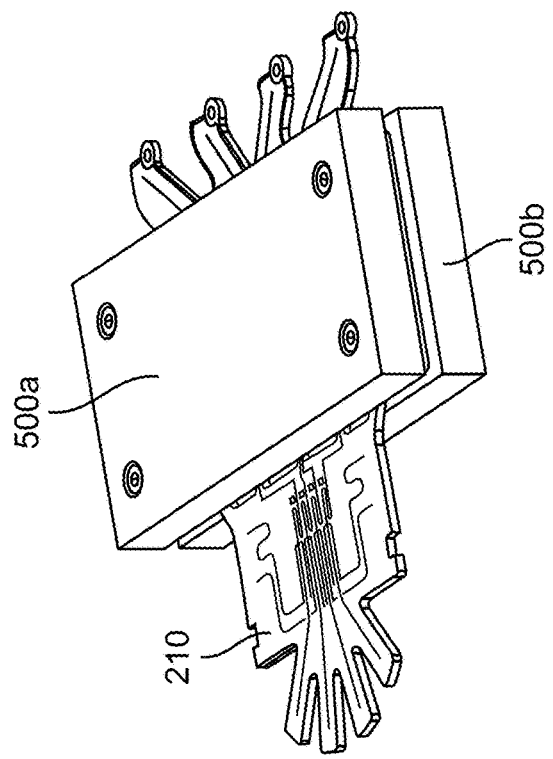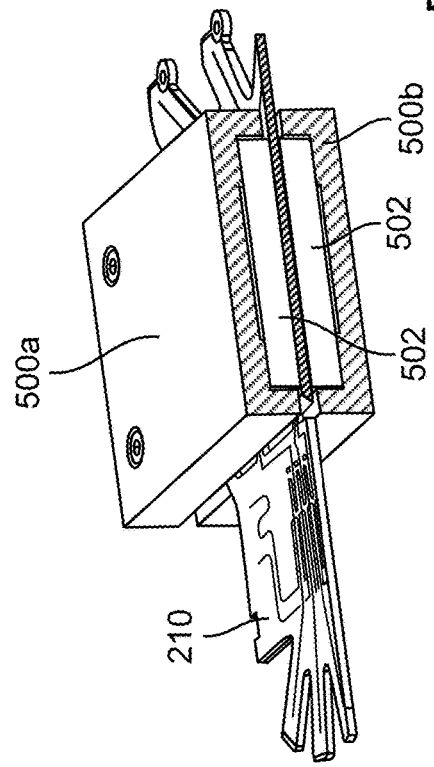

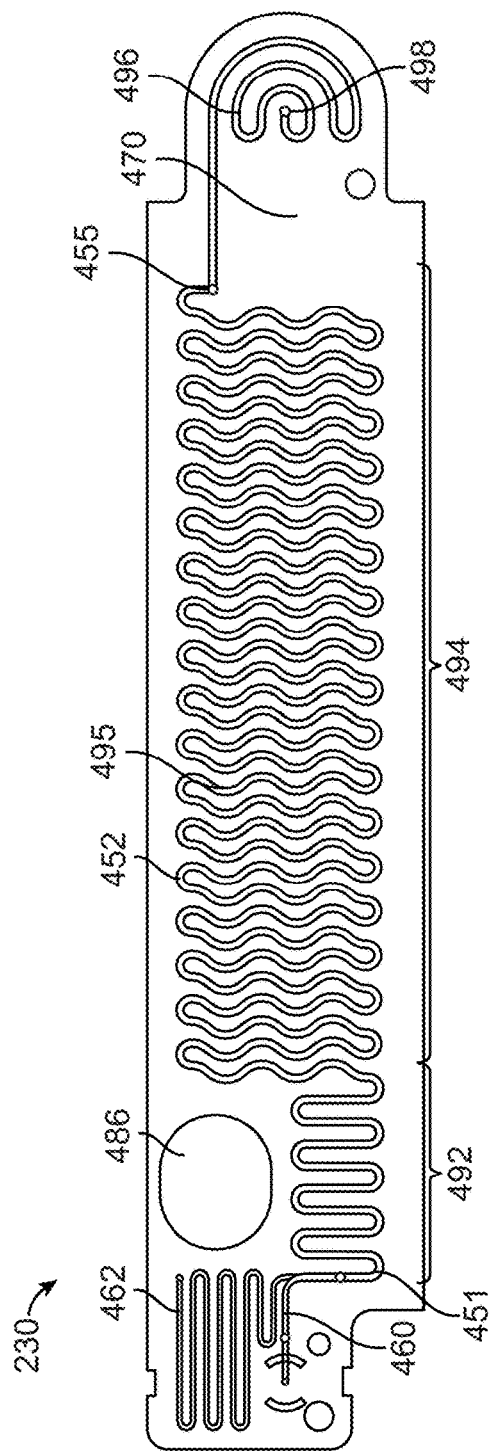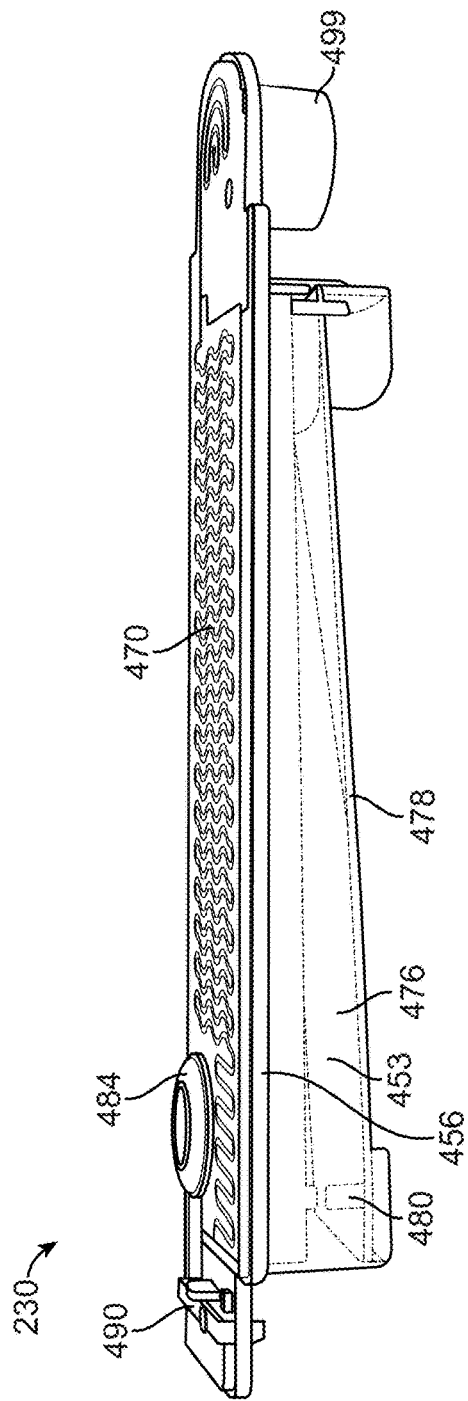

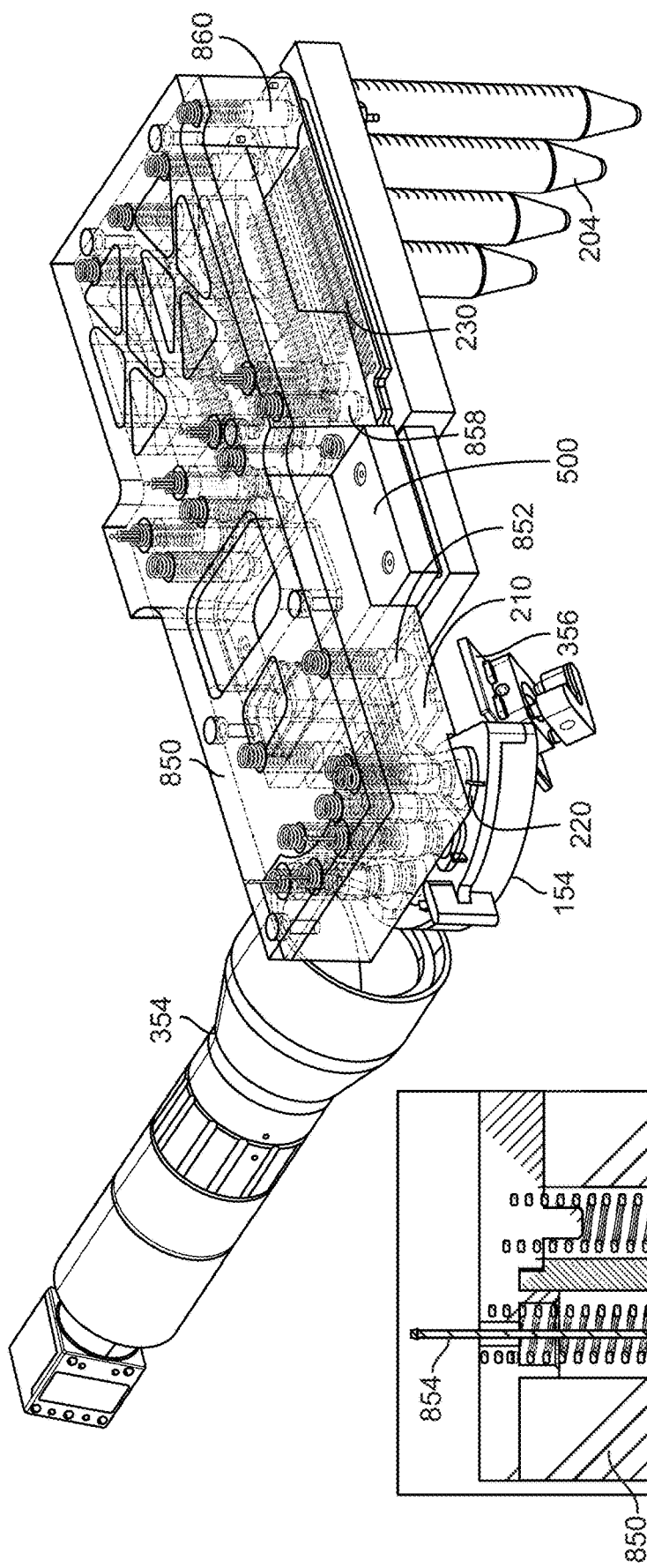
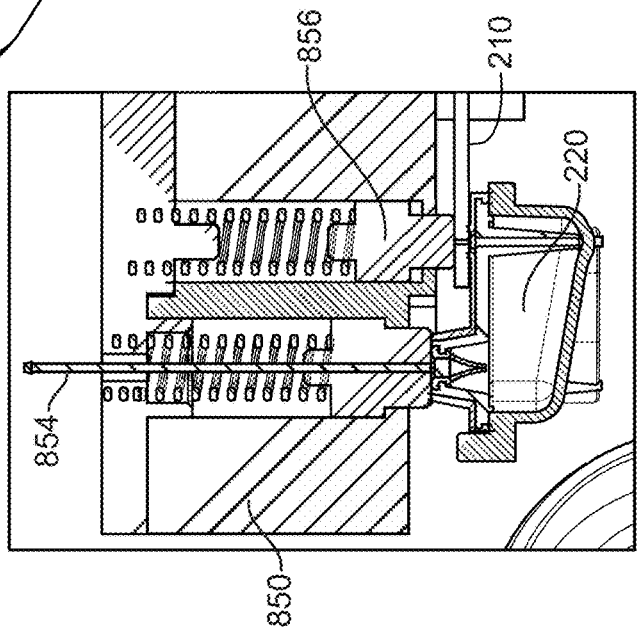
FIG. 18A
FIG. 18B

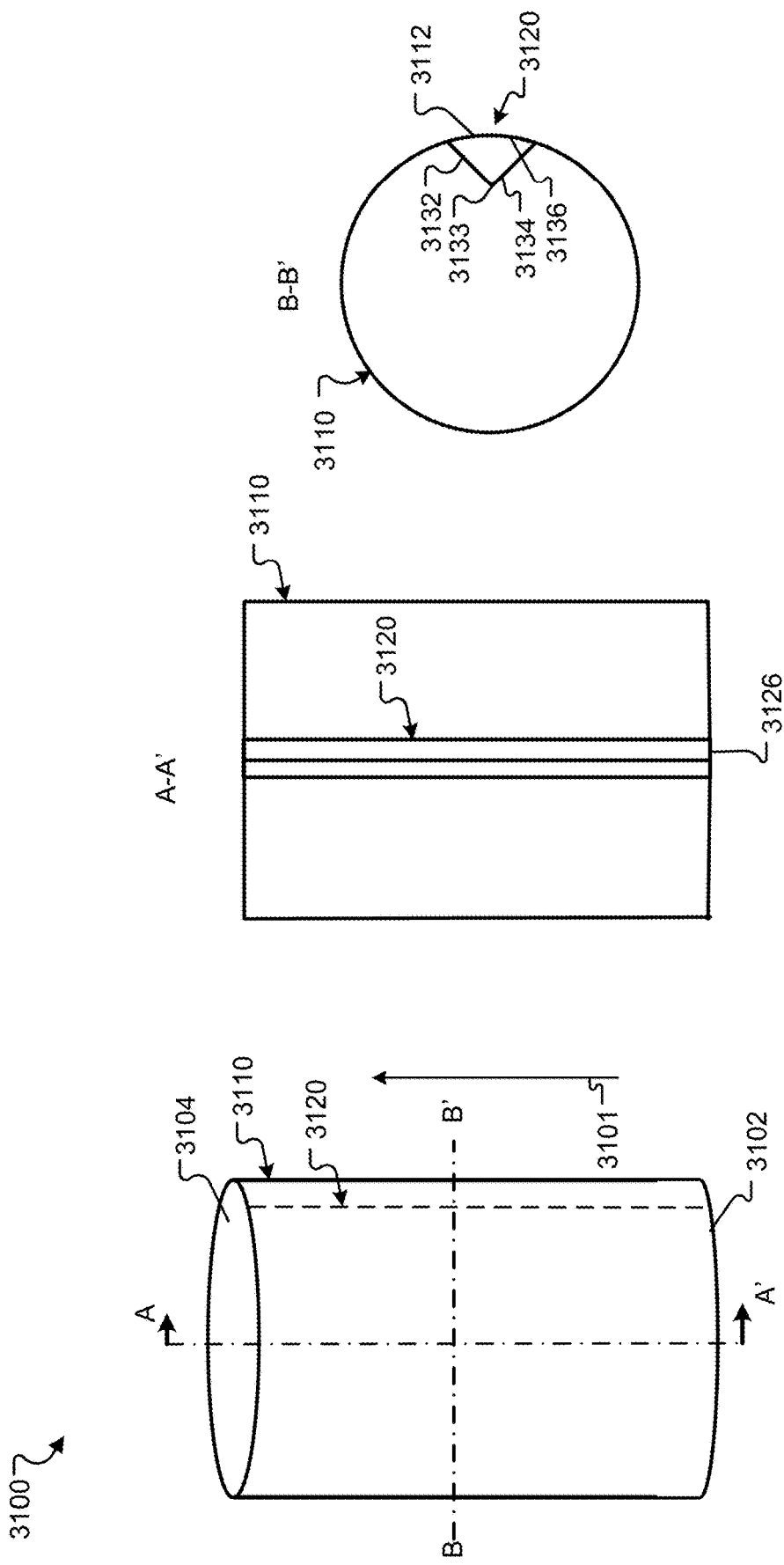

INTEGRATED MICROFLUIDIC SYSTEM FOR GENERATION OF MICROORGANOSPHERES (MOS)

CLAIM OF PRIORITY

This application claims the benefit of priority of U.S. Patent Application Ser. No. 63/415,228, filed on Oct. 11, 2022, U.S. Patent Application Ser. No. 63/415,240, filed on Oct. 11, 2022, U.S. Patent Application Ser. No. 63/415,232, filed on Oct. 11, 2022, and U.S. Patent Application Ser. No. 63/415,235, filed on Oct. 11, 2022, the entire contents of each of which are hereby incorporated by reference.

BACKGROUND

Biological materials derived from a patient, such as cells obtained from biopsied or resected tissue, can be used to screen for treatments to which the patient responds effectively. Treatment screening can be performed using microfluidic devices.

SUMMARY

In a first aspect, a microfluidic apparatus includes a microfluidic chip for generation of MicroOrganoSpheres (MOS), in which a first microfluidic channel is defined in a surface of the microfluidic chip, the first microfluidic channel including: a droplet generation portion including an inlet portion, a junction between the inlet portion and an emulsifying fluid channel, and a chamber downstream of the junction, in which a cross-sectional area of the chamber is larger than a cross-sectional area of the inlet portion, and a polymerization portion downstream of the droplet generation portion, the polymerization portion having a serpentine configuration; and a cartridge for MOS demulsification, the cartridge including: a collection container; a substrate disposed on the collection container, in which a second microfluidic channel is defined in a surface of the substrate that faces the collection container, and in which the second microfluidic channel is fluidically connected to an output of the polymerization portion of the first microfluidic channel; and a membrane disposed between the collection container and the surface of the substrate.

Embodiments can include one or any combination of two or more of the following features.

The droplet generation portion of the first microfluidic channel includes an outlet portion downstream of the chamber, in which a cross-sectional area of the chamber is larger than a cross-sectional area of the outlet portion. In some cases, at least some of the outlet portion extends in a direction parallel to the chamber.

The surface of the microfluidic chip is a first surface, and in which the polymerization portion of the microfluidic channel is defined on the first surface of the microfluidic chip and on a second surface of the microfluidic chip opposite the first surface.

The junction includes a junction with two hydrophobic fluid channels. In some cases, the junction is a right-angle junction.

The membrane includes a hydrophobic membrane. In some cases, the membrane is both hydrophobic and oleophilic.

The second microfluidic channel includes: an upstream section that has a simple serpentine configuration, and a downstream section that has a double serpentine configuration.

A cross-sectional area of the second microfluidic channel decreases from an input end of the second microfluidic channel to an output end of the second microfluidic channel.

The surface of the substrate is a first surface, and in which a media inlet channel is defined on a second surface of the substrate opposite the first surface of the substrate, the media inlet channel fluidically connected to an upstream section of the second microfluidic channel and configured to be connected to a media reservoir. In some cases, the demulsification cartridge includes the media reservoir. In some cases, the media inlet channel is fluidically connected to the media reservoir via a tube extending through the substrate and the collection container. In some cases, the collection container is disposed in a cavity defined in the media reservoir such that the collection container is positioned between the media reservoir and the substrate. In some cases, a bottom surface of the media reservoir is angled relative to a plane of the substrate. In some cases, the demulsification cartridge includes a duckbill valve extending through the substrate and the collection container, the duckbill valve configured to provide fluidic access to the media reservoir.

The demulsification cartridge includes a hydrophobic material disposed within the collection container.

A vacuum flow pathway is defined through a body of the collection container, the vacuum flow pathway configured to enable application of a vacuum to a surface of the membrane opposite the substrate.

The microfluidic apparatus includes a reservoir fluidically connected to the first microfluidic channel via an input port defined at an input end of the first microfluidic channel. In some cases, the reservoir includes a base and a cover, the base and cover defining a cavity for a fluidic sample. In some cases, the microfluidic apparatus includes an input port in the cover of the reservoir, the input port including a duckbill valve. In some cases, the microfluidic apparatus includes an output port in the cover of the reservoir, the output port connected to a tube extending into the cavity of the reservoir. In some cases, a bottom surface of the base of the reservoir is angled relative to the cover. In some cases, the microfluidic apparatus includes a reservoir holder configured to receive the reservoir, the reservoir holder including a cooling system configured to cool the reservoir. In some cases, the cooling system includes a thermoelectric cooling system.

One or more cutouts are defined in the microfluidic chip between the droplet generation portion and the polymerization portion. In some cases, edges of the one or more cutouts are angled relative to the surface of the microfluidic chip. In some cases, the one or more cutouts extend through an entire thickness of the microfluidic chip.

The microfluidic apparatus includes a cover disposed on the surface of the microfluidic chip. In some cases, the cover includes an optically transparent cover.

Multiple first microfluidic channels are defined in the surface of the microfluidic chip, and the apparatus includes multiple cartridges, in which the second microfluidic channel of each cartridge is fluidically connected to a corresponding one of the first microfluidic channel of the microfluidic chip.

The apparatus includes an output vial fluidically connected to the second microfluidic channel via an output port defined at the output end of the second microfluidic channel.

In a second aspect, combinable with any embodiment of the previous aspect, a system includes the microfluidic apparatus of the first aspect; a housing, in which the microfluidic apparatus is disposed in the housing; and a polymerization block housed in the housing and positioned to apply a stimulus to the polymerization portion of the first microfluidic channel.

Embodiments can include one or any combination of two or more of the following features.

The polymerization block includes a thermal polymerization block configured to apply heat to the polymerization portion of the first microfluidic channel. In some cases, the thermal polymerization block includes a heater. In some cases, the thermal polymerization block includes a temperature sensor. In some cases, the temperature sensor includes one or more of a thermistor, a thermocouple, or a resistance temperature detector. In some cases, the system includes a controller configured to control operation of the resistance heater responsive to temperature data received from the temperature sensor. In some cases, the heater includes a resistance heater. In some cases, the thermal polymerization block includes a thermally insulating cover, and in which the heater is disposed within a cavity defined within the thermally insulating cover.

The polymerization block includes a light polymerization block configured to illuminate the polymerization portion of the first microfluidic channel. In some cases, the light polymerization block includes a light emitting diode (LED). In some cases, the light polymerization block includes a photodetector. In some cases, the system includes a controller configured to control operation of the LED responsive to light intensity data received from the photodetector. In some cases, the LED is disposed within a cavity defined in a housing of the light polymerization block. In some cases, a wall of the cavity is formed of a material that is capable of reflecting light at a wavelength of light output by the LED. In some cases, the system includes a controller configured to control the LED to emit pulsed illumination.

The surface of the microfluidic chip is a first surface, and the polymerization block includes: a first block disposed adjacent the first surface of the microfluidic chip; and a second block disposed adjacent a second surface of the microfluidic chip, the second surface opposite the first surface. In some cases, the first and second blocks are secured against the microfluidic chip by springs. In some cases, the first and second blocks are clamped to the microfluidic chip.

The system includes a reservoir for emulsifying fluid, in which the emulsifying fluid channel of the microfluidic apparatus is fluidically connected to the reservoir. In some cases, the reservoir includes a reflective rib for fluid volume measurement disposed in a chamber of the reservoir. In some cases, the system includes a pump disposed between the reservoir for emulsifying fluid and the emulsifying fluid channel. In some cases, the system includes a controller configured to control operation of the pump. In some cases, the controller is configured to control operation of the pump to achieve a target fluid velocity in the second microfluidic channel. In some cases the pump is a syringe pump. In some embodiments, a valve, such as a servo valve, may be used in place of the pump.

The system includes an imaging system positioned to capture images of at least a portion of the chamber. In some cases, the system includes a controller configured to control a flow rate of fluid through the inlet portion of the microfluidic channel based on the images captured by the imaging system. In some cases, the controller is configured to control the flow rate of the fluid by controlling a pressure applied to a reservoir fluidically connected to the inlet portion of the microfluidic channel. In some cases, the controller is configured to control the flow rate of the fluid by controlling a syringe pump. In some cases, the flow rate of a sample-containing fluid is controlled by pressure, and the flow rate of an emulsifying fluid such as an oil is controlled by a syringe pump.

In a third aspect, combinable with any embodiment of either or both of the previous aspects, a microfluidic chip includes multiple first microfluidic channels for generation of an emulsion of droplets of a first fluid in a second fluid, in which the first microfluidic channels are defined in a first surface of the microfluidic chip, in which each first microfluidic channel is fluidically independent from each other first microfluidic channel, and in which each first microfluidic channel includes: an inlet portion configured to receive the first fluid from a respective source of the first fluid; a junction between the inlet portion and a corresponding second fluid channel configured to carry the second fluid; and a chamber downstream of the junction, in which a cross-sectional area of the chamber is larger than a cross-sectional area of the inlet portion; and multiple second microfluidic channels for polymerization of the droplets of the emulsion to thereby generate MOSs, in which each second microfluidic channel is fluidically connected to an outlet of a corresponding one of the first microfluidic channels, in which each second microfluidic channel is a serpentine channel including a first portion defined on the first surface of the microfluidic chip and a second portion defined on a second surface of the microfluidic chip opposite the first surface.

Embodiments can include one or any combination of two or more of the following features.

Each first microfluidic channel includes an outlet portion downstream of the chamber, in which the cross-sectional area of the chamber is larger than a cross-sectional area of the outlet portion. In some cases, a region of the outlet portion of each first microfluidic channel extends in a direction parallel to the respective chamber.

The microfluidic chip includes a cover disposed on each of the first surface and the second surface of the microfluidic chip. In some cases, the cover includes an optically transparent cover.

The multiple first microfluidic channels are defined in a first region of the microfluidic chip, and in which the multiple second microfluidic channels are defined in a second region of the microfluidic chip distinct from the first region. In some cases, one or more cutouts are defined in the microfluidic chip between the first region and the second region. In some cases, edges of the one or more cutouts are angled relative to the first and second surfaces of the microfluidic chip. In some cases, the one or more cutouts extend through an entire thickness of the microfluidic chip.

Each junction is a junction between the respective inlet portion and two corresponding second fluid channels. In some cases, the junction is a right-angle junction.

The microfluidic chip includes multiple inlet fingers, each inlet finger extending away from at least one other inlet finger and separated from each adjacent inlet finger by a gap, and in which at least some of the inlet portion of each first microfluidic channel is defined on a surface of a corresponding inlet finger.

The microfluidic chip includes multiple outlet fingers, each outlet finger extending away from at least one other outlet finger and separated from each adjacent outlet finger by a gap, and in which an outlet portion of each second microfluidic channel is defined on a surface of a corresponding outlet finger.

An output port of each second microfluidic channel is configured to be connected to a corresponding cartridge for demulsification of the emulsion.

In a fourth aspect, combinable with any embodiment of one or more of the previous aspects, an apparatus includes a cartridge for transferring MOSs from an emulsion in a hydrophobic fluid into a suspension in aqueous fluid, e.g., an aqueous, hydrophilic fluid such as growth media, the demulsification cartridge including: a collection container defining a cavity for receiving the hydrophobic fluid; a substrate disposed on the collection container, in which a microfluidic channel is defined in a first surface of the substrate that faces the collection container, and in which a media inlet channel for aqueous fluid aqueous fluid is fluidically connected to an upstream portion of the microfluidic channel; and a hydrophobic membrane disposed between the collection container and the surface of the substrate. In some cases, the hydrophobic membrane is both hydrophobic and oleophilic.

Embodiments can include one or any combination of two or more of the following features.

The apparatus includes a media reservoir having a cavity configured to contain the aqueous fluid, in which the media inlet channel is fluidically connected to the media reservoir. In some cases, the apparatus includes a tube extending through the substrate and the collection container, in which the media inlet channel is fluidically connected to the media reservoir via the tube. In some cases, the collection container is disposed in the cavity of the media reservoir such that the collection container is positioned between the media reservoir and the substrate. In some cases, a bottom surface of the media reservoir is angled relative to a plane of the substrate. In some cases, the apparatus includes a duckbill valve disposed through an opening in the substrate and an opening in the collection container, the duckbill valve configured to allow aqueous fluid to be provided into the cavity of the media reservoir, but not spill back out.

The surface of the substrate is a first surface, and in which the media inlet channel is defined on a second surface of the substrate opposite the first surface.

A cross-sectional area of the microfluidic channel is larger at an upstream end of the microfluidic channel than at a downstream end of the microfluidic channel.

An upstream portion of the microfluidic channel has a different configuration than a downstream portion of the microfluidic channel. In some cases, the upstream portion of the microfluidic channel has a simple serpentine configuration and in which the downstream portion of the microfluidic channel has a double serpentine configuration.

The apparatus includes a hydrophobic absorbent material disposed in the cavity of the collection container. In some cases, the apparatus includes a material that is both hydrophobic and oleophilic.

In a fifth aspect, combinable with any embodiment of one or more of the previous aspects, a method includes in a droplet generation portion of a first microfluidic channel defined in a surface of a microfluidic chip, generating droplets of a first fluid in the hydrophobic fluid, the first fluid including biological material and a matrix material, and in a polymerization portion of the first microfluidic channel, applying a stimulus to the generated droplets to polymerize the matrix material, thereby forming MOSs emulsified in the hydrophobic fluid; transferring the MOSs from the emulsion into a suspension in aqueous fluid, including: flowing a mixture of aqueous fluid and the emulsion of MOSs in the hydrophobic fluid along a second microfluidic channel defined in a substrate; as the mixture flows along the second microfluidic channel, transferring the hydrophobic fluid across a membrane forming a wall of the second microfluidic channel.

Embodiments can include one or any combination of two or more of the following features.

Generating droplets of the first fluid includes generating the droplets at a junction between the first microfluidic channel and one or more channels carrying the hydrophobic fluid. In some cases, the method includes controlling a flow rate of the hydrophobic fluid.

The method includes controlling a flow rate of the first fluid based on a determined size of the generated droplets. In some cases, the method includes determining the size of the generated droplets based on images of the droplets in the droplet generation portion of the first microfluidic channel.

Applying a stimulus to the generated droplets includes heating the droplets.

Applying a stimulus to the generated droplets includes illuminating the droplets with light having a wavelength configured to induce polymerization of the matrix material. In some cases, the surface of the microfluidic chip is a first surface, and in which the polymerization portion of the first microfluidic channel is defined on both the first surface and a second surface of the microfluidic chip, and in which illuminating the droplets includes illuminating the first and second surfaces of the microfluidic chip. In some cases, illuminating the droplets includes illuminating the droplets with pulsed illumination.

The method includes receiving the transferred hydrophobic fluid into a collection container, in which the membrane is disposed between the collection container and the substrate.

Transferring the hydrophobic fluid across the membrane by the pressure differential of the positive drive pressure above and ambient pressure below, plus the additional force of gravity. In some cases, transferring the hydrophobic fluid across the membrane includes applying a vacuum to the membrane.

The method includes providing the suspension of MOSs in aqueous fluid to an output vial.

The method includes generating droplets of each of multiple first fluids in each of multiple, fluidically independent first microfluidic channels defined in the surface of the microfluidic chip; and applying the stimulus to the generated droplets in each first microfluidic channel to form MOSs.

The approaches described here can have one or more of the following advantages. MicroOrganoSpheres (MOS) can be generated and extracted from an immiscible generation fluid in a fast, high throughput process that provides high recovery rates. The system is fully automated and thus provides consistent performance across samples. The system utilizes disposable components in the sample processing path, thus reducing the need for downtime for cleaning and disinfecting.

The details of one or more implementations are set forth in the accompanying drawings and the description below. Other features and advantages will be apparent from the description and drawings, and from the claims.

BRIEF DESCRIPTION OF DRAWINGS

FIGS. 5A-5C are diagrams of heat blocks for a MOS generation system.

FIGS. 16A-16C are diagrams of a demulsification subsystem of a MOS generation system.

FIGS. 18A and 18B are diagrams of a loading system.

FIGS. 33A to 33C illustrate an example container including a protrusion for liquid level sensing.

DETAILED DESCRIPTION

Figure 1:
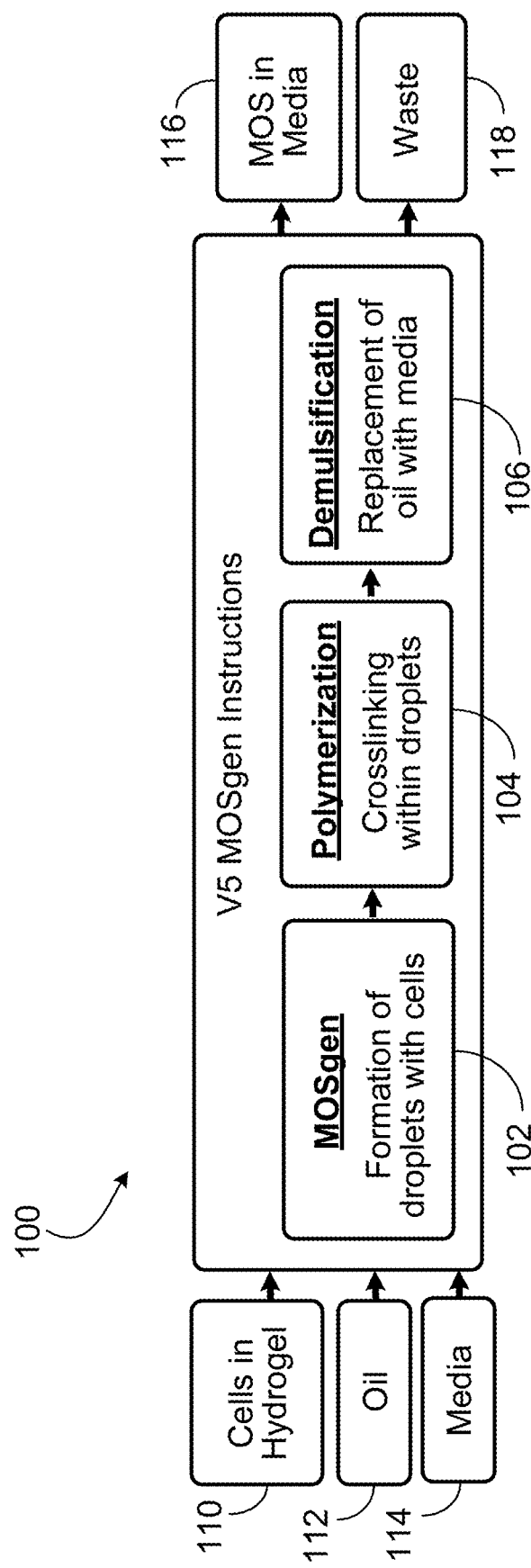
FIG. 1 is a block diagram of a system for MicroOrganoSphere (MOS) generation.

This disclosure describes an integrated microfluidic pathway for generation of droplets containing biological material, polymerization of the droplets to form MicroOrganoSpheres (MOSs), and demulsification and transfer of the MOSs into a suspension in aqueous fluid, e.g., an aqueous, hydrophilic fluid such as growth media. Specifically, multiple, fluidically independent microfluidic channels are defined on a microfluidic chip. Each channel has droplet generation region that is configured for generation of an emulsion of droplets in a hydrophobic fluid, and a serpentine polymerization region where a stimulus, such as light or heat, is applied to polymerize a matrix material in the droplets, thereby forming MOSs. Downstream of the polymerization region, each channel is fluidically connected to a microfluidic channel in a demulsification cartridge. A mixture of aqueous fluid and the MOSs in the hydrophobic fluid is flowed along this microfluidic channel, and the hydrophobic fluid is drawn across a hydrophobic membrane, leaving the MOSs suspended in the aqueous fluid.

The process for droplet generation and polymerization and MOS demulsification using this system is an automated, continuous process and can be performed to process multiple samples concurrently, but independently. The automated MOS generation and demulsification process is efficient and reliable, e.g., not prone to errors that may occur during a manual process. For instance, a 100 µL sample of biological material can be fully processed in under 10 minutes, e.g., in 6 minutes, and a 1 mL sample can be processed in under 40 minutes; all hands-off automated processing time.

MicroOrganoSpheres (MOSs) are generally spherical structures that contain biological material, such as dissociated tissue, e.g., cells, dispersed (e.g., suspended) in a matrix material. MOSs can be used for high throughput, patient-specific screening, e.g., for effective therapeutics. The biological material in MOSs can be cells extracted from a small biopsy, from resected tissue (e.g., from a tumor or organ), or from other sources (e.g., stored cells or cultured cells). Each MOS contains a small number of cells, e.g., clusters of 5-10 cells, suspended in a matrix material. The matrix material is a material that is polymerizable upon application of a stimulus (e.g., heat, light, or a chemical reaction) to form a support or support network for the biological material. For instance, the matrix material can be a hydrogel.

A large number of MOSs can be created from a single patient sample, e.g., a single biopsy or tissue resection. For instance, over 10,000 MOSs of substantially uniform size (e.g., over 20,000, over 30,000, over 40,000, over 50,000, over 60,000, over 70,000, over 80,000, over 90,000, over 100,000) can be created from a tissue sample (e.g., a needle biopsy sample) with a volume of about 10-1000 µL. This large number of MOSs can be used for high throughput screening of a large number of treatments to identify treatments to which that particular patient is responsive. For instance, MOSs containing cells from a patient biopsy can be used for high-throughput screen for drug compositions that may predict what therapies may be applied effectively to that patient. This screening may allow, for instance, efficient screening of a large number of potential treatments (e.g., pharmaceutical treatments) to identify effective treatments for a cancer patient before the patient is treated. The generation of MOSs and their use for screening is described further below and in US 2020/0377861, the contents of which are incorporated here by reference in their entirety.

The recovered MOSs are used, e.g., for screening of therapies for the patient who supplied the biological material in the MOSs. For instance, the recovered MOSs are placed in a culture media to allow the cells within the MOSs to grow. After culturing, the cells can be assayed substantially immediately or can be cryopreserved for future use.

Referring to FIG. 1, an instrument 100 for MOS generation houses an integrated microfluidic flow pathway that provides three aspects of MOS generation functionality: droplet generation 102, droplet polymerization 104, and demulsification 106. In droplet generation 102, droplets including patient-specific biological material and a matrix material (e.g., a hydrogel) are generated as an emulsification in a fluid that is immiscible with the matrix material (e.g., an oil). In droplet polymerization 104, the matrix material in the generated droplets is polymerized to thereby form MOSs. In demulsification 106, the MOSs are transferred from the oil emulsion into a suspension in an aqueous fluid. The resulting suspension can be used for downstream processing (e.g., further cell growth) and/or testing. The instrument 100 receives as input the patient-specific biological material 110 (e.g., dissociated tissue, such as cells), oil for the emulsion 112, and aqueous fluid 114, and outputs the MOSs in aqueous fluid 116 and waste 118, such as the oil from the emulsion. Droplet generation 102 and droplet polymerization 104 take place on a microfluidic chip that is fluidically connected to demulsification cartridges for demulsification 106.

The instrument 100 is capable of processing multiple samples, such as four samples (e.g., samples from multiple patients), in parallel (e.g., concurrently) along multiple, fluidically isolated flow paths. The portions of the instrument 100 that contact a sample are disposable, such that no cleaning or disinfection needs to be performed between processing of multiple samples.

Droplet polymerization is performed by cross-linking of a matrix material within which the biological material is suspended. Matrix materials can be cross-linked by application of a thermal stimulus (e.g., heat), by a photoinitiated process, or by a chemical reaction. The instrument 100 can be configured to be compatible with one or multiple of these cross-linking approaches. For instance, the instrument 100 can be equipped with hardware for either thermal or photoinitiated polymerization, and can also be compatible with chemical polymerization with use of a suitable microfluidic chip.

Figure 2:
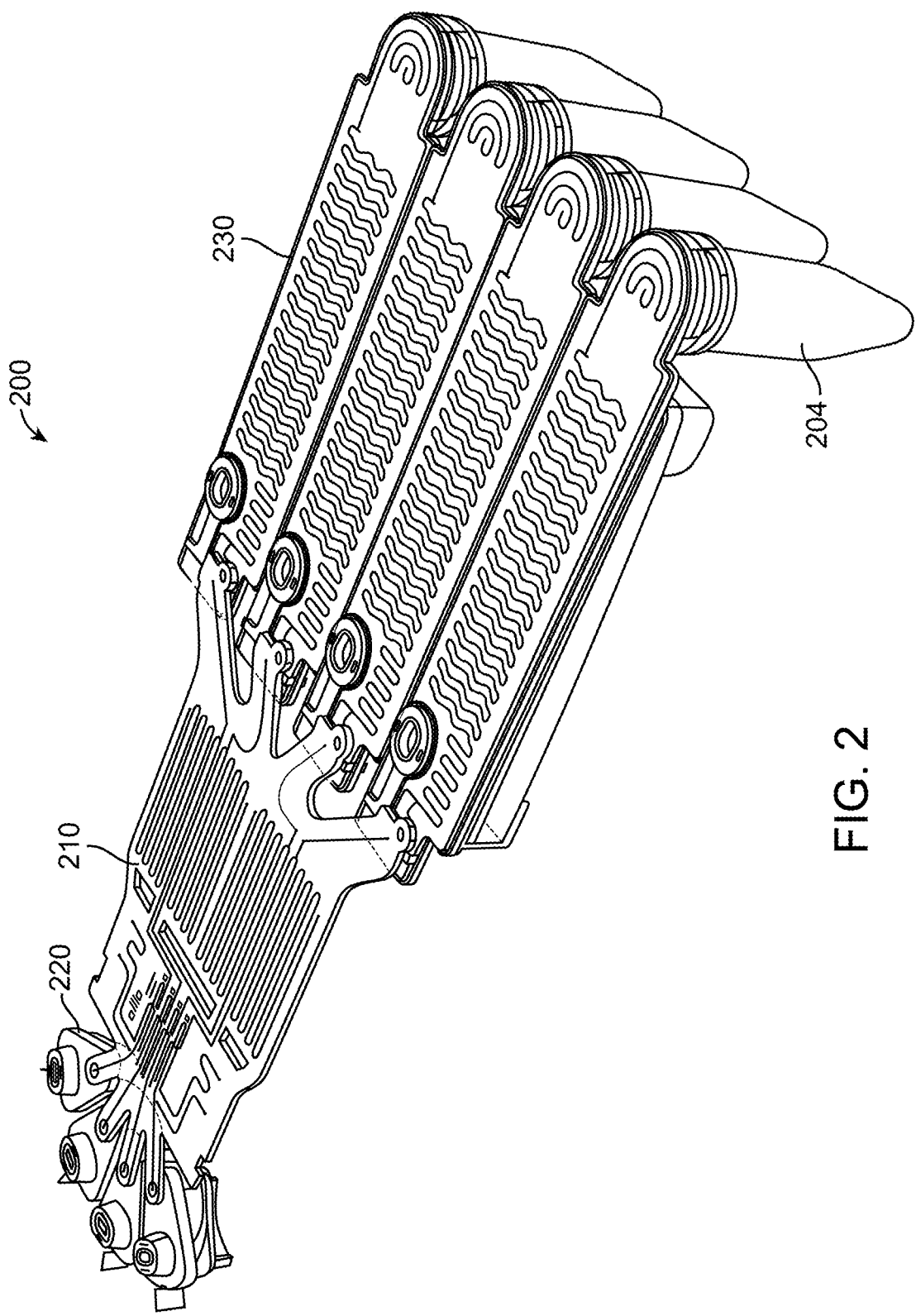
FIG. 2 is a diagram of consumables of an MOS generation system.

FIG. 2 shows an example of an MOS generation system 200 that can be used for generation of MOSs, e.g., in the instrument 100 of FIG. 1. The MOS generation system 200 is configured for parallel processing of multiple samples that are provided to the system in respective reservoirs 220. In the illustrated example, the MOS generation system can process up to four samples concurrently. Each sample contains biological material (e.g., patient-specific biological material such as tumor cells) suspended in a matrix material, such as a hydrogel. The sample from each reservoir 220 is processed on an independent microfluidic flow path (e.g., fluidically isolated and controllable independently from each other flow path) defined in a microfluidic chip 210, where the droplet generation and polymerization processes occur. Following droplet polymerization, the MOS emulsion in each flow path is provided to a corresponding demulsification cartridge 230, where the MOSs are transferred from in oil into a suspension in aqueous fluid. The MOSs in aqueous fluid are output into output vials 240.

For processing of a set of up to four samples, the MOS generation system 200 is loaded into the MOS generation instrument. Optionally, the desired type of polymerization stimulus is enabled, e.g., by inserting a heat block or light block into the instrument for thermal or photoinitiated polymerization, respectively. Once processing of the set of samples is complete, the MOS generation system 200 (including the reservoirs 220, microfluidic chip 210, demulsification cartridges 230, and output vials 240) is discarded. Because no other components of the instrument have contact with the samples, no cleaning or disinfection is necessary prior to processing another set of samples with another MOS generation system 200.

Tracking information, such as industry standard 2D barcodes (e.g., QR codes or Data Matrix codes) or other types of identifiers, can be used to track the chain of custody of each patient-specific sample from its origin, to the reservoir 220 containing the sample, and to the output vials 240. For instance, the instrument 100 can be equipped with barcode scanning capabilities, laboratory information management systems (LIMS), or other tracking techniques. In some examples, similar tracking techniques are also used to track reagents, such as matrix material and oil, e.g., to ensure that appropriate and non-expired reagents are used.

Figure 3A:
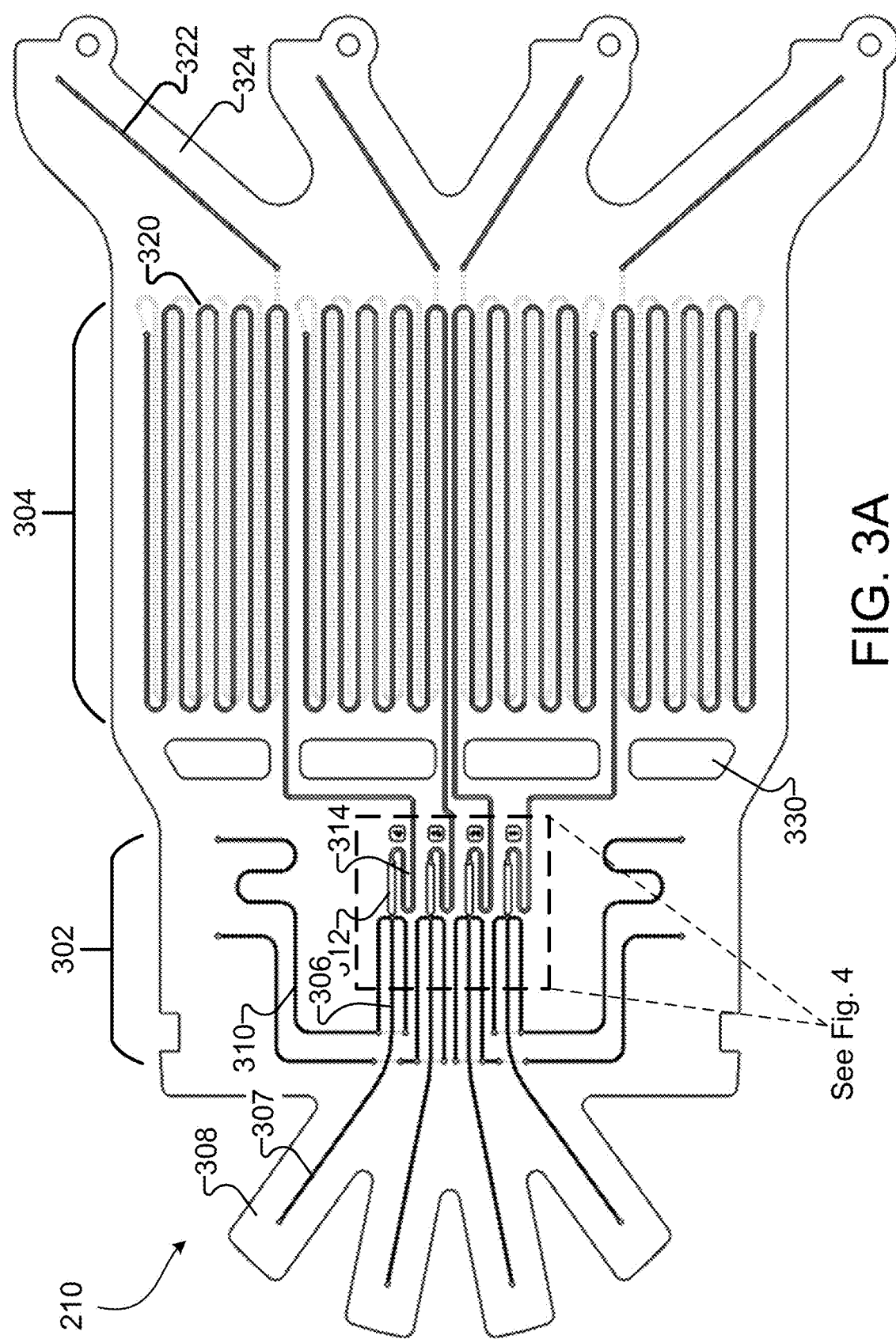
FIGS. 3A and 3B are diagrams of a microfluidic chip of an MOS generation system.
Figure 3B:
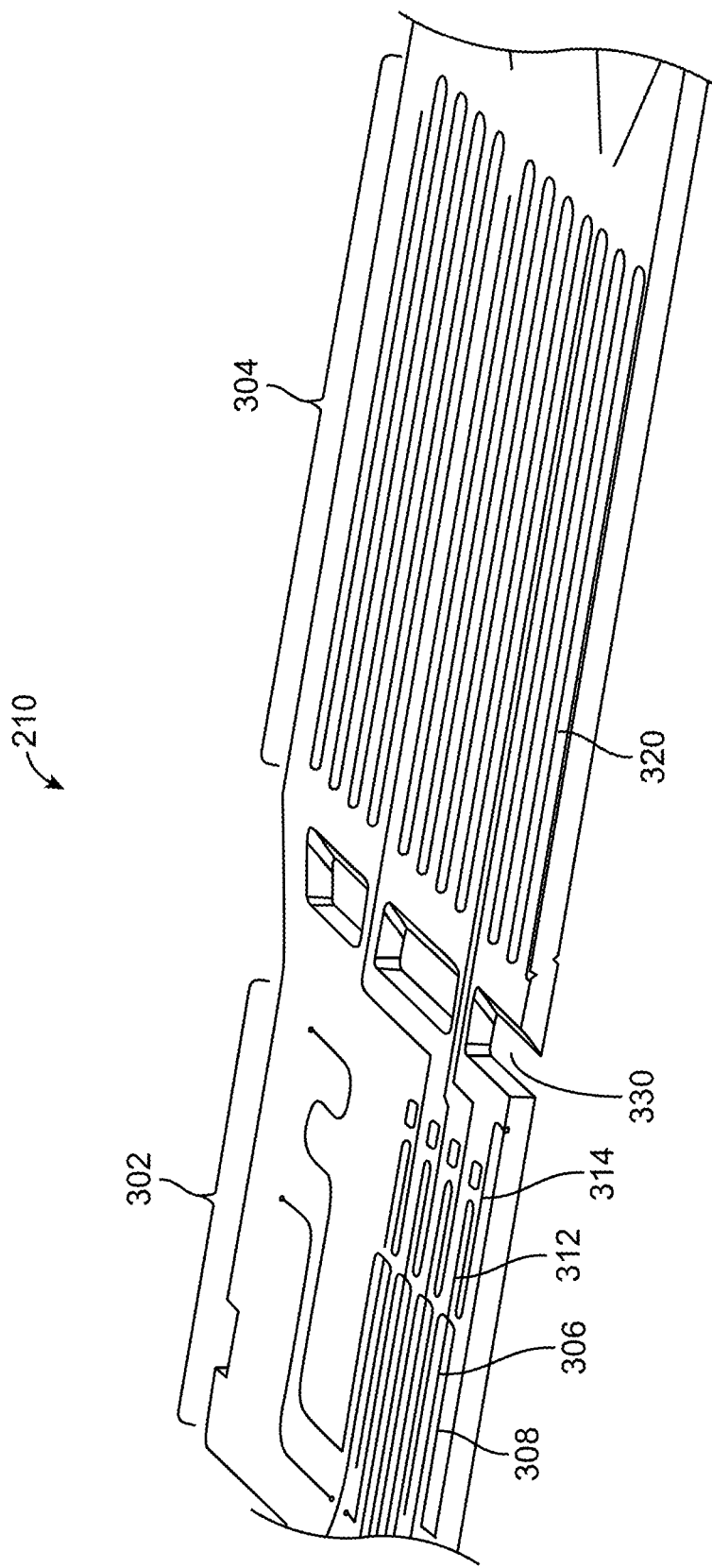

FIGS. 3A and 3B are top and sectioned perspective views, respectively, of the microfluidic chip 210, which has a droplet generation region 302 and a polymerization region 304. Four independent flow pathways are defined through the microfluidic chip 210 for concurrent processing of four biological samples; other numbers of pathways can also be defined. Each pathway is for processing of a different biological sample.

Each flow pathway includes an inlet channel 307 defined on a respective inlet finger 308 of the microfluidic chip 210. Each inlet channel 307 includes a port for connection to a corresponding one of the reservoirs 220, which is a source for the first fluid containing the patient-specific biological material and the unpolymerized matrix material. The inlet fingers 308 are spread apart from one another (e.g., each outlet finger 324 is separated from adjacent fingers by a gap) to allow for sufficient space for each reservoir. Moreover, the spread-apart inlet fingers 308 allow each finger to flex and seal against the corresponding reservoir 220 independently of each other finger, thereby avoiding the problem of tolerance variations preventing sealing (e.g., avoiding a situation in which a taller reservoir prevents sealing on adjacent shorter reservoirs). Each flow pathway also includes one or more (here, two) second channels 310 that each includes a port for connection to an oil source (e.g., an oil reservoir 700, see FIG. 7).

In the droplet generation region 302, a continuous stream of droplets is generated in each flow pathway by combining a stream of a first fluid that contains the biological material (e.g., patient-specific biological material) suspended in an unpolymerized matrix material (e.g., a hydrogel) with one or more streams of a second fluid. The second fluid is a low viscosity fluid that is immiscible with the first fluid such that an emulsion of the first fluid in the second fluid can be generated. For instance, the first fluid can be a hydrophilic (e.g., water-based) fluid and the second, immiscible fluid can be a hydrophobic material such as an oil. Although this document sometimes refers specifically to oil or a hydrophobic fluid, it should be understood that the disclosed approach applies generally to any suitable second fluid that is immiscible with the first fluid. Generally, the flow of the first fluid and the flow of the second fluid are controlled by separate flow regulator devices controlled by respective controllers, such as proportional-integral-derivative (PID) controllers. For instance, the flow of the first fluid is controlled by pressurizing the reservoirs 220, e.g., using a syringe pump or other suitable flow regulator, and the flow of the second fluid is controlled by a pump with programmable flow rate.

When the streams of the first and second fluids meet, droplets of the first fluid are formed in the second fluid. Each generated droplet contains the unpolymerized matrix material and a small amount of the biological sample from the corresponding reservoir and are dispersed (e.g., emulsified) in the oil. The droplets have a stable, substantially spherical geometry, and the relative flow rates of the first fluid and the oil controls the size (e.g., diameter, volume) of the droplets. In the polymerization region 304, the matrix material in the droplets is polymerized by exposure to a stimulus, such as heat, light, a chemical stimulus, or another suitable stimulus, thereby forming an emulsion of MOSs in the oil. Following polymerization, the MOSs are recovered from the oil by demulsification in demulsification cartridges 230 (shown in FIG. 2) fluidically connected to the microfluidic chip 210. For instance, as the flow rate of the first fluid is increased relative to that of the second fluid, larger droplets are generated. As the flow rate of the first fluid is decreased relative to that of the second fluid, smaller droplets are generated. The relative flow rates of the first and second fluid also affect the flow rate of the emulsion containing the generated droplets.

The microfluidic chip 210 is, e.g., an injection molded chip-on-chip device that is sealed on its top surface and bottom surface (not shown) by a thin cover, such as a glass cover or a polymer film. The cover is a thin film with a thickness of, e.g., between 50 µm and 100 µm, e.g., 80 µm. This two-sided geometry allows the flow channels to cross over one another and allows the density of the channels in the polymerization region 304 to be doubled as compared to a similarly structured but single-sided chip. In some examples, such as when the microfluidic chip 210 is designed for thermal or photoinitiated polymerization, the cover is a film that is substantially non-absorbing of heat or light, respectively. For instance, the cover film can be optically transparent (e.g., allowing transmission of at least 50%, at least 60%, at least 80%, at least 90%, or at least 95%) of light intensity at the wavelength(s) of light used for photoinitiated polymerization (e.g., 405 nm blue light).

Figure 4:
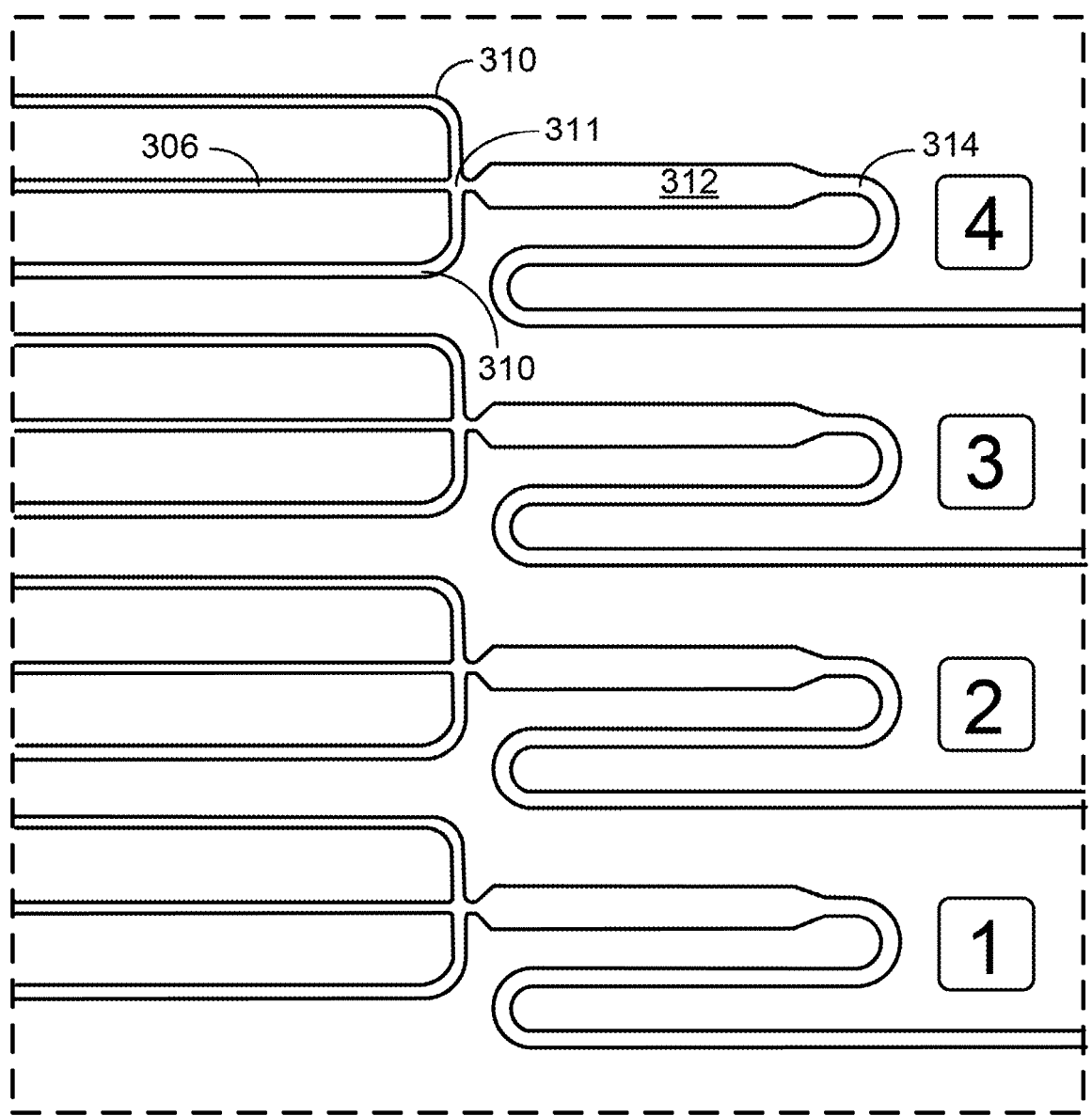
FIG. 4 is a diagram of a portion of a microfluidic chip of a MOS generation system.

FIG. 4 is a blown up view of the portion of the droplet generation region contained in the dashed-line box of FIG. 3A. As shown in FIG. 4, the first and second channels 306, 310 in each flow pathway intersect, e.g., at right-angles, at a junction 311 in the droplet generation region 302. As the first fluid flows out of the first channel 306 and the oil flows out of the second channels 310 and into the junction, the opposing convergence of the flowing oil (e.g., flowing from two sides of the junction) permits a small amount of the first fluid to pass into the junction before pinching off the first fluid, thereby initiating formation of droplets of the first fluid encapsulated in the oil. From the junctions, the droplets in each flow pathway flow into respective droplet generation chambers 312. In some examples, the droplet generation chambers 312 are a flared chamber that have cross-sectional dimensions (e.g., cross-sectional area) that is greater than the cross-sectional dimensions of the first channels 306. The transition between the narrower first channel 306 and the wider droplet generation chamber 312 along each flow pathway causes the fluid flow to slow and the pressure to rise, triggering the pinching off of the droplets. Continuous flow of the first fluid and the oil forms a continuous stream of evenly spaced droplets of substantially uniform shape and volume. Each droplet contains the patient-specific biological material and the unpolymerized matrix material.

From the droplet generation chamber 312 in each flow pathway, the droplets flow into a narrower outlet channel 314. For instance, the height and width of the outlet channels 314 are slightly larger than the diameter of the droplets, e.g., between about 10% and about 25% larger. The decrease in cross-sectional dimensions from the droplet generation chamber 312 to the outlet channel 314 generates back pressure to support droplet generation. This decrease in size also causes the droplets to form into a single file line with substantially even spacing, preventing the droplets from touching one another and merging prior to a downstream polymerization process. In an example, the spacing between droplets in the outlet channel 314 can be about twice the spacing between droplets in the droplet generation chamber 312.

In a specific example, for droplets having a diameter of 260 µm, the outlet channels 314 have cross-sectional dimensions of 300 µm×300 µm, the droplet generation chambers 312 have cross-sectional dimensions of 200 µm×700 µm, and the first and second channels 306, 310 have cross-sectional dimensions of 200 µm×200 µm.

An imaging subsystem (not shown; see FIG. 13) is positioned to acquire images (e.g., still or video images) of droplets as they pass through the droplet generation chambers 312, outlet channels 314, or both. The images can be used to determine characteristics of the droplets, such as droplet size (e.g., droplet volume or droplet diameter), droplet size distribution, droplet velocity, separation between adjacent droplets, a number density of the droplets (e.g., number of droplets per unit length of the outlet channels 314, number of droplets per unit volume of the second fluid), an estimated total number of droplets generated from a given starting volume of the first fluid, or other droplet characteristics. In some examples, discussed further below, droplet characteristics can be used for closed loop feedback control of the droplet generation process. For instance, the flow rate of the oil, the first fluid, or both, can be adjusted in real time based on determined droplet characteristics in order to obtain droplets of a target size.

In the illustrated example, each outlet channel 314 doubles back alongside the corresponding droplet generation chamber 312, e.g., in a serpentine configuration such that a portion of each outlet channel 314 extends in a direction parallel to the corresponding droplet generation chamber 312. This geometry allows the droplets to remain in the field of view of the imaging subsystem for a longer time. Moreover, the droplets can be imaged in an evenly spaced, single file line in the outlet channels 314, facilitating analysis of the images. Moreover, the ability to image droplets and calculate their velocity in adjacent channels of different cross sections allows an internal QC that the velocity ratio corresponds to the channel area ratio. Moreover, the droplet generation chambers 312 and outlet channels 314 are compressed into a relatively small area of the microfluidic chip 210, which allows the imaging subsystem to operate with a small field of view, thereby permitting images to be captured with a high resolution, e.g., a resolution of microns per pixel.

Referring again to FIGS. 3A and 3B, from the outlet channel 314 of each flow pathway, the droplets flow into a respective polymerization channel 320 in the polymerization region 304. The polymerization channels 320 are arranged such that the droplets flowing therethrough are exposed to a stimulus, such as heat, light (e.g., blue light), a chemical stimulus, or another suitable stimulus. The stimulus induces polymerization of the unpolymerized matrix material in the droplets, thereby forming MOSs emulsified in the oil. In some examples, the stimulus is applied to both the top surface and the bottom surface of the microfluidic chip 210; in some examples, the stimulus is applied to only one surface.

In the illustrated example, the polymerization channels 320 are serpentine channels, with a portion of the channel length arranged on the top surface of the microfluidic chip 210 and the remainder arranged on the bottom surface of the microfluidic chip 210. For instance, for a polymerization channel with a 1 meter total length, 0.5 m of channel length is arranged on the top surface and 0.5 m of channel length is arranged on the bottom surface. This arrangement enables a high density of polymerization channels 320, thereby providing a long fluid path length to maximize the time of exposure to the stimulus. In addition, the positioning of the polymerization channels 320 on the top and bottom surfaces of the microfluidic chip 210 means that there is only a small separation between the droplets in the channels 320 and the applied stimulus, e.g., a separation approximately equal to the thickness of the transparent film covering the microfluidic chip. This small separation minimizes delay in the stimulus reaching the polymerization channels and mitigates energy loss, thus contributing to efficient polymerization. The combination of the serpentine pathway on both surfaces of the microfluidic chip 210 and the small separation between the channels 320 and the applied stimulus enables polymerization to be achieved with a relatively short dwell time, e.g., a dwell time of between 30 seconds and 2 minutes, e.g., 1 minute, along polymerization channels with a length of about 1 meter. The dwell time refers to the time it takes a given droplet to flow along the length of one of the polymerization channels 320.

The geometry of the polymerization channels 320 is designed to contribute to efficient polymerization. For instance, the cross-sectional area of the channels 320 can be slightly larger than that of the droplets. This prevents the droplets from stacking on top of one another in the channels, instead keeping the droplets substantially evenly separated in a single file line, which in turn helps to avoid clogs and to ensure that all droplets are exposed evenly to the applied stimulus. The serpentine path of the polymerization channels 320 provides a long path length even in the limited area of the microfluidic chip 210. Moreover, the tight turns, e.g., 180° turns, along the polymerization channels 320 promotes mixing of the fluid stream in the channels, thereby facilitating thermal transfer, e.g., by inducing convection, and thus promoting polymerization efficiency.

The parameters for polymerization of the matrix material in the droplets can depend on the size of the droplets. For instance, the duration of an exposure of a droplet to the stimulus that is sufficient to induce complete polymerization of the matrix material in the droplet can depend on the size of the droplet. A larger droplet may take longer to polymerize than a smaller droplet because of the larger volume of material and the greater distance between the edge of the droplet and its center. For instance, droplets of a certain size may need an exposure time of at least 90 seconds, while droplets of a different, smaller size may need an exposure time of only 30 seconds. The microfluidics system can be tuned such that the stimulus is sufficient to obtain complete polymerization of the matrix material in droplets of a target size, e.g., such that droplets flowing through the system at a target flow rate are exposed to the stimulus for an amount of time sufficient to polymerize droplets of the target size. Specifically, length of the polymerization channel 320 is fixed. Thus, the flow rate (velocity) of the droplets along the polymerization channel 320 determines the exposure time of the droplets amount.

In some examples, the system is designed to achieve complete polymerization when droplets of a target size flow through the polymerization channel 320 at a target flow rate. In some examples, various combinations of target sizes and target flow rates are available. For instance, the system may be designed such that droplets in a first size range achieve complete polymerization when they flow at a first flow rate, and droplets in a second, smaller size range achieve complete polymerization when they flow at a second, faster flow rate.

The downstream end of each polymerization channel 320 is fluidically connected to a corresponding outlet channel 322, each of which is connected to a corresponding demulsification cartridge (not shown). Each outlet channel 322 is formed in a respective outlet finger 324 of the microfluidic chip 210. The outlet fingers 324 are spread apart from one another (e.g., each outlet finger 324 is separated from adjacent fingers by a gap) to allow for sufficient space for each demulsification cartridge 230. Moreover, the spread-apart outlet fingers 324 allows each finger to flex and seal against the corresponding demulsification cartridge 230 independently of each other finger, thereby avoiding the problem of tolerance variations preventing sealing.

Referring to FIGS. 5A-5C, for thermal polymerization, the matrix material is a temperature-sensitive material, such as Matrigel, that polymerizes responsive to exposure to heat. Heat blocks 500a, 500b (collectively referred to as heat blocks 500) are positioned to apply heat to the top and the bottom surface in the polymerization region of the microfluidic chip 210. The heat blocks 500 are designed to expose the droplets in the polymerization channels 320 to a temperature that is sufficient to induce polymerization but not so high as to destroy the biological material, e.g., a temperature of between 35° C. and 45° C., e.g., 37° C. Moreover, the heat blocks 500 are designed to induce a rapid rise in temperature to the target temperature, and to provide accurate temperature control. In some examples, thermal polymerization of droplets having Matrigel as the polymerizable matrix material can be achieved with an exposure time of less than 2 minutes, e.g., less than 1 minute.

The heat blocks 500 are secured in place, e.g., with clamps. In some examples, the heat blocks 500 are secured in place in a way that promotes contact with the surfaces of the microfluidic chip 210. For instance, the heat blocks 500 can be spring loaded to press them against the surfaces of the microfluidic chip 210. In some cases, springs on both sides of the heat blocks 500 are used to secure the heat blocks against the microfluidic chip. For example, a first spring secures the heat block 500a against the microfluidic chip and a second spring secures the heat block 500b against the microfluidic chip. The heat blocks 500 do not contact the droplet generation region 302 to avoid inducing polymerization of the matrix material before it reaches the polymerization region 304.

As shown in the cross-sectional view of FIG. 5B and the exploded view of FIG. 5C, each of the heat blocks includes a heating element 502 that contacts the respective surface of the microfluidic chip 210 in the polymerization region 304. The heating elements 502 are enclosed on all sides except the side facing the microfluidic chip 210 by a thermally insulating cover 504, such as a polytetrafluoroethylene (PTFE) or ultra-high-molecular-weight polyethylene (UHMWPE) cover. Referring specifically to FIG. 5C, in an example, the heating elements 502 are copper blocks, e.g., 6 mm thick copper blocks heated on the side opposite the microfluidic chip by respective resistance heaters 506, such as Kapton film resistance heaters, e.g., Minco 24 VDC resistance heaters. In an example, the resistance heaters 506 are wired in parallel and are controlled by a controller under closed loop feedback control, with temperature feedback provided by a temperature sensor, such as a thermistor, thermocouple, resistance temperature detector, or other suitable temperature sensor, attached to one or both of the heating elements 502. The controller has a serial interface to allow a computer to control operation of the heating elements 502 and to read the current temperature of the heating elements. In some examples, a temperature sensor is attached to each of the heating elements 502, and each heating element 502 is independently controllable by a corresponding thermostat controller, thereby enabling precise temperature control.

Figure 6A:
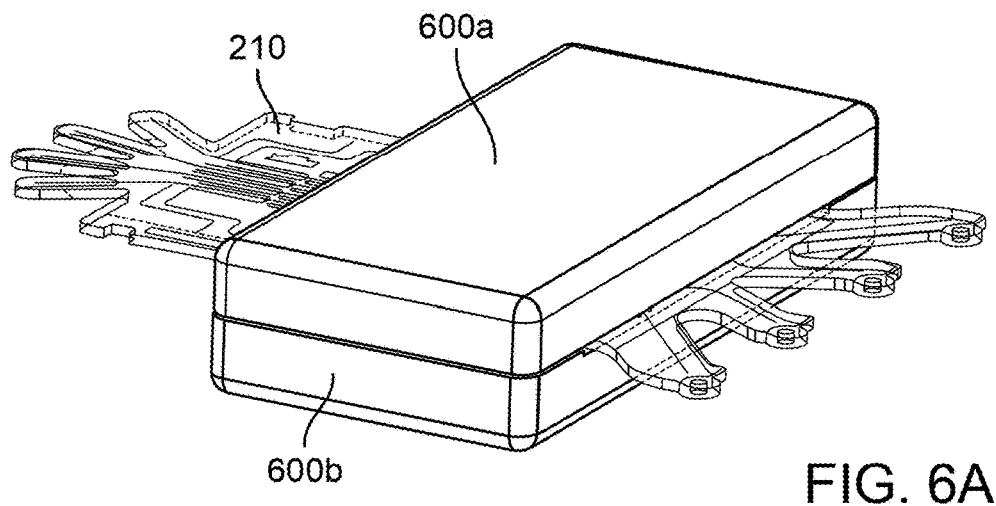
FIGS. 6A-6C are diagrams of light blocks for a MOS generation system.
Figure 6B:
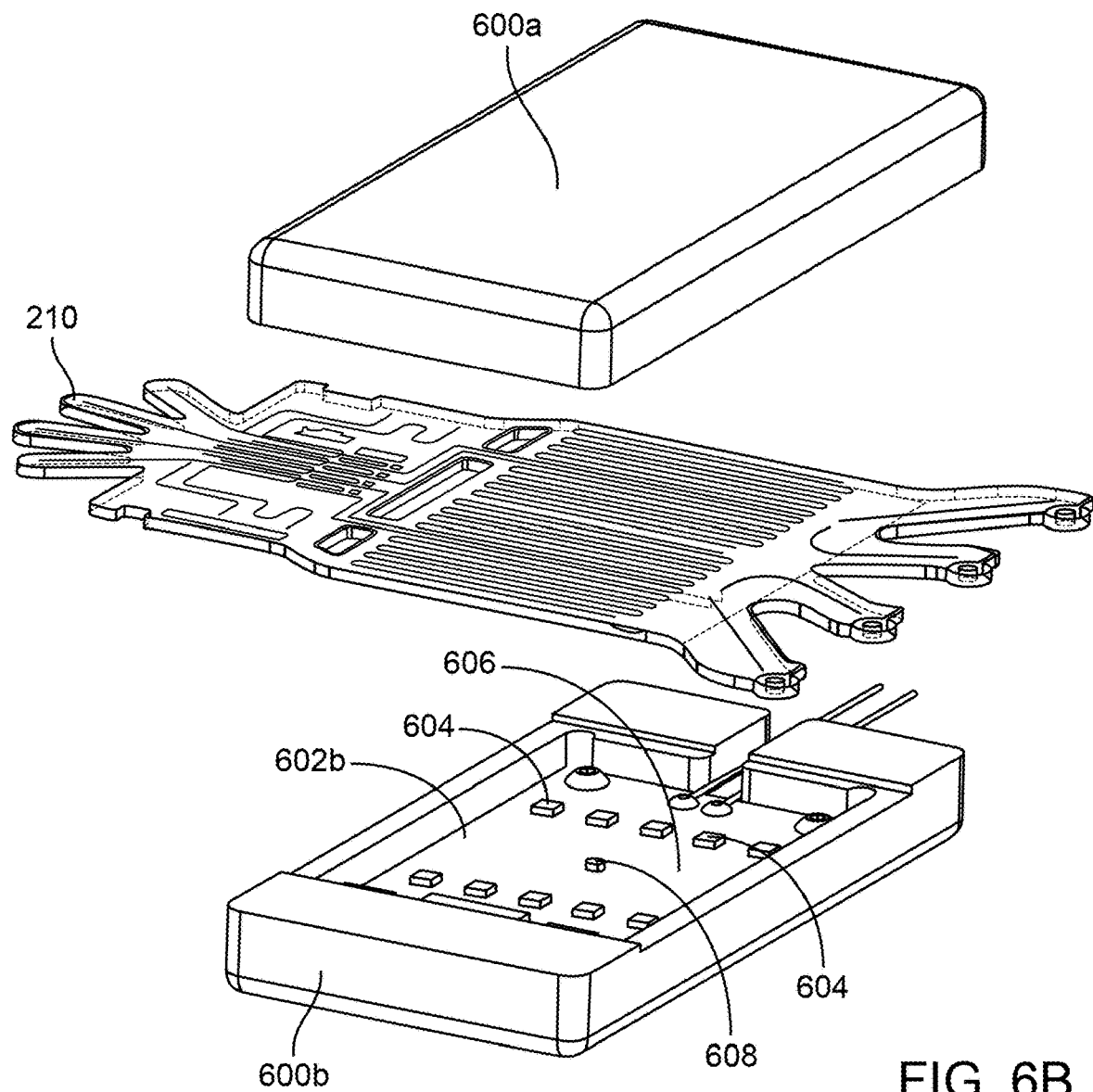
Figure 6C:
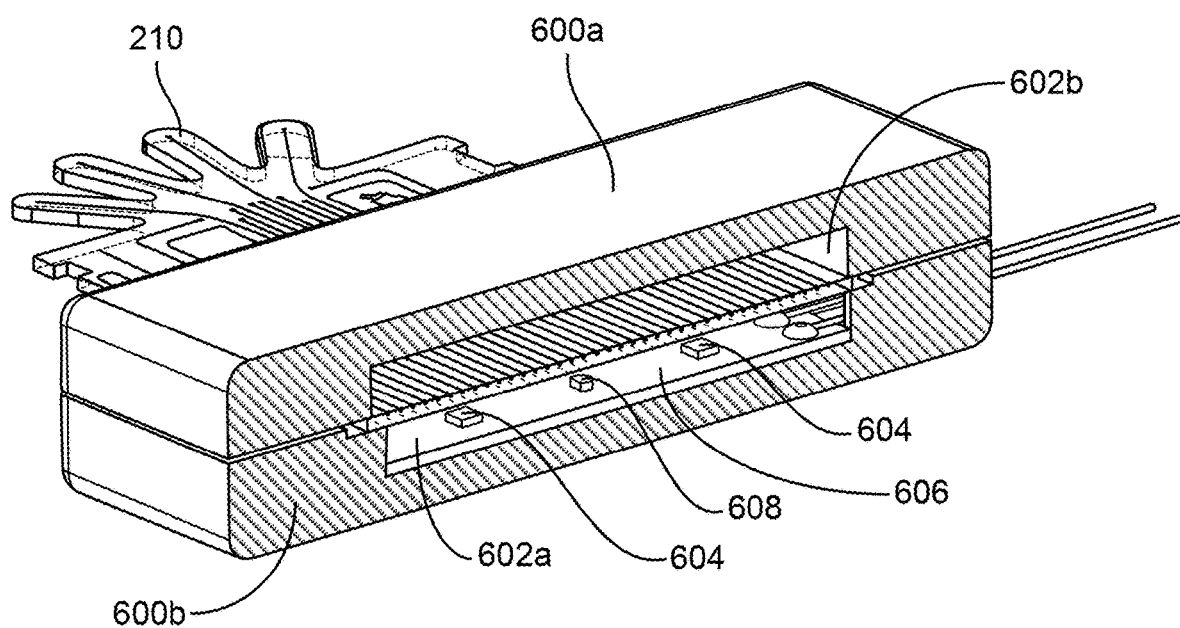

Referring to FIG. 6A-6C, when light-induced polymerization is used, the matrix material is a material that polymerizes responsive to exposure to certain wavelengths of light, such as 405 nm blue light. For light polymerization, light blocks 600a, 600b are positioned to illuminate the droplets in the polymerization channels of the microfluidic chip. Each light block 600a, 600b defines a respective integrating chamber 602a, 602b. The light block 600b houses a light source, such as one or more light emitting diodes (LEDs) 604, e.g., 405 nm blue LEDs, disposed in the integrating chamber 602b. For instance, the LEDs 604 are mounted on a printed circuit board (PCB) 606, such as a metal core PCB, to disperse heat generated by the LEDs. The LEDs can be arranged in a one- or two-dimensional array. In some examples, LEDs are disposed in both integrating chambers 602a, 602b. A heat sink is disposed on the exterior of one or both of the light blocks 600a, 600b to further disperse the heat.

The integrating chambers 602a, 602b are designed to repeatedly reflect the light around and through the microfluidic chip to maximize exposure and exposure uniformity. For instance, the integrating chambers 602a, 602b are formed of a material, such as white PTFE or UHMWPE, that has high diffuse reflectivity and that is not yellowing. The high diffuse reflectivity of both integrating chambers 602a, 602b causes the light from the LEDs 604 to pass through the transparent microfluidic chip 210 multiple times. A material that has sufficiently high reflectivity is a material that reflects at least 90%, at least 95%, or at least 99% of visible light, and that has a constant reflectance across all visible wavelengths (e.g., a reflectance that varies less than 20%, less than 10%, less than 5%, or less than 1% across the spectrum of visible wavelengths). Diffuse reflectivity refers to a property of a material by which every ray of light incident on the material is dispersed in many directions and not specularly reflected.

To further facilitate light reflectance and to prevent light from escaping the integrating chambers 602a, 602b, the light blocks 600a, 600b are secured in place and pressed against the surfaces of the microfluidic chip, e.g., by spring loading. In some cases, springs on both sides of the light blocks 600a, 600b are used to secure light blocks 600a, 600b against the microfluidic chip. For example, a first spring secures the light block 600a against the microfluidic chip and a second spring secures the light block 600b against the microfluidic chip. A photodetector 608, such as a photodiode, is disposed in the integrating chamber 602b of the light block 600b to measure the intensity of light in the integrating chamber 602b. In some examples, the signal from the photodetector is used to verify that there is sufficient light intensity to complete the light-induced polymerization process; if not, sample processing does not proceed. In some examples, the signal from the photodetector is used for closed-loop computer control of the light sources. In some examples, a photodetector is also disposed in the integrating chamber 602a.

In some examples, light-induced polymerization is sufficiently fast that polymerization occurs in less than the dwell time of the droplets in the polymerization channels 320. For instance, light-induced polymerization can be a photo-initiated process that, once triggered with light of the appropriate wavelength, continues to propagate until complete even without continued exposure to the light. In these examples, the light sources can be pulsed for energy efficiency and to reduce heating of the droplets. The light blocks are positioned to avoid illumination of the droplet generation region to avoid inducing polymerization of the matrix material before it reaches the polymerization region.

In some examples, the matrix material is polymerized by chemical polymerization. In chemical polymerization, two liquid materials (such as two hydrogels, one of which contains biological material) are mixed, and an emulsion of the mixed hydrogels in the hydrophobic fluid is generated in the droplet generation region. Polymerization begins substantially immediately upon mixing of the two hydrogels. The ratio of the hydrogel containing the biological material to the other hydrogel is between about 1:1 and about 2:1. Droplet size is controlled by the combined flow rate of the two hydrogels.

In a specific example, a microfluidic chip designed for chemical polymerization includes two independent flow pathways for concurrent processing of two biological samples. Each flow pathway includes two channels for the two hydrogels. The two hydrogel channels merge into a single channel just upstream of a junction with flow channels for the hydrophobic fluid. A droplet generation chamber is located downstream of the junction, e.g., as illustrated in FIG. 4. The droplet generation chamber and a subsequent outlet channel have a length such that the residence time of the emulsion allows for complete chemical polymerization of the droplets. The emulsion of polymerized droplets in the hydrophobic fluid are output into demulsification cartridges.

Referring again to FIGS. 3A-3B, cutouts 330 are defined in the microfluidic chip 210 between the droplet generation region 302 and the polymerization region 304. The cutouts 330 provide thermal and/or optical isolation between the regions to prevent unwanted early polymerization of the matrix material that is still in the droplet generation region. The cutouts 330 can have angled sides (see FIG. 2B), e.g., sloped at a 45° angle relative to the surface of the microfluidic chip 210, to create a total internal reflection (TIR) mirror. When light is used as a polymerization stimulus, this TIR mirror reflects the stimulus light away from the droplet generation region 302, thereby protecting the matrix material in the droplet generation region 302 from exposure to the light. When heat is used as a polymerization stimulus, the cutouts 330 act as thermal insulators, protecting the matrix material in the droplet generation region 302 from exposure to the applied heat. For instance, the cutouts 330 extend through the entire thickness of the microfluidic chip 210.

Figure 7A:
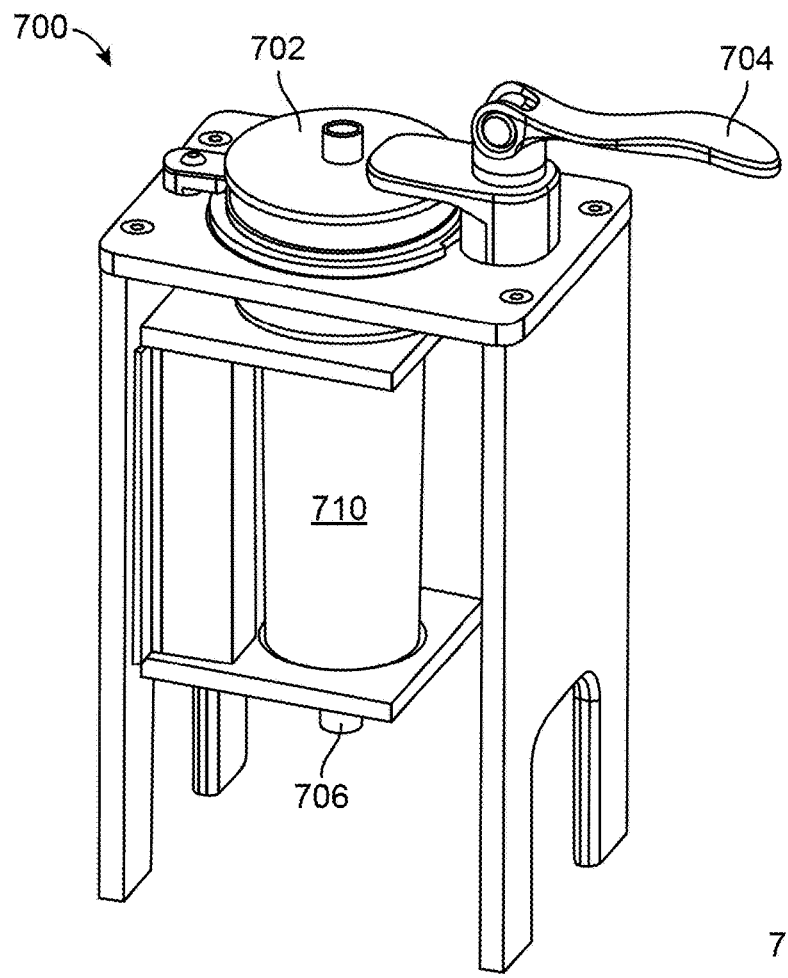
FIGS. 7A-7C are diagrams of an example oil reservoir.
Figure 7B:
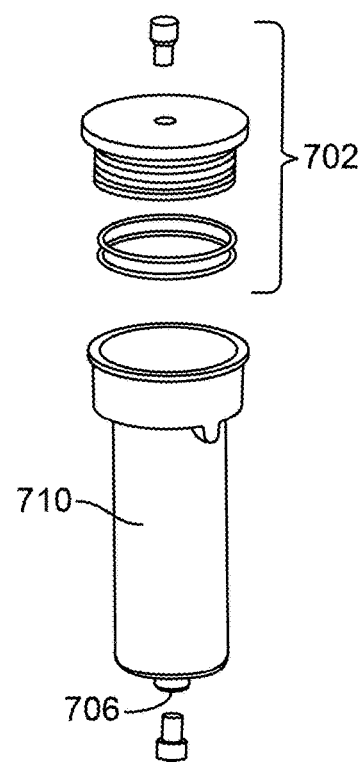
Figure 7C:
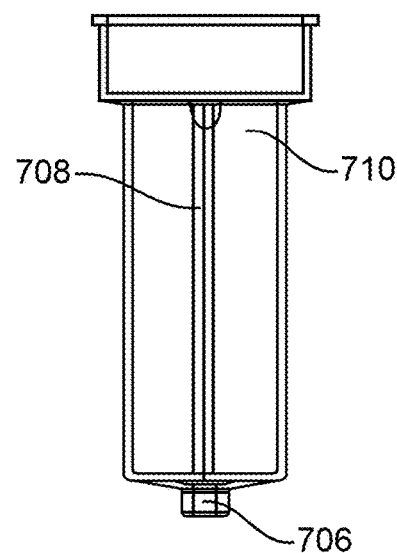

Referring to FIGS. 7A-7C, an oil reservoir 700 stores oil to be used for droplet generation. Oil is poured into a chamber 710 of the reservoir 700 through an opening at the top of the reservoir, which is closable by a cover 702. In some examples, the cover 702 is a pressure cap that is secured in place with a toggle clamp 704 such that the pressure cap can be removed without a screwing motion. Oil exits the chamber 710 through a port 706 at the bottom of the chamber, e.g., such that no dip tube is used. In some examples, the port 706 is a threaded port to facilitate a reliable seal to tubing connected thereto.

An internal, retro-reflective rib 708 extends along the height of the chamber 710 to allow measurement of the volume of oil in the chamber 710, e.g., in discrete increments. In some examples, the rib is designed to enable measurement of five distinct volumes of oil. Based on the number and volumes of samples to be processed, the system can verify that sufficient oil is present before starting.

Figures 7D, 7E:
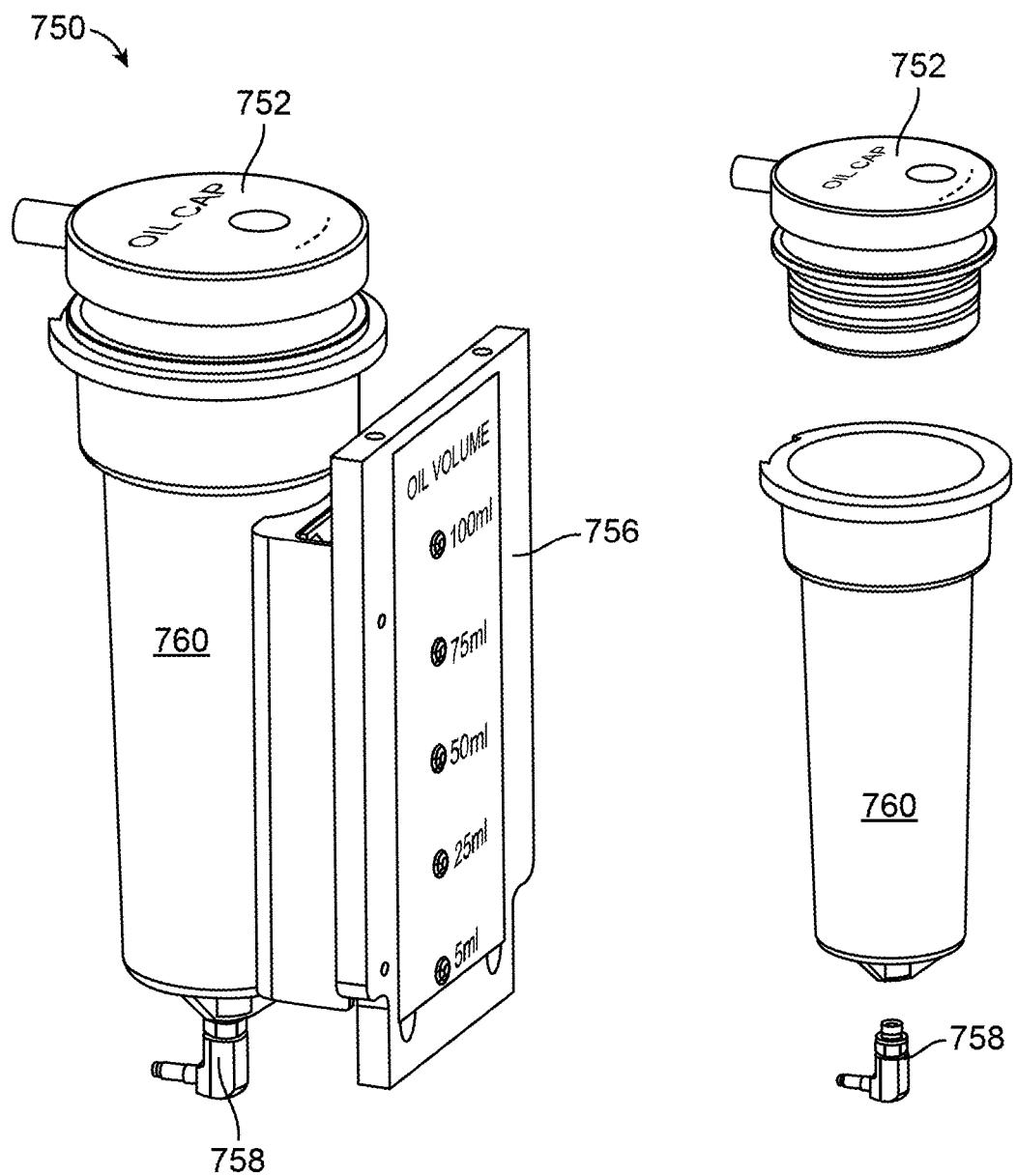
FIGS. 7D-7E are diagrams of an example oil reservoir.

FIGS. 7D-7E illustrate an example of an oil reservoir 750 for storing oil to be used for droplet generation. Oil is poured into a chamber 760 of the reservoir 750 through an opening at the top of the reservoir, which is closable by a cover 752, which can be a filter vented cap used to keep particulates out of the oil. In some cases, the oil is not pressurized, and the oil reservoir 750 does not include a pressure camp and/or a toggle clamp. The oil reservoir 750 is configured with (e.g., includes) an interface 756 indicating a volume of oil in the oil reservoir 750. The interface 756 may display other measures instead of or in addition to volume. Oil exits the chamber 760 through a port 758 at the bottom of the chamber.

Figure 8A:
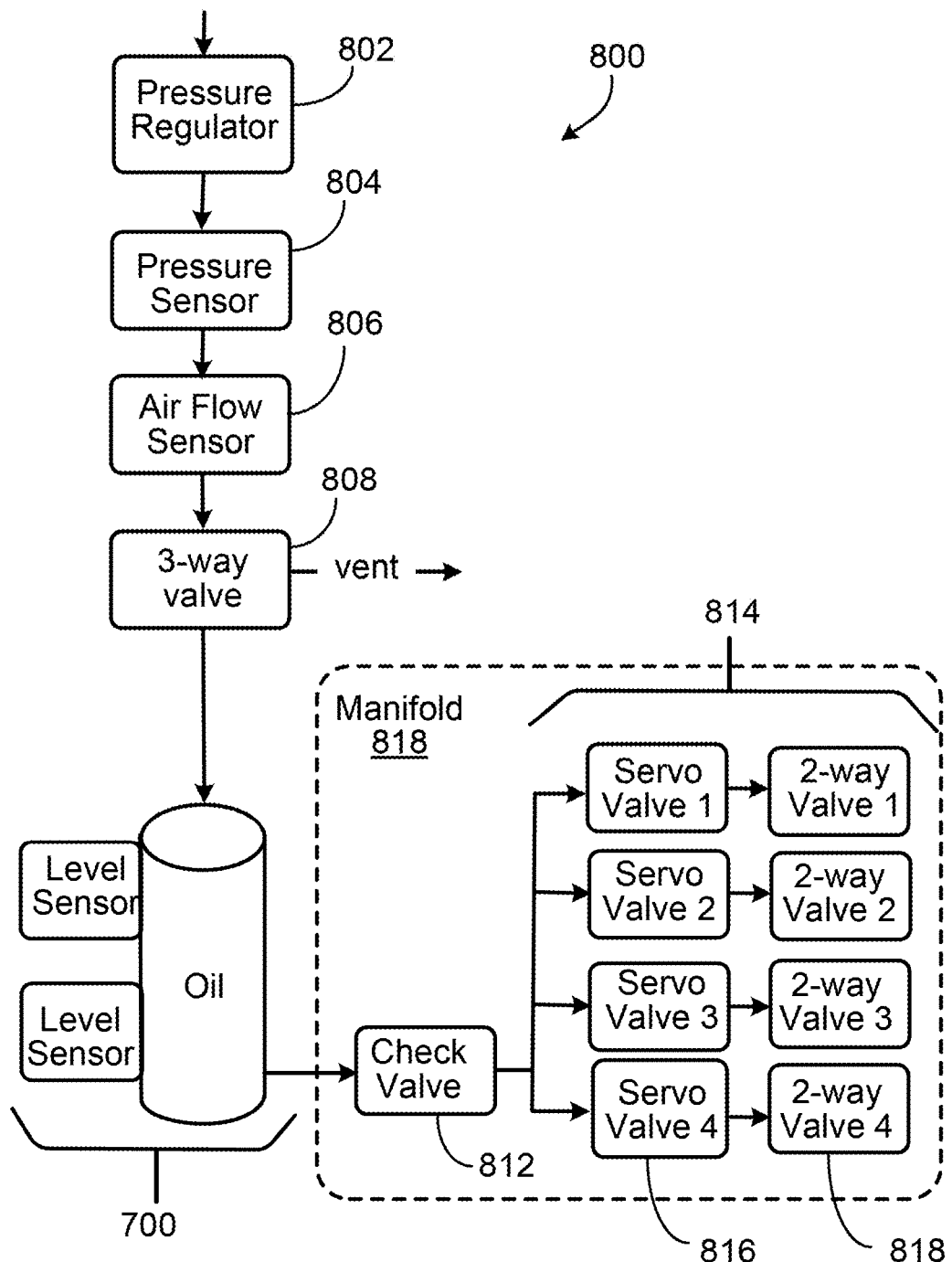
FIG. 8A is a diagram of an example oil delivery subsystem.

FIG. 8A is a schematic block diagram of an example oil delivery subsystem 800 for delivery of oil from the reservoir 700 to the microfluidic chip 210. Generally, during the droplet generation process, the oil flow to each of the four droplet generation channels is individually metered to thereby control the velocity of the droplet stream through the polymerization section of the microfluidic chip.

The oil delivery subsystem 800 includes a pressure regulator 802 that supplies a single fixed air pressure, e.g., an air pressure of 2 bar, to the oil reservoir 700 to push oil out through the port 706. A pressure sensor 804 and an air flow sensor 806 positioned between the pressure regulator 802 and the oil reservoir 700 provide feedback for error checking. A three-way valve 808 is also positioned between the fixed pressure regulator 802 and the oil reservoir 700. The three-way valve 808 has a default open configuration to vent pressure in the oil reservoir 700, and is closed by a controller in order to pressurize the reservoir 700. This is a safety feature that ensures, e.g., that the reservoir 700 is not pressurized when opened for refilling.

The oil leaving the oil reservoir 700 passes into a manifold 810 with a single check valve 812 to prevent contamination from backflow and then branches to four flow control channels 814. The flow for each of the four channels 414 is controlled by a respective servo flow valve 816 (e.g., Enidine PFV-W24E01-P050E-0300 servo flow valves) mounted on the manifold 810. In some examples, control of the servo valves 816 is through a 0-10 VDC analog control signal providing closed-loop control of the oil flow rate, e.g., to control the size of the generated droplets. A two-way valve 818 is disposed along each channel 814 to serve as flow shut off valves. Downstream of the valves 818, tubing connects the channels 814 to oil ports in a mount for the microfluidic chip 210.

Figure 8B:
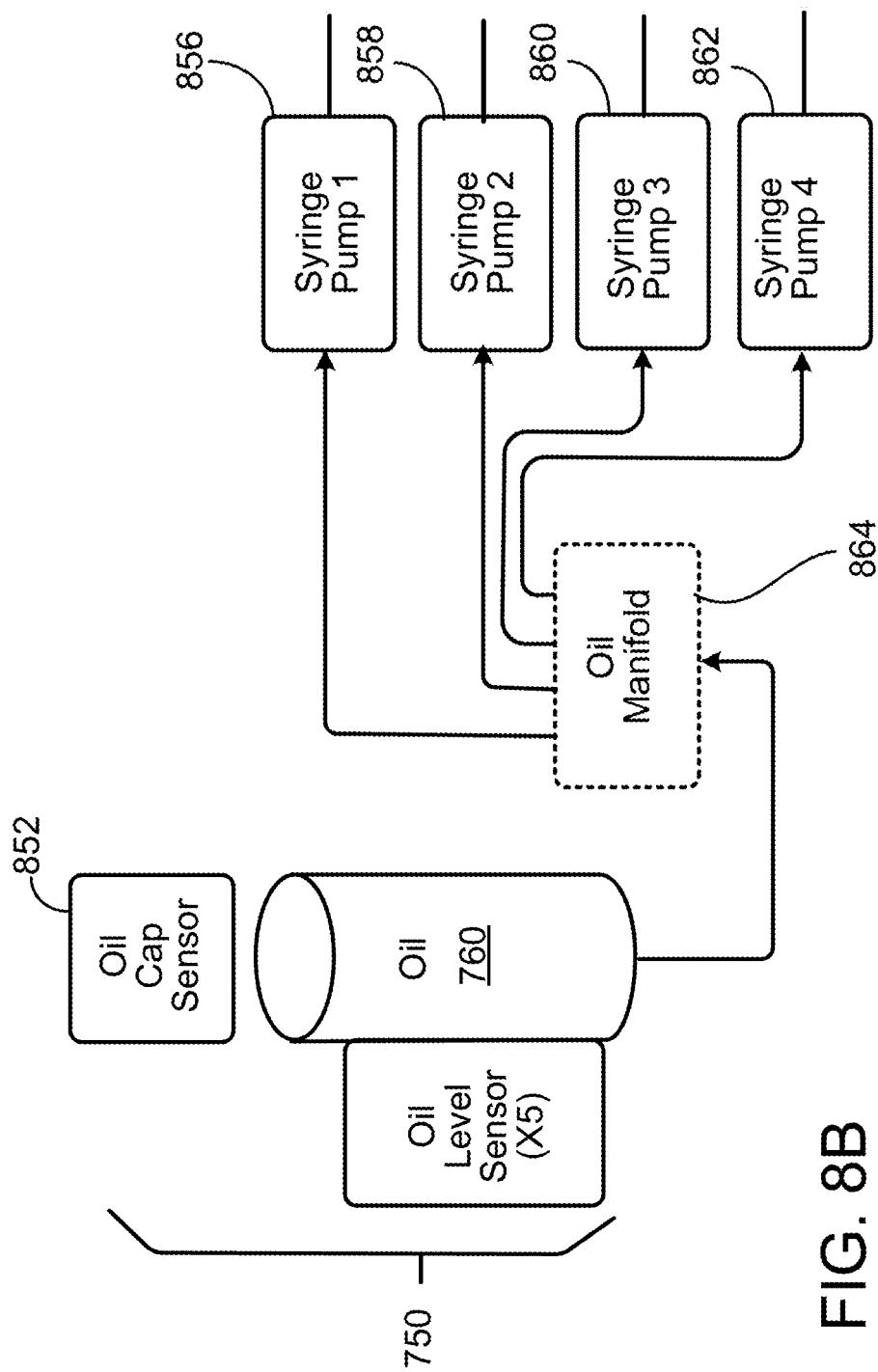
FIG. 8B is a diagram of an example oil delivery subsystem.

FIG. 8B is a schematic block diagram of an example oil delivery subsystem 850 for delivery of oil from the chamber 760 of the oil reservoir to the microfluidic chip 210. The oil delivery system includes a manifold 864 to distribute the single oil reservoir output to four independent syringe pumps 856, 858, 860, and 862 with programmable flow rate, controlled by a controller such as a PID controller. Outputs from the four syringe pumps 856, 858, 860, and 862 connect to the four oil input ports of the droplet generation chip. Each syringe has a volume capacity sufficient to do an entire droplet generation run without stopping and refilling. The oil delivery subsystem 850 includes one or more level sensors 854 configured to measure the volume of oil in the oil chamber 760, and an oil cap sensor 852. In one specific example, the oil reservoir 750 includes five level sensors 854.

Figure 9A:
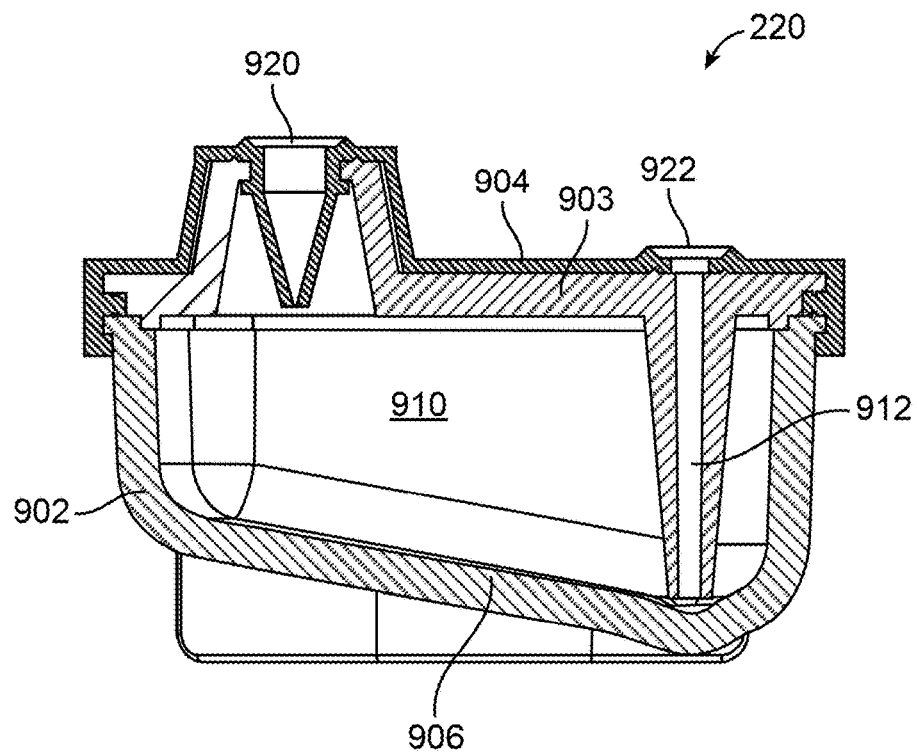
FIGS. 9A and 9B are cross-sectional and perspective view diagrams, respectively, of a sample reservoir.
Figure 9B:
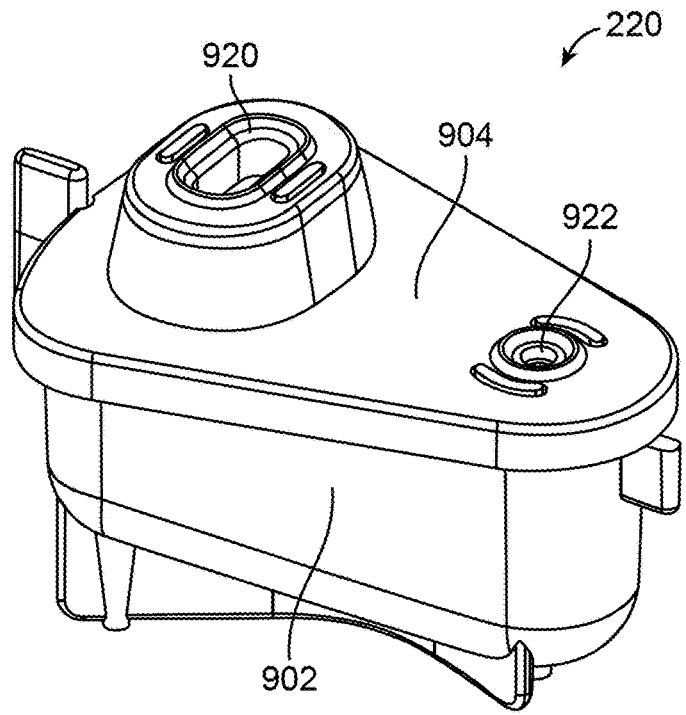

Referring to FIGS. 9A-9B, each biological sample is packaged in a closed, disposable (single-use) reservoir 220. The reservoir 220 is designed for transportation from a sample preparation area to the MOS generation instrument and for direct insertion into the instrument. The reservoir 220 includes a plastic base 902 and a plastic top cover 903, e.g., a polypropylene base and top cover. The base 902 and top cover 903 are attached together to form a hermetic seal, e.g., by ultrasonic welding. The base 902 defines a single well 910 in the interior of the reservoir 220, with capacity for a single biological sample, e.g., a capacity of less than 5 mL, less than 2 mL, less than 1 mL, or less than 500 µL; and greater than 5 µL, greater than 10 µL, or greater than 20 µL. The well has a sloping bottom 906 that slopes to a low point beneath a tube 912 that extends from the bottom 906 of the well 910 to the cover 904. This geometry facilitates processing of a high percentage, e.g., substantially 100%, of the sample contained in the well 910. This geometry also facilitates loading of the reservoir 220 into the MOS generation instrument with proper orientation.

The reservoir 220 includes a flexible cover 904, e.g., an elastomeric cover, disposed over the top cover 903. An input port 920 and an output port 922 are defined in the flexible cover 904. The input port 920 and the output port 922 are flexible seals that, when not in use, are fluidically sealed by the flexible cover 904. The input port 920 is, e.g., a duckbill valve. To insert the biological sample into the well 910 of the reservoir 220, an operator pushes a pipette tip through a slit in the duckbill valve of the input port 920 and dispenses the sample. Air gaps along the slit on either side of the pipette tip allow air to exit as the sample is dispensed. When the pipette is withdrawn, the duckbill valve closes and seals, preventing spillage.

The duckbill valve of the input port 920 is also sized and shaped to mate with a pressure manifold when the reservoir is positioned in the MOS generation instrument. This configuration allows the well 910 to be pressurized without penetration of the duckbill valve of the input port, which thereby reduces the risk of contamination of the biological sample contained in the well 910.

The output port 922 is a seal that couples the reservoir output to the microfluidic chip input. When the well 910 is pressurized, the sample contained in the well 910 is forced through the tube 912 and out through the output port 922, from where the sample enters into the microfluidic chip 210.

Figure 10A:
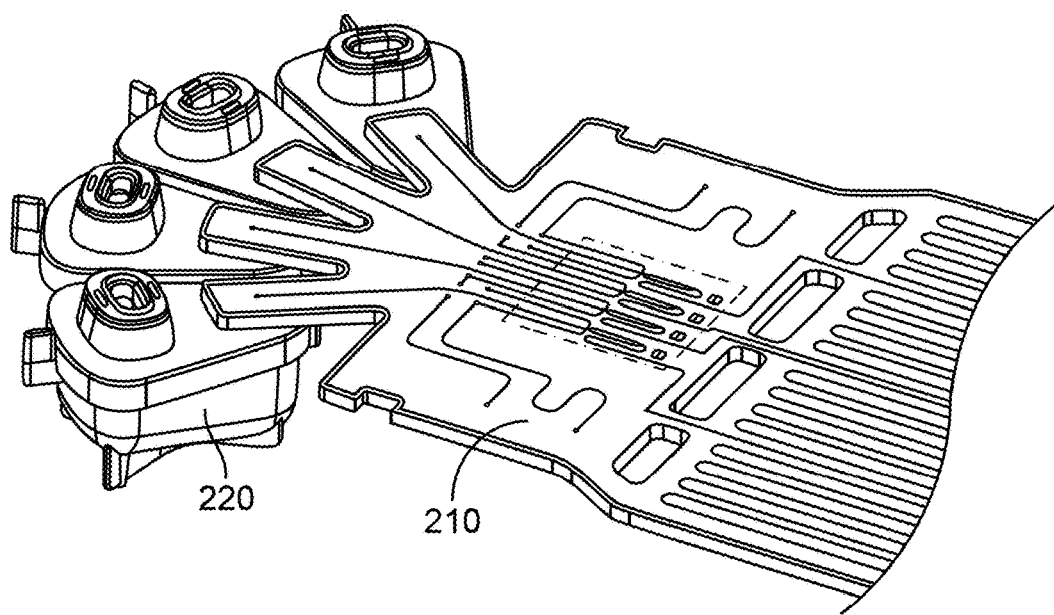
FIGS. 10A and 10B are diagrams of multiple reservoirs.
Figure 10B:
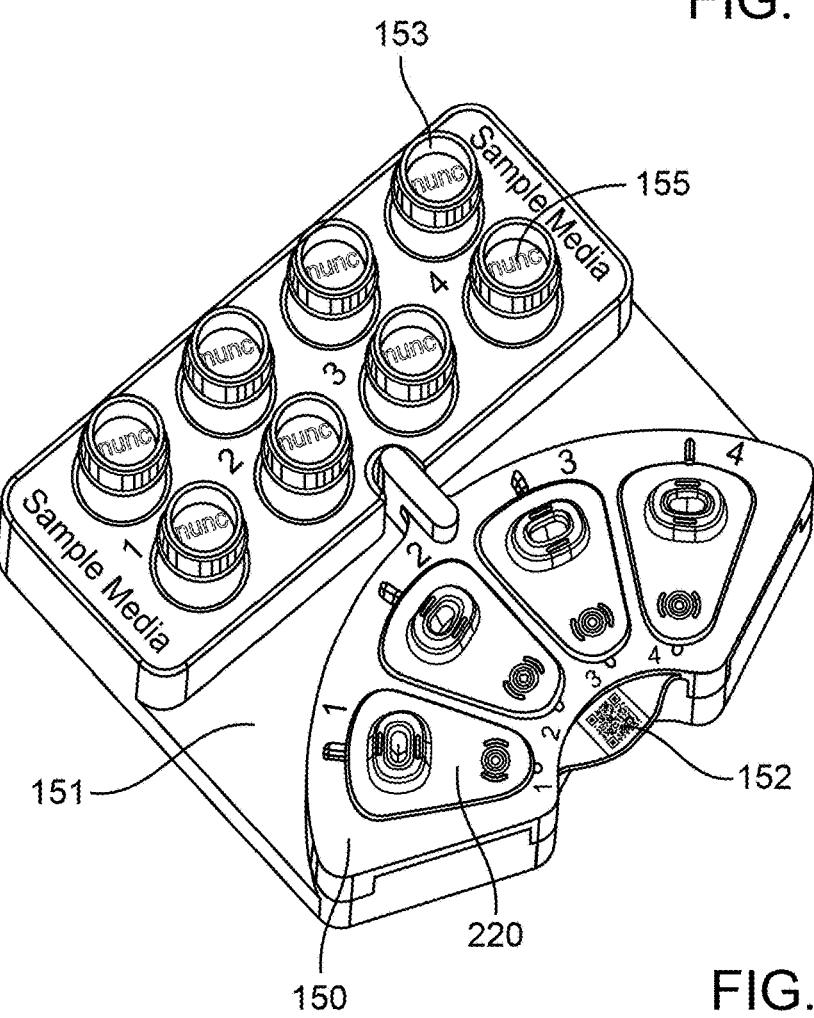

Referring to FIGS. 10A and 10B, samples from multiple reservoirs 220 (e.g., up to four reservoirs, in the illustrated example) can be processed concurrently by the MOS generation instrument. Each reservoir 220 is fluidically connected, via its outlet port 922 (FIGS. 8A-8B), to the inlet port of one of the fluid flow pathways through the microfluidic chip 210. In some examples, a set of multiple reservoirs 220 are handled collectively in a carrier 150, e.g., for transportation to the MOS generation instrument. The carrier 150 can have an identifier 152, such as a bar code (e.g., QR code or Data Matrix), serial number, or other identifier, printed or attached thereto, that is usable to identify the samples contained in the reservoirs 220 carried by the carrier 150. In some examples, each reservoir 220 also has an identifier that is usable to identify the sample contained therein.

The carrier 150 resides in a sample preparation station 151 for sample preparation prior to transportation to the MOS generation instrument. The sample preparation station 151 houses sample tubes 153 that contain biological material (e.g., minced tissue) suspended in processing media or buffer, and media tubes 155 that contain fresh media for dilution. A user dilutes the sample in each sample tube 153 to a desired concentration using media from the corresponding media tube 155, then transfers the diluted suspension into the corresponding reservoir 220.

Figure 11B:
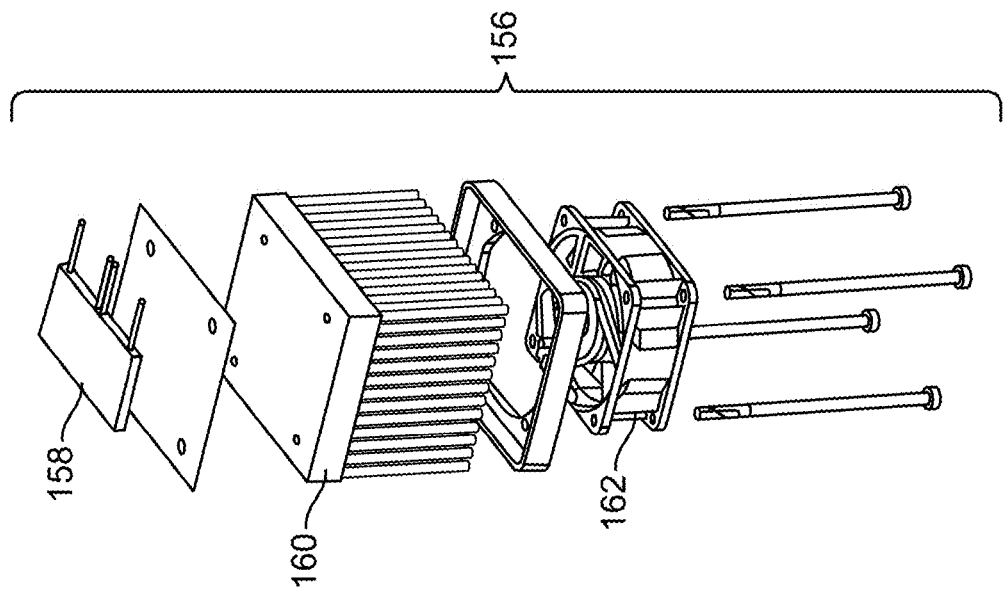
FIG. 11B is a diagram of a thermoelectric cooling subsystem.
Figure 11A:
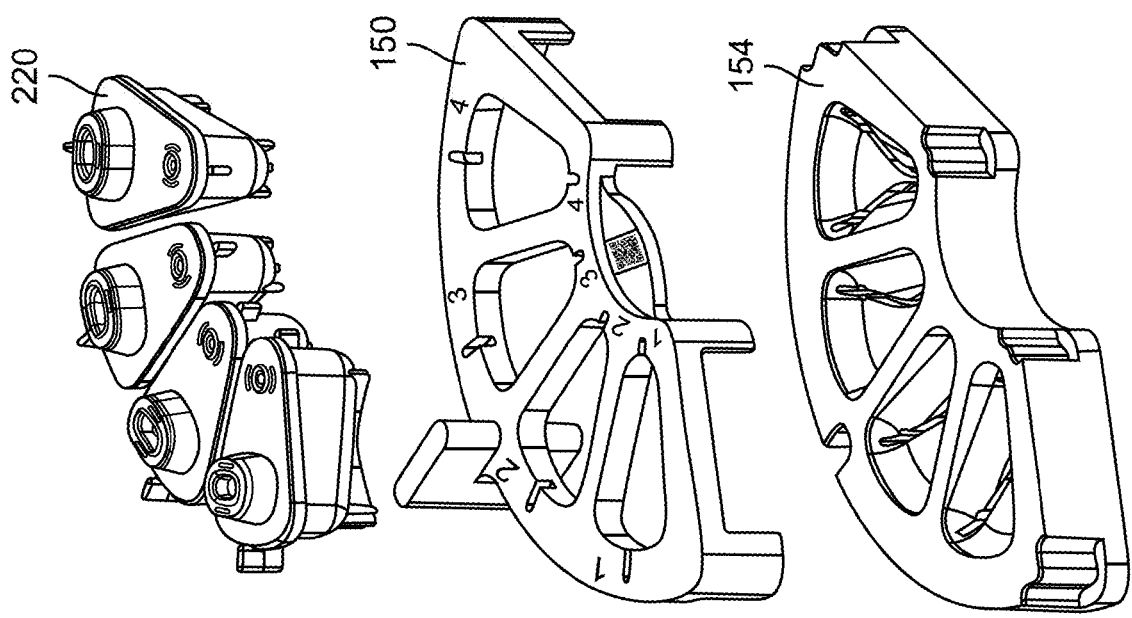
FIG. 11A is a diagram of a cold block.

In some examples, it is important to maintain the biological samples at a sufficiently low temperature prior to processing in the MOS generation instrument. During transportation to the instrument, the carrier 150 carrying the reservoirs 220 can be cooled, e.g., by placing the carrier in an ice bath or by using another cooling mechanism. Referring to FIGS. 11A and 11B, in some examples, the MOS generation instrument includes a cold block 154 that receives the carrier 150 carrying the reservoirs 220 to keep the biological samples cold while they are at the instrument. In an example, the cold block 154 is cooled by a thermoelectric cooling subsystem 156 including a thermoelectric cooler 158, with a heat sink 160 (e.g., a pin-fin heat sink) and a fan 162 to dissipate the heat.

Figure 12:
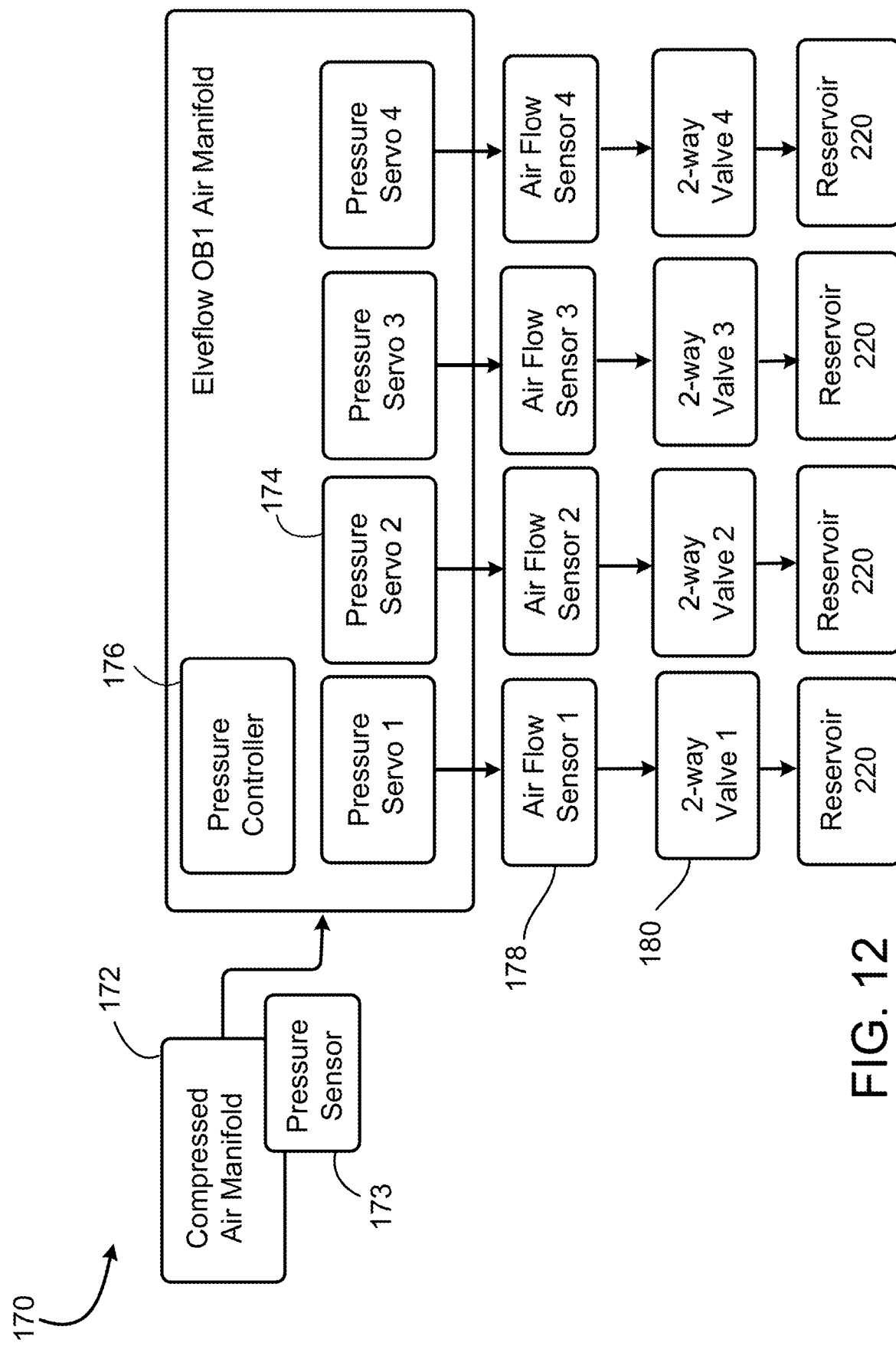
FIG. 12 is a diagram of a sample drive subsystem of a MOS generation system.

Referring to FIG. 12, a sample drive subsystem 170 applies air pressure independently to each reservoir 220 to drive the biological sample out of the reservoir through the tube 912 (FIG. 9A) and into the corresponding flow channel of the microfluidic chip 210. The air pressure applied to each reservoir is controllable independently from the air pressure applied to each other reservoir, and thus the fluid flow rate along each flow channel is independently controllable. The fluid flow rate affects the size of the droplets generated in the microfluidic chip, and in some examples the sample drive subsystem 170 implements closed loop feedback control of the fluid flow rate to achieve target droplet size, e.g., based on droplet size measurements obtained from the imaging subsystem.

A compressed air manifold 172 serves as a central distribution and monitoring point to supply air to multiple subsystems such as pressure servo valve 174. The integration of a pressure sensor 173 in the manifold allows the system to not operate if the supply pressure is too low. The pressure servo valves 174 are, for instance, Elveflow regulators with a maximum of 2 bar and a resolution of 0.0001 bar. The pressure servo valves 174 are controlled by a controller 176, such as a proportional-integral-derivative (PID) controller. An air flow sensor 178 and a two-way valve 180 are positioned in series between each servo valve 174 and the respective reservoir 220. The air flow sensors 178 provide feedback about the air flow, e.g., for error detection. The two-way valves 180 act as shut-off valves, preventing backflow when the pressure regulators are shut down.

In the illustrated example, the sample drive subsystem 170 is shown as implemented with pressure servo valves. In some examples, other types of flow regulators are used, such as pressure regulators, valves, or pumps, e.g., a peristaltic pump, diaphragm pump, syringe pump, or other suitable flow regulator. Control of the flow regulator can effect precise variation of the pressurization in the respective reservoir, e.g., in increments of 0.1 mbar or 0.01 mbar.

In general, the sample drive subsystem 170 is operable to control the fluid flow rate within the range of about 100-200 μL/minute by pressurizing the reservoir using an air pressure of between about 50-800 mbar. The sample drive subsystem 170 enables continuous fluid flow for the entire volume of a sample, e.g., for a sample volume of between about 10 μL and 1 mL. The sample drive subsystem 170 can implement a purge capability that involves higher air pressures, e.g., an air pressure of up to about 2000 mbar.

Figure 13A:
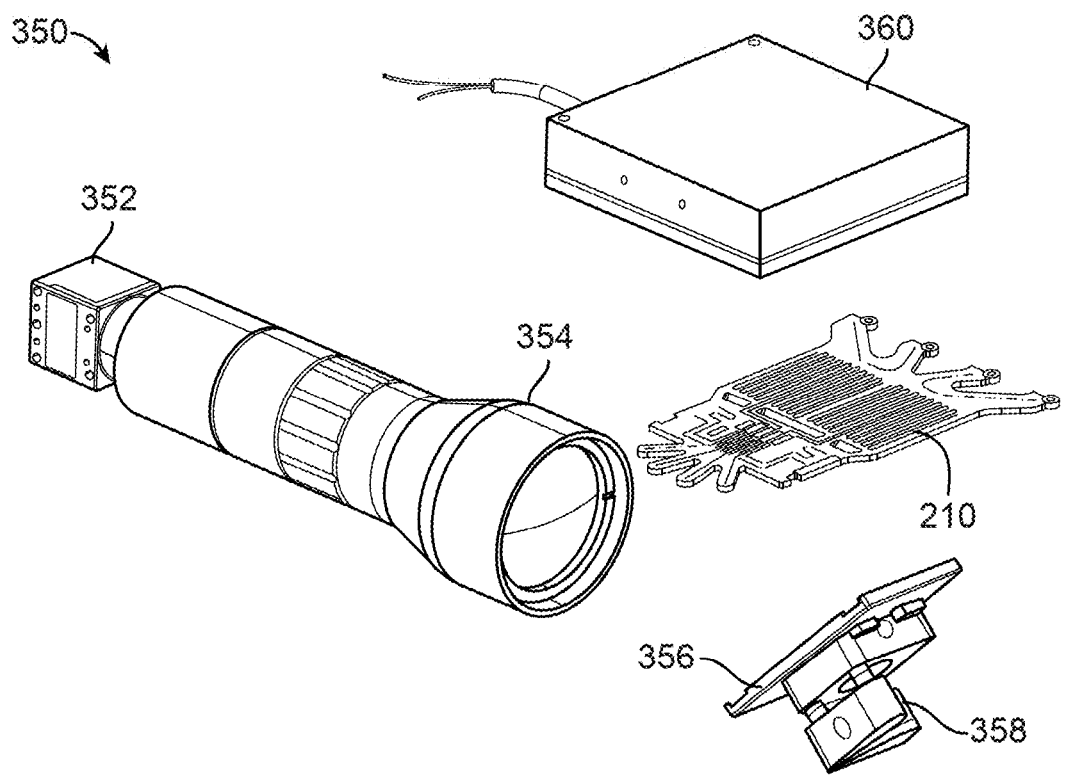
FIGS. 13A and 13B are diagrams of an imaging system of a MOS generation system.
Figure 13B:
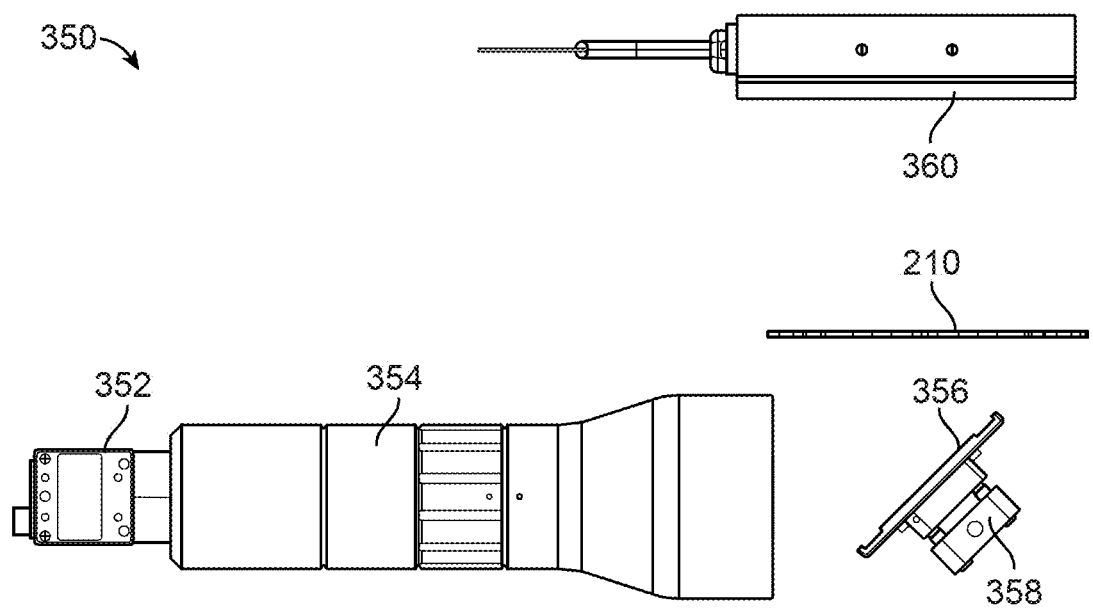

Referring to FIGS. 13A and 13B, an imaging subsystem 350 is positioned to acquire images (e.g., still or video images) of droplets as they pass through the droplet generation chambers 312 and outlet channels 314 (see FIGS. 3A-3B) of the microfluidic chip 210. The images acquired by the imaging subsystem are used for measurement or other characterization of the droplets, as part of a real-time, closed loop flow control feedback system, and/or for user visualization of the generated droplets. For instance, droplet characteristics determined based on the images can be provided as input into a closed loop control system that controls the flow rate of the first fluid, the second fluid, or both, to achieve droplets with target characteristics (e.g., target sizes) or to obtain a desired number of droplets (e.g., for a screening library).

The imaging subsystem 350 includes a camera 352, such as a still camera or a video camera, a lens 354 attached to the camera 352, a mirror 356 on a kinematic mount 358, and a backlight 360. The camera 352 and lens 354 and the mirror 356 on its mount 358 are positioned on one side of the microfluidic chip 210. The backlight 360 is positioned on the opposite side of the microfluidic chip 210. A mount (not shown) houses the camera 352, the lens 354, and the mirror 356. In some examples, to protect the components of the imaging subsystem from drips and debris, the imaging subsystem 350 is separated from the microfluidic chip by a transparent window, e.g., a glass window. Images captured by the camera 352 are provided to a computing device such as a local computer or a cloud-based server having one or more processors coupled to a memory.

In general, the camera 352 and lens 354 have a field of view of about 20 mm×25 mm, a pixel resolution of about 5 μm, and a frame rate of 42 frames per second. The imaging subsystem 350 can be a monochromatic or a polychromatic imaging system. The imaging subsystem 350 has a global shutter, does not exhibit parallax or distortion in outer channels, and is capable of sub-frame region-of-interest transfer.

The backlight 360 is positioned to illuminate the droplet generation chambers and outlet channels of the microfluidic chip 210 so that images can be captured. The backlight 360 can be monochromatic or polychromatic, and illuminates the chip 210 with a wavelength that does not induce polymerization and does not heat the droplets to a degree sufficient to induce polymerization. In a specific example, the light is a green light mounted at least 75 mm from the chip. In some examples, multiple light sources of different colors are used to facilitate image analysis. The liquids, including the first fluid containing the patient-specific biological material and unpolymerized matrix material and the second, immiscible fluid, are generally both clear liquids, and the droplets are visible in the immiscible fluid because of a difference in the index of refraction between the droplets and the surrounding fluid. The curvature of the droplet edges, combined with the difference in refractive index, causes the droplets to act as lenses that bend the light from the backlight 360.

In some examples, the backlight 360 is a source of diffuse light, resulting in the edges of the droplet being visible in images captured by the camera 352. In some examples, the light is a collimated light source to facilitate image analysis. For instance, when illuminated with collimated light, the focusing effect of the lens-like droplets deflects light off of its original axis and away from the line of sight of the camera 352. This focusing effect enhances the contrast of the droplets in the resulting images as compared to droplets that are illuminated with diffuse light, which can facilitate identification of the droplets and/or their edges in the images. In some examples, a light is positioned on the same side of the microfluidic chip 210 as the camera, e.g., instead of the backlight 360.

In some examples, the imaging subsystem applies strobed illumination to capture multiple exposures of each of one or more of the droplets in a single image captured during a single frame of the camera 352. Because of the timing of the two exposures, e.g., the interval between the two exposures and the duration of each exposure, the same droplet is captured in both exposures, without artifacts such as blurring that can arise due to motion of a subject in an image. The two exposures of the same droplet are analyzed to determine characteristics of the droplet, such as droplet size (e.g., droplet volume or droplet diameter), droplet size distribution, droplet velocity, separation between adjacent droplets, a number density of the droplets (e.g., number of droplets per unit length of the outlet channel (e.g., outlet channels 314 of FIG. 4), number of droplets per unit volume of the second fluid), an estimated total number of droplets generated from a given starting volume of the first fluid, or other droplet characteristics. These characteristics are applied in a closed loop feedback system that can adjust the flow rate of source material (e.g., first or second fluid) to affect the size and flow rate of the droplets that are generated, thereby enabling continuous generation of droplets of a target size at a target flow rate. This closed loop feedback system is described in more detail below.

Following polymerization, the polymerized droplets pass through a demulsification subsystem, in which the droplets are moved from their emulsion in the second fluid (e.g., oil) into an aqueous fluid in a continuous, microfluidic based demulsification process. The demulsification subsystem is designed to minimize loss of droplets, e.g., to achieve recovery of at least 90% of the droplets into the aqueous fluid, and to migrate the droplets into the aqueous fluid without physical damage to the droplets. The demulsification subsystem is also designed to prevent residual oil from being brought into the aqueous fluid. Moreover, the demulsification subsystem can achieve high throughput processing, e.g., processing input volumes ranging from 10-1000 µL, and has the capacity to remove large amounts of oil, such as up to 5 mL of oil.

Figure 14:
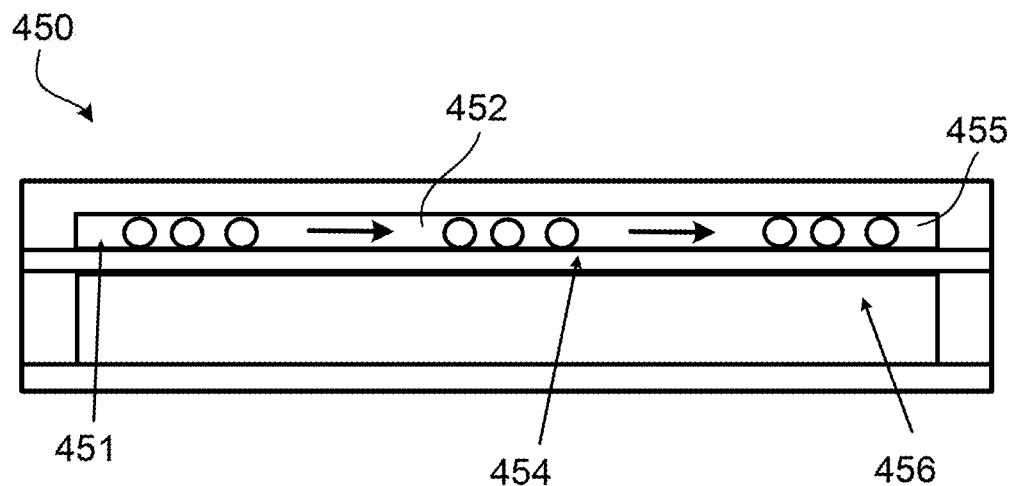
FIG. 14 is a schematic diagram of a portion of a demulsification subsystem of a MOS generation system.

FIG. 14 is a schematic illustration of a portion of a demulsification subsystem 450. The demulsification subsystem 450 uses transverse flow filtration in a microfluidic chip format, in which a combined stream of aqueous fluid and oil containing the polymerized droplets is enters into an inlet end 451 of a microfluidic channel 452 and flows along the channel 452 over a membrane 454. The membrane is a hydrophobic and oleophilic membrane, such as a polyvinylidene fluoride (PVDF) or PTFE membrane. A pressure bias across the membrane 454 drives the oil through the membrane into a collection container 456 below the membrane 454. For instance, a vacuum can be applied to the surface of the membrane 454 that faces the collection container 456. In some examples, the collection container 456 is vented to atmosphere. In some examples, a positive pressure is applied to the surface of the membrane 454 that faces the microfluidic channel 452. In some examples, the oil is driven through the membrane due to the pressure differential between the applied positive pressure above the membrane and ambient pressure below the membrane, aided by the force of gravity.

Because the membrane 454 is hydrophobic, the aqueous fluid and the polymerized droplets are repelled from the membrane 454 and thus continue to flow along the microfluidic channel 452 to an output end 455 of the microfluidic channel.

As the oil is drawn across the membrane, the polymerized droplets exchange into the aqueous fluid. By the output end 455 of the microfluidic channel, the oil has been drawn across the membrane, such that only the polymerized droplets in the aqueous fluid remain in the channel.

The microfluidic channel 452 of the demulsification subsystem 450 is serpentine to promote mixing of oil and aqueous fluid within the channel, thereby facilitating contact between the oil and the membrane 454 even when only a small fraction of the volume of the fluid is constituted by oil (e.g., toward the output end 455 of the microfluidic channel).

Figure 15:
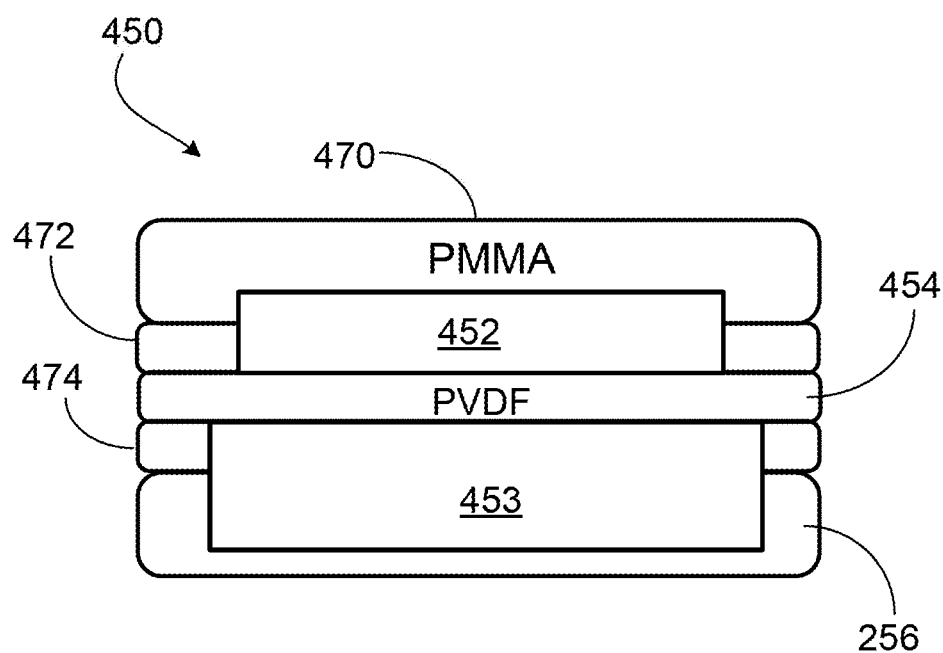
FIG. 15 is a cross-sectional view of a portion of a demulsification subsystem.

FIG. 15 illustrates a cross-sectional view of a portion of the demulsification subsystem 450. The microfluidic channel 452 is defined in a substrate 470, such as a molded plastic substrate (e.g., polymethylmethacrylate (PMMA) or polystyrene). A first side of the hydrophobic membrane 454 (e.g., a PVDF membrane) is attached to the substrate 470 by an adhesive 472, which is cut to expose the microfluidic channel 452 in the substrate 470. The opposite side of the membrane 454 is attached to the collection container 456, such as a plastic container, e.g., PMMA, by an adhesive 474. The adhesive 474 is disposed around the outside edge of the membrane 454 such that oil in the microfluidic channel can be drawn through the membrane 454 and into the collection container 456. The collection container 456 itself has a central chamber 453 positioned under the portion of the membrane that is not covered by the adhesive 474, such that the oil drawn through the membrane 454 is collected in the cavity of the collection container 456. The adhesives 472, 474 are biocompatible adhesives that are inert with respect to the oil and aqueous fluid.

The membrane 454 has pores that are sized to readily permit flow of oil through the membrane while preventing the passage of the droplets. For instance, the pores have a diameter of between 0.25 µm and about 1 µm, e.g., 0.45 µm.

Figure 16C:
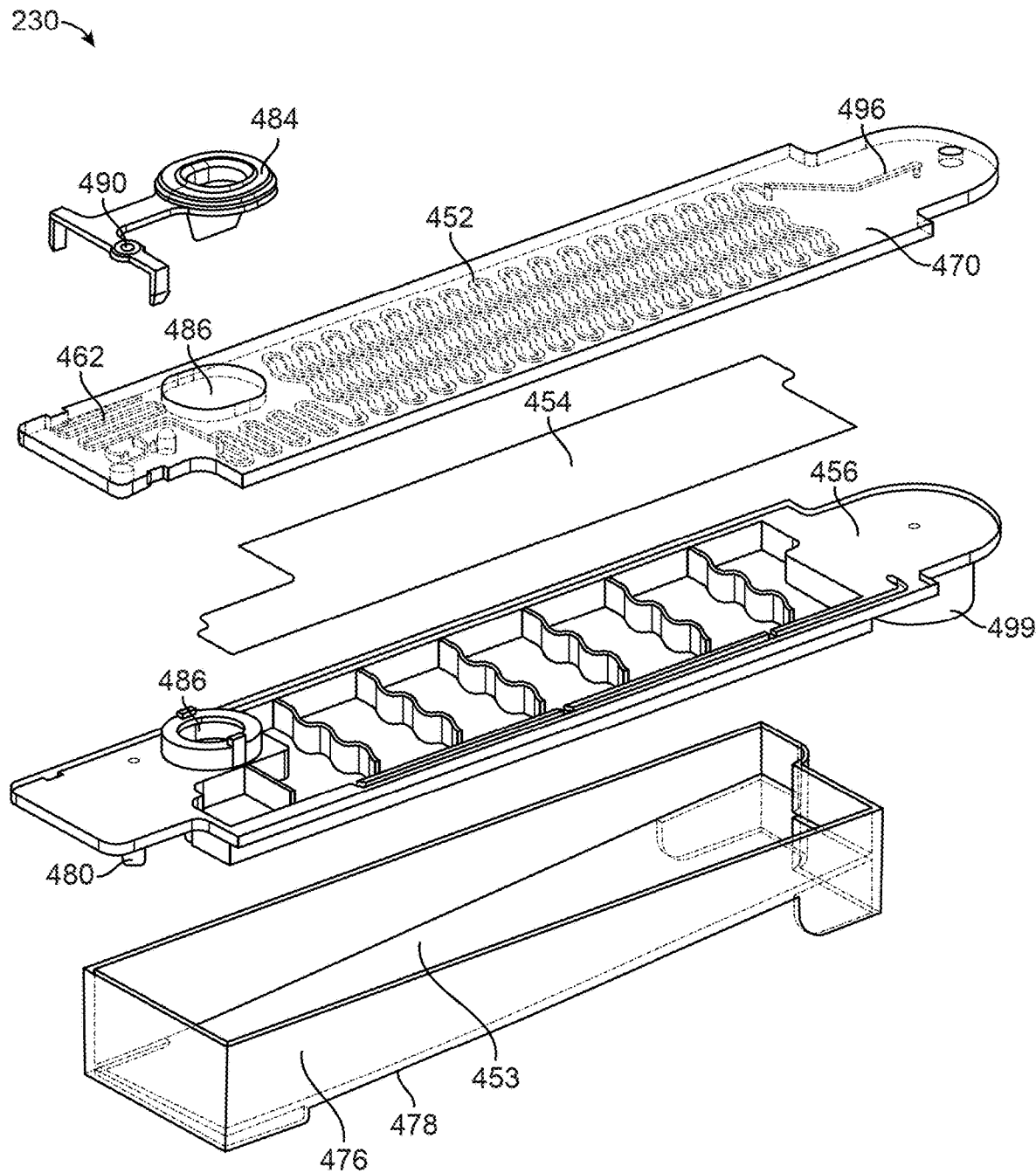

FIGS. 16A-16C are a top view, side view, and an exploded view, respectively, of an example demulsification cartridge 230. A sample input channel 460, a media input channel 462, and the microfluidic channel 452 are defined in the substrate 470. The substrate 470 is connected to the collection container 456, with the membrane 454 disposed therebetween such that the membrane 454 forms the bottom wall of the microfluidic channel 452. A media reservoir 476 is disposed below the collection container 456. The substrate, collection container 456, and media reservoir 476 are connected, e.g., by ultrasonic welding.

The microfluidic channel 452 is defined in a surface of the substrate 470 that faces the collection container 456 such that fluid in the microfluid channel 452 comes into contact with the membrane 454 and such that oil is pulled through the microfluidic channel 452 into the collection container 456. In some examples, the media input channel 462 is defined on the same surface of the substrate 470 as the microfluidic channel 452, and in some examples the media input channel 462 is defined on the opposite surface of the substrate 470.

The collection container 456, e.g., a molded plastic (e.g., PMMA or polystyrene) structure, defines one or more chambers 453 for holding oil removed from the fluid flowing along the microfluidic channel 452. Generally, the volume of the chambers in the collection container 456 is larger than the expected volume of oil to be removed from the fluid, e.g., between about 10-25% greater. For instance, if the expected volume of oil is about 5 mL, the chamber capacity can be about 6 mL. In some examples, the collection container 456 contains an oil trap material, such as a sponge-like material, e.g., disposed on the bottom surface of the chambers. The oil trap material is a hydrophobic material that captures oil in the chambers 453 of the collection container 456, thereby preventing oil from being pulled back through the membrane 454 into the microfluidic channel 452. In some examples, vacuum channels are defined in the body of the collection container 456 for application of a vacuum to the membrane 454.

The media reservoir 476, e.g., a molded plastic (e.g., PMMA or polystyrene) structure, defines a chamber that holds aqueous fluid to be supplied into the microfluidic channel 452. In some examples, the chamber of the media reservoir 476 has a capacity of between about 10-20 mL, e.g., 4-8 mL of aqueous fluid. In some cases, the media reservoir 476 capacity is constrained by the volume of the final output tubes. For example, if the capacity of the final output tubes is 15 mL, then the capacity of the chamber of the media reservoir should not exceed 15 mL. A bottom surface 478 of the chamber is angled relative to the plane of the substrate 470 such that aqueous fluid accumulates under a sipper tube 480. Aqueous fluid is extracted from the media reservoir 476 via the sipper tube 480, which is fluidically connected to the media input channel 462. In the illustrated example, the sipper tube 480 is integral with the collection container 456 and is sealed to the substrate 470 with an adhesive. In some examples, the sipper tube is a distinct element that extends through a hole in the collection container 456. In some examples, the sipper tube 480 is integral with the substrate 470 (e.g., molded as part of the substrate 470) such that no separate seal element between the sipper tube 480 and the substrate 470 is used.

The media reservoir 476 can be filled with aqueous fluid through a valve 484. The valve 484 extends through openings 486, 488 in the substrate 470 and collection container 456, respectively. In some examples, the valve 484 is a molded duckbill valve, e.g., a thermoplastic elastomer valve, that allows a pipette tip to be inserted through the valve 484 to fill the media reservoir 476, but that remains closed otherwise to prevent spillage or contamination of the aqueous fluid. The valve 484 also forms a seal against the pressure port and can open to allow entry of air pressure to drive flow of aqueous fluid into the media input channel 462. A media pressure subsystem, such as a bank of precision pressure regulators protected by shut-off valves, provides individual drive pressures to each media reservoir 476 to thereby drive the flow of aqueous fluid into the media input channel 462.

A seal 490 is positioned to provide a sealed coupling between the microfluidic chip 210 and the sample input channel 460. The seal 490 can be a thermoplastic elastomer seal. In the illustrated example, the valve 484 and the seal 490 are a single, integral element. In some examples, the valve 484 and the seal 490 are two distinct elements.

As discussed previously, the sample input channel 460 is fluidically connected to the output of the polymerization section (see FIGS. 3A-3B) and to the microfluidic channel 452. The media input channel 462, which is configured to receive aqueous fluid through a valve, is also connected to the microfluidic channel 452, such that the fluid flowing along the microfluidic channel 452 near the inlet end 451 is a mixture of aqueous fluid and droplets in oil. In some examples, the sample input channel 460 and the media input channel 462 have a three-dimensional channel structure, e.g., that is raised above a bottom surface of the substrate 470, thus preventing the oil and aqueous fluid from contacting the membrane 454 until they are combined in the microfluidic channel 452. In some examples, the media input channel 462 is a long channel (e.g., between about 50 mm and 150 mm in length) with a small cross-sectional dimension (e.g., 125 µm×225 µm) to allow for operation at high back pressure, thereby preventing backflow of oil into the microfluidic channel 452 when the flow over the membrane 454 slows down.

A first section 492 of the microfluidic channel 452 has a simple serpentine pattern, which allows the initial, oil-rich fluid to wet the membrane 454, thereby facilitating rapid removal of oil from the fluid flowing in the channel 452. A second section 494 of the microfluidic channel 452 has a double serpentine pattern, with small turns (e.g., turn 495) formed within each back-and-forth pass of the channel 452. These small turns facilitate mixing of the fluid in the channel so that the shrinking boluses of oil in the fluid are brought into repeated contact with the membrane 454. This repeated contact helps to prevent the situation where a small oil bolus (e.g., an oil bolus less than a certain percentage of the channel depth, e.g., less than 50%) fails to contact the membrane 454 along the entire length of the channel 452.

In some examples, the cross-sectional dimension (e.g., cross-sectional area) of the microfluidic channel 452 decreases along the length of the channel to increase fluid resistance, thereby increasing the residence time of the fluid on the membrane 454 and promoting complete removal of the oil. This tapering also helps to maintain back pressure against the membrane 454 as the volume of fluid decreases with oil removal. In a specific example, the microfluidic channel 452 is tapered from an initial dimension of 300 µm×600 µm to a final dimension of 300 µm×325 µm. The tapering can be gradual or in discrete increments.

At the output end 455 of the microfluidic channel 452, droplets in aqueous fluid, with substantially no oil present, flow through an outlet channel 496 to an outlet port 498 that extends through a shield element 499, e.g., formed integrally with the collection container 456. The shield element 499 prevents contamination of the rim of an output vessel connected to the outlet port 498 that could otherwise occur due to spattering caused by the processing air that pushes liquid out of the outlet port 498. The outlet channel 496 can be a long channel, e.g., with a length of between about 50-100 mm, and with a cross-sectional dimension similar to the final cross-sectional dimension of the microfluidic channel 452, to create a back pressure equivalent to that of external tubing in the breadboard. In some examples, the outlet port 498 has a pipette-like tip that is configured to connect to an output vessel, such as a conical output vessel (see FIG. 18). The demulsified MOSs can be transported elsewhere in the output vessels, e.g., for further organoid growth and testing.

Figure 17A:
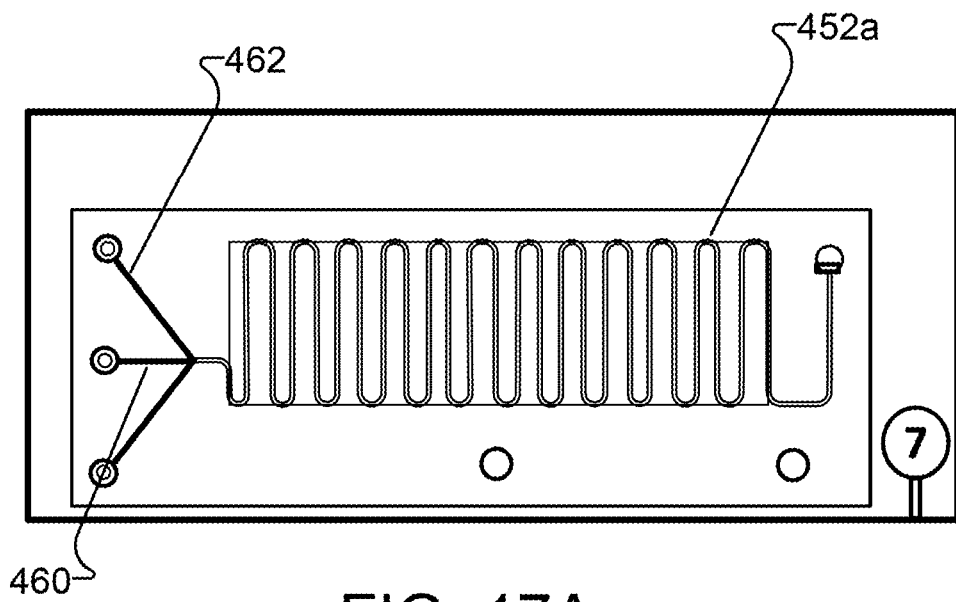
FIGS. 17A and 17B are diagrams of configurations for microfluidic channels in a demulsification subsystem of a MOS generation system.
Figure 17B:
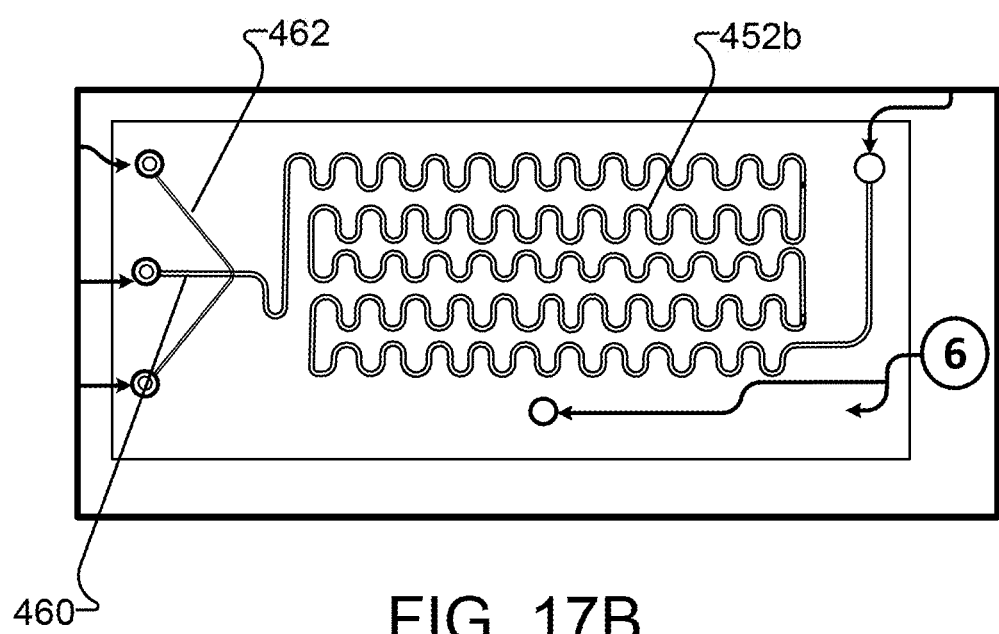

FIGS. 17A-17B illustrate two example configurations for the serpentine microfluidic channel 452, including a single serpentine channel 452*a* (FIG. 17A) and a double serpentine channel 452*b* (FIG. 17B). Other configurations are also possible. In each configuration, the emulsion of droplets in oil is received via the sample input channel 460, and aqueous fluid is received via the one or more media input channels 462. At the output end 455 of the microfluidic channel 452, droplets in aqueous fluid are output via the outlet port 498 to an output vial, such as a centrifuge tube (not shown).

The components of the MOS generation instrument that come into contact with samples (e.g., with patient-specific biological material) are disposable. These components, and other disposable components, are referred to as consumables. Referring to FIGS. 18A and 18B, the consumables are positioned, e.g., in holders or nests, such that the various fluidic interfaces are aligned and fluidically connected.

The positioned consumables are clamped in place by a clamp 850, interface seals are pressed together, and air supplies are mated to air drive ports. For instance, the clamp 850 is lowered by operation of an actuator, such as a lever. In the example of FIGS. 18A and 18B, the clamp 850 includes spring plungers that bear down on certain components to provide good sealing. For instance, pressure feeds 854 and chip input ports 856 press down on the top of each sample reservoir 220. Oil ports 852 press down on the microfluidic chip 210. Pressure feeds 858 press down on the demulsification cartridges 230 to connect to the media reservoirs 476. Plungers 860 apply a downward force on the demulsification cartridges to keep them seated in a nest when a sealing pressure is applied on the other side.

Figure 19:
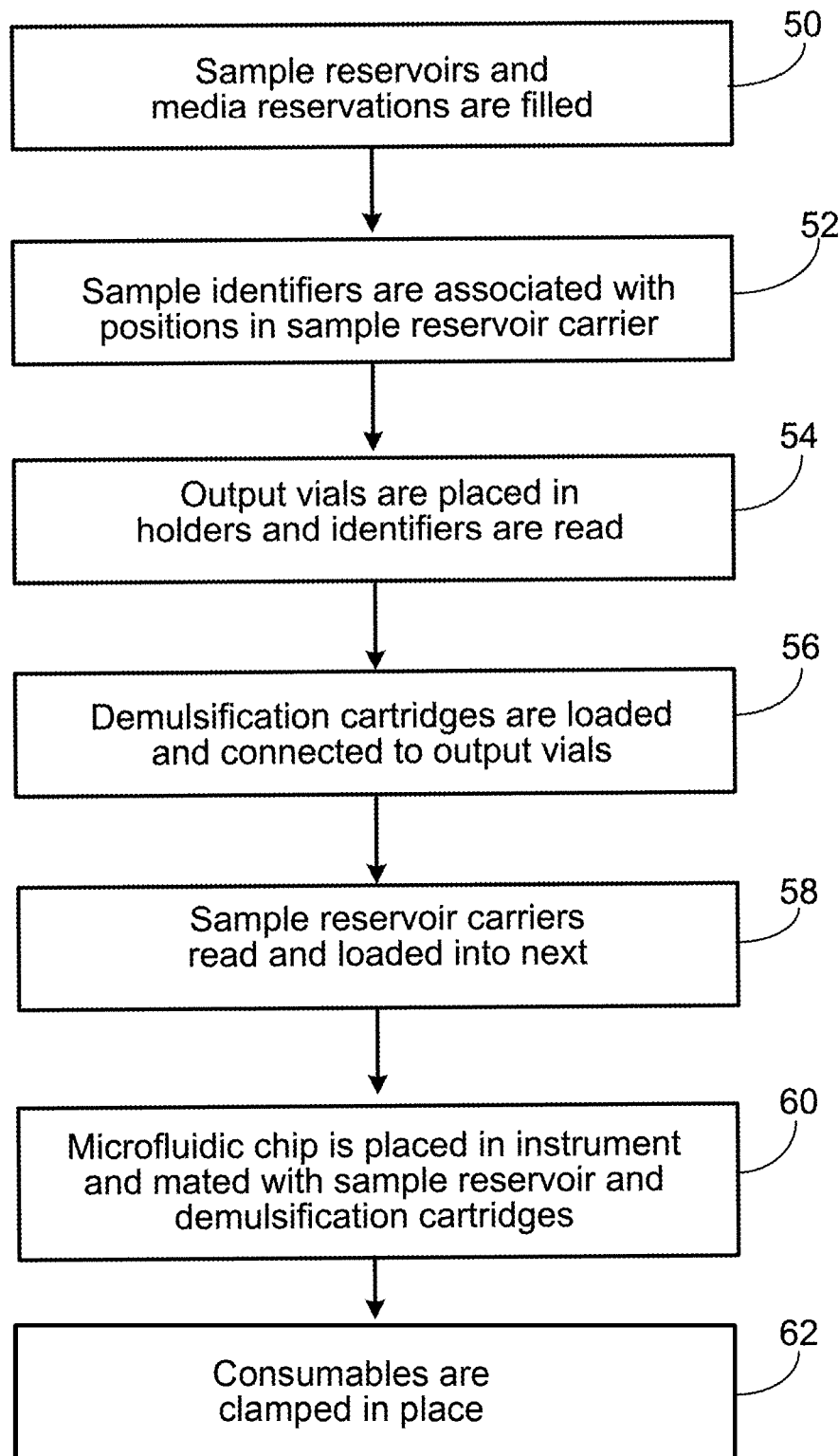
FIG. 19 is a flow chart.

Referring to FIG. 19, in some examples, the consumables loading follows a prescribed order. Sample reservoirs and media reservoirs in the demulsification cartridges are pre-filled away from the instrument (50). Prior to operating, a sample identifier is associated with each position in the sample reservoir carrier (52). Output vials are placed into their holders and their identifiers (e.g., barcodes) are read (e.g., scanned) as each vial is loaded, thereby linking each output vial identifier to a corresponding channel (54).

Demulsification cartridges are loaded in their holders and the output port of each demulsification cartridge is inserted into the corresponding output vial (56). The sample reservoir carrier containing multiple sample reservoirs is read (e.g., scanned) and placed into a refrigerated input nest in the instrument (58), thereby linking a sample identifier for each sample with the corresponding channel and thus with the corresponding specific output vial identifier.

The microfluidic chip is placed in the instrument and aligned and mated with the sample reservoirs and demulsification cartridges (60). The consumables are clamped, forming seals to open ports of the various components (62).

Figure 20:
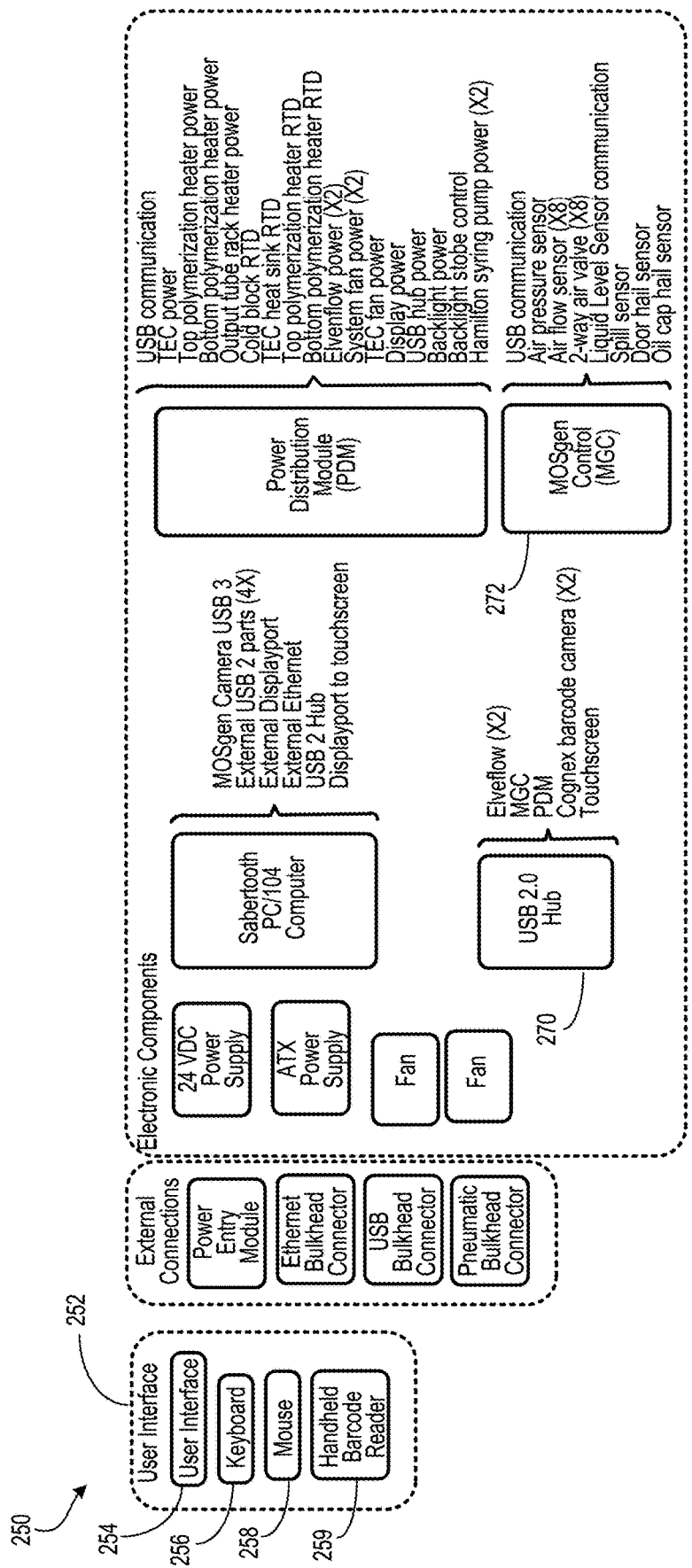
FIG. 20 is a diagram of an electronics subsystem of a MOS generation system.

Referring to FIG. 20, the droplet generation system 200 operates under control by an electronics subsystem 250, e.g., implemented in a computing device (e.g., local or cloud-based) that communicates with various electronically-controlled subsystems via interfaces such as USB or I2C serial interfaces. The electronics subsystem provides a graphical user interface that enables development, diagnostic testing, and service to be performed on the droplet generation system. The electronics subsystem also is operable to control the hardware of the droplet generation system 200 to process a sample according to a selected protocol and to communicate results, e.g., to the graphical user interface or to another computing device. In some examples, the electronics subsystem implements closed loop feedback control of the operation of the droplet generation system 200 based on analysis of data received from the system. For instance, the electronics subsystem can determine the size of the generated droplets based on images acquired by the imaging subsystem and can control the droplet generation system to adjust the fluid flow rate through the droplet generation chambers 212 to achieve a target droplet size.

The electronics subsystem 250 includes user interface components 252 such as a display 254 (e.g., a touchscreen display), a keyboard 256, a mouse 258, and a barcode reader 259. Additional and/or alternative user interface components can also be included. The electronics subsystem 250 includes data acquisition components, including data input and data output components. Digital output components include controls for features such as two-way valves (e.g., for solenoid valves or syringe pumps), heat, and lights. Digital input components include, e.g., a door closed sensor. Analog input components include, e.g., a polymerization light intensity sensor and a spill sensor.

Figure 21A:
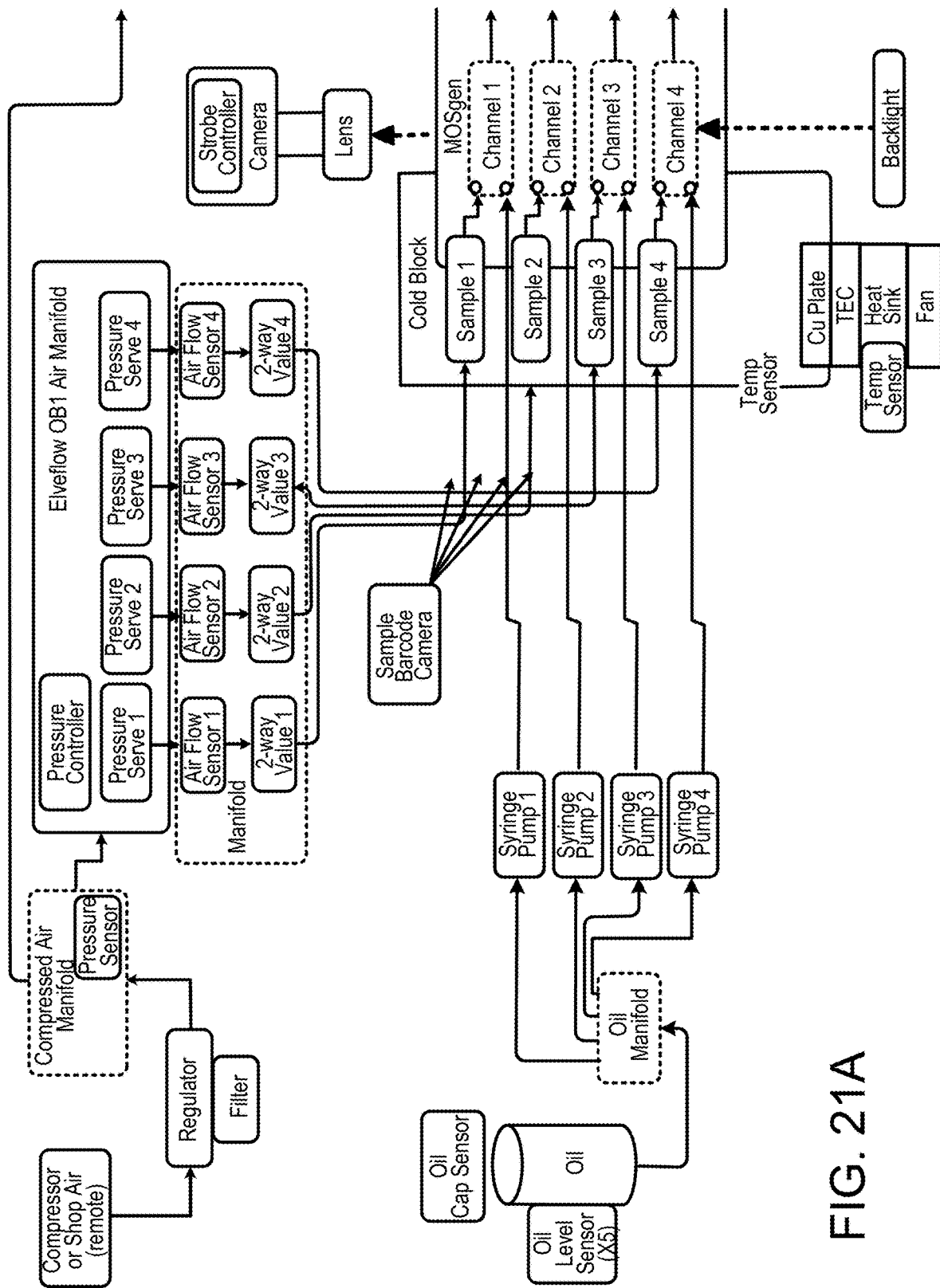
FIG. 21 is a block diagram of a MOS generation system.
Figure 21B:
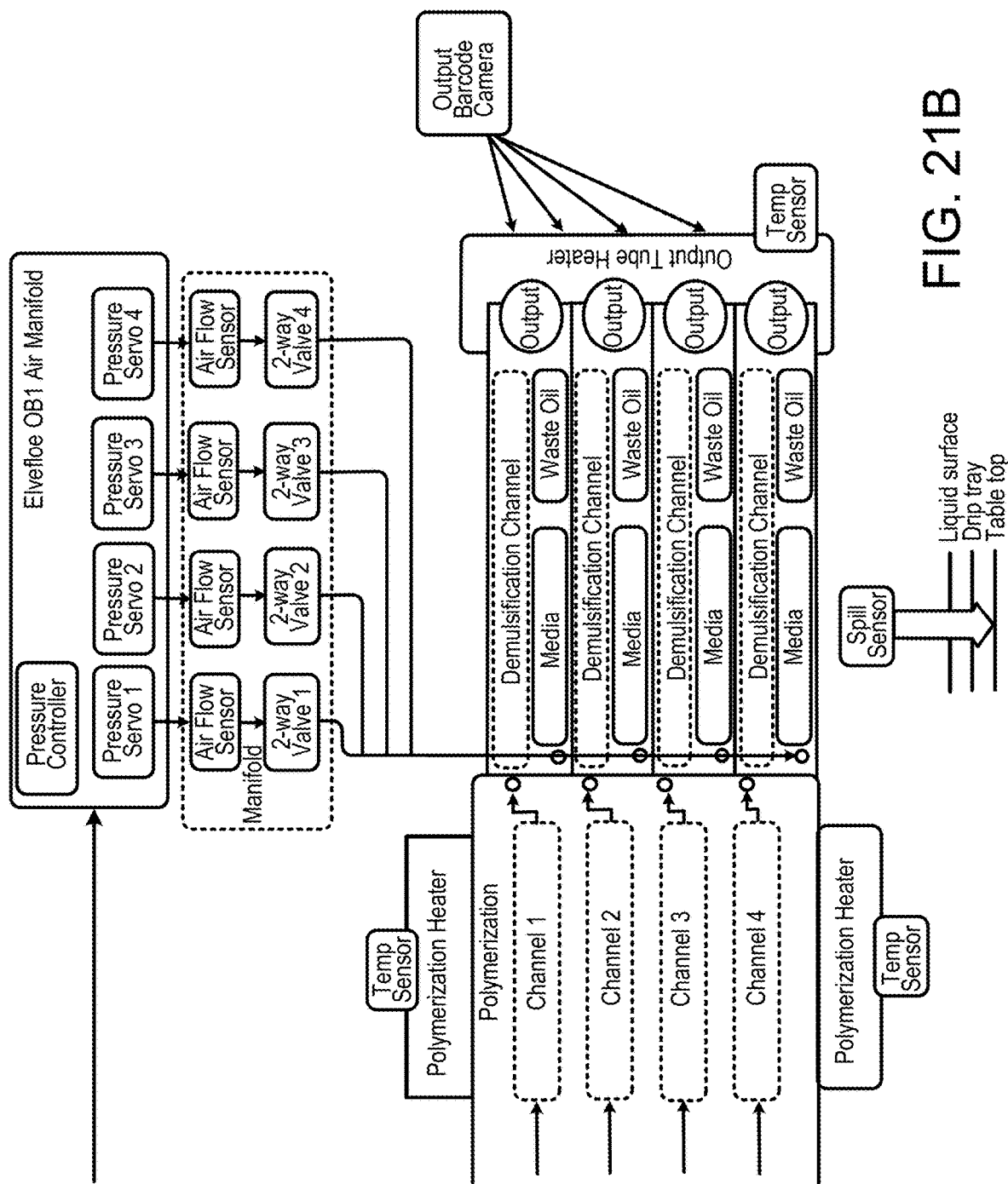

The electronics subsystem 250 includes devices that are connected to the controlling computing device via one or more types of interfaces. In the example of FIG. 21, these devices include USB devices 270, such as cameras, pressure regulators (e.g., Elveflow precision pressure regulators), thermal controllers, strobe controllers, and barcode readers; and I2C sensor input devices 272, such as sensors for pressure, air flow, and temperature.

Additional components for the electronics subsystem include, e.g., a power entry module, a power supply, a USB hub, an Ethernet bulkhead pass-through, a cooling fan, and other components, e.g., as illustrated in FIG. 20.

FIG. 21 is a block diagram of an MOS generation system showing integration of certain elements of the electronics subsystem.

Figure 22:
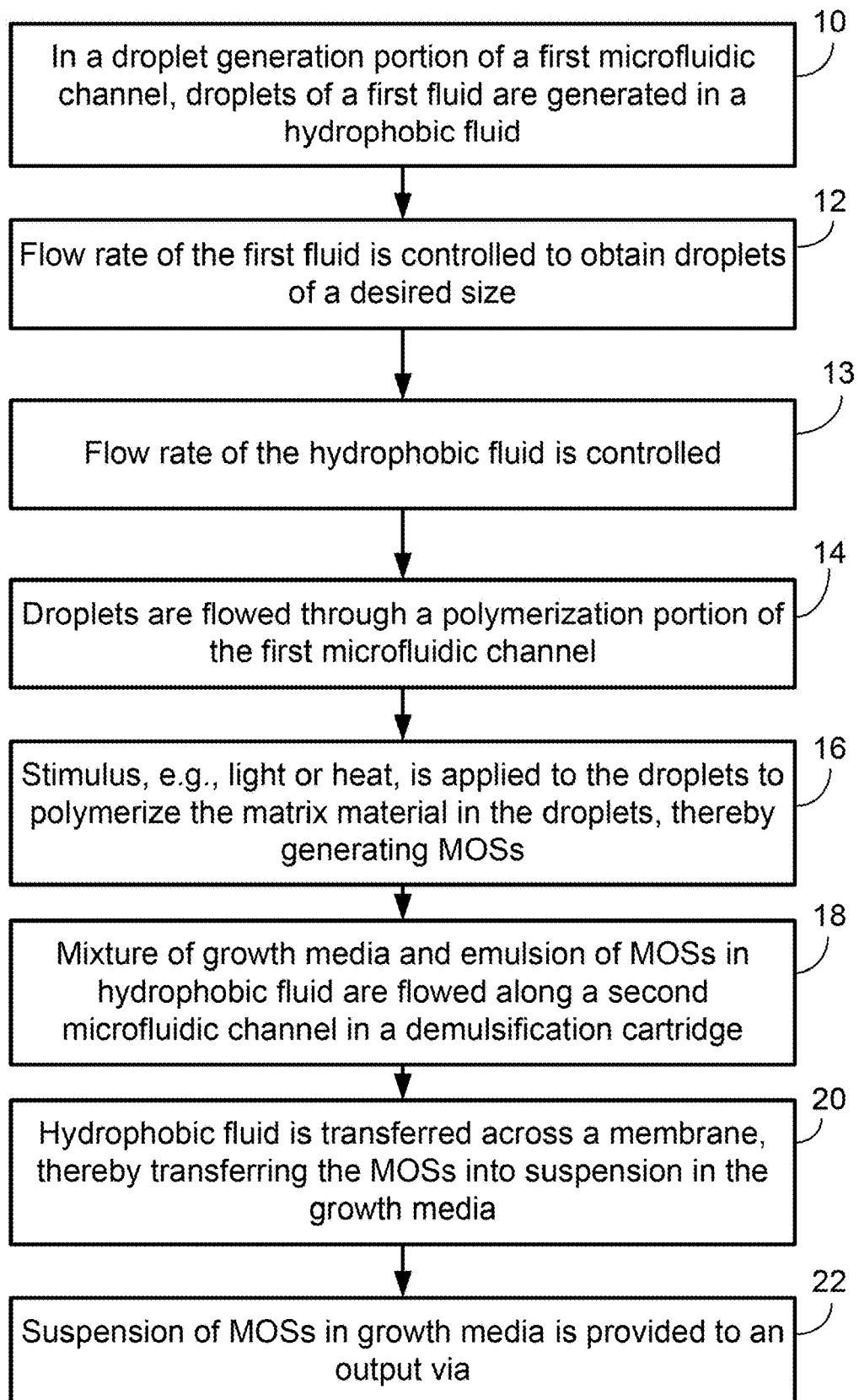
FIG. 22 is a flow chart.

Referring to FIG. 22, in an example method for MOS generation (e.g., generation and demulsification), in a droplet generation portion of a first microfluidic channel defined in a surface of a microfluidic chip, droplets of a first fluid (e.g., patient-specific biological material in a polymerizable matrix material) are generated in a hydrophobic fluid, such as an oil (10). For instance, the droplets are generated at a junction between the first microfluidic channel and one or more channels carrying the hydrophobic fluid. In some examples, the microfluidic chip has multiple, fluidically independent first microfluidic channels, and droplets are generated in parallel (e.g., concurrently) in each first microfluidic channel, e.g., such that samples from multiple patients can be processed concurrently.

In some examples, a flow rate of the first fluid (the fluid containing the biological material suspended in the unpolymerized matrix material) is controlled, e.g., in a closed loop feedback control system, to obtain droplets of a desired size (12). For instance, the flow rate is controlled based on a size of generated droplets as determined from images of the droplets in a droplet generation chamber of the first microfluidic channel. The flow rate of the hydrophobic fluid is also controlled (13) to control the velocity of the emulsion stream (e.g., the stream of fluid flowing through the outlet channels 314; see FIG. 4), which determines the residency time of the fluid in the polymerization region (e.g., in the polymerization channel 320; see FIGS. 3A-3B). The flow rate of the emulsion stream is also relevant for coordinating the start time and velocity of the media input into the demulsification channel (e.g., through the media input channel 462; see FIGS. 16A-16C).

The generated droplets are flowed through a polymerization portion of the first microfluidic channel (14), where a stimulus, e.g., light or heat, is applied to polymerize the matrix material, thereby forming MOSs emulsified in the hydrophobic fluid (16). When there are multiple, fluidically independent first microfluidic channels, the droplets in each channel are polymerized concurrently as they flow through the respective polymerization portions of the first microfluidic channels. In some examples, when light is applied as the stimulus, the droplets are illuminated with a pulsed illumination pattern. In some examples, the stimulus (e.g., light or heat) is applied to two opposing surfaces of the microfluidic chip.

A mixture of aqueous fluid and the emulsion of MOSs in the hydrophobic fluid is flowed along a second microfluidic channel defined in a substrate of a demulsification cartridge for demulsification of the MOSs, e.g., to transfer the MOSs into a suspension in aqueous fluid (18). When there are multiple first microfluidic channels defined in the microfluidic chip, each first microfluidic channel is fluidically connected to a respective second microfluidic channel in a corresponding demulsification cartridge. As the mixture flows along the second microfluidic channel, the hydrophobic fluid is transferred across a membrane that forms a wall of the second microfluidic channel, thereby removing the hydrophobic fluid and allowing the MOSs to transfer into the aqueous fluid (20). In some examples, a vacuum is applied to the side of the membrane opposite the second microfluidic channel to facilitate removal of the hydrophobic fluid from the second microfluidic channel.

The suspension of MOSs in aqueous fluid is provided to an output vial (22) for downstream use, e.g., for cell growth, testing, or other uses.

Closed Loop Control of MOS Generation Systems

In some examples, real-time, closed loop feedback is used for real-time quantification and control of droplet size and flow rate in the MOS generation systems and methods described above. Based on the measured droplet size and flow rates, the microfluidic system can be controlled to adjust the size of the generated droplets, the flow rate of the droplets, or both. These adjustments can enable target droplet sizes, flow rates, or both, to be achieved in order to allow for efficient and complete polymerization of the matrix material of the MOSs. These adjustments can also enable the droplet generation process to be controlled to produce a target number of droplets, e.g., to obtain a desired number of MOSs for a screening library.

These approaches to closed loop feedback can have one or more of the following advantages. The closed loop feedback system described here provides a mechanism to reliably and non-invasively capture multiple images of a single droplet as it flows along a microfluidic channel. Quantitative measurements of the size and velocity of a single droplet, and estimates of total numbers of droplets, can be obtained using short exposure times and high intensity illumination pulses. The images are obtained without artifacts, such as blurring, due to droplet motion. The timing of the illumination pulses is controllable independently from the camera shutter and is independent from the frame rate of the camera, and can be adjusted to achieve consistent imaging quality across a wide range of flow rates. The ability to sense physical parameters such as size and velocity in a non-contact and non-invasive approach enhances the precision of the process being performed in the microfluidic device. In addition, because these imaging approaches can be achieved using low camera frame rates, the computing power burden to analyze the generated images is relatively low. Moreover, the configuration of the optical system used in the closed loop feedback approaches described here is less expensive and smaller than typical optical systems used in life science systems, e.g., because the optical system described here does not require expensive aspects such as sub-millimeter alignment, florescent dyes, dichroic components, or lasers. In addition, the closed loop feedback system described here is non-invasive to the microfluidic system, which allows the potential for clogging or contamination to be avoided.

In the approaches to closed-loop feedback described here, multiple exposures of each of one or more droplets are obtained within a single image, and the size of the droplets, the flow rate of the droplets, or both are determined based on these exposures. Because of the timing of the two exposures, e.g., the interval between the two exposures and the duration of each exposure, the same droplet is captured in both exposures, without artifacts such as blurring that can arise due to motion of a subject in an image. The two exposures of the same droplet are analyzed to determine characteristics of the droplet, such as size and flow rate. The exposures can also be analyzed to determine other characteristics of the droplets, such separation between adjacent droplets, number density of droplets, or an estimated total number of droplets generated in the system. These characteristics are applied in a closed loop feedback system that can adjust the first and second fluids are adjusted as appropriate such that droplets of the target size are generated, such that the generated droplets flow at the target flow rate, or both, thereby enabling continuous generation of droplets of a target size at a target flow rate. In a specific example, the flow rate of the first fluid is adjusted to achieve droplets of the target size, and the flow rate of the second fluid is adjusted such that the generated droplets flow at the target flow rate.

In some examples, the closed loop feedback approach can be used to control the number of droplets generated in the microfluidics system. For instance, the microfluidics system can have a performance goal indicative of a target number of droplets of a certain size to be generated from a sample of a given volume, e.g., a 10 µL sample of biological material from a needle biopsy is to generate 10,000 drops of a specified size. Based on the size of the droplets as determined from the multiple images, the flow rates of the first and second fluids can be adjusted to achieve generation of the target number of droplets.

Referring again to FIGS. 13A and 13B, the closed loop feedback system including the imaging subsystem 350, a computing device, such as a local computer or a cloud-based server having one or more processors coupled to a memory, the controllers controlling flow of the first and second fluids, and a controller that controls the operation of the imaging system 350. The closed loop feedback system captures and analyzes images of the droplets to quantify the size of the generated droplets, the flow rate of the generated droplets, or both. In some examples, the closed loop feedback system controls operational parameters of the MOS generation system based on the analysis of the images to obtain droplets of the target size, target flow rate, or both, suitable for complete and efficient polymerization. In some examples, the closed loop feedback system controls operational parameters of the MOS generation system based on the analysis of the images to obtain a target number of droplets from a given sample of the first fluid. For instance, the closed loop feedback system controls operation of flow regulators controlling the flow of the first and second fluids, e.g., controlling operation of the sample drive subsystem 170 (see FIG. 12) to control flow of the first fluid and/or controlling operation of one or more of the programmable flow rate pumps 856-862 (see FIG. 8B) to control flow of the second fluid.

The liquids, including the first fluid containing the patient-specific biological material and unpolymerized matrix material and the second, immiscible fluid, are generally both clear liquids, and the droplets are visible in the immiscible fluid because of a difference in the index of refraction between the droplets and the surrounding fluid. The curvature of the droplet edges, combined with the difference in refractive index, causes the droplets to act as lenses that bend the light from the light source 360. In some examples, the light source 360 is a source of diffuse light, resulting in the edges of the droplet being visible in images captured by the camera 352. In some examples, the light source 360 is a collimated light source, and the focusing effect of the lens-like droplets deflects light off of its original axis and away from the line of sight of the camera 352. This focusing effect enhances the contrast of the droplets as compared to droplets that are illuminated with diffuse light.

Operation of the camera 352 and light source 360 is controlled by a controller of the closed loop feedback system. The controller is, e.g., a programmable control board that can produce multiple concurrent outputs of control pulses (e.g., current pulses or voltage pulses) for synchronized control of the camera and the light source with programmable timing.

The camera 352 includes a shutter, e.g., a global shutter. For instance, the shutter can be an electronic shutter internal to the camera. The opening of the shutter is controllable by an external trigger, such as a current or voltage pulse received from the controller of the closed loop feedback system. The exposure time (e.g., the amount of time the shutter remains open) can be specified, e.g., by direct interaction with the camera 352 or by interaction with a computing device communicatively coupled with the camera 352. In a specific example, the shutter of the camera 352 is responsive to a transistor-transistor logic (TTL) input, e.g., a 3.3 V or 5 V TTL input, received from the controller. When the shutter receives an input from the controller, the shutter opens, starting an integration period that lasts for the specified exposure time. A single integration period, such as a single still photographic frame or a single frame of a video camera, is sometimes referred to as a single frame of the camera 352.

The light source 360 is controllable by an external trigger, such as a current or voltage pulse, e.g., received from the controller of the closed loop feedback system. The light source 360 is a light source capable of producing strobed illumination, e.g., multiple (e.g., two, three, four, or more than four) brief illumination pulses in rapid succession. For instance, the light source 360 can be a light emitting diode (LED), an arc lamp, or another suitable light source. In some examples, the light source 360 is a collimated light source, e.g., a collimated LED. The light source 360 can be a monochromatic light source (e.g., a monochromatic LED) or a polychromatic light source (e.g., a white light source). In a specific example, a monochromatic blue LED is used as a light source. The short wavelength of the blue LED helps to prevent blurring of the edges of the droplets in the images. In some examples, such as when the droplets contain absorbing dyes, the light source 360 includes multiple light sources of different colors, e.g., multiple differently colored LEDs.

The controller of the closed loop feedback system is configured to control the camera 352 and the light source 360 such that the light source 360 produces the multiple (e.g., two, three, four, or more than four) illumination pulses during a single frame of the camera 352, e.g., while the camera shutter remains open. The result is a double exposure within one frame: two exposures of the droplet generation chamber 312 (see FIGS. 3A-3B) (with droplet(s) therein) within a single image captured during a single frame of the camera 352. In some examples, the outlet channels 314 also fall within the field of view of the camera 352 and thus are also captured by the two exposures. The two exposures are separated in time by the time between the two successive illumination pulses produced by the light source 360. Because of the brief temporal separation between the two illumination pulses, the same droplet or droplets appear in both exposures. A given droplet appears in a slightly different position in the two exposures because of the flow of the droplet along the droplet generation chamber 312 in the time interval between the two illumination pulses.

In some examples, the camera 352 runs at a fixed frame rate and outputs a TTL signal at the beginning of each frame integration (e.g., when the shutter opens). The controller of the closed loop feedback system is programmed to generate strobe output pulses at a specific delay from start, duration, and separation. In some examples, the controller of the closed loop feedback system triggers the camera exposure and the strobe pulses such that the time between exposures can be varied. In some examples, a modified sequence can be implemented in which the strobe is fired in an alternating sequence of a single pulse in one frame followed by a double pulse in the next frame. This modified sequence allows the system to gather two image streams, one that includes double exposures to analyze for, e.g., velocity, and the other that includes single exposures, e.g., for display to a user.

The ability to image droplets in both the droplet generation chamber 312 and the outlet channel 314 has advantages. Specifically, because the geometry of the droplet generation chamber 312 is different from that of the outlet channel 314, the ability to image droplets in both locations affords the opportunity to image droplets having different shapes. In an example, the first and second channels 306, 310 have cross sectional dimensions of 200 μm×200 μm, the droplet generation chamber 312 has cross sectional dimensions of 200 μm×700 μm, and the outlet channel 314 has cross sectional dimensions of 300 μm×300 μm. With a nominal spherical droplet size of 255 μm, the droplets are flattened into a pancake shape with full-round edges while in the droplet generation chamber 312, and become spherical when they exit the droplet generation chamber 312 and enter the outlet channel 314. The ability to image droplets in both the droplet generation chamber 312 and the outlet channel 314 allows the droplets to be imaged in both geometries, e.g., facilitating volume calculations.

The ability to image droplets and determine droplet velocity in both the generation chamber and the outlet channel also provides a mechanism for error checking. Because the generation chamber and the outlet channel have different cross-sectional areas, the expected velocity ratio between the two locations is known (e.g., the velocity ratio is the inverse ratio of the cross sectional areas). The measured droplet velocity in the two locations can be compared to act as an error check, e.g., preventing a wrong velocity from being reported from a single location measurement and facilitating reporting instead a velocity that is concordant with the data for both channels.

Figure 23A:
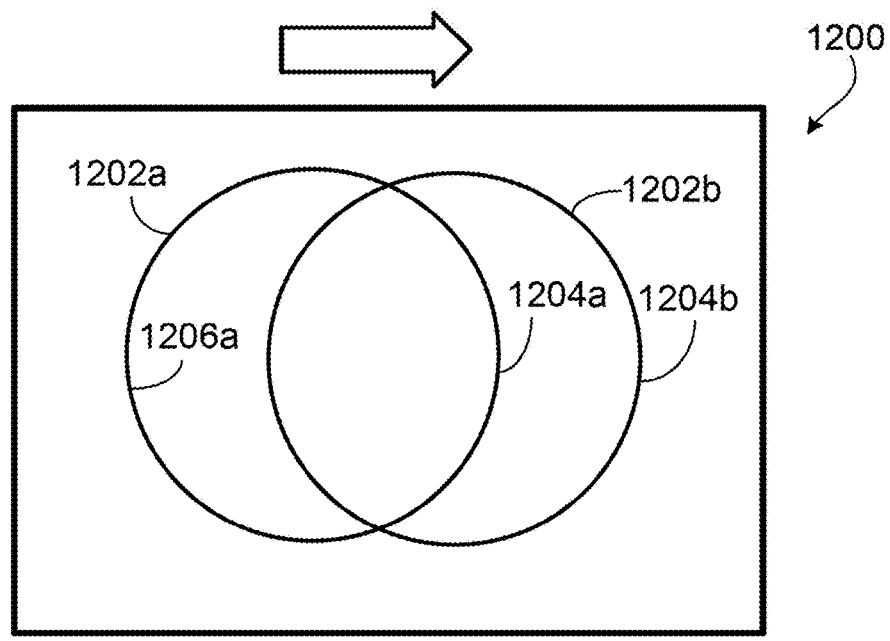
FIG. 23A is a schematic diagram of multiple images of a droplet.

FIG. 23A shows an example of a single image 1200 captured during one frame of the camera 352 (FIG. 13A-13B) of the imaging system. The image 1200 contains an image of a portion of the generation chamber with two captured positions 1202a, 1202b of the same droplet. The two positions 1202a, 1202b of the droplet were captured as a double exposure by two successive illumination pulses while the camera shutter remained open. The two positions 1202a, 1202b within a single image are sometimes referred to as two exposures 1202a, 1202b of the same droplet. Because the droplet is flowing along the generation chamber in the direction indicated by the arrow, the droplet appears at a different location in each of the two exposures 1202a, 1202b. The position of the droplet in the exposure 1202a is the position of the droplet when the first flash of illumination was produced, and the position of the droplet in the exposure 202b is the position of the droplet when the second flash of illumination was produced. The droplet is at a different location in each of the two exposures 1202a, 1202b, because it has moved along the chamber in the interval between the flashes. As discussed more below, analysis of the multiple exposures 1202a, 1202b of a single droplet within one frame can be performed to determine characteristics of the droplet, such as droplet size, droplet velocity, or other characteristics.

Figure 23B:
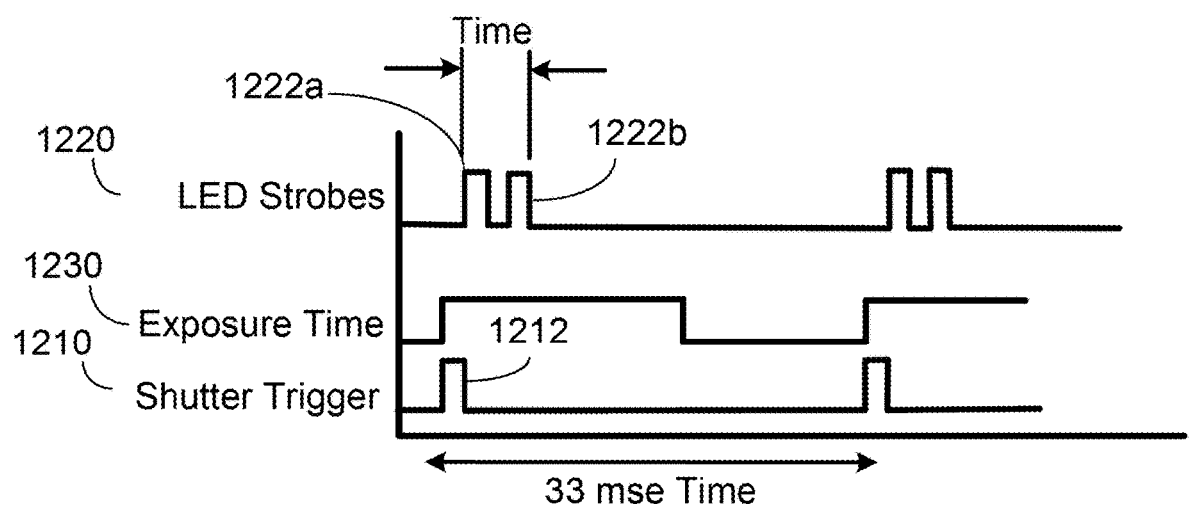
FIG. 23B is a diagram of control signals.

FIG. 23B shows an example of control signals provided from a controller to the camera and light source that result in the generation of the double exposure image of FIG. 23A. For instance, the controller of the closed loop feedback system can generate the control signals of FIG. 23B to control the operation of the shutter of the camera 352 (see FIGS. 13A-13B) and the operation of the light source 360. The control signals include camera drive signals 1210, e.g., square wave current pulses, that cause the shutter of the camera 352 to open. The control signals also include light source drive signals 1220, e.g., square wave current pulses, each drive signal 1220 causing the light source 360 to produce an illumination pulse. The middle line in FIG. 23B illustrates an integration period 1230 of the camera, e.g., the time during which the shutter of the camera 352 remains open.

In the example of FIGS. 23A and 23B, the controller first sends a camera drive signal 1212 to control the shutter of the camera to open, thereby beginning a single frame (integration period) of the camera for the capture of the single image 1200. The controller then sends two successive light source drive signals 1222a, 1222b, each signal causing the light source to produce a brief flash of illumination. As shown by the integration period 1230 of the camera, the camera shutter remains open during both illumination pulses. Each flash of illumination generates one exposure of the droplet (e.g., the flashes triggered by the pulses 1222a, 1222b give rise to the exposures 1202a, 1202b of the droplet, respectively) within the single image 1200. After the integration period 230 ends, the shutter of the camera closes. The resulting image 1200, including the two exposures 1202a, 1202b, is sent to a computing device for analysis.

In some examples, the time interval between the two pulses 1222a, 1222b is short enough that the separation between a leading edge 1204a of the droplet in the exposures 1202a and a leading edge 1204b of the same droplet in the successive exposures 1202b is less than a size (e.g., the radius or the diameter) of the droplet. This brief time interval ensures that the same droplet appears in both exposures 1202a, 1202b (e.g., that a given droplet travels a distance that is less than its diameter during the time interval between pulses). For instance, the time interval (pulse separation) between the two pulses 1222a, 1222b can be between 1 millisecond (ms) and 50 ms, e.g., between 1 ms and 30 ms or between 5 ms and 10 ms. The time interval is adjustable, e.g., by programming the controller, to be applicable to various flow rates. For instance, the time interval can be adjusted to produce a consistent separation between the leading edge of the droplet in each image regardless of the flow rate. The time interval can be consistent throughout the imaging process or can vary.

In some examples, the time interval between the two pulses 1222a, 1222b has a duration such that the droplet moves by a distance of between about ¼ of its radius to about 4 times its radius between exposures. Droplet identification and analysis can be achieved even if the droplet does not overlap itself in the two exposures. This flexibility allows the image analysis to be performed across a large dynamic range of velocities.

The pulses 1222a, 1222b can be sufficiently brief to avoid artifacts (e.g., blurring) due to droplet motion in the respective exposures 1202a, 1202b. The duration of each pulse can be set based on system factors such as lens light gathering, lens aperture setting, camera imager sensitivity, and camera gain. For instance, each pulse 1222a, 1222b can have a duration of between about 5 microseconds (μsec) and about 125 μsec, e.g., between about 10 μsec and about 50 μsec or between about 25 μsec and about 50 μsec, e.g., 10 μsec, 20 μsec, 25 μsec, 30 μsec, 35 μsec, 40 μsec, 45 μsec, 50 μsec, 75 μsec, 100 μsec, or 120 μsec. In a specific example, the two pulses 1222a, 1222b are 125 μsec duration pulses that are separated by a time interval of 25 ms. The pulse duration the pulse separation do not necessarily have the same value. Because the pulses 1222a, 1222b are brief, high intensity light can be used, which facilitates image analysis.

The multiple exposures 1202a, 1202b in a given image 1200 are analyzed by a computing device that has one or more processors coupled to a memory for executing the image analysis, e.g., using machine vision analysis processing techniques. The analysis can determine characteristics of the droplet(s) in the exposures 1202a, 1202b, such as the size (diameter, volume) of the droplets, the flow rate (velocity) of the droplets, the separation between adjacent droplets, the number density of droplets, or an estimated total number of droplets generated from a sample of a specified volume.

Analysis by the computer can include identifying the droplet in each exposure 1202a, 1202b of a given image 1200 and identifying a leading edge or trailing edge of the droplet in each exposure (e.g., the leading edge 1204a of the droplet in the exposure 1202a and the leading edge 1204b of the droplet in the exposure 1202b). The leading edge of a droplet is the edge of the droplet that faces the direction of motion of the droplet; the trailing edge is the edge facing opposite the direction of motion of the droplet. In some examples, the leading edge, trailing edge, or both edges of the droplet in each exposure is identified directly without first identifying the droplet itself.

In an example, a droplet is identified in an exposure by frequency-domain techniques or machine vision analysis processes that identify circular or substantially circular objects (the two-dimensional projection of a spherical droplet) in the exposure, e.g., creating best fit circles. Frequency domain techniques such as autocorrelation or fast Fourier transform processes can allow for holistic analysis of some or all of each image. In some cases, the machine vision analysis processes identify circular or substantially circular features that fall within a prespecified target size range, e.g., to avoid erroneous identification of foreign objects, such as debris or bubbles, as droplets.

In an example, a leading edge of a droplet is identified in an exposure as a feature in the exposure that has a positive curvature in a prespecified direction corresponding to the direction of motion of the droplets, and a trailing edge of a droplet is identified as a feature that has a negative curvature in that same direction. In some cases, the machine vision processes identify features that have a curvature that falls within a prespecified range of suitable curvatures, e.g., to avoid erroneous identification of foreign objects as droplets.

In some examples, once a droplet is identified in each exposure, the exposures 1202a, 1202b in the image 1200 are analyzed to determine the distance between corresponding edges of the droplet in the two successive exposures 1202a, 1202b. In the example of FIG. 23A, the distance d between the leading edge 1204a of the droplet in the exposure 1202a and the leading edge 1204b of the droplet in the exposure 1202b is determined. In some examples, the distance between the trailing edges of the droplets in the two successive exposures 1202a, 1202b is determined. The distance between corresponding edges of the same droplet in two successive exposures is the distance traveled by the droplet along the imaging channel in the time between the two successive illumination pulses triggered by the two light source drive signals 1222a, 1222b. Because the time interval between the two light source drive signals 1222a, 1222b is known, the velocity of the droplet can then be determined as the distance traveled by the droplet divided by the time interval between the two light source drive signals 1222a, 1222b. The velocity of a given droplet is the flow rate of the droplets along the imaging channel.

In some examples, once a droplet is identified in each exposure, the exposures 1202a, 1202b of the image 1200 are analyzed to determine the size of the droplet. In the example of FIG. 23A, the diameter D of the droplet is determined as the separation between the leading edge 1204a of the droplet in the exposure 1202a and a trailing edge 1206a of the droplet in the same exposure 1202a. The volume of the droplet can also be determined based on the determined droplet diameter, e.g., based on an expected or observed shape of the droplet given the geometry of the channels. An estimate of the total number of droplets generated from a given starting volume of a sample can be determined based on the determined volume of a single droplet.

The number density of droplets per unit length of channel or unit volume of second fluid can be determined based on a distance between adjacent droplets, e.g., a separation between a trailing edge of a first droplet and a leading edge of the next successive droplet in the channel.

The closed loop feedback system controls operational parameters of the MOS generation system 200 based on the droplet characteristics determined from the image analysis. Specifically, a computing device communicates with the controllers controlling the flow of the first fluid, the second fluid, or both to control the flow rate of the first fluid, the second fluid, or both, e.g., to adjust the size of the droplets generated at the junction 311 (see FIG. 4), the flow rate of the droplets through the droplet generation chamber 312, or both. In a specific example, the flow rate of the first fluid is adjusted to achieve droplets of the target size, and the flow rate of the second fluid is adjusted such that the generated droplets flow at the target flow rate. For instance, if the image analysis reveals that droplets larger than the target size are generated, the computing device communicates with the controller controlling the flow rate of the first fluid to reduce the flow rate of the first fluid. If the image analysis reveals that the flow rate of the droplets along the droplet generation chamber 312 is greater than the target flow rate, the computing device communicates with the controller controlling the flow rate of the second fluid to reduce the flow rate of the second fluid, or both.

In one implementation, the controller controlling the flow rate of each of the first fluid and the second fluid is implemented as a PID controller to facilitate stable control. This implementation enables consideration of interactions among parameters of the system, e.g., providing independent control over oil flow rate and sample pressure despite dependencies between these two parameters. For instance, one PID controller considers velocity and oil flow rate and the other PID controller considers droplet size and sample pressure, thus enabling stable control over both droplet size and velocity.

The camera of the closed loop feedback system can be run at a frame rate of between 1 Hz and 30 Hz. In some examples, the frame rate of the camera is faster than the cycle rate of the flows of the first and second fluids. In this way, dynamic adjustments can be made in real time to maintain generation of droplets of the target size at the target flow rate. In a specific example, the flows of the first and second fluids are controlled by a pressure that has a cycle rate of between 2 Hz and 5 Hz. In this example, a camera having a frame rate of 15 Hz, 30 Hz, or 40 Hz can be used for capturing the multiple images. For instance, when multiple image streams are gathered (e.g., a double exposure image stream and a single exposure image stream) at a frame rate of 30-40 Hz, the double exposure image stream for analysis can be collected at 15-20 Hz, and the single exposure image stream for display to a user can be interleaved with the double exposure image stream and also collected at 15-20 Hz.

In some examples, the closed loop feedback system can determine when a performance issue arises in the MOS generation system 200. For instance, when the supply of the first fluid is exhausted, no droplets will be formed and thus no droplets will be identified in images of the droplet generation chamber 312. To avoid the circulation of air bubbles from an empty reservoir for the first fluid (e.g., the reservoir 220, see FIGS. 3A-3B), the closed loop feedback system can control the flow regulator of fluid flow from the reservoir 220 to shut off flow from the reservoir 220, while maintaining a flow of the second fluid from the oil reservoir 700 at the target flow rate. For instance, a two-way shut-off valve is positioned between the flow regulator for the reservoir of first fluid (e.g. a syringe pump) and the reservoir 220 to prevent pressure from the second fluid from causing backflow into the reservoir 220. The continued flow of the second fluid ensures that previously generated droplets will flow through the entire length of the outlet channel 314 at the target flow rate for complete polymerization.

Figure 24A:
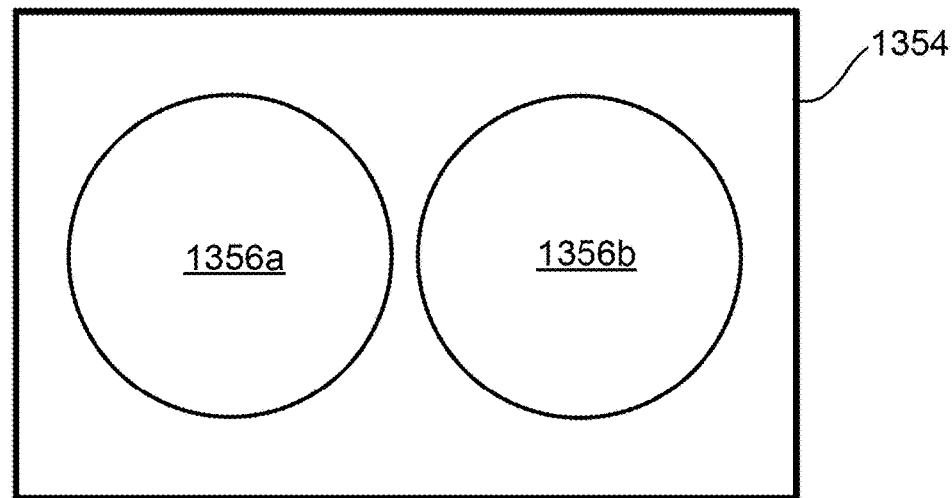
FIG. 24A is a diagram of a light source.

Referring to FIG. 24A, in some examples, a light source 1354 of an imaging system includes multiple individual light sources 1356a, 1356b, each individual light source 1356a, 1356b emitting light of a different color. For instance, the light source 1356a can be a first LED emitting red light and the light source 1356b a second LED emitting green light.

Figure 24B:
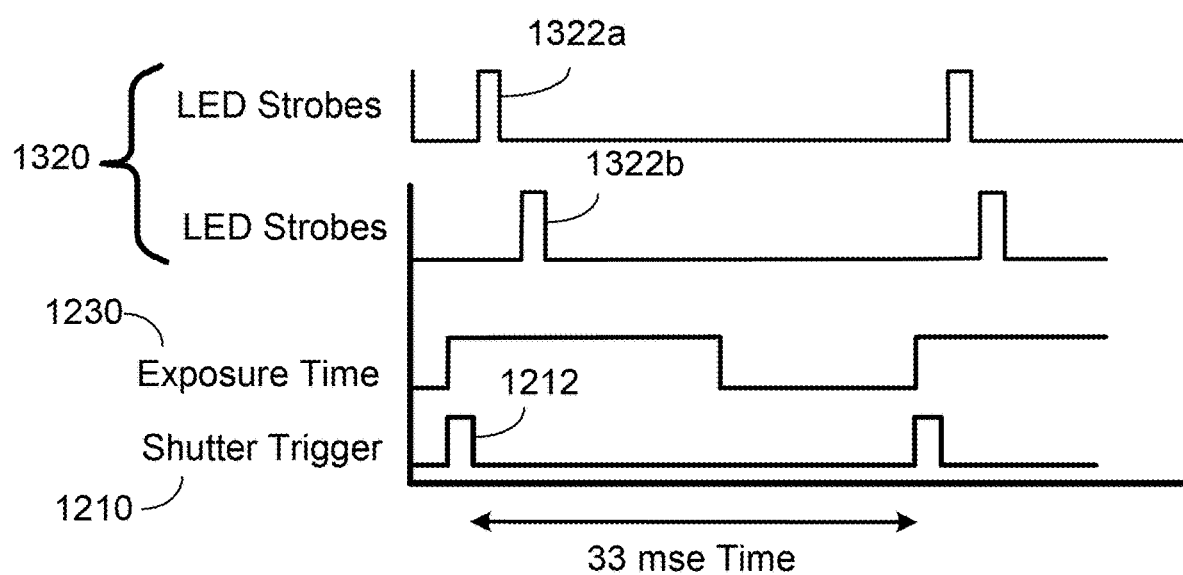
FIG. 24B is a diagram of control signals.

FIG. 24B shows drive signals for an imaging system including the multiple individual light sources 1356a, 1356b of FIG. 24A. The camera drive signal 1210 and the integration period 1230 of the camera are as described above with respect to FIG. 23B. In this example, the controller sends a light source drive signal 1320 to the light source. The light source drive signal 1320 includes a first light source drive signal 1322a sent to the first individual light source 1356a, which causes the first light source to emit light of its color (e.g., red light). The light source drive signal 1320 also includes a second light source drive signal 1322*b* sent to the second individual light source 1356*b* to cause the second light source to emit light of its color (e.g., green light). In this way, two successive illumination pulses of two different colors are produced.

In the two exposures that result from the two differently colored successive illumination pulses within a single frame, the first exposure is in the first color (e.g., red) and the second exposure is in the second color (e.g., green). Identification of a droplet in each exposure is facilitated by this color difference; a droplet in red belongs to the first exposure and a droplet in green belongs to a second exposure.

Figure 25:
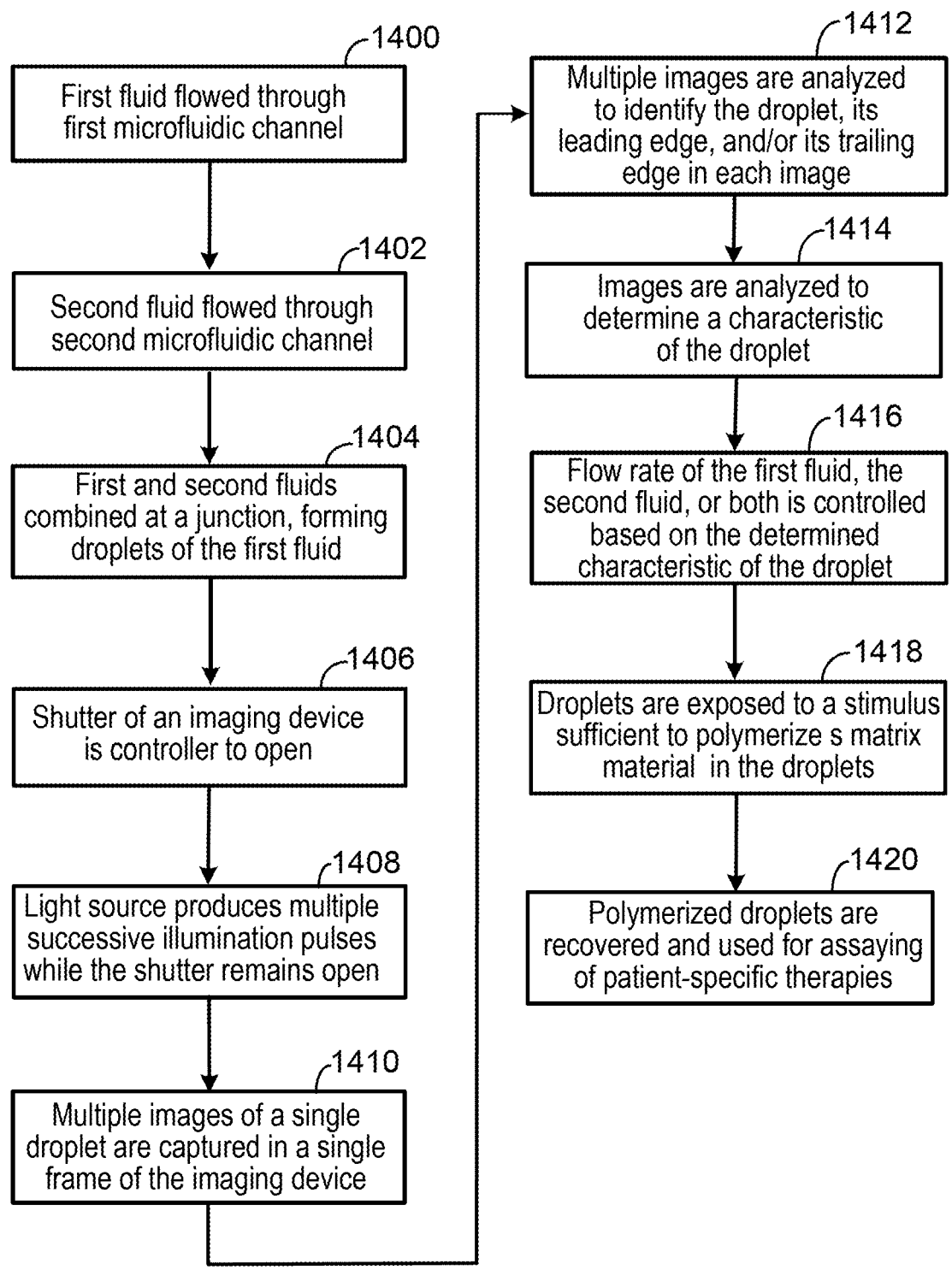
FIG. 25 is a flow chart.

Referring to FIG. 25, in an example process for generating MOSs, a first fluid is flowed through a first microfluidic channel of an MOS generation system (1400). The first fluid includes biological material, e.g., patient-derived biological material, and an unpolymerized matrix material. A second fluid is flowed through one or more second microfluidic channels of the microfluidic apparatus (1402). The first fluid and the second fluid are immiscible.

The first and second fluids are combined at a junction where the first microfluidic channel and the second microfluidic channels meet, thereby forming droplets of the first fluid dispersed in the second fluid (1404). The droplets of the first fluid in the second fluid flow from the junction into a third microfluidic channel.

A shutter of an imaging device is controlled to open (1406). A light source illuminates a region of the third microfluidic channel with multiple successive illumination pulses while the shutter remains open (1408) such that multiple exposures are captured of a single droplet of the first fluid in the third microfluidic channel in a single image captured by the imaging device (1410).

The multiple exposures of the single droplet are analyzed to identify the droplet in each image, or to identify a leading edge, a trailing edge, or both, of the droplet in each exposure (1412). In some examples, the image analysis is performed using frequency domain techniques or machine vision techniques or by creation of best fit circles. The multiple exposures of the single droplet are analyzed to determine a characteristic of the droplet (1414), such as a size of the droplet, a velocity of the droplet, a separation between adjacent droplets, a number density of droplets, an estimated total number of droplets generated in the system, or a droplet generation rate (e.g., number of droplets per second).

Based on the determined characteristic of the droplet, the flow rate of the first fluid in the first microfluidic channel, the flow rate of the second fluid in the one or more second microfluidic channels, or both is controlled (1416). For instance, the flow rate of the first fluid can be controlled to obtain droplets of a target size, and the flow rate of the second fluid can be controlled to obtain droplets flowing at a target velocity.

The droplets are exposed to a stimulus sufficient to polymerize the matrix material in the droplets (1418), and the polymerized droplets are used, e.g., for assaying patient-specific therapies (1420).

Measurement and Control of Droplet Sizes

Images of generated droplets in conjunction with the MOS generated systems and methods described above can be processed to identify any imaged droplets and to estimate a size of the imaged droplet(s). Then, based on the estimated size of the imaged droplet(s), a control system is configured to adjust at least one fluid flow rate within the device (e.g., by adjusting the pressure of at least one fluid flow within the device) to actively control the size of droplets that are subsequently generated. These approaches to measurement and control of droplet size can be used in combination with aspects of the MOS generations systems and methods described above, including in combination with aspects of the closed loop feedback approaches described above.

Various implementations of the approaches to measurement and control of droplet sizes described herein may provide one or more of the following advantages.

Implementing a feedback system based on the size of generated droplets can provide for a robust microfluidic system that adapts to various operating conditions. For example, the technology described herein can ensure consistent generation of droplets within a target size range even when there are variations in the purity of input materials, the viscosity of the input materials, a temperature of the device, etc.

The technology described herein can also have the advantage of more rapidly identifying an appropriate pressure to apply to a fluid input reservoir (sometimes referred to herein as a "holding chamber") to affect the rate of fluid flow within the device and to generate droplets of a target size. Some devices rely on a careful and time-intensive experimental process to determine the appropriate pressure for a very specific set of operating conditions. Unlike such devices, the technology described herein enables real-time automatic pressure adjustments to rapidly converge to (e.g., in the order of seconds) an appropriate pressure for a specific set of operating conditions. For simplicity, this specification describes example implementations of the invention where the rate of fluid flow is adjusted by changing the pressure applied to a fluid input reservoir. It is to be understood, however, that the disclosed techniques are equally applicable to other suitable approaches to adjusting fluid flow rates including, for example, adjusting a programmable pump flow rate applied to the fluid.

Another advantage of the technology described herein is its enablement of sub-pixel radial resolution for circle detection, which is used for identifying and estimating the size of the imaged droplets. The term "circle detection" is used herein to refer to identifying the circular or near-circular shapes in an image (e.g., based on detected edges in the image) and fitting a circle to represent such shapes (e.g., using a polynomial representation). For example, even if the droplets do not appear as exactly circular in an image, a circle detection process may still be able to detect the near-circular shape of a droplet and generate a circular representation corresponding to the droplet. In some cases, shapes other than circles can be used to represent the near-circular shape. For example, polygons having 10 edges, 50 edges, 100 edges, 500 edges, etc. can be used to represent the near-circular shape in some implementations. In some implementations, in addition to or in alternative to polynomial representations, the circular or near-circular shapes can be represented by their spectral decomposition, their angular symmetry, etc. Compared to other shape detection algorithms that implement a single-pass approach, the technology described herein uses a multi-pass approach that yields a circular representation with sub-pixel radial resolution. This advantage is especially important for microfluidic applications, where imaged droplets (sometimes referred to herein simply as "droplets") can sometimes have radii ranging from only 5-20 pixels (although, in other examples, radii can have lengths of up to 50 pixels, up to 100 pixels, up to 250 pixels, etc.).

In some implementations, the technology described herein provides for various filtering criteria that can potentially avoid undesired results when processing real-world images of droplets in microfluidic devices. For example, the filtering criteria implemented by the technology disclosed herein can prevent the false positive detection of circles in the spaces between droplets, prevent the false positive detection of intersecting circles, exclude the detection of any circles located too close to a wall of the droplet-generating device, and exclude the detection of any circles that have abnormal signals within the circle's perimeter.

Furthermore, in some implementations, the technology disclosed herein can be used to not only identify droplets, but also air bubbles generated by the device. This detection of air bubbles can be indicative of a fault condition or a near depletion of an input material, and can be used to accordingly control the flow rate of at least one fluid within the device (e.g., by controlling the pressure applied to a fluid reservoir that affects the rate of fluid flow). For example, in response to an identification of air bubbles in the device, the pressure of a fluid flow can be decreased to avoid streaming a continuous flow of air into a channel of the device.

Generally, in some applications, it can be desirable to control the size of the droplets generated by a device. For example, referring to MOS generation, it can be desirable to ensure that the MOSs are generated to have a particular size (e.g., 220 microns to 300 microns). If the MOS is too small, there can be a lack of space for the cells to grow and divide, and there can be a shortage of nutrient media within the MOS. MOSs also tend to shrink over time, and a growing cluster of cells might rupture a droplet that is too small. This rupture, in turn, may interfere with tracking individual cells within the MOS to identify individual cell responses. On the other hand, if a MOS is generated to be too large, there can be an excess of nutrient media within the MOS and a shortage of cells, and diffusion of drugs to the cells can be slow. MOSs that are excessively large can also get stuck within a channel of the device (e.g., a microfluidic chip), which may have, for example, a channel width of approximately 300 microns at some locations.

To achieve a target droplet size, existing devices for droplet generation require specific conditions to operate reliably. As described in greater detail below, droplet size is sensitive to the flow rates of one or more fluid flows (e.g., a ratio of flow rates of two fluid flows) within a droplet-generating device. It is therefore desirable to control the flow rates, which can be affected by various factors including, for example, a viscosity of the fluids, a surface tension of the fluids, a pressure applied to the fluids, one or more dimensions of the fluid flow path, etc. In some implementations, the flow rates can be controlled directly using positive displacement pumps (e.g., syringe pumps). In other implementations, such as in the examples described herein, the flow rate for each fluid can be controlled by adjusting the pressure applied to a corresponding input fluid reservoir that feeds into a fluid flow path within the droplet-generating device. Thus, while the current application describes examples in which fluid flow rates are controlled by applying pressure to input fluid reservoirs, the technology described herein is equally applicable to other flow rate control mechanisms.

In examples where the flow rates are controlled by adjusting applied pressures to input fluid reservoirs, the appropriate pressure to apply to each reservoir can be highly dependent on various operating conditions. For example, existing devices may require a consistent purity of input materials, a consistent viscosity of the input materials, precise temperature conditions, etc. to ensure a consistent and desired droplet size. The appropriate pressure to apply under a very specific set of conditions is often determined through a time-intensive experimental process and can leave the droplet generation process vulnerable to slight changes in the operating conditions. Therefore, consistent and robust generation of droplets of a target size is a difficult technological challenge.

Figure 26A:
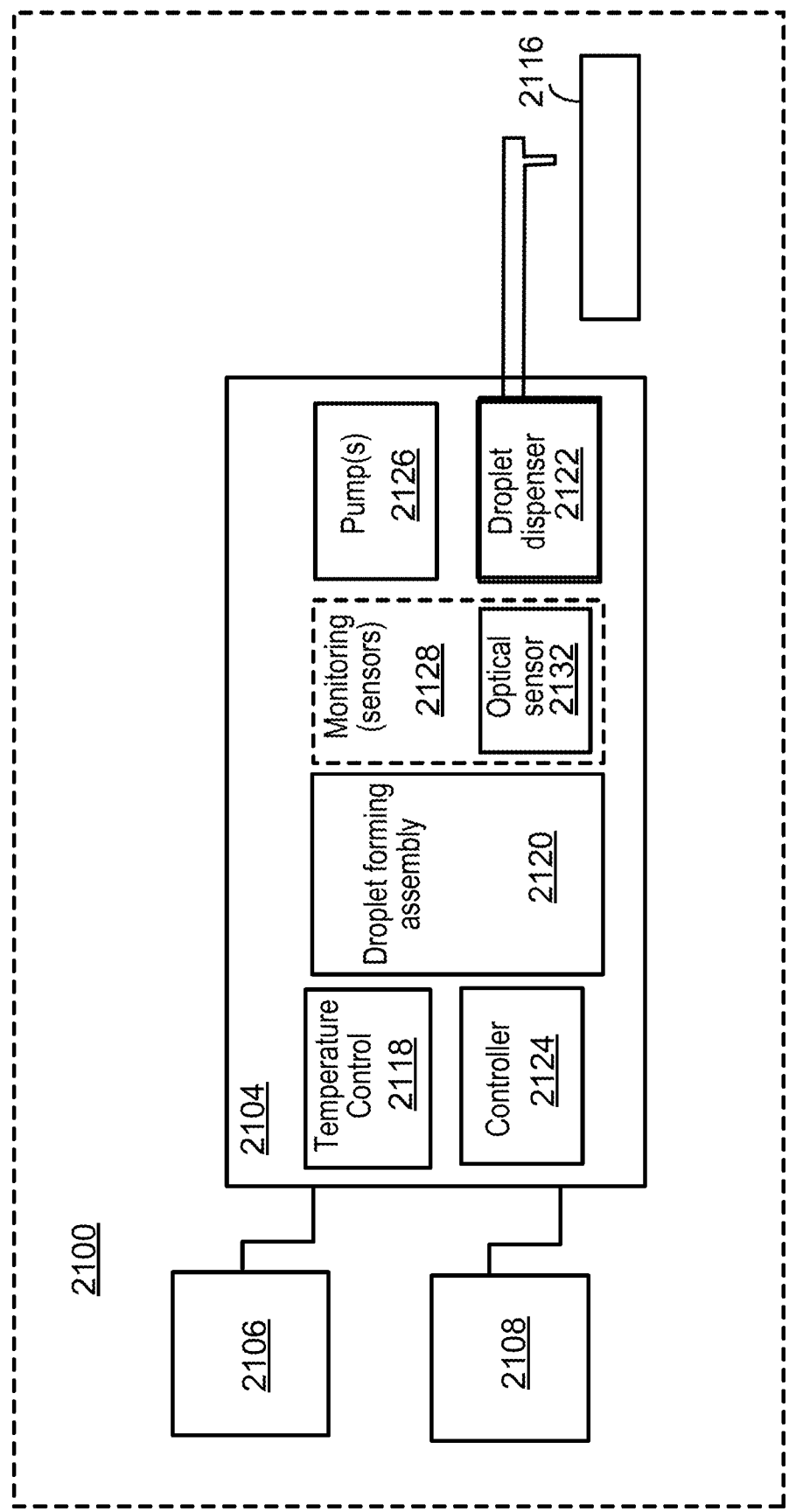
FIG. 26A is a block diagram of an example device for generating droplets.

FIG. 26A illustrates an example of a device 2100 for forming droplets (e.g., MOSs). The device 2100 can be, e.g., an implementation of aspects of the MOS generation system 200 discussed above. The device 2100 includes an input for inputting either an unpolymerized mixture of cells and a fluid matrix material (already combined) or may separately receive the cells, e.g., in a holding solution, and a fluid matrix material. As described above, in some droplet applications, no cells may be included at all.

In some variations the device 2100 includes a holding chamber 2106 for holding the unpolymerized mixture and/or holding chambers (not shown) for holding the cell sample (e.g., tumor cells) and holding the fluid matrix material. For instance, the holding chamber 2106 can be implemented as the reservoir 220 discussed above. Any or all of these holding chambers may be pressurized to control and/or speed up fluid flow out of the chambers and into the device. The device may either receive the unpolymerized mixture or it may receive the components and mix them. In some variations the device may control the concentration of the cells in the unpolymerized mixture and may dilute the mixture (e.g., by adding additional fluid matrix material to achieve a desired density. For example, the device 2100 may include one or more sensors 2128 for reading the density (e.g., the optical density) of the cells in the unpolymerized mixture. The sensor may also be coupled to the controller 2124, which may automatically or semi-automatically (e.g., by indicating to a user) control the dilution of the cells in the unpolymerized mixture. The device 2100 may also include a port for receiving the unpolymerized mixture. The port may include a valve or may be coupled to a valve and the valve may be controlled by the controller 2124 (or a separate controller).

The device 2100 may include another holding chamber 2108 and/or port for holding and/or receiving an immiscible or hydrophobic fluid such as oil. For instance, the holding chamber 2108 can be implemented as the oil reservoir 700 described above. In some variations the immiscible fluid may be held in a pressurized chamber so that the flow rate of the immiscible fluid within the device 2100 may be controlled. Any of the pressurized chambers may be controlled by the controller 2124 which may use one or more pumps 2126 to control the pressure and therefore the flow through the device 2100. One or more pressure and/or flow sensors (e.g., sensors 2128) may be included in the system to monitor the flow through the device.

In FIG. 26A, the entire device 2100 may be enclosed in a housing or a portion of the device 2104 may be enclosed in a housing. In some variations the housing may include one or more openings or access portions on the device 2100, e.g., for adding the immiscible fluid and/or the unpolymerized mixture to the chambers 2106, 2108.

As mentioned, the device 2100 may also include one or more sensors 2128 for monitoring all or key portions of the droplet generation process. In some variations, the sensors may include optical sensors, mechanical sensors, voltage and/or resistance (or capacitance, or inductance) sensors, force sensors, temperature sensors, mass air flow sensors, mass liquid flow sensors, pressure sensors, etc. These sensors may be used to monitor the ongoing operation of the assembly, including the formation of the droplets. For example, the device 2100 can include an optical sensor 2132 among the sensors 2128. The optical sensor 2132 can be a camera configured to capture imagery (e.g., photographs or videos) of the droplets generated by the device 2100, and as described below, can be used to control a size of the droplets generated by the device 2100. For instance, the optical sensor 2132 can be part of the closed loop feedback system discussed above. The device 2100 may also include one or more thermal/temperature regulators 2118 for controlling the temperatures of either or both the immiscible fluid and/or the unpolymerized mixture (and/or the fluid matrix material). In some implementations, the monitoring sensors 2128 and/or the optical sensor 2132 can be external to the device 2100.

The device 2100 can also include one or more droplet forming assemblies 2120 that may be monitored (e.g., using the one or more sensors 2128) as will be described in further detail below. The droplet forming assembly may include, or may be coupled with, a dispenser (e.g., a droplet dispenser) 2122. The dispenser may dispense, for example, into one or more collection tubes or a multi-well plate 2116.

Figure 26B:
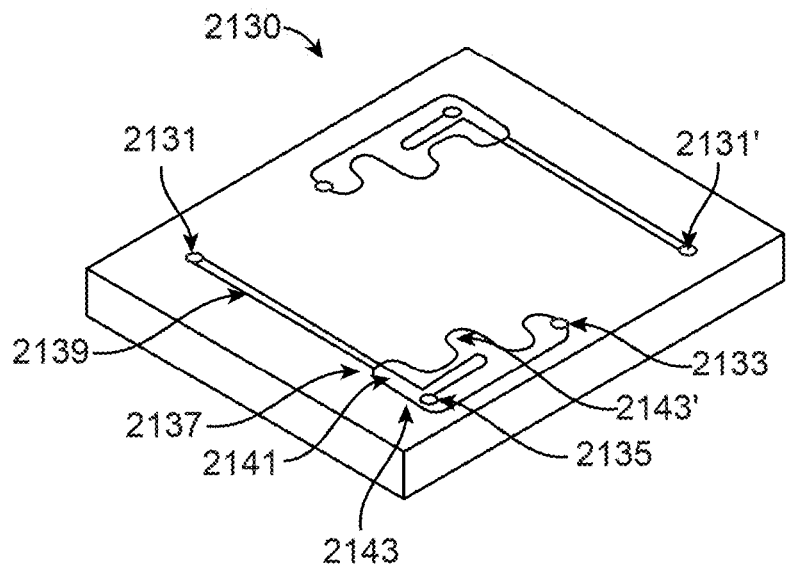
FIG. 26B is a perspective view of an example device for generating droplets.

In general, the droplet forming assembly 2120 may include one or more microfluidic chips (e.g., microfluidic chip 2130 shown in FIG. 26B, or the microfluidic chip 210 of FIG. 2) or structures that form and control the streams of the unpolymerized mixture and form the actual droplets. FIG. 26B illustrates one example of a microfluidic chip 2130 for forming droplets; other examples of microfluidic chips are illustrated and discussed above, e.g., in conjunction with the microfluidic chip 210. In FIG. 26B, the chip 2130 includes a pair of parallel structures for forming droplets (e.g., MOSs). In other implementations, the microfluidic chip can include additional structures (e.g., 3 structures, 4 structures, 5 structures, etc.).

Figure 26C:
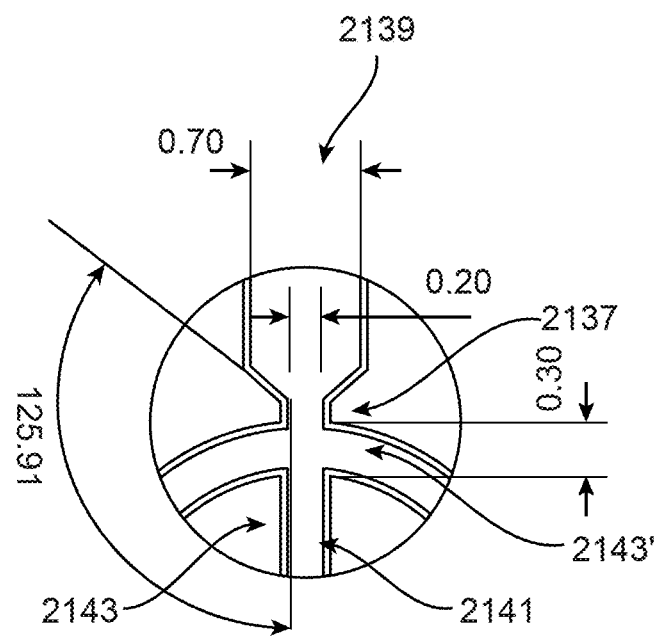
FIG. 26C is a schematic illustration of a portion of the example device shown in FIG. 1B.

FIG. 26C illustrates the droplet-forming region of the microfluidic chip 2130 for forming MOSs, including an unpolymerized channel outlet 2141 that opens into the outlet channel 2139 and is intersected by the immiscible fluid outlet(s) or channels, 2143, 2143'. In some implementations, the outlet channel 2139 can be wider than the unpolymerized channel outlet 2141 to create a slowing of flow and back pressure to assist in droplet formation. In some implementations, a junction region 2137 can be configured as a "+" junction, with the immiscible fluid channels 2143, 2143' intersecting the unpolymerized channel outlet 2141 and the outlet channel 2139 to form four right angles. In some implementations, the region of intersection 2137 can be configured such that a single immiscible fluid channel (e.g., the immiscible fluid channel 2143) enters a straight sample channel (e.g., unpolymerized channel outlet 2141) at a right angle. In some variations the input from the immiscible fluid channel(s) may be configured to intersect with the unpolymerized material at a non-perpendicular angle. In FIG. 26C, as in all figures in this description showing dimensions, the dimensions shown are exemplary only, and are not intended to be limiting, unless otherwise specified. Other implementations of the droplet-forming region are discussed above in conjunction with the microfluidic chip 210.

In FIG. 26B, the microfluidics chip 2130 includes an inlet (input port) 2133 for the immiscible fluid into the chip (e.g., from the inlet port or storage chamber shown in FIG. 26A). A second inlet port 2135 into the chip may be configured to receive the unpolymerized material and transport it down a semi-tortious path to the junction region. Similarly the inlet port for the immiscible fluid may be securely coupled to the outlet from the immiscible fluid chamber or inlet, described above.

The inlet port 2135 for the unpolymerized material into the chip 2130 may be coupled through a delivery pathway connecting the inlet 2135 to the junction region 2137 (as shown in FIG. 26C). Similarly, the inlet 2133 for the immiscible fluid may connect to two (or more) connecting channels 2143, 2143' to the junction region 2137. A channel leaving the junction region 2137 may pass the formed droplets (in the immiscible fluid) down the channel to an outlet 2131 that may connect to a dispenser (e.g., dispenser 2122 shown in FIG. 26A) for dispensing the droplets into one or more chambers (e.g., multi-well plate 2116 shown in FIG. 26A) for culture and/or assaying.

In the example shown in FIGS. 26B and 26C the formed droplets (e.g., unpolymerized MOSs), may be transmitted down a long temperature-controlled microfluidics environment (e.g., channel 2139), prior to being dispensed from the apparatus.

In FIGS. 26B and 26C, the junction region 2137 is shaped as described above, so that the channel 2141 carrying the unpolymerized mixture intersects one or more (e.g., two) channels 2143, 2143' carrying a hydrophobic fluid (e.g., oil) that is immiscible with the unpolymerized mixture. As the unpolymerized mixture is pressurized to flow at a first rate out of the first channel 2141, the flowing immiscible fluid in the intersecting channels, 2143, 2143', permits a predefined amount of the unpolymerized mixture to pass before pinching it off to form a droplet that is passed into the outlet channel 2139. The size of the droplet, therefore, is dependent and highly sensitive to changes in the pressure (and corresponding flow rate) of both the unpolymerized mixture and the immiscible fluid.

In some variations, a minced (e.g., dissociated) clinical (e.g., biopsy or resected) sample of disassociated cells, such as <1 mm in diameter, can be mixed with a temperature-sensitive gel (i.e. MATRIGEL, at 4 degrees C.) to form the unpolymerized mixture. This unpolymerized mixture may be placed into the device 100 that generates droplets of a particular volume and material composition, and the dissociated cells (e.g., tumor cells) may be partitioned into these droplets. In some cases, each droplet can be approximately 260 microns in diameter (e.g., 220 microns to 300 microns), and can contain a tumorsphere including 2-100 tumor cells (e.g., 2-15 tumor cells, 15-50 tumor cells, 50-100 tumor cells, etc.). The gel in the unpolymerized material may solidify upon heating (e.g., at 37 degrees Celsius), to form polymerized MOSs. In some variations this method may be used to produce over 10,000 (e.g., over 20,000, over 30,000, over 40,000, over 50,000, over 60,000, over 70,000, over 80,000, over 90,000, over 100,000) MOSs from a single biopsy. These MOSs are compatible with traditional 3D cell culture techniques and can be used for observing cell responses to various stimuli through assays, as previously described.

FIGS. 27A-27E are examples of images 2200A-2200E of a droplet-generating device (such as the device 2100 of FIGS. 26A-26C) in operation. Each of the images 2200A-2200E shows an outlet channel 2239 that provides egress from a junction region 2237. The representations of the outlet channel 2239 and junction region 2237 can correspond respectively to the outlet channel 2139 and the junction region 2137 of the microfluidic chip 2130 described in relation to FIGS. 26B and 26C. For instance, the outlet channel 2239 and the junction region 2237 can correspond to the droplet generation chamber 312 and junction 311, respectively, of FIG. 4. The images were captured by a camera (corresponding to the optical sensor 2132 of the device 2100) to monitor the droplet-generation process of the device. Each of the images 2200A-2200E includes overlays representative of the output of an image processing module, which can be implemented by a controller of a droplet-generating device (e.g., the controller 124 of the device 100 shown in FIG. 1A). The image processing module and the steps it performs is described below with reference to FIGS. 28, 429 and 32.

Referring to FIGS. 27A-27E, the overlay 2250 corresponds to the detected walls of the imaged outlet channel 2239 (sometimes referred to herein simply as "outlet channel 2239") in a widened region (e.g., a chamber) of the outlet channel 2239. The overlay 2252 corresponds to edges detected by the image processing module within the widened region (e.g., by an edge detection algorithm such as Canny edge detection, Gaussian edge detection, threshold-based edge detection, etc.). The overlay 2254 corresponds to circles detected by the image processing module based on the detected edges (e.g., using a Hough transform).

In some implementations, it can be beneficial to capture imagery of the widened region and process the image content within the widened region because the droplets generated by the device may be less likely to interact with the side walls of the outlet channel when the droplets are in this region. Therefore, it can be useful to capture imagery of the generated droplets in the widened region to estimate their sizes absent any interactions with the side walls of the outlet channel 2239.

In some implementations, it can be useful to capture imagery of the generated droplets in other portions of the system, for example, in a narrower portion 2260 of the outlet channel2 239. Capturing imagery of the narrower portion 2260 of the outlet channel 2239 can be beneficial in some cases because the droplets in this portion are likely to be lined up in a single file and separated from one another (e.g., by the immiscible fluid). In some implementations, the narrower portion 2260 can also be deeper than the widened region of the outlet channel 2239 (e.g., 300 microns in depth compared to 200 microns in depth), enabling measurement of droplet sizes absent compression by the top or bottom walls of the outlet channel 2239. In some implementations, the narrower portion 2260 can be wide enough such that droplets inside the narrower portion 2260 are not compressed by the side walls of the narrower portion 260.

Figure 27A:
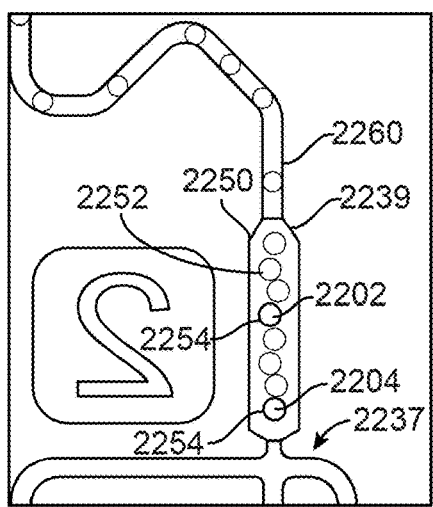
FIGS. 27A-27E are example images captured of a droplet-generating device.
Figure 27B:
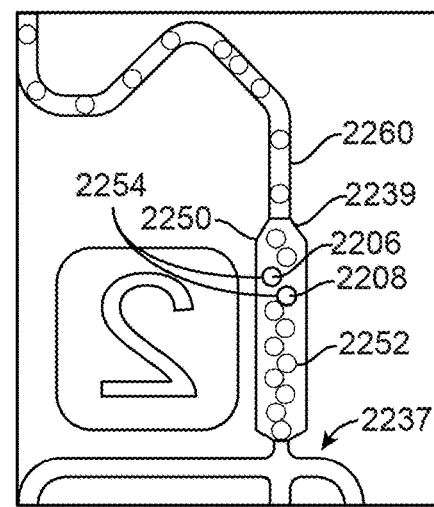

In FIGS. 27A-27B, the overlay 2252 indicates the presence of several droplets in the widened region of the outlet channel 2239. However, in each of the images 2200A, 2200B, only two circles (circles 2202, 2204 in image 2200A; circles 2206, 2208 in image 2200B) are detected. In some implementations, this behavior can be desirable since false positives can be much more detrimental than false negatives for estimating the size of generated droplets. Since consecutively generated droplets are often likely to have similar size and because droplets are made quickly (e.g., 40 droplets per second in some implementations), detecting only a few representative droplets (e.g., less than 5) in the outlet channel 2239 may be sufficient to monitor and control droplet sizes. Typically, it can be detrimental to detect circles that do not actually correspond to droplets, because the sizes of these false positives can bias estimates of true droplet sizes in the outlet channel 2239.

Referring still to FIGS. 27A and 27B, it is also readily observable that the circles 2202, 2204 are larger than the circles 2206, 2208 in image 2200B. This demonstrates the ability of the image processing module to accurately detect circles (and corresponding droplets) of various sizes.

Figure 27C:
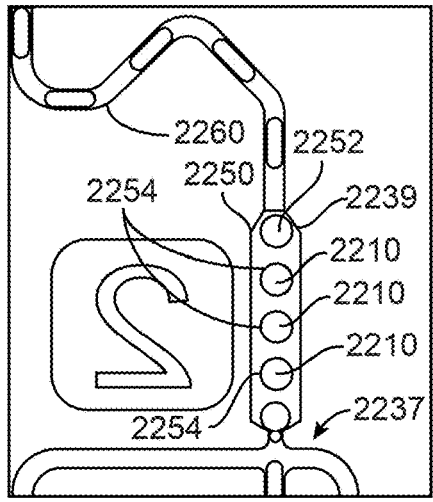

Similar to FIGS. 27A and 27B, FIG. 27C shows an image 2200C with detected edges (overlay 2254) indicating the presence of various spherical objects in the widened region of the outlet channel 2239. In FIG. 27C, the image processing module detected three circles 2210 based on these detected edges. However, unlike in FIGS. 27A-27B, the detected circles 2210 in the image 2200C represent air bubbles rather than droplets. Imaged air bubbles (e.g., the circles 2210) can be distinguished from droplets (e.g., detected circles 2202, 2204, 2206, 2208) based on the darkness of the imaged edges. For example, the edges in the image 2200C that correspond to the detected circles 2210 are much darker than the edges in the images 2200A, 2200B that correspond to the detected circles 2202, 2204, 2206, 2208. This is because the difference between the refractive indices of air and the immiscible fluid (e.g., oil) is greater than the difference between the refractive indices of the unpolymerized mixture and the immiscible fluid. Thus, in an example implementation, imaged air bubbles can be distinguished from droplets by estimating, for each detected circle, a value reflective of an intensity of the detected circle's perimeter (e.g., a ratio of an average on-perimeter intensity to an average off-perimeter intensity). This value can in turn be used to classify the detected circle as an imaged air bubble or a droplet using one or more classification techniques (e.g., a classification threshold, naïve Bayesian inference, a machine learning-based classifier, etc.).

Figure 27D:
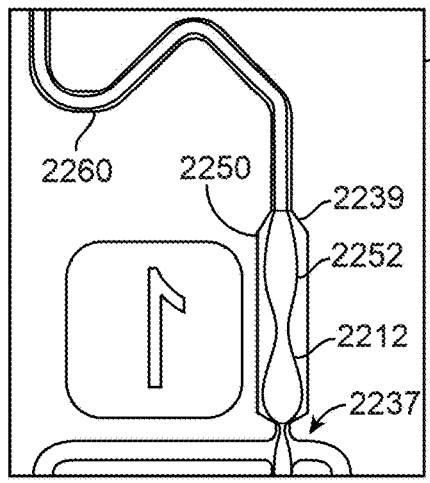

In some implementations, the detection of air bubbles in the outlet channel 2239 can be indicative of a fault condition of the device or a near depletion of the unpolymerized mixture. Therefore, in some implementations, in response to a detection of air bubbles in the outlet channel 2239, the pressure of the fluid flow corresponding to a channel for transporting the unpolymerized mixture (e.g., channel 2141 shown in FIGS. 26B and 26C) can be decreased to prevent the continued formation of air bubbles and/or the streaming of air into the outlet channel. In circumstances where the pressure is not sufficiently decreased, an undesirable situation (sometimes referred to as a "blowout scenario") can arise, in which a stream of air flows into the outlet channel. The image 2200D shown in FIG. 27D depicts an example of a blowout scenario, in which a stream of air 2212 is forced into the outlet channel 2239.

Figure 27E:
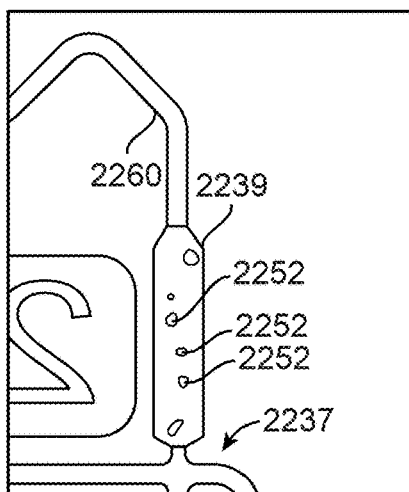

FIG. 27E shows an image 2200E, in which no droplets or air bubbles appear in the outlet channel 2239. Consequently, no circles were detected in the image 2200E. In some implementations, a scenario like this can be indicative of a fault condition. For example, the image 2200E may result when the pressure of the fluid flow of the unpolymerized mixture is too low or too high to support stable droplet generation. In these scenarios, the outlet channel 2239 can become entirely filled with either the immiscible fluid (e.g., if the pressure of a fluid flow of the unpolymerized mixture is too low) or the unpolymerized matrix (if a pressure of a fluid flow of the unpolymerized mixture is too high). In some implementations, in response to a failure to detect any circles within the outlet channel 2239, a controller of the device (e.g., the controller 2124 of the device 2100) can implement a fault recovery routine to restart stable droplet generation. Actions taken by the controller, including fault recovery routines, are described in further detail herein.

Figure 28:
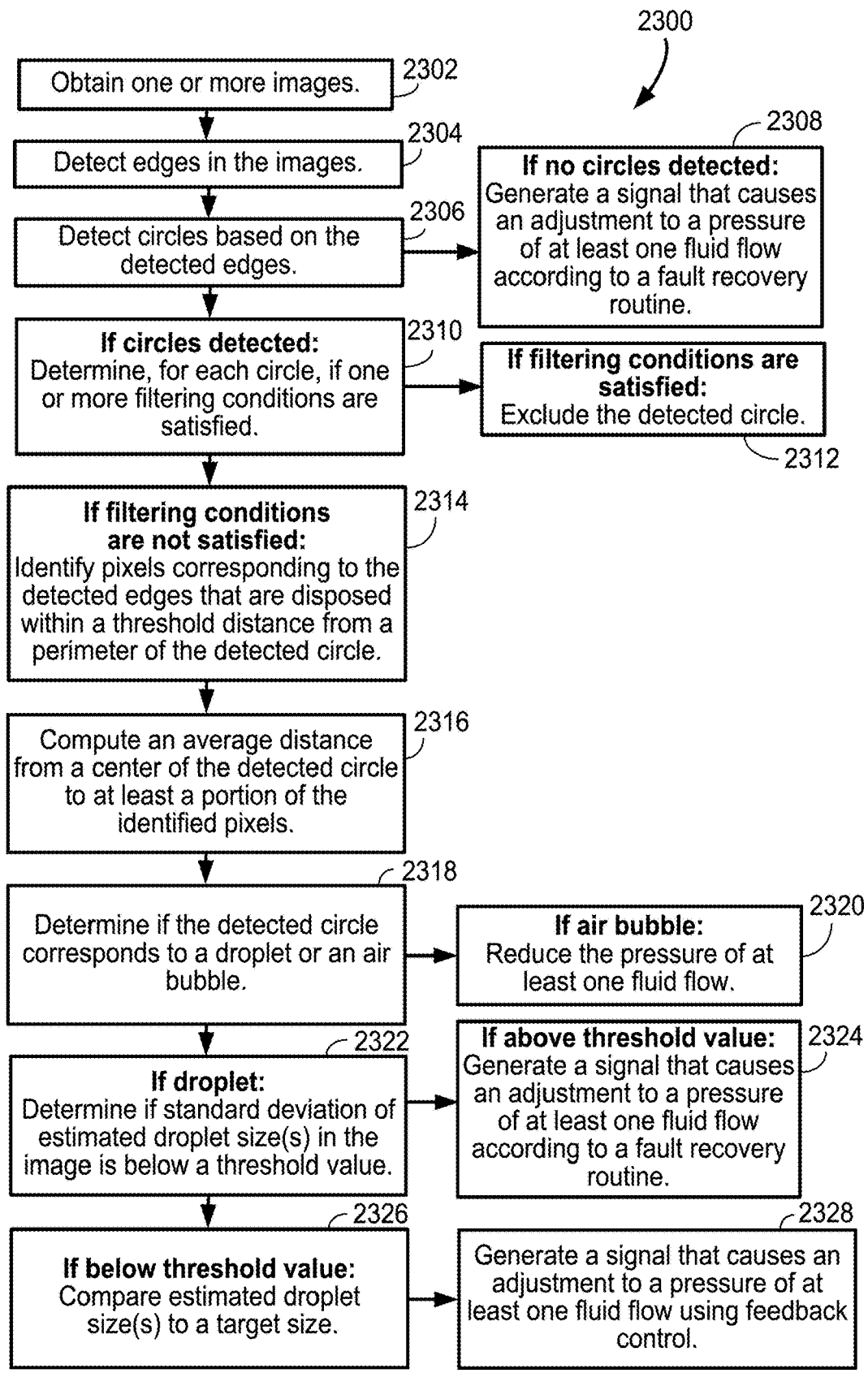
FIG. 28 is a flowchart of a process for controlling a pressure of a fluid flow in a droplet-generating device.

FIG. 28 illustrates an example process 2300 for controlling a pressure of a fluid flow in a droplet-generating device, for example, to control the sizes of generated droplets. At least some operations of the process 2300 can be executed by a microfluidic system such as the device 2100 or a portion thereof (e.g., by the controller 2124). In some implementations, one or more operations of the process 2300 can be executed by one or more remote computing systems external to the device 2100.

Operations of the process 2300 include obtaining one or more images (2302). For example, the images can be captured by a camera such as the optical sensor 2132 of the device 2100. The images can correspond to the images 2200A-2200E described in relation to FIGS. 27A-27E. Like the images 2200A-2200E, the obtained images can be framed to include a widened region of an outlet channel (e.g., the outlet channel 2139), which in some cases, can include droplets and/or air bubbles. In some implementations, after obtaining the one or more images (2302), a gamma correction can be applied to the one or more images. The gamma correction can convert pixel array data retrieved from the camera to numbers that are proportional to actual photon intensity, which can, for example, optimize the usage of bits to account for the non-linear manner in which humans perceive light and color.

Operations of the process 2300 can also include detecting edges in the images (2304) (sometimes after applying a gamma correction to the one or more images) and detecting circles based on the detected edges (2306). Both of these operations can be executed by an image processing module implemented on a controller of a microfluidic device (e.g., the controller 2124 of the device 2100). In some implementations, the operations 2304, 2306 can be implemented on a remote computing device external to the device 2100. Detecting the edges (2304) can include implementing an edge detection algorithm such as a Canny edge detector, Gaussian edge detector, a threshold-based edge detector, etc. In some implementations, detecting the edges (2304) can also include using asymmetric filtering to mitigate bias caused by the outline of the channel of the microfluidic device. For example, in the one or more images, the outline of the chamber can appear, at least in part, as two dark vertical lines in the image (as they do in FIGS. 27A-27E). In such cases, by using a difference-of-Gaussians kernel along the vertical axis or by using the kernel [[0.5, 1, 0.5], [0, −4, 0], [0.5, 1, 0.5]], a filter can be intentionally biased to be more sensitive to vertical changes in pixel intensity. Various filters can be selected and used depending on the specific optical and droplet characteristics of the system. Detecting the circles based on the detected edges (2306) can be implemented using one or more shape detection algorithms such as a Hough transform. In some implementations, the one or more images can be downsized (e.g., via down-sampling) prior to detecting the edges in the images (2304) and/or prior to detecting circles based on the detected edges (2306). For example, the one or more images can be down-sampled (e.g., digitally down-sampled) to ¼-½ of the original resolution (e.g., 25% of the original resolution, 30% of the original resolution, 40% of the original resolution, 50% of the original resolution, etc.). This down-sampling can have the advantage of increasing the speed of edge detection and/or circle detection. For example, the number of operations involved in performing a Hough transform (an example algorithm that can be used to detect circles), can scale with the fourth power of an image's size. Therefore, down-sampling the image prior to performing the circle detection using a Hough transform can yield substantial time savings (e.g., enabling performance of the Hough transform 5 times to 15 times faster, enabling performance the complete process (2300) 2 times to 10 times faster, etc.). For example, in implementations where an original image having a resolution of 100×100 pixels was down-sampled to an image having a resolution of 50×50 pixels prior to performing the Hough transform, the Hough transform was performed approximately 10 times faster, and the process 2300 performed about 6 times faster, than in implementations without down-sampling. In implementations where down-sampling is performed, subsequent to detecting the edges in the images (2304) and/or subsequent to detecting circles based on the detected edges (2306), the resulting image data can be magnified. For example, the image can be magnified by a factor ranging from 2 to 4. In some cases, the magnification factor can be selected to restore a down-sampled image to its original size subsequent to detecting the edges in the images (2304) and/or subsequent to detecting circles based on the detected edges (2306).

If no circles are detected at the operation 2306, then the process 2300 can include generating a signal that causes an adjustment to a pressure of at least one fluid flow according to a fault recovery routine (2308). For example, the one or more images may be similar to the image 2200E shown in FIG. 27E, which includes no detected circles. In some implementations, a controller of a microfluidic device (e.g., the controller 2124 of the device 2100) can control one or more pumps (e.g., pumps 2126) to control the flow rate (e.g., by controlling the pressure) of a fluid flow within the device 2100. In some implementations, this fluid flow can correspond to the flow of the unpolymerized mixture through the device. However, in other implementations, both the pressure of the flow of the unpolymerized mixture and the flow of the immiscible fluid can be adjusted.

The fault recovery routine can include implementing a control scheme for controlling the flow rate (e.g., by controlling the pressure) of a fluid flow, the control scheme operating without the use of feedback control. For example, the fault recovery routine can include implementing a naïve control scheme that gradually increases the pressure of the fluid flow of the unpolymerized mixture until stable droplet generation begins or until a maximum pressure value is reached. In some implementations, the fault recovery routine can include implementing a naïve control scheme that gradually decreases the pressure of the fluid flow of the unpolymerized mixture until stable droplet generation begins or until a minimum pressure value is reached. In some implementations, the fault recovery routine can include implementing a naïve control scheme that continually oscillates the pressure of the fluid flow of the unpolymerized mixture between a minimum pressure value and maximum pressure value until stable droplet generation begins. The use of a naïve static controller instead of feedback control in the presence of fault conditions can prevent undesired or erratic behavior from a feedback controller when no droplets are detected or when droplets of extreme sizes are detected.

Alternatively if circles are detected at operation 2306, the process 2300 can include determining, for each circle, if one or more filtering conditions are satisfied (2310). For example, the obtained images with detected circles might correspond to the images 2200A, 2200B, or 2200C. The one or more filtering conditions can include criteria for excluding circles in order to prevent biasing size estimates with data from false positives or low-quality circles.

In some implementations, the filtering conditions can include an indication that the detected circle is based on the detected edges of a plurality of droplets. For example, this can result from mistakenly identifying a space between multiple droplets as a detected circle. In some implementations, the indication that the detected circle is based on the detected edges of a plurality of droplets can arise from a determination that a detected circle is substantially smaller than one or more other detected circles in the same image. The indication can also arise from a determination that a detected circle shares an edge with one or more other detected circles of substantially larger size.

In some implementations, the filtering conditions can include an indication that the detected circle overlaps with at least one additional circle within the same image. Although droplets can sometimes be tangent to one another in the outlet channel (e.g., the outlet channel 2139), they typically do not overlap. Thus, detected circles should also not be overlapping in the imaged outlet channel (e.g., the outlet channel 2239). Receiving an indication that a detected circle overlaps with at least one additional circle can therefore suggest that at least some of the overlapping circles are potentially false positives.

In some implementations, the filtering conditions can include an unexpected detected signal within the perimeter of the detected circle. In some implementations, detected signals (e.g., dark pixels) in the one or more images are only expected to be present at edges corresponding to the droplets, air bubbles and/or the microfluidic device itself. In some implementations, one may also expect a particular type of detected signal (e.g., a faint signal or a signal of a particular size and/or shape) corresponding to tumorspheres or other cells located within a detected droplet. However, if an unexpected signal different from these expected signals is detected within the perimeter of a detected circle, this could suggest that the detected circle is potentially a false positive or is abnormal for other reasons. In some implementations, the unexpected detected signal can correspond to a detected signal originating from within a perimeter of the detected circle, the detected signal exceeding a threshold signal level.

In some implementations, the filtering conditions can include a determination that the detected circle is less than a threshold proximity from an imaged wall (sometimes referred to herein simply as a "wall") of the device. A droplet that is located at a wall of the device may be compressed against the wall and may lose its spherical shape. This can in turn result in poor performance of the circle detection algorithm and/or result in biased estimates of the droplet's size. Moreover, because the walls of the device may appear in the image as edges with high contrast, there is a risk of incorrectly identifying these edges as portions of a detected circle, which can lead to false positives. Therefore, it can be beneficial in some implementations to exclude detected circles that are very close to a wall of the device.

If any of the filtering conditions are satisfied at operation 2310 for a particular detected circle, the process 2300 can include excluding the detected circle (2312). As discussed above, the operation 2312 can result in more accurate estimates of droplet size by excluding false positive and low-quality detected circles.

If none of the filtering conditions are satisfied at operation 2310, the process 2300 can include identifying pixels corresponding to the detected edges that are disposed within a threshold distance from a perimeter of the detected circle (2314) and computing an average distance from the center of the detected circle to at least a portion of the identified pixels (2316). This computed average (which can be a weighted average) can be used as an updated radius of the detected circle. In some implementations, a metric other than an average can be computed, as long as the metric is derived from and representative of a distance from the center of the detected circle to at least a portion of the identified pixels. Compared to single-pass circle detection algorithms that detect circles with a radial resolution greater than or equal to 1 pixel, this multi-pass approach to estimating the detected circle's size yields sub-pixel radial resolution. This resolution is particularly important for microfluidic applications, where droplets can sometimes have radii ranging from only 5-20 pixels (although, in other examples, radii can have lengths of up to 50 pixels, up to 100 pixels, up to 250 pixels, etc.). A visual representation of this process is provided in FIG. 29 and is described in further detail below.

After detecting a high-quality circle and estimating its size with sub-pixel radial resolution, the process 2300 can include determining if the detected circle corresponds to a droplet or an air bubble (2318). As described previously, with respect to FIGS. 27A-27C, air bubbles can be distinguished from droplets based on a darkness of the pixels corresponding to the edges of the detected circles, with air bubbles (e.g., detected circles 2210) having darker edges than droplets (e.g., detected circles 2202, 2204, 2206, 2208).

If the detected circle is an air bubble, the process 2300 can include reducing the pressure of at least one fluid flow (2320). For example, the operation 2320 can include reducing the pressure (and therefore the flow rate) of the fluid flow corresponding to a channel for transporting the unpolymerized mixture (e.g., the channel 1241 shown in FIGS. 26B and 26C). In some implementations, the fluid flow can be stopped entirely and/or the droplet-generating device can be powered off. As described previously, this can prevent the continued formation of air bubbles and/or the streaming of air into an outlet channel of the device (e.g., the outlet channel 2139). The operation 2320 can also prevent the loss or waste of the unpolymerized mixture (e.g., a sample) in operating conditions where droplets are not being properly generated. The operations 2300 and 2320 can further provide the advantage of automatically detecting when a sample has been depleted (resulting in air bubble formation), which can eliminate the need for the droplet-generating device to store and keep track of the remaining available sample volume.

If the detected circle is a droplet, the process 2300 can include determining if the standard deviation (or any other measure of spread) of the estimated droplet size(s) in the image is below a threshold value (2322). In some implementations, a large standard deviation of the estimated droplet size(s) in the image can be indicative of a fault condition since consecutively generated droplets should not typically vary substantially in size. Consequently, if the standard deviation is above the threshold value, the process 2300 can include generating a signal that causes an adjustment to a pressure (and flow rate) of at least one fluid flow according to a fault recovery routine (2324). The fault recovery routine can be substantially similar to the example fault recovery routines previously described above.

In some implementations, if the estimated sizes of droplets identified in a single image vary more than a threshold amount, the largest estimated size can be treated as the most indicative of the actual droplet sizes. For example, the smaller estimated sizes can be discarded, or a weighted average of all the estimated sizes can be taken, wherein less weight is placed on the smaller estimated sizes than the larger estimated sizes. This can prevent the false positive detection of small droplets, which can be more frequent than the false detection of larger droplets due to noise and/or other factors.

If the standard deviation (or other measure of spread) of the estimated droplet size(s) in the image is below the threshold value, the process 2300 can include comparing the estimated droplet size(s) to a target size (2326). For example, the target size of the droplet can be between 220 microns and 300 microns. In some implementations, the target size can be manually adjusted by a user of the device.

The comparison of the estimated droplet size(s) to a target size can be used to calculate an error signal.

Operations of the process 2300 can also include generating a signal that causes an adjustment to a pressure (and flow rate) of at least one fluid flow using feedback control (2328). For example, as described above, the pressure can be adjusted using a controller of the device (e.g., controller 2124 of device 2100) to control one or more pumps (e.g., pumps 2126) to control the pressure of a fluid flow within the device 2100. The fluid flow can correspond to the flow of the unpolymerized mixture through the device (e.g., the channel 2141). The feedback control can be implemented using an error signal calculated based on comparing the estimated droplet size(s) to a target size at operation 2326. In some cases, the error signal or the estimated droplet size(s) can be averaged over multiple previous images (e.g., 3 images, 5 images, 10 images, 20 images, etc.) to reduce noise. The feedback control can include proportional control, integral control, derivative control, or any combination of the above. We use the term "proportional control" broadly to include control system technology based on a response that is in proportion to an error signal. The error signal can be a difference between a desired process value (or set point) and a current value of a controlled process variable (e.g., a size of a detected droplet). We use the term "integral control" broadly to include control system technology based on a response that is proportional to an integral (e.g., a time integral) of the error signal. We use the term "derivative control" broadly to include control system technology based on a response that is proportional to a derivative (e.g., a derivative with respect to time) of the error signal.

Once feedback control is initiated, it can continue until either an air bubble is detected or a fault condition is identified (e.g., no circles are detected in a captured image or a standard deviation of estimated droplet size(s) in an image exceeds a threshold value). To enable this continuous control, the process 2300 can be repeated for multiple images captured by a camera (e.g., optical sensor 2132) of a microfluidic device. For example, in some implementations, the multiple images can be frames from a single captured video.

Figure 29:
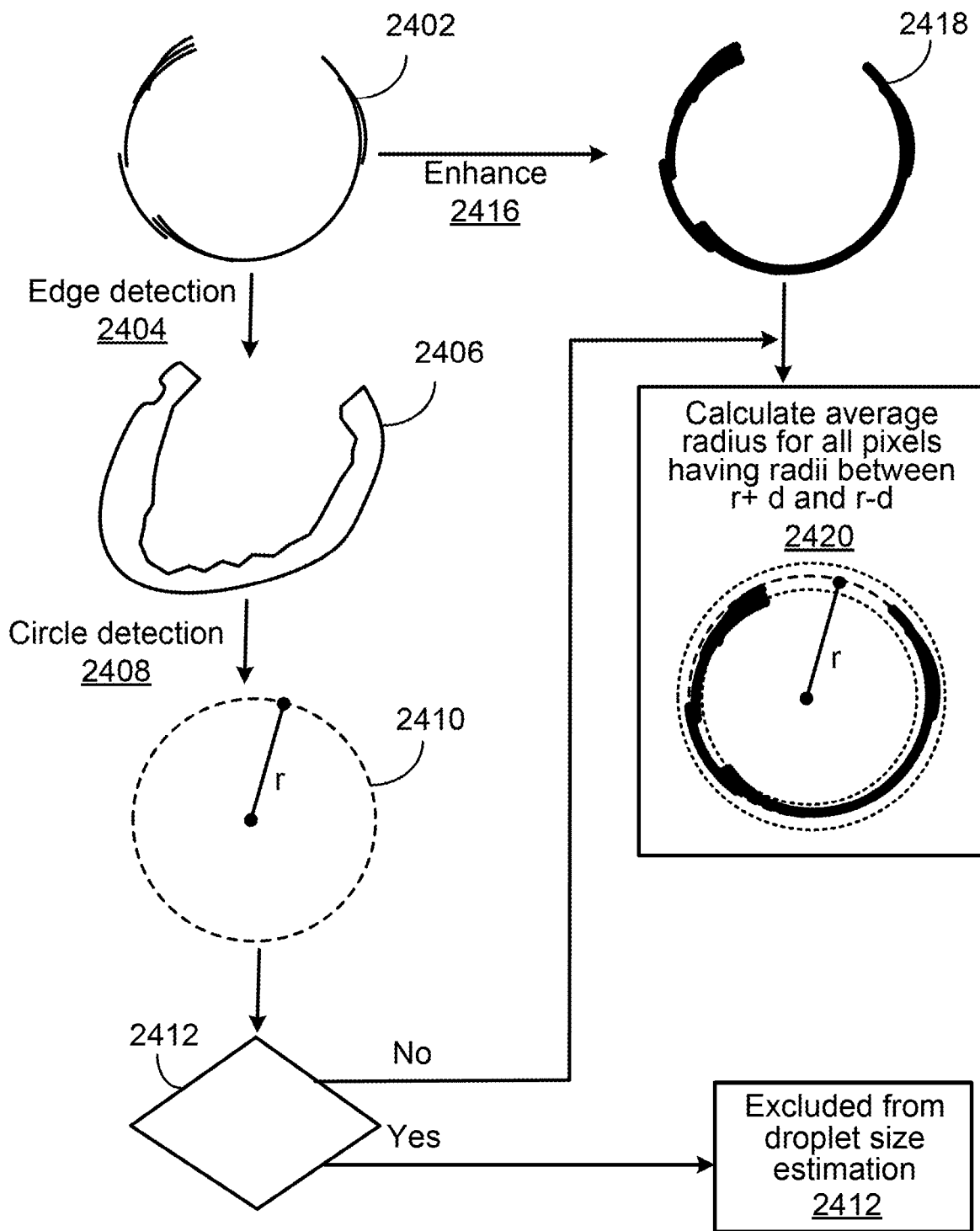
FIG. 29 illustrates a process for estimating the size of a droplet.

FIG. 29 illustrates, in greater detail, a process for estimating the size of a droplet, corresponding to the operations 2302, 2304, 2306, 2310, 2312, 2314, 2316 of the process 2300 shown in FIG. 28. All of these operations can be executed by an image processing module (e.g., an image processing module of a microfluidic device) and can be implemented on a controller (e.g., controller 2124).

Imaged object 2402 represents an illustration of a zoomed-in original image (e.g., captured at operation 2302 of the process 2300), focusing on a single droplet. At operation 2404, edge detection (corresponding to operation 2304 of the process 2300) can be implemented to generate detected edges 2406 corresponding to the imaged object 2402. The imaged object 2402 can also be enhanced (at operation 2416) to yield an enhanced object 2418. For example, the imaged object 2402 can be enhanced using conventional feature enhancement or edge sharpening techniques such as edge sharpening filters or a "difference of Gaussians" process to increase the visibility of the imaged object's edges. In one example, the "difference of Gaussians" process can include computing a difference between two Gaussian-blurred versions of the imaged object (e.g., with a first version blurred using a Gaussian function having a standard deviation of 2 pixels and a second version blurred using a Gaussian function have a standard deviation of 1 pixel, although other parameter values are possible and may be preferred depending on the hardware and lighting conditions used to acquire the image). In this particular example, the resulting image can retain visual (e.g., spatial) information with frequencies ranging from between about 1 pixel and 3 pixels (such as the imaged object's edges), while blurring or removing other features.

The detected edges 2406 can be used as input to a circle detection process (at operation 2408) to yield a detected circle 2410 having a radius r. The operation 2408 corresponds directly to the operation 2306 of the process 2300, and can similarly be implemented using a Hough transform. In some implementations, the detected circle 2410 can have a radial resolution greater than or equal to 1 pixel.

As described above in relation to FIG. 28, in some implementations, the original image including the imaged object 2402 can be downsized (e.g., via down-sampling) prior to edge detection (operation 2404) or prior to circle detection (operation 2408). For example, the one or more images can be down-sampled (e.g., digitally down-sampled) to ¼-½ of the original resolution (e.g., 25% of the original resolution, 30% of the original resolution, 40% of the original resolution, 50% of the original resolution, etc.). This down-sampling can have the advantage of increasing the speed of edge detection and/or circle detection. In implementations where down-sampling is performed, the resulting image data can be magnified subsequent to edge detection (operation 2404) and/or subsequent to circle detection (operation 2408). For example, the image can be magnified by a factor ranging from 2 to 4. In some cases, the magnification factor can be selected to restore a down-sampled image to its original size.

At decision point 2412 (corresponding to operation 2310 of the process 2300), the image processing module can determine whether one or more filter conditions are satisfied. As described previously in relation to operation 2312 of FIG. 28, if the filter conditions are satisfied, the detected circle 2410 can be excluded from droplet size estimation (2414). However, if the filter conditions are not satisfied, the detected circle 2410 can be jointly processed with the enhanced object 2418 to calculate a representative radius based on all pixels in the enhanced object 2418 having radii between r+d and r−d (2420), where d represents a threshold distance from a perimeter of the detected circle 2410. In some implementations, the representative radius calculation can be based on only a portion of these pixels. The operation 2420 corresponds to the operations 2314, 2316 of the process 2300, and has similar advantages of yielding sub-pixel radial resolution as previously described. The representative radius calculated at operation 2420 can be an average of distances, a weighted average of distances, or another metric derived from and representative of a distance from the center of the detected circle to at least a portion of the identified pixels. For example, the representative radius can be calculated using the following formula:

$$\text{Representative Radius} = \frac{\sum_{i=1}^{n} w_i r_i}{\sum w_i}$$

where $w_i$ is a weight value reflective of an intensity value of pixel i, $r_i$ is reflective of a distance from the center of the detected circle to pixel i, and where n represents the total number of pixels included in the calculation. Although various alternative metrics can be used, the representative radius calculation described by the formula above can have the advantage of placing higher weight on the radii corresponding to pixels having greater intensity. The computed representative radius from operation 2420 can then be used to update the radius of the detected circle 2410 for further processing (e.g., as described in relation to the process 2300).

Figure 30:
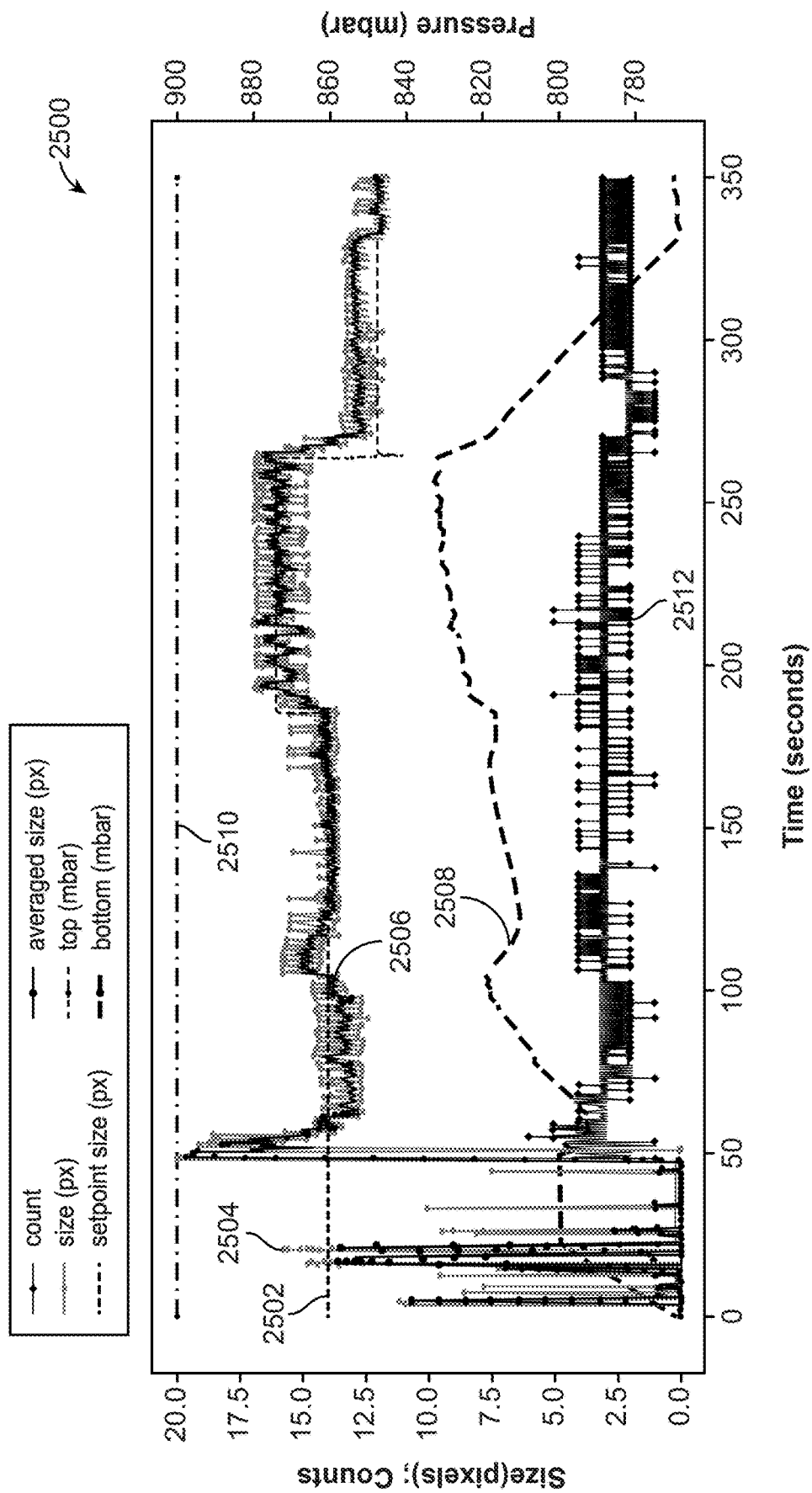
FIGS. 30-31 are graphs showing experimental data.
Figure 31:
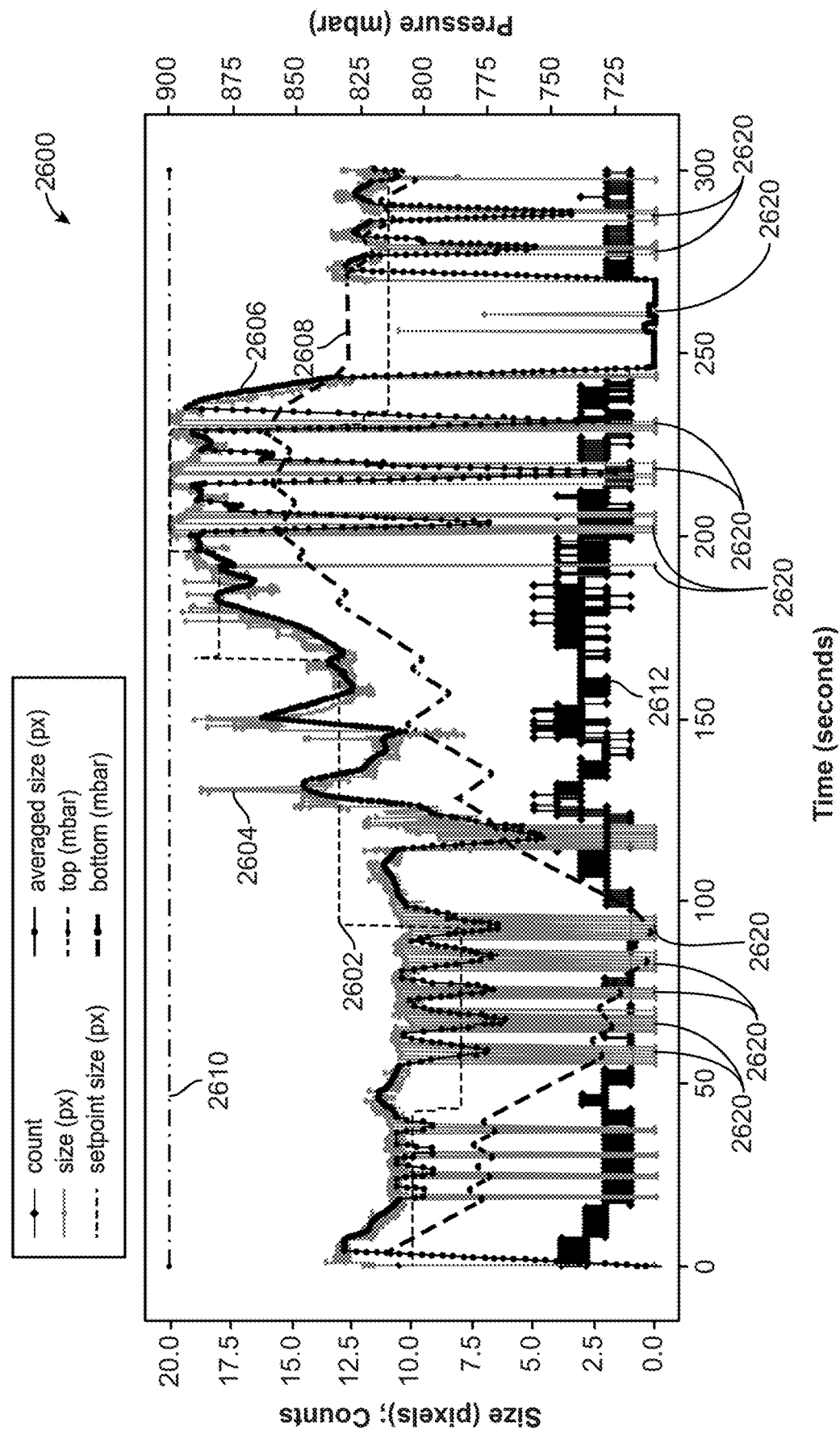

Referring now to FIGS. 30 and 31, experimental data is presented demonstrating capabilities and advantages of the technologies described herein.

FIG. 30 shows a graph 2500 from an experiment, in which a user manually set a target size or "set point size" of the droplets generated by a microfluidic device, increased the target size at around 180 seconds, and decreased the target size at around 260 seconds. It is noted, however, that in some implementations, the set point can be set (and changed) automatically by a computer system, for example, based on one or more characteristics of the sample, one or more characteristics of the droplet-generating device, etc. The set point size (corresponding to a target radius of droplets) is shown by the trace 2502 and is represented in pixels. The trace 2504 corresponds to the estimated droplet sizes for each captured image (e.g., each frame of a video captured by a camera of the microfluidic device) and is also represented in pixels. The trace 2506 is a running average of the trace 2504 to reduce noise effects, and is also represented in pixels. The trace 2508 shows a pressure applied to a holding chamber for the unpolymerized mixture in order to control its flow rate. The pressure is controlled directly by a controller of the microfluidic device and is measured in millibars. The trace 2510 shows a pressure applied to a holding chamber for the immiscible fluid (held constant in this experiment) and is measured in millibars. The trace 2512 shows a count of circles detected in each captured image.

For the first 50 seconds, stable droplet generation had not yet begun, which is apparent from the many image frames where the count (trace 2512) and size (trace 2504) are at zero. Just as described above, in response to failing to detect droplets in the first 50 seconds, the applied pressure for the unpolymerized mixture flow was gradually increased to a maximum pressure of 800 millibars and held constant until stable droplet generation began. Once stable droplet generation began (at about 50 seconds), feedback control of the pressure for the unpolymerized mixture flow (trace 2508) successfully enabled the estimated size traces (trace 2504 and trace 2506) to track the setpoint size (trace 2502). Graph 2500 therefore demonstrates the successful control of pressure to control a fluid flow rate within a microfluidic device to control the size of generated droplets.

FIG. 31 shows a graph 2600 from a second experiment, in which a user manually set and altered, over time, a target size or "set point size" of the droplets generated by a microfluidic device. The traces in the graph 2600 are analogous to the traces in the graph 2500. The set point size (corresponding to a target radius of droplets) is shown by the trace 2602 and is represented in pixels. The trace 2604 corresponds to the estimated droplet sizes for each captured image (e.g., each frame of a video captured by a camera of the microfluidic device) and is also represented in pixels. The trace 2606 is a running average of the trace 2604 to reduce noise effects, and is also represented in pixels. The trace 2608 shows a pressure applied to a holding chamber for the unpolymerized mixture in order to control its flow rate. The pressure is controlled directly by a controller of the microfluidic device and is measured in millibars. The trace 2610 shows a pressure applied to a holding chamber for the immiscible fluid (held constant in this experiment) and is measured in millibars. The trace 2612 shows a count of circles detected in each captured image.

Similar to the graph 2500, the general trend of the estimated sizes (trace 2606) tracks the fluctuations in set point size (trace 2602). However, in several instances, fault conditions 2620 occurred, where no droplets were detected, and the count trace (trace 2612) and estimated size trace (trace 2604) accordingly dropped to zero. While this behavior is not ideal, the experimental data shown in graph 2600 demonstrates the ability of the technology described herein to recover from these fault conditions 2620. Just as described above in relation to FIG. 28, when each fault condition 2620 was identified, a controller of the microfluidic device replaced the use of feedback control of the pressure with a fault recovery routine involving a naïve pressure controller that gradually increased, decreased, or maintained the pressure applied to generate the unpolymerized mixture flow (trace 2608) until stable droplet generation resumed. In each instance of the fault conditions 2620, droplet generation was able to be successfully resume without further user intervention.

While the experiments shown in relation to FIGS. 30 and 31 demonstrate active control of the pressure applied to only a single fluid flow (i.e., the flow of the unpolymerized mixture), this disclosure is not intended to be limiting. As described previously, the size of droplets can be dependent on the pressure (and therefore the flow rate) of both the unpolymerized mixture flow and the immiscible fluid flow. Consequently, in some implementations, the pressure (and flow rate) of the immiscible fluid flow can also be controlled, in addition or alternatively to controlling the pressure (and flow rate) of the unpolymerized mixture flow. For example, in some implementations, simultaneously controlling the pressure of both fluid flows in a microfluidic device can enable additional control of the droplet generation process, including controlling the speed of generation as well as the size of the generated droplets.

Figure 32:
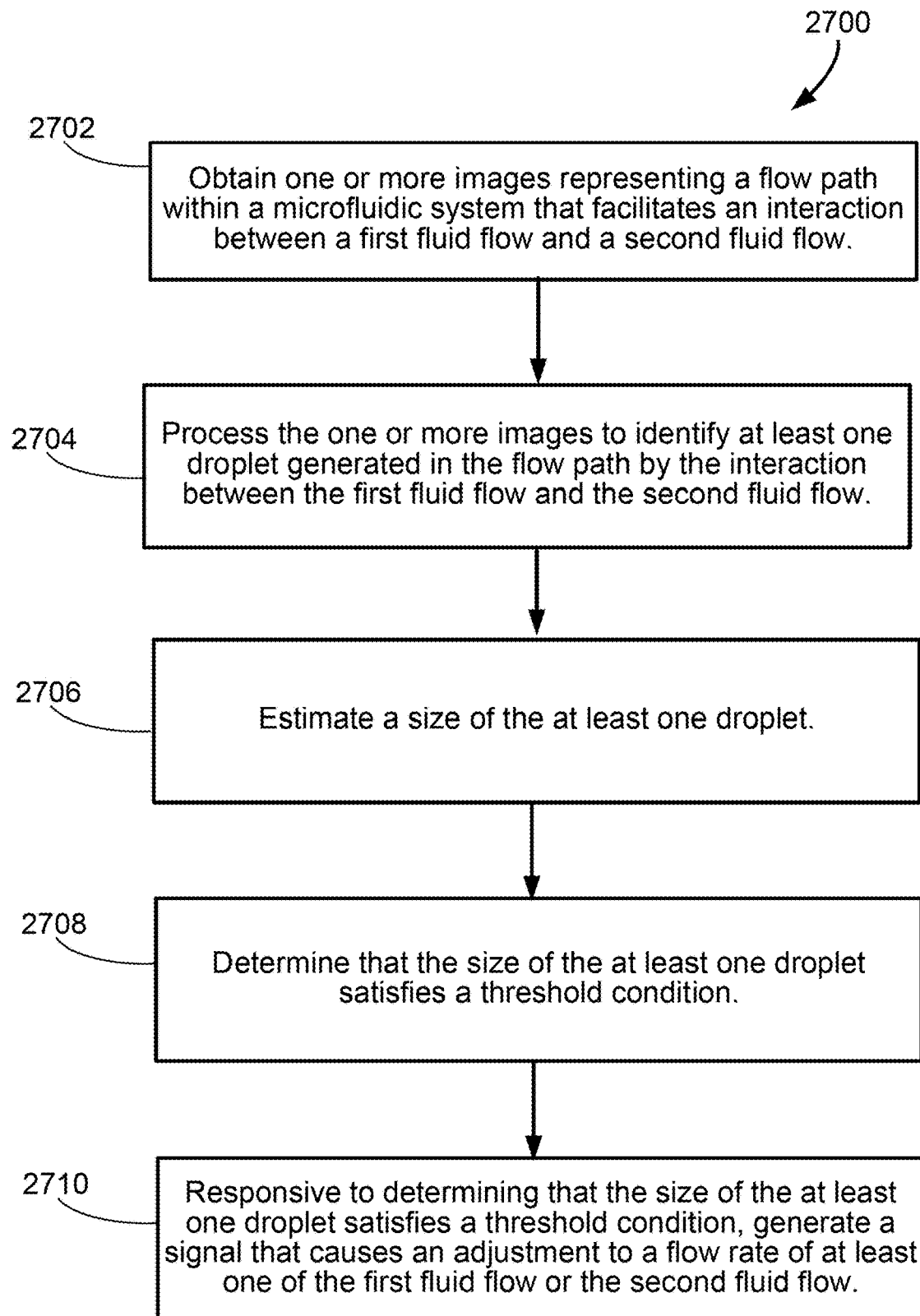
FIG. 32 is a flowchart of a process for controlling the size of droplets generated by a device.

FIG. 32 illustrates an example process 2700 for controlling the size of droplets generated by a device (e.g., a microfluidic device such as the device 2100). Operations of the process 2700 can be executed by a microfluidic system such as the device 2100 or a portion thereof (e.g., controller 2124). In some implementations, one or more operations of the process 2700 can be executed by one or more remote computing systems external to the device 2100.

Operations of the process 2700 can include obtaining one or more images representing a flow path within a microfluidic system that facilitates an interaction between a first fluid flow and a second fluid flow (2702). Obtaining the one or more images can include capturing the images with an optical sensor (e.g., the optical sensor 2132), which in some cases, can be a camera. The one or more images can include an image of at least one droplet generated in the flow path in an area of a device where the at least one droplet is not compressed by one or more walls of the device. For example, the at least one droplet can be imaged in a widened region of an outlet channel of the device (e.g., the outlet channel 2139).

Operations of the process 2700 also include processing the one or more images to identify at least one droplet generated in the flow path by the interaction between the first fluid flow and the second fluid flow (2704). The first fluid flow can include a flow of a hydrophilic solution (e.g., an unpolymerized mixture including a fluid matrix material and cells) and the second fluid flow can include a flow of a hydrophobic solution (e.g., an immiscible fluid such as oil). Processing the one or more images can include detecting edges of the at least one droplet in at least one of the one or more images (e.g., using a Canny edge detector) and identifying a first set of pixels corresponding to the detected edges of the at least one droplet. For example, the first set of pixels can be a circle representation generated based on the detected edges of the at least one droplet (e.g., using a Hough transform). Processing the one or more images to identify the at least one droplet can also include downsizing the one or more images prior to detecting edges of the at least one droplet and/or prior to identifying the first set of pixels corresponding to the detected edges of the at least one droplet. For example, as described above, the one or more images can be down-sampled (e.g., digitally down-sampled) to ¼-½ of the original resolution (e.g., 25% of the original resolution, 30% of the original resolution, 40% of the original resolution, 50% of the original resolution, etc.). In implementations where down-sampling is performed, processing the one or more images to identify the at least one droplet can further include magnifying the one or more down-sampled images subsequent to detecting edges of the at least one droplet and/or subsequent to identifying the first set of pixels corresponding to the detected edges of the at least one droplet. For example, the image can be magnified by a factor ranging from 2 to 4. In some cases, the magnification factor can be selected to restore a down-sampled image to its original size. Processing the one or more images can also include identifying a second set of pixels that are disposed within a threshold distance from the first set of pixels and computing an average distance of at least a portion of the second set of pixels from a predetermined location within the at least one droplet. In some examples, the predetermined location within the at least one droplet can be a center of the at least one droplet (or a center of a circular representation of the at least one droplet). In some implementations, identifying the second set of pixels can be performed subsequent to any down-sizing and re-magnification of the one or more images being processed. Processing the one or more images can further include excluding data corresponding to the detected edges of the at least one droplet if one or more filtering conditions is satisfied. The filtering conditions can include an indication that the first set of pixels corresponds to the detected edges of a plurality of droplets; an indication that the first set of pixels overlaps with at least one additional set of pixels (e.g., pixels corresponding to another circular representation of a another droplet); a detected signal that satisfies a threshold signal level condition, the detected signal originating from within a perimeter of the first set of pixels; and/or a determination that the first set of pixels is less than a threshold proximity from an imaged wall of a device.

Operations of the process 2700 also include estimating a size of the at least one droplet (2706) and determining that the size of the at least one droplet satisfies a threshold condition (2708). Estimating the size of the at least one droplet can include estimating the size based on the averaged distance of at least a portion of a set of pixels (e.g., the second set of pixels described above) from a predetermined location within the at least one droplet. In some implementations, estimating the size of the at least one droplet can include estimating the size with sub-pixel radial resolution. Determining that the size of the at least one droplet satisfies the threshold condition can include comparing the size of the at least one droplet to a target size obtained via a user-input (e.g., to generate an error signal).

Operation of the process 2700 also include, responsive to determining that the size of the at least one droplet satisfies the threshold condition, generating a signal that causes an adjustment to a pressure of at least one of the first fluid flow or the second fluid flow (2710). The signal can be configured to increase or decrease the pressure of at least one of the first fluid flow or the second fluid flow based on the size of the at least one droplet. In some implementations, generating the signal can include using a feedback controller to generate the signal using proportional control, integral control, and/or derivative control. In some implementations, generating the signal can include generating the signal without feedback control (e.g., using a naïve static controller) when no droplets are identified in the one or more images and/or when a standard deviation of the size of the at least one droplet (e.g., two or more droplets) exceeds a threshold value. In some implementations, generating the signal can be based on the estimated sizes of multiple droplets from the same captured image or from different images (e.g., consecutive frames in a video).

Additional operations of the process 2700 can include the following. In some implementations, the process 2700 can include processing the one or more images to identify air bubbles in the flow path. In some implementations, the process 2700 can include storing, on a storage device, the one or more images and/or data representing the estimated size of the at least one droplet. In some implementations, the process 2700 can include transmitting, to a remote computing device, the one or more images and/or data representing the size of the at least one droplet.

Liquid Level Sensing Using Optical Reflection

Measuring and monitoring liquid levels in containers (e.g., tubes) accurately and precisely is important in many applications including chemical or biological analysis and medical diagnosis, e.g., in the context of the MOS generation systems and methods described above. For instance, the liquid level sensing approaches described here can be used in combination with one or more aspects of the MOS generation systems and methods described above, including in combination with the approaches to closed loop control and/or droplet size determination described here. In some examples, liquid levels are sensed in these MOS generation systems and methods using optical reflection such as total internal reflection (TIR). Optical reflection approaches for liquid level sensing have advantages over other liquid level sensing approaches, such as capacitive approaches, ultrasonic approaches, or pressure based approaches, in that optical-based approaches are effective, inexpensive, and accurate.

The approaches described here for liquid level sensing use optical total internal reflection (TIR). The liquid level sensing is based on integrating an optical interface in a container (e.g., a tube), and the optical interface is between a medium (air or liquid) in the container and an internal surface that light is incident on. When a liquid level in the container is lower than the optical interface, TIR occurs and light incident on the optical interface is totally reflected back by the optical interface; when the liquid level is higher than or equal to the optical interface, there is no TIR and light incident on the optical interface is substantially (or totally) transmitted through the liquid and/or the container. The liquid level can be determined based on a result of measuring the reflected light and/or the transmitted light.

In some embodiments, a liquid level sensor includes a container having at least one internal surface (e.g., for an optical interface) and a pair of light source (e.g., a light emitted diode (LED) or a laser diode) and light detector (e.g., a photodetector, a photodiode, or a phototransistor). The pair of light source and light detector can be closely spaced and packaged as an electro-optical package. The light source and the light detector can be arranged on a same side of the container and can be positioned adjacent to (e.g., about a certain distance away such as 0 mm, 1 mm, 2 mm, 3 mm, 4 mm, 5 mm, or any suitable distance) the container for measurement. Light from the light source is incident on the at least one internal surface through an external surface of the container, and reflected by the at least one internal surface and detected by the light detector.

In some embodiments, the pair of light source and light detector can be moved along a longitudinal direction of the container to measure a liquid level in the container. In some embodiments, multiple pairs of light sources and light detectors can be arranged at a series of positions along the longitudinal direction of the container, and the liquid level in the container can be determined based on multiple measurements of the multiple pairs of light sources and light detectors.

The container in which liquid levels are sensed is a structure defining a space for holding a fluidic medium to be measured. The container can be a reservoir, a vessel, a tube, a canister, a tank, a bottle, or any suitable structure.

In some embodiments, the container includes a protrusion extending along a longitudinal direction of the container. In some embodiments, the protrusion and the container can be separately formed and then the protrusion is attached to the container (e.g., through an index matching material). In some embodiments, the container and the protrusion can be integrably formed, e.g., by molding or 3D printing such as Stereolithography (SLA) printing. The container and/or the protrusion can be optically transparent or at least partially transparent. A material of the container can be glass, plastic or polymer, e.g., a polypropylene, polyethylene, polystyrene, polycarbonate, polymethyl methacrylate (PMMA), Acrylonitrile butadiene styrene (ABS), high-clarity photopolymer Somos Watershed or Waterclear resins, or any substantially transparent resin with a high polish on the surface which can transmit light with minimal diffusion. The container can be custom finished with highly polished surfaces.

The protrusion can include the at least one internal surface. For example, the protrusion can be a 90° V-shape raised rib on a body of the container. The body defines a space for holding liquid. The protrusion can include first and second sides defining an angle of 90 degrees and a third side being part of the body of the container. The protrusion can be configured for retro-reflection of light.

In some embodiments, light can enter along a horizontal direction into the container to be incident on a first internal surface of the first side with an incident angle (e.g., 45°), sequentially be reflected by the first internal surface towards a second internal surface of the second side in the protrusion (e.g., with an incident angle of 45°), and then be reflected by the second internal surface back toward the light detector along the horizontal direction. When a liquid level is below an incident position of the light on the first and second internal surfaces of the protrusion, an incident angle is greater than a critical angle (defined by a refractive index of a material of the protrusion and a refractive index of air) on each of the first and second internal surfaces, and total internal reflection occurs on an interface between air and the protrusion; when the liquid level is higher than or identical to the incident position of the light on the first internal surface, e.g., light is submerged in the liquid, an incident angle is smaller than or identical to a critical angle (defined by the refractive index of the material of the protrusion and a refractive index of the liquid), and total internal reflection is eliminated as the liquid has a closer refractive index (e.g., 1.3) than air (e.g., 1.0) with respect to a material of the protrusion (e.g., 1.5). The light then exits into the liquid and transmits through the container, and the light detector receives much less or zero reflected light. In some cases, if the refractive index of the liquid is close to that of the material of the protrusion (e.g., plastic), the critical angle can be a large angle, and total internal reflection occur only if the light is hitting the protrusion at a very small grazing angle.

These techniques for liquid level sensing can address existing challenges for liquid level sensing. For example, the techniques for liquid level sensing can improve an accuracy of liquid level measurement, which makes it possible to reduce biological or chemical-process variability, resulting in higher product quality, reduced cost, and less waste. These techniques can provide liquid level sensors or systems that can be cost-effective, compact, and easy fabricated. These techniques can provide precise and reliable liquid level measurement sensors and systems, which can satisfy the demands of sophisticated automated processing systems, the need for ever-tighter process control, and an increasingly stringent regulatory environment. The techniques can also provide non-contact liquid level sensing through a wall of a sealed container, such that neither the liquid level sensor nor the liquid is contaminated. The techniques described herein can be applicable for any fluid-related process requiring precise amounts of liquid in containers. The techniques described herein can be used in many applications, e.g., chemical/biological analysis and medical diagnosis. Besides liquid, the techniques can be applied to any other types of fluidic medium, e.g., any medium with a higher refractive index than air. The liquid can include one or more different types of fluidic media.

FIGS. 33A to 33C illustrate an example of a container 3100 for liquid level sensing, where FIG. 33A is a schematic diagram of the container 3100, FIG. 33B is a side view A-A' of the container 3100, and FIG. 33C is a cross-section view B-B' of the container 3100. The container 3100 includes a protrusion including at least one internal surface as an optical interface for total internal reflection that can be used for liquid level sensing. For instance, the container can be a container for a sample or an output used in the context of the MOS generation system described above. For instance, when liquid levels are sensed in both sample and output containers, an initial volume and/or an ending volume of liquid in the input container can be determined and a volume of sample or waste in an output container can be determined. In some cases, a difference between a volume of the liquid in the input container and a volume of the sample or waste in the output container can be obtained for further analysis.

As shown in FIGS. 33A to 33C, the container 3100 includes a body 3110 extending from a bottom 3102 to a top 3104 along a longitudinal direction 3101. The body 3110 defines a space for holding liquid, e.g., water, solution, oil, or any suitable fluidic medium. The bottom 3102 of the container 3100 can have a flat surface, a cone shape, or any suitable shape. The top 3104 can include a cover having a recess or groove for sealing.

The container 3100 can be configured to have a holding volume of liquid, e.g., 1 milliliter (mL), 2 mL, 5 mL, 10 mL, 20 mL, 50 mL, 100 mL, 200 mL, 500 mL, 1 liter (L), 2 L, 5 L, 10 L, 100 L, or any suitable volume. Different liquid levels in the container 3100 can correspond to different volumes of liquid held in the container 3100. In some embodiments, the container 3100 includes a series of volume level labels corresponding to a series of positions on the body 3110 along the longitudinal direction, each volume level label corresponding to a respective volume.

In some embodiments, as illustrated in FIGS. 33A to 33C, the container 3100 has a cylindrical shape with a circular cross section. A container can also have any other suitable shape, e.g., a cuboid shape with a rectangular cross section. In some embodiments, the container 3100 can have an equal size (e.g., a diameter) along the longitudinal direction, or variable sizes changing from small to large or from large to small along the longitudinal direction. For illustration purposes only, a container having a cylindrical shape with a circular cross section is used as an example in the descriptions herein.

In some embodiments, as illustrated in FIGS. 33A to 33C, the container 3100 includes a protrusion 3120 that can inwardly protrude from the body 3110 of the container 3100. The protrusion 3120 can extend along the longitudinal direction 3101 of the container 3100, e.g., from the bottom 3102 to the top 3104, as illustrated in FIG. 33B. The protrusion 3120 can include a first side 3122, a second side 3124, and a third side 3126. FIG. 33C shows a cross-section view B-B', where a cross section of the protrusion 3120 includes a first internal surface 3132 on the first side 3122, a second internal surface 3134 on the second side 3124, and a third surface 3136 on the third side 3126. As discussed with further details below, the protrusion 3120 is configured such that light entering from an external surface 3112 (e.g., a surface open to an external environment) of the body 3110 can be totally internally reflected by a first internal surface 3132 of the first side towards a second internal surface 3134 of the second side and then be totally internally reflected by the second internal surface 3134 back out of the container 3100.

In some embodiments, the protrusion 3120 is a V-shaped rib, as illustrated in FIGS. 33B and 33C. The first side 3122 and the second side 3124 can be connected together at an edge 3123, and the first internal surface 3132 and the second internal surface 3134 can be connected at a corner 3133. The edge 3123 can be a straight line along the longitudinal direction 3101, and the corner 3133 can be a point. In some embodiments, the edge 3123 can be any other suitable shape, e.g., an arc or curved shape, and accordingly the corner 3133 can have an arc or curved shape. In some embodiments, the first internal surface 3132 and/or the second internal surface 3134 are straight lines, as illustrated in FIG. 33C. An angle defined by the first internal surface 3132 and the second internal surface can be substantially identical to 90 degrees. In some embodiments, the first internal surface 3132 and/or the second internal surface 3134 can at least partially have an arc or curved shape.

The body 3110 and the protrusion 3120 can be optically transparent or at least partially transparent, such that light can propagate in the body 3110 and the protrusion 3120. In some embodiments, the body 3110 of the container 3100 can be made of a first material, e.g., glass, plastic, or polymer. The protrusion 3120 can be made of a second material, e.g., glass, plastic, or polymer. In some embodiments, the second material is same as the first material. The third side 3126 of the protrusion 3120 can be part of the body 3110 and integrated with a remaining part of the body 3110. In some embodiments, the second material is different from the first material. The third side 3126 of the protrusion 3120 can be attached or adhered to an internal surface of the body 3110.

Figures 34A, 34B:
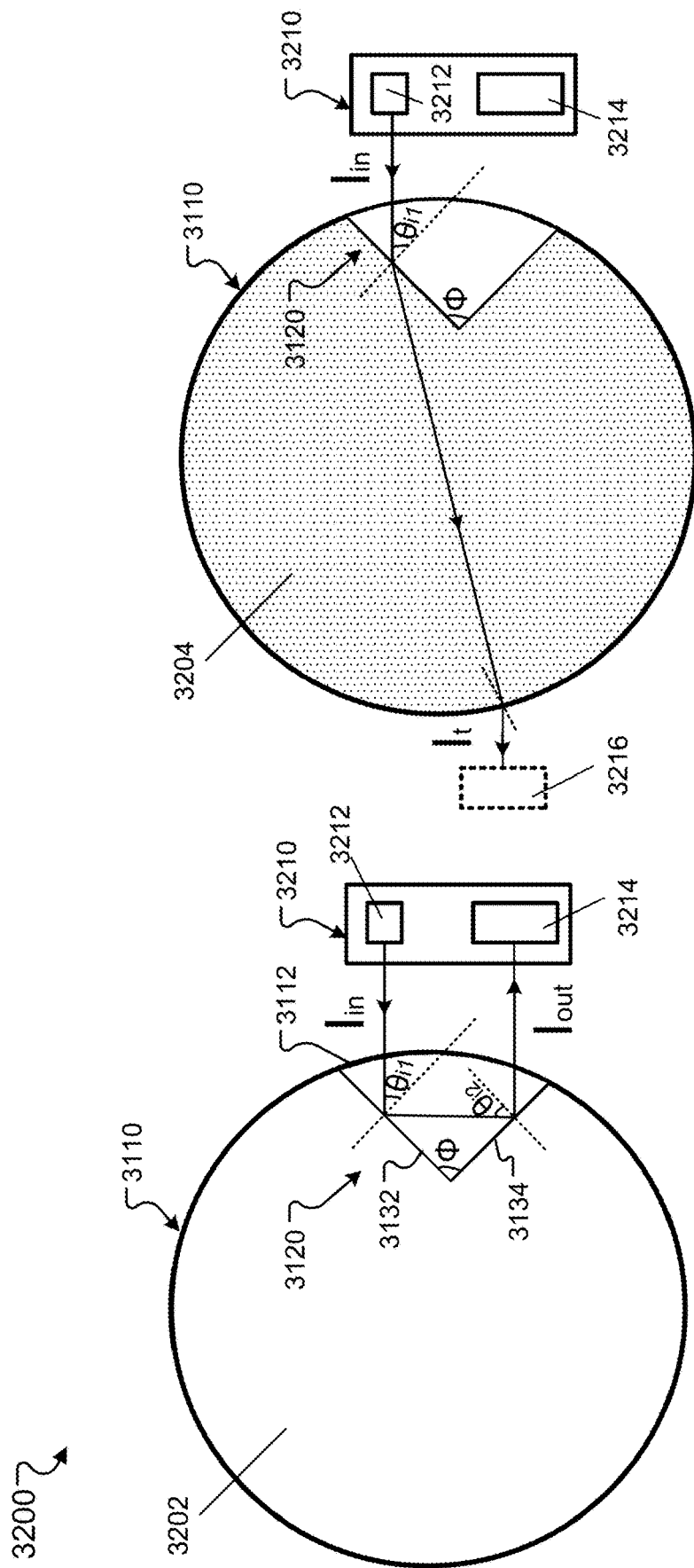
FIGS. 34A-34B illustrate an example of a liquid level sensor measuring a liquid level in the container of FIGS. 33A-33C, when the liquid level is below a light incident position (FIG. 34A) or higher than a light incident position (FIG. 34B).

FIGS. 34A-34B illustrate an example of a liquid level sensor 3200 measuring a liquid level in the container 3100 of FIGS. 33A-33C, when the liquid level is below a light incident position (FIG. 34A) or higher than a light incident position (FIG. 34B), respectively, according to one or more embodiments of the present disclosure. The liquid level sensor 3200 includes a container 3100 having a protrusion 3120 and a sensing pair 3210 of a light source 3212 and a light detector 3214.

The protrusion 3120 can be a V-shape rib having an angle 1 defined by the first internal surface 3132 and the second internal surface 3134. Light emitted from the light source 3212 can enter through an external surface 3112 of the body 3110 to be incident at the first internal surface 3132 with an incident angle $\theta_{i1}$ at an incident position.

According to Snell's law, a critical angle for total internal reflection (TIR) is $\sin^{-1}(n_i/n_o)$, where $n_i$ is a refractive index of the protrusion 3120, and $n_o$ is a refractive index of a medium interacting with the first internal surface 3132 in the container 3100. When the liquid level is below the incident position, as illustrated in FIG. 34A, the medium interacting with the first internal surface 3132 is gas 3202, e.g., air having a refractive index $n_o$ identical to 1. When the liquid level is higher or identical to the incident position, as illustrated in FIG. 34B, the medium interacting with the first internal surface 3132 is liquid 3204, e.g., a water solution having a refractive index $n_o$ that can be identical to 1.3. A material of the protrusion 3120 has a refractive index $n_i$ that can be larger than 1.3 and smaller than 2.0.

For illustration purposes only, a refractive index $n_i$ of the material of the protrusion 3120 is set to be identical to 1.5. Thus, when the liquid level is below the incident position, $n_o=1$, and the TIR critical angle is 41.8°; when the liquid level is higher than or identical to the incident position, $n_o=1$, and the TIR critical angle is 60.1°. Thus, by configuring the protrusion 3120 (e.g., an angle between of the first internal surface and the external surface) and/or an incident position of the light from the light source 3212, the incident angle $\theta_{i1}$ can be configured to be larger than 41.8° and smaller than 60.1°, e.g., 45°. In such a way, TIR can occur when the liquid level is below the incident position and there is no TIR when the liquid level is higher than or identical to the incident position.

As illustrated in FIG. 34A, when the liquid level is below the incident position, the medium is gas and TIR occurs at the first internal surface 3132, and the light is reflected in the protrusion 3120 to be incident at the second internal surface 3134 with an incident angle $\theta_{i2}$. Similarly, when the incident angle $\theta_{i2}$ can be configured to be larger than 41.8° and smaller than 60.1°, e.g., 45°. In such a way, TIR can occur when the liquid level is below the incident position and there is no TIR when the liquid level is higher than or identical to the incident position. The angle Φ defined by the first internal surface 3132 and the second internal surface 3134 can be identical to $\theta_{i1}+\theta_{i2}$.

In some examples, Φ=90°, and $\theta_{i1}=\theta_{i2}=45°$, and TIR can occur on both the first internal surface 3132 and the second internal surface 3134. Reflected light intensity $I_{out}$ can be substantially identical to the input light intensity Imo. Moreover, the input light towards the container 3100 and the reflected light back from the container 3100 can be parallel to each other, which can be considered as retro-reflection and can be used for aligning the light detector 3214 for receiving the output light.

As illustrated in FIG. 34B, when the liquid level is higher than or identical to the incident position, the medium is liquid 3204, e.g., the first internal surface is submerged in the liquid 3204, no TIR occurs at the first internal surface and light is transmitted through the first internal surface, with a large transmittance, e.g., about 96%, into the liquid 3204, which can further propagate out of the container 3100.

The light detector 3214 configured to receive reflected light may receive substantially no reflected light. In some examples, a light detector 3216 can be positioned on a different side from the light source 3212 and configured to receive transmitted light $I_t$ from the container 3100. The light detector 3216 can be calibrated or adjusted to receive the transmitted light.

In some embodiments, the sensing pair 3210 includes the light source 3212 and the light detector 3214 on the same side of the container 3100. A power of the reflected light detected by the light detector 3214 can determine whether the liquid level is higher or lower than the incident position. For example, if the power of the detected reflected light is greater than a predetermined threshold, it indicates that TIR occurs and the level of the liquid is lower than the incident position. If the power of the detected light is smaller than or equal to the predetermined threshold, it indicates that no TIR occurs and the level of the liquid is higher than or identical to the incident position.

In some embodiments, the sensing pair 3210 includes the light source 3212 and the light detector 3216 on different sides of the container 3100. A power of transmitted light detected by the light detector 3216 can determine whether the liquid level is higher or lower than the incident position. For example, if a power of the detected transmitted light is smaller than a predetermined threshold, it indicates that TIR occurs and the level of the liquid is lower than the incident position. If the power of the detected light is greater than or equal to the predetermined threshold, it indicates that no TIR occurs and the level of the liquid is higher than or identical to the incident position.

Figures 35A, 35B:
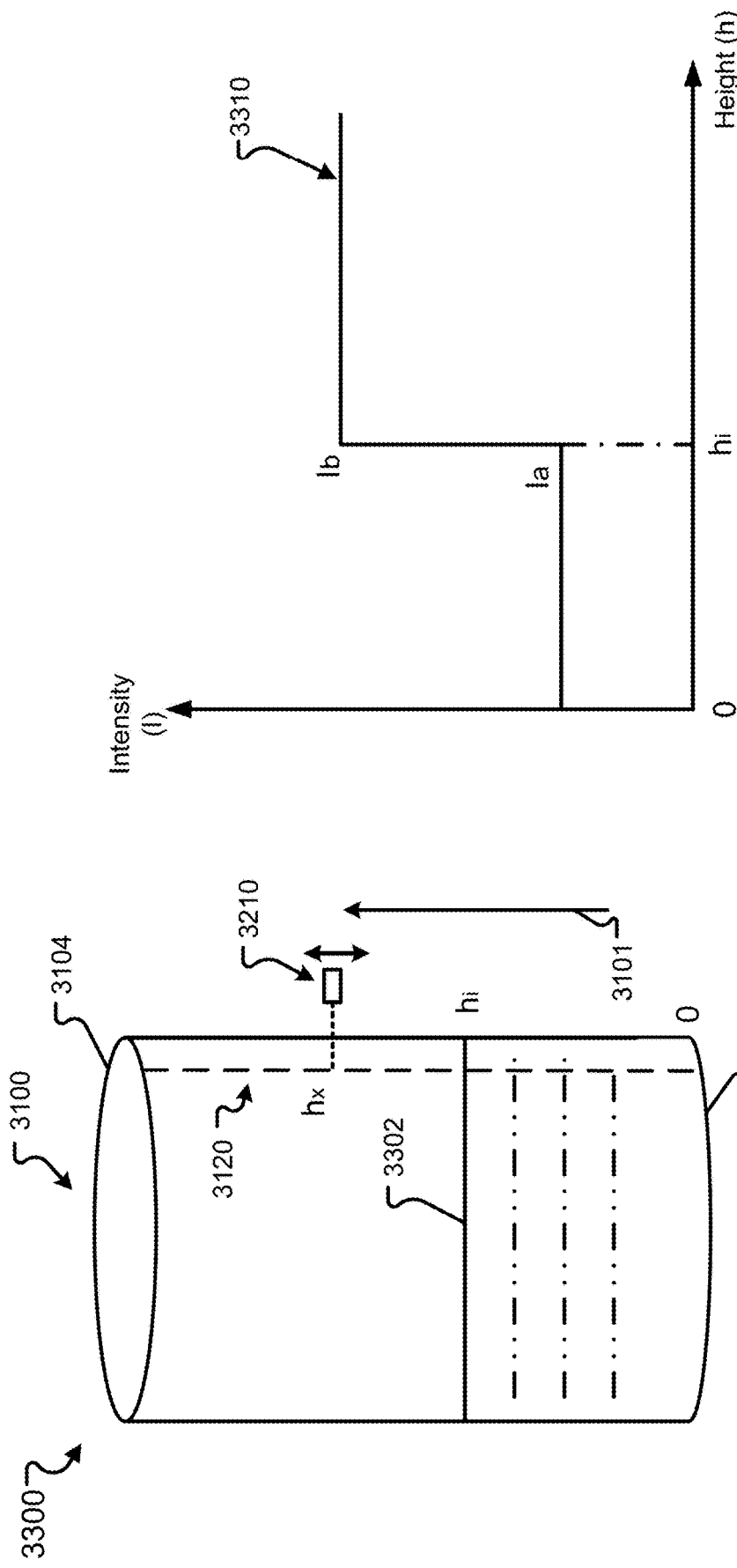
FIG. 35A illustrates an example liquid level measurement by moving a pair of light source and light detector along a longitudinal direction of a container.
FIG. 35B illustrates an example measurement result using the liquid level measurement of FIG. 35A.

FIG. 35A illustrates an example liquid level measurement by moving a pair of light source and light detector of a liquid level sensor along a longitudinal direction of a container, according to one or more embodiments of the present disclosure.

The container can be the container 3100 of FIGS. 33A-33C and 34A-34B, including a protrusion 3120. The pair of light source and light detector can be the pair 3210 of FIG. 34A or FIG. 34B. The pair 3210 can be moved continuously along a longitudinal direction 3101. An incident position of light on an internal surface 3132 of the protrusion 3120 is represented by a height $h_x$ with respect to a bottom 3102 of the container 100. When the pair 3210 is moved, the incident position is also moved, e.g., $h_x$ is increasing or decreasing.

To measure a liquid level 3302 in the container 3100 that has a corresponding height $h_i$, the pair 3210 can be continuously moved from the bottom 3102 (h=0) towards a top 3104 of the container 3100. An intensity of reflected light can be monitored and continuously detected. FIG. 35B illustrates an example measurement result 3310 using the liquid level measurement of FIG. 35A. The result 3310 shows, when the incident position $h_x$ is below the liquid level hi, TIR does not occur and the intensity of detected reflected light has a lower value Ia, and when the incident position $h_x$ is identical to or higher than the liquid level hi, TIR occurs and the intensity of detected reflected light has a higher value Ib. There is a substantially change across the liquid level $h_i$. In some examples, a ratio of Ib/Ia can be larger than 2, 3, 4, 5, 10, 20, 50, 100, or any suitable value. In some embodiments, a predetermined threshold can be set to be a value between Ia and Ib, e.g., an average of Ia and Ib, that is, (Ia+Ib)/2. Thus, by monitoring the detected light intensity while moving the pair 3210 along the longitudinal direction, an accurate measurement of the liquid level hi can be obtained.

In some embodiments, a reference signal can be first detected by the light detector, e.g., detecting light reflected from a container without protrusion. The reference signal can be used as a background noise. The detected reflected light from the container with protrusion can be subtracted with the reference signal to further improve the detection accuracy.

Figures 36A, 36B:
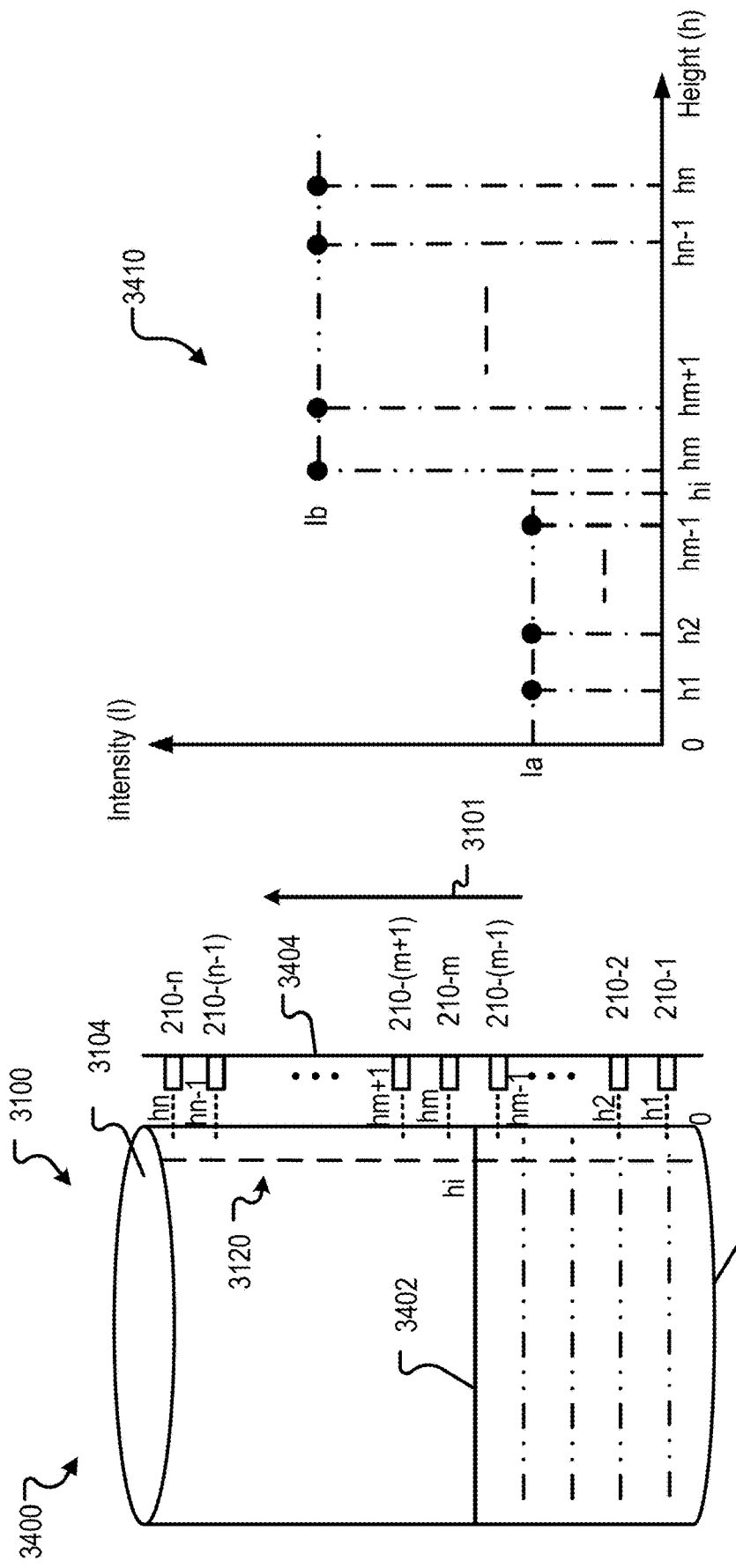
FIG. 36A illustrates another example liquid level measurement by multiple pairs of light source and light detector arranged at a series of positions along a longitudinal direction of a container.
FIG. 36B illustrates another example measurement result using the liquid level measurement of FIG. 36A.

FIG. 36A illustrates another example liquid level measurement by a liquid sensing system 3400, according to one or more embodiments of the present disclosure. FIG. 36B illustrates an example measurement result 3450 using the liquid level measurement of FIG. 36A.

The liquid sensing system 3400 can include multiple pairs of light source and light detector 3210-1, 3210-2, . . . , 3210-(m−1), 3210-m,3 210-(m+1), . . . , 3210-(n−1), 210-n (referred to generally as pairs 3210 or individually as pair 3210), where m, n are integers. The pairs 3210 can be arranged at a series of positions along a longitudinal direction 3101 of a container 3100, e.g., from a bottom 3102 to a top 3104. The series of positions of the pairs 3210 correspond to a series of incident positions h1, h2, hm−1, hm, hm+1, . . . , hn−1, hn along the longitudinal direction. The pairs 3210 can be static and mounted on a support 3404 extending along the longitudinal direction. The number of pairs 3210 can be 5, 10, 20, or any suitable number.

To determine a liquid level 3402 in the container 3100 that has a corresponding height hi, a respective intensity of detected reflected light for each pair 3210 corresponding to different incident positions is obtained. The respective intensities can be plotted as discrete points 3410, as illustrated in FIG. 36B. It shown that, when the incident position, e.g., h1, h2, . . . hm−1, is lower than the corresponding height hi of the liquid level 3402, no TIR occurs and the intensity of the detected reflected light has a lower intensity value Ia; when the incident position, e.g., hm, hm+1, . . . , hn−1, hn, is identical to or higher than the liquid level hi, TIR occurs and the intensity of detected reflected light has a higher value Ib. There is a substantially change across the liquid level $h_i$. In some examples, a ratio of Ib/Ia can be larger than 2, 3, 4, 5, 10, 20, 50, 100, or any suitable value. Thus, by measuring the detected light intensities of the series of pairs 3210, the liquid level hi can be determined to be in a range between $h_{m-1}$ and $h_m$.

In some embodiments, the liquid level sensing system 400 includes one pair 3210 of light source and light detector which can be arranged at a predetermined position, e.g., corresponding to a predetermined liquid level or a predetermined volume level. Liquid can be gradually injected into the container 3100. The light detector can keep monitoring the reflected light from the container 3100. When a substantial change occurs, it indicates that TIR occurs and the liquid level increases to the predetermined liquid level, the liquid level sensing system 3400 can send a signal to stop injecting the liquid. In such a way, an accurate amount of liquid can be obtained in the container 3100. In some embodiments, the liquid level sensing system 3400 include two or more pairs 3210 to control injecting a certain amount of liquid into a container.

Figure 37:
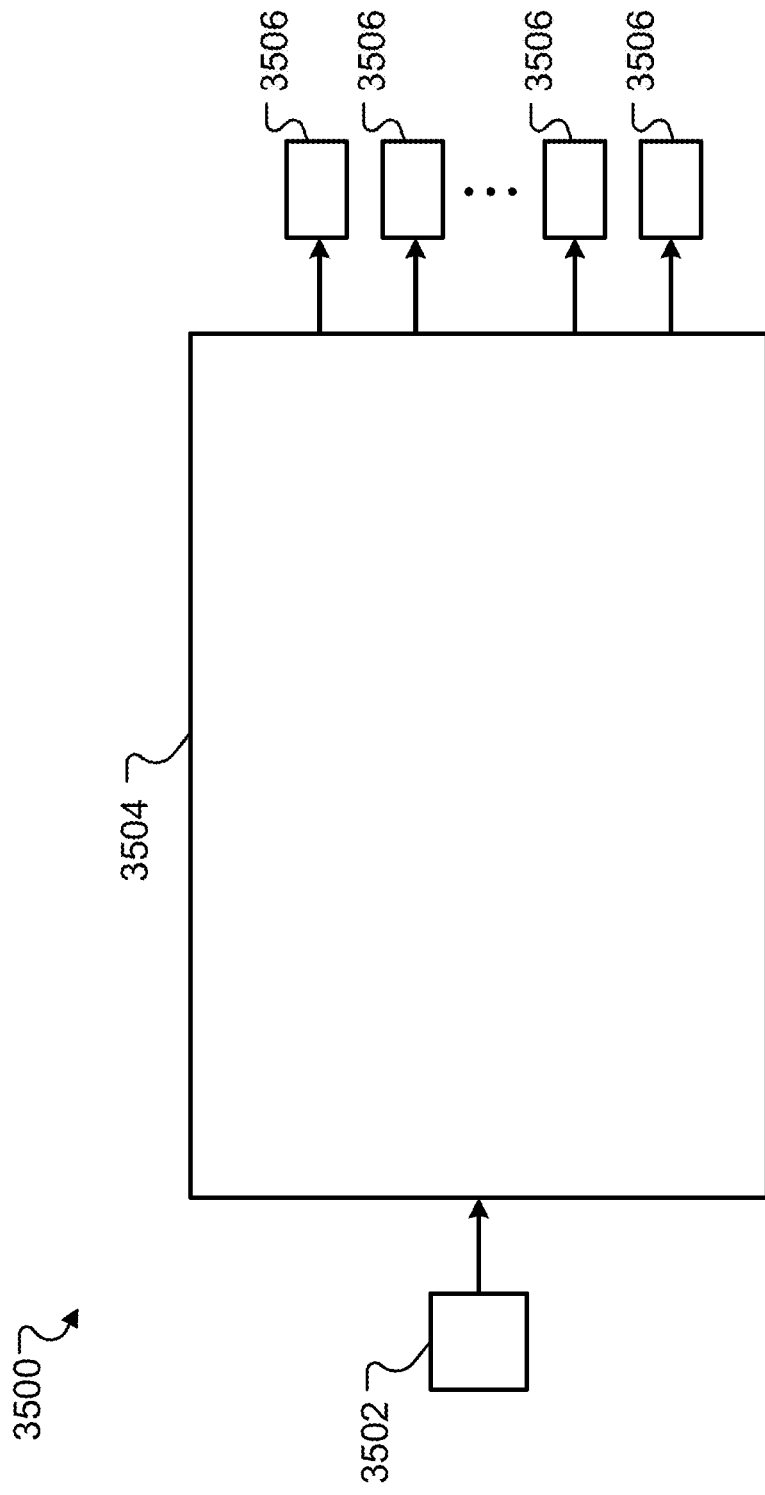
FIG. 37 illustrates an example fluidic system including at least one liquid level sensor.

FIG. 37 illustrates an example fluidic system 3500 for liquid level sensing, according to one or more embodiments of the present disclosure. The fluidic system 3500 can include at least one input container 3502, a fluidic channel system 3504 including one or more fluidic channels, and one or more output containers 3506.

In some embodiments, liquid (e.g., a mixture of solutions) contained in the input container 3502 can flow through the fluidic channel system 3504 for processing, e.g., filtering, separation, or any suitable processing steps. The fluidic channel system 3504 can output processed liquid into the one or more output containers 3506. In some embodiments, the one or more output containers 3506 include at least one sample container 3506 and at least one waste container 3506.

In some embodiments, at least one container, among the at least one input container 3502 and the one or more output containers 3506, can be a container 3100 and be assembled with one or more pairs 3210 of light source and light detector to form one or more liquid level sensors 3200 or 3300 or systems 3400. In such a way, an initial volume and/or an ending volume of liquid in the input container 3502 can be determined. A volume of sample or waste in an output container 3506 can be determined. In some cases, a difference between a volume of the liquid in the input container and a volume of the sample or waste in the output container 3506 can be obtained for further analysis.

Figure 38:
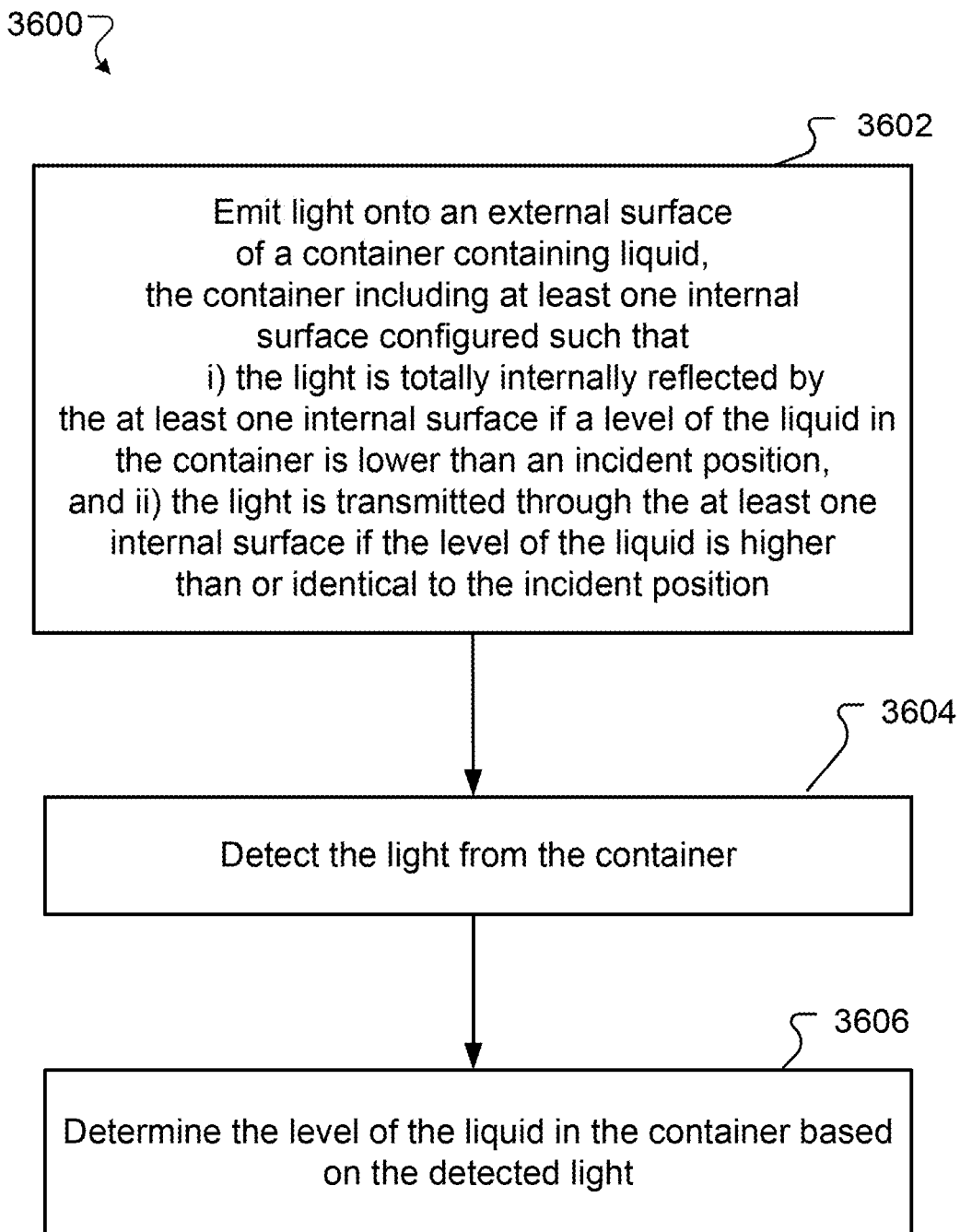
FIG. 38 is a flowchart of an example process for liquid level sensing using optical reflection.

FIG. 38 is a flowchart of an example process 3600 for liquid level sensing using optical reflection, according to one or more embodiments of the present disclosure. The process 3600 can be performed by a liquid level sensor (e.g., the liquid level sensor 3200 of FIGS. 34A-34B, 3300 of FIG. 35A), a liquid level system (e.g., the liquid level system 3400 of FIG. 36A), or a fluidic system (e.g., the fluidic system 3500 of FIG. 37). Liquid is held in a container, e.g., the container 3100 of FIGS. 33A-33C, FIGS. 34A-34B, FIG. 34A, FIG. 36A, or FIG. 36. A liquid level sensor includes a pair of light source (e.g., 3212 of FIGS. 34A-34B) and light detector (e.g., 3214 or 3216 of FIGS. 34A-34B).

Light is emitted, e.g., from the light source, onto an external surface of the container containing the liquid (3602). The container includes at least one internal surface configured such that i) the light is totally internally reflected by the at least one internal surface if the level of the liquid in the container is lower than an incident position where the light is incident on the at least one internal surface, and ii) the light is transmitted through the at least one internal surface if the level of the liquid is higher than or identical to the incident position where the light is incident on the at least one internal surface.

The light from the container (e.g., transmitted light or reflected light) is detected, e.g., by the light detector (3604), and then the level of the liquid in the container is determined based on the detected light (3606).

The container can extend along a longitudinal direction (e.g., 3101 of FIG. 33A) and a level of the liquid can be defined from a bottom of the container along the longitudinal direction. In some embodiments, the container includes a protrusion (e.g., 3120 of FIGS. 33A-33C, 34A-34B, 35A or 36A) having the at least one internal surface. The protrusion can continuously extend along the longitudinal direction or include multiple parts spaced along the longitudinal direction.

In some embodiments, the protrusion includes a first internal surface (e.g., 3132 of FIGS. 33B-33C or 34A-34B) on a first side (e.g., 3122 of FIGS. 33B-33C) and a second internal surface (e.g., 3134 of FIGS. 33B-33C or 34A-34B) on a second side (e.g., 3124 of FIGS. 33B-33C). As illustrated in FIG. 34A, the light can be totally internally reflected by the first internal surface and then by the second internal surface if the level of the liquid in the container is at or beyond the incident position (e.g., at a position higher than the incident position along the longitudinal direction).

In some embodiments, an angle defined by the first internal surface and the second internal surface is substantially identical to 90 degrees, e.g., as illustrated in FIGS. 33C and 34A-34B. A first incident angle at which the light is incident on the first internal surface can be substantially identical to a second incident angle at which the incident on the second internal surface. For example, each of the first incident angle and the second incident angle can be substantially identical to 45 degrees.

In some embodiments, the first side and the second side of the protrusion are connected together at an edge, e.g., 3123 of FIG. 33B. The container can include a body (e.g., 3110 of FIGS. 33A-33C or 34A-34B) for containing the liquid. The protrusion can include a third side (e.g., 3126 of FIG. 33B) that is part of the body of the container, the first side and the second side being externally connected to the body of the container. In some examples, the protrusion has a triangle shape having the first side, the second side, and the third side, e.g., as illustrated in FIG. 33C or 34A-34B.

In some embodiments, the body includes a first material, and the protrusion includes a second material. In some cases, the second material is same as the first material, and the protrusion and the body are an integrated piece. In some cases, the second material is different from the first material, and the protrusion and the body are attached together.

In some embodiments, the light is normally incident on the external surface of the container, and the light exits normally from the container, e.g., as illustrated in FIGS. 34A-34B. In some embodiments, as illustrated in FIG. 34A, if the level of the liquid in the container is below the incident position, the light propagates along a first direction to be incident on the first internal surface, and is reflected away from the second internal surface along a second direction that is substantially parallel but opposite to the first direction.

The light is emitted from a light source, and the light is detected by a light detector, the light source and the light detector forming a pair. The incident position can be predetermined based on a position of the light source, e.g., as illustrated in FIG. 35A or 36A.

In some embodiments, the light source and the light detector are arranged on a same side of the container, e.g., FIGS. 34A and 34B. Determining the level of the liquid in the container based on the detected light can include: in response to determining that a power of the detected light is greater than a predetermined threshold, determining that the level of the liquid is lower than the incident position, or in response to determining that a power of the detected light is smaller than or equal to the predetermined threshold, determining that the level of the liquid is higher than or identical to the incident position.

In some embodiments, the light source and the light detector are arranged on opposite sides of the container, e.g., as illustrated in FIG. 34B. Determining the level of the liquid in the container based on the detected light can include: in response to determining that a power of the detected light is smaller than a predetermined threshold, determining that the level of the liquid is lower than the incident position, or in response to determining that a power of the detected light is greater than or equal to the predetermined threshold, determining that the level of the liquid is higher than or identical to the incident position.

In some embodiments, as illustrated in FIGS. 35A-35B, the process 3600 can include: gradually moving at least one of the container or the pair of the light source and the light detector along the longitudinal direction until a power of the detected light substantially changes across a predetermined threshold, and determining the level of the liquid based on a position of the bottom of the container and a position of the light source when the power of the detected light substantially changes across the predetermined threshold.

In some embodiments, the process 3600 can include: monitoring a power of the detected light while the level of the liquid in the container is increasing due to injection of the liquid into the container, the incident position of the light corresponding to a predetermined level in the container; and in response to determining that the power of the detected light substantially changes across a predetermined threshold, controlling to stop the injection.

In some embodiments, as illustrated in FIG. 36A, the light is emitted from a plurality of light sources spaced along the longitudinal direction, and the light is detected by a plurality of light detectors spaced along the longitudinal direction. Each light source of the plurality of light sources can be associated with a respective light detector of the plurality of light detectors and configured to emit a corresponding portion of the light, and the respective light detector can be configured to detect the corresponding portion of the light emitted from the light source.

In some cases, each light source of the plurality of light sources and the respective light detector are arranged in a plane that passes through the longitudinal axis of the container. For example, when a beam size of the light is relatively small compared to a size of the container, the light is emitted into the container, reflected in the protrusion, and reflected out of the container in the same plane, and the respective light detector can be arranged side by side to the light source in the same plane. The light emitted from the light source can be configured to be focused at least in the longitudinal direction, such that the incident positions on the first and second internal surfaces are both in the plane perpendicular to the longitudinal direction. A distance between the light source and the respective light detector can be determined based on an input position and an output position of the light on the container. As illustrated in FIG. 34A, the farther the input position is to the intersection of the two internal surfaces (e.g., the edge 3133 of FIG. 33C) along the longitudinal direction, the larger the distance is. That is, after the distance between the light source and the respective light detector is determined, the input position of the light on the body can be adjusted, e.g., to maximize the intensity of the detected reflected light by the respective light detector.

In some cases, each light source of the plurality of light sources and the respective light detector are arranged along the longitudinal direction. For example, when a beam size of the light is relatively large compared to a size of the container, the light is emitted into the container, reflected in the protrusion, and reflected out of the container in different planes along the longitudinal direction. The respective light detector can be arranged under or above the light source along the horizontal direction. A position of the respective light detector can be calibrated or adjusted to maximize the intensity of the detected reflected light.

The protrusion extends along a vertical direction to make multiple depth (volume) measurements on the protrusion. A light source and a light detector can be arrayed either side-by-side or over-and-under if they are within a width of the protrusion. A molding draft angle can be doubled by a specular reflection. If the molding draft angle is 1 degree, the incident light can be reflected down by 2 degrees by the protrusion. In some embodiments, the light detector is arranged under the light source, e.g., for considering alignment tolerances. A distance between entering light rays and returning light rays can be no further apart than the width of the protrusion. With the light detector under the light source, the pair of the light detector and the light source can move horizontally along almost the entire protrusion width, as the first and second reflections on the first and second internal surfaces can occur on either surface.

In some embodiments, determining the level of the liquid in the container based on the detected light includes: determining the level of the liquid in the container based on detected corresponding portion of light by each of the plurality of light detectors. For example, as illustrated in FIGS. 36A-36B, step 3606 can include: determining that the level of the liquid in the container is higher than a first incident position at which a first corresponding portion of light from a first light source is incident on the first internal surface based on detected first corresponding portion of light by a first light detector, determining that the level of the liquid in the container is lower than a second incident position at which a second corresponding portion of light from a second light source is incident on the first internal surface based on detected second corresponding portion of light by a second light detector, and determining that the level of the liquid in the container is between the first incident position and the second incident position. The first incident position is predetermined based on a first position of the first light source, and the second incident position is predetermined based on a second position of the second light source.

In some embodiments, the container is a tube, a vessel, a tank, a bottle, or any suitable structure configured to hold liquid.

In some embodiments, the container can be formed by forming the body of the container and forming the protrusion together such that the body and the protrusion are formed as an integrated piece, e.g., by SLA 3D printing or molding. In some embodiments, the container is formed by attaching the protrusion onto the body of the container.

In some embodiments, the liquid level sensor includes at least one processor configured to determine the level of the liquid based on the detected light by the light detector. In some embodiments, the liquid level sensor is coupled to at least one processor and configured to provide the detected light to the at least one processor that is configured to determine the level of the liquid based on the detected light. In some embodiments, the at least one processor is configured to multiplex a number of liquid level sensors, e.g., by controlling to turn on one liquid level sensor at a time to prevent crosstalk due to light piping and scattering.

In some embodiments, as illustrated in FIG. 37, a fluidic system (e.g., 3500 of FIG. 37) includes: at least one input container configured to contain liquid, at least one fluidic channel configured to receive the liquid from the input container and output the liquid from at least one output, and at least one output container coupled to the at least one output and configured to receive the liquid through the at least one fluidic channel. At least one container of the input container or the at least one output container is configured for liquid level sensing, each container of the at least one container including at least one internal surface configured such that i) light is totally internally reflected by the at least one internal surface if a level of liquid in the container is lower than an incident position where the light is incident on the at least one internal surface, and ii) the light is transmitted through the at least one internal surface if the level of the liquid is higher than or identical to the incident position where the light is incident on the at least one internal surface.

The fluidic system can further include at least one processor configured to: determine the level of the liquid in the container based on the detected light from the container as described above. In some embodiments, the at least one processor is configured to: determine a difference between a volume of the liquid in the input container and a volume of the liquid in the at least one output container.

MicroOrganoSpheres (MOSs)

Historically, the most common practice for testing cell responses to various stimuli includes culturing the cells in two-dimensional (2D) conditions such as in a Petri dish or in a well plate. However, these 2D conditions can stress the cells, and they do not always correlate well with individual patient responses to the tested stimuli. On the other hand, droplets can provide a three-dimensional (3D) environment for a cluster of 3D cell aggregates and may yield experimental results that better correlate with patient outcomes. The 3D cell aggregates can include organoids or spheroids. Organoids are in-vitro cell aggregates, typically having a diameter greater than one mm, that include a population of stem cells that can differentiate into cells of major cell lineages. Spheroids are simple clusters of broad-ranging cells, such as from tumor tissue, embryoid bodies, heptaocytes, nervous tissue, or mammary glands. Unlike organoids, spheroids typically do not have the ability to self-assemble or regenerate.

Droplets that are generated to include 3D cell aggregates such as organoids or spheroids are sometimes referred to as "Patient-Derived MicroOrganoSpheres" (PMOSs) or simply "MicroOrganoSpheres" (MOSs). MOSs, including methods and apparatuses for generating them, are described in further detail in U.S. patent application Ser. No. 16/838,010, which is incorporated herein by reference in its entirety.

It is important to note that while MOSs are described in this application as an example of droplets that can be generated by a microfluidic device, this disclosure is not intended to be limiting. Microfluidic-formed droplets can be used in a wide range of applications including drug discovery and evaluation of drug efficacy, and one skilled in the art would appreciate that the technologies described herein can be applied to droplets used for many of these alternative applications.

In some examples, MOSs contain dissociated cells from patient-derived tissue samples (e.g., biopsy samples). Tissues may be from a healthy tissue biopsy or from cancerous (e.g., tumor) cell biopsy. The cells are dissociated and dispersed (e.g., suspended) in the matrix material. Once generated, MOSs can be patterned onto a microfluidic microwell array, to be incubated, dosed with drug compounds, and imaged at repeated time intervals to monitor the growth of each organoid. This miniaturized assay maximizes the use of patient samples, and enables high throughput screening of a large number of therapeutics (e.g., drugs or drug formulations) from a core biopsy at a relatively low cost per sample.

The matrix material used in generation of MOSs can be a gel, a semi-solid, or a liquid, such as a low-viscosity liquid, at room temperature (e.g., at about 25° C.). Example matrix materials include polymers or hydrogels including collagen, fibrin, or chitosan; MATRIGEL™ (Corning, Corning, NY); polyethylene glycol; dextrans including chemically cross-linkable or photo-crosslinkable dextrans, electrospun biological, synthetic, or biological-synthetic blends; or other suitable polymerizable matrix materials. In some examples, the matrix material is a gel, such as a synthetic or natural gel. Examples of synthetic gels include gels derived from any of polyethylene glycol (PEG), polyhydroxyethyl methacrylate (PHEMA), polyvinyl alcohol (PVA), poly ethylene oxide (PEO).

In some examples, once polymerized, the matrix material forms a hydrogel. The term "hydrogel" refers to a two- or multi-component gel including a three-dimensional network of polymer chains, where water acts as the dispersion medium and fills the space between the polymer chains. Example hydrogels that can be used for MOSs include alginate, collagen (including collagen types I and VI), elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, or derivatives and copolymers thereof; inorganic materials such as glass such as bioactive glass, ceramic, silica, alumina, calcite, hydroxyapatite, calcium phosphate, bone; or combinations of the foregoing. In a specific example, the hydrogel includes a material selected from the group consisting of agarose, alginate, collagen type I, a polyoxyethylene-polyoxypropylene block copolymer (e.g., Pluronic® F127 (BASF Corporation, Mount Olive, N.J.)), silicone, polysaccharide, polyethylene glycol, and polyurethane.

In some examples, the MOSs include one or more biologically relevant materials in addition to the patient-derived cells and the matrix material. Example biologically-relevant materials included in the MOSs can include one or more of: an extracellular matrix protein (e.g. fibronectin), a drug (e.g. small molecules), a peptide, an antibody (e.g., to modulate any of cell survival, proliferation or differentiation); or an inhibitor of a particular cellular function. Biologically-relevant materials in MOSs can be used, for example, to increase cell viability by reducing cell death and/or activation of cell growth/replication or to otherwise mimic the in vivo environment. Biologically-relevant materials incorporated in MOSs can include or mimic one or more of the following components: serum, interleukins, chemokines, growth factors, glucose, physiological salts, amino acids, or hormones. When the matrix material is a gel, the gel itself can include one or more biologically relevant materials including extracellular matrix components such as collagen, fibrinogen, laminin, fibronectin, vitronectin, hyaluronic acid, fibrin, alginate, agarose, or chitosan. For example, MATRIGEL includes bioactive polymers that are important for cell viability, proliferation, development and migration. In a specific example, the matrix material is a gel including collagen type 1, such as collagen type 1 obtained from rat tails, alone or in addition to other biologically relevant materials, such as other extracellular matrix proteins.

The MOSs described here can have a diameter of between about 50 μm and about 500 μm (e.g., between about 50 μm and about 400 μm, about 50 μm and about 300 μm, about 50 μm and about 250 μm, etc.). Each MOS initially can contain between about 1 and 1000 dissociated primary cells distributed within the matrix material (e.g., between about 1 and 750, between about 1 and 500, between about 1 and 400, between about 1 and 300, between about 1 and 200, between about 1 and 150, between about 1 and 100, between about 1 and 75, between about 1 and 50, between about 1 and 40, between about 1 and 30, between about 1 and 20, etc.). The number of cells per MOS can be set based on an intended use of the MOSs. For instances, MOSs having a small number of cells per MOS (e.g., 1-5 cells per MOS) may be useful for studying clonal diversity (e.g., for tumor heterogeneity), e.g., for observing which clones are drug resistant and for determining genomic (mutation) diversity related to the particular clone (e.g., by genomic sequencing). MOSs having a moderate number of cells per MOS (e.g., between about 3-30 cells, 5-30 cells, 5-25 cells, 5-20 cells, 10-25 cells, etc.) may be useful for rapid drug testing, such as toxicity testing, as these MOSs tend to grow quickly. MOSs having a large number of cells per MOS (e.g., between about 20-100 cells, e.g., 30-100 cells, 40-100 cells, or greater than 50 cells, etc.) may be suitable for mimicking tissue composition in each MicroOrganoSphere, as the MicroOrganoSphere may contain different lineages, potentially including epithelial (or cancer, etc.) and mesenchymal (or stromal, immune, blood vessel, etc.) cells.

MOSs generated in the microfluidics system described here can be used substantially immediately upon formation or cultured for a brief period of time (e.g., 14 days or less, 10 days or less, 7 days or less, 5 days or less, etc.). Cells within the MOSs can survive while maintaining much, if not all, of the characteristics of the tissue, including tumor tissue, from which they were extracted. The survival rate of the cells within the MOSs is high, and the MOSs may be cultured for a period of time (e.g., days or weeks) through multiple passages, in which the cells will divide, cluster and form structures similar to the parent tissue, sometimes referred to as tumorspheres. In some cases, the cells from the dissociated tissue within the MOSs form morphological structures inside the MOSs.

Figures 39A, 39B, 39C:
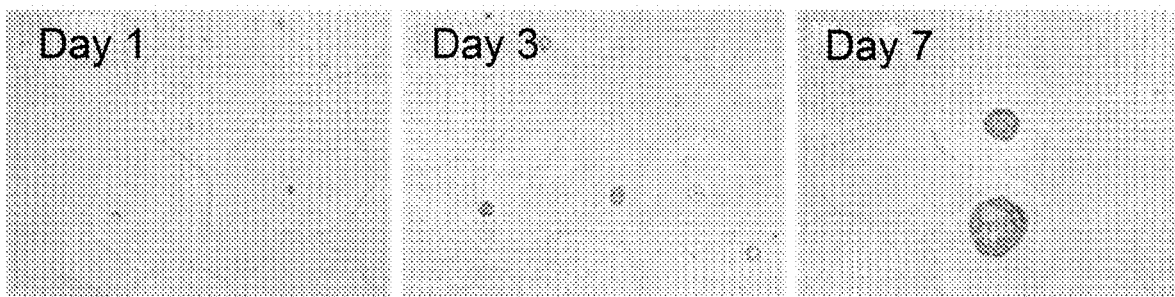
FIGS. 39A-39C are images of MicroOrganoSpheres.

FIGS. 39A-39C show example MOSs. Referring specifically to FIG. 39A, upon generation, each MOS includes a single cell and has a diameter of approximately 300 μm. FIG. 39B shows the MOSs after 3 days in culture. The cells have expanded in size, e.g., doubling or growing. Referring to FIG. 39C, after seven days in culture, the cells have doubled multiple times, forming clusters or masses of cells, or tumorspheres.

Figure 40:
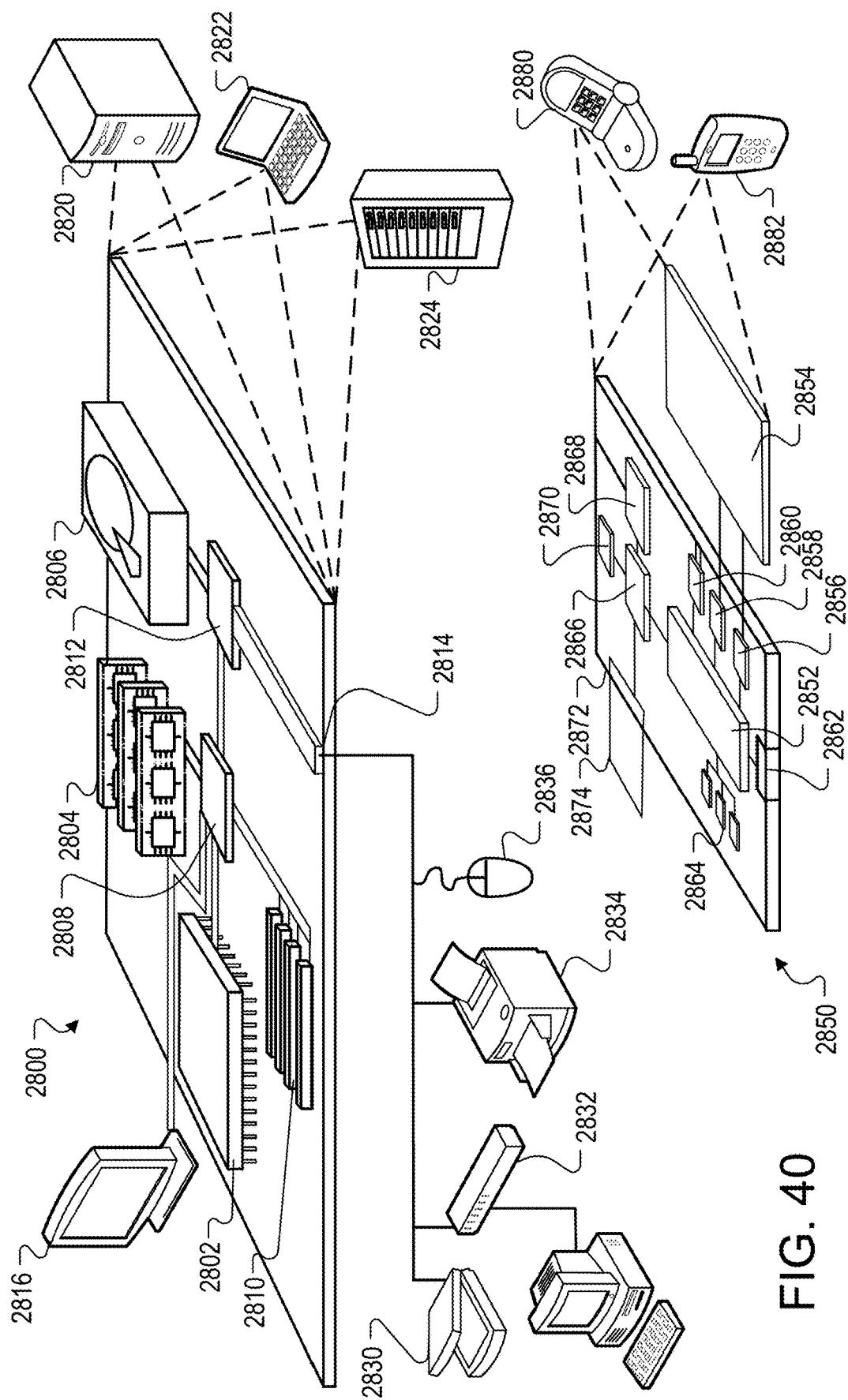
FIG. 40 is a diagram illustrating an example of a computing environment.

FIG. 40 shows an example of a computing device 2800 and a mobile computing device 2850 that are employed to execute implementations of the present disclosure. The computing device 2800 is intended to represent various forms of digital computers, such as laptops, desktops, workstations, personal digital assistants, servers, blade servers, mainframes, and other appropriate computers. The mobile computing device 2850 is intended to represent various forms of mobile devices, such as personal digital assistants, cellular telephones, smart-phones, AR devices, sensor devices, smart cameras, and other similar computing devices. The components shown here, their connections and relationships, and their functions, are meant to be examples only, and are not meant to be limiting. The computing device 2800 and/or the mobile computing device 2850 can form at least a portion of a microfluidic system such as the controller 2124 of the device 2100 described above. The computing device 2800 and/or the mobile computing device 2850 can also form at least a portion of a remote computing device external to the device 2100, which can perform one or more of the image processing operations described in relation to FIGS. 28, 29, and 30 or can interact with the device 2100 to receive data transmitted from the device 2100 (e.g., captured images and/or estimated sizes of one or more droplets). For example, in some implementations, the computing device 2800 and/or the mobile computing device 2850 can form at least a portion of a remote camera or smart camera that is external to the device 2100.

The computing device 2800 includes a processor 2802 (e.g., a digital signal processor [DSP], a graphics processing unit [GPU], a field-programmable gate array [FPGA], etc.), a memory 2804, a storage device 2806, a high-speed interface 2808, and a low-speed interface 2812. In some implementations, the high-speed interface 2808 connects to the memory 2804 and multiple high-speed expansion ports 2810. In some implementations, the low-speed interface 2812 connects to a low-speed expansion port 2814 and the storage device 2804. Each of the processor 2802, the memory 2804, the storage device 2806, the high-speed interface 2808, the high-speed expansion ports 2810, and the low-speed interface 2812, are interconnected using various buses, and may be mounted on a common motherboard or in other manners as appropriate. The processor 2802 can process instructions for execution within the computing device 2800, including instructions stored in the memory 2804 and/or on the storage device 2806 to display graphical information for a graphical user interface (GUI) on an external input/output device, such as a display 2816 coupled to the high-speed interface 2808. In other implementations, multiple processors and/or multiple buses may be used, as appropriate, along with multiple memories and types of memory. In addition, multiple computing devices may be connected, with each device providing portions of the necessary operations (e.g., as a server bank, a group of blade servers, or a multi-processor system).

The memory 2804 stores information within the computing device 2800. In some implementations, the memory 2804 is a volatile memory unit or units. In some implementations, the memory 2804 is a non-volatile memory unit or units. The memory 2804 may also be another form of a computer-readable medium, such as a magnetic or optical disk.

The storage device 2806 is capable of providing mass storage for the computing device 2800. In some implementations, the storage device 2806 may be or include a computer-readable medium, such as a floppy disk device, a hard disk device, an optical disk device, a tape device, a flash memory, or other similar solid-state memory device, or an array of devices, including devices in a storage area network or other configurations. Instructions can be stored in an information carrier. The instructions, when executed by one or more processing devices, such as processor 2802, perform one or more methods, such as those described above. The instructions can also be stored by one or more storage devices, such as computer-readable or machine-readable mediums, such as the memory 2804, the storage device 2806, or memory on the processor 2802.

The high-speed interface 2808 manages bandwidth-intensive operations for the computing device 2800, while the low-speed interface 2812 manages lower bandwidth-intensive operations. Such allocation of functions is an example only. In some implementations, the high-speed interface 2808 is coupled to the memory 2804, the display 2816 (e.g., through a graphics processor or accelerator), and to the high-speed expansion ports 2810, which may accept various expansion cards. In the implementation, the low-speed interface 2812 is coupled to the storage device 2806 and the low-speed expansion port 2814. The low-speed expansion port 2814, which may include various communication ports (e.g., Universal Serial Bus (USB), Bluetooth, Ethernet, wireless Ethernet) may be coupled to one or more input/output devices. Such input/output devices may include a display device, a printing device 2834, or a keyboard or mouse 2836. The input/output devices may also be coupled to the low-speed expansion port 2814 through a network adapter. Such network input/output devices may include, for example, a switch or router 2832.

The computing device 2800 may be implemented in a number of different forms, as shown in FIG. 40. For example, it may be implemented as a standard server 820, or multiple times in a group of such servers. In addition, it may be implemented in a personal computer such as a laptop computer 2822. It may also be implemented as part of a rack server system 2824. Alternatively, components from the computing device 2800 may be combined with other components in a mobile device, such as a mobile computing device 2850. Each of such devices may contain one or more of the computing device 2800 and the mobile computing device 2850, and an entire system may be made up of multiple computing devices communicating with each other.

The mobile computing device 2850 includes a processor 2852; a memory 2864; an input/output device, such as a display 2854; a communication interface 2866; and a transceiver 2868; among other components. The mobile computing device 2850 may also be provided with a storage device, such as a microSD card or other device, to provide additional storage. Each of the processor 2852, the memory 2864, the display 2854, the communication interface 2866, and the transceiver 2868, are interconnected using various buses, and several of the components may be mounted on a common motherboard or in other manners as appropriate. In some implementations, the mobile computing device 2850 may include a camera device(s).

The processor 2852 can execute instructions within the mobile computing device 2850, including instructions stored in the memory 2864. The processor 2852 may be implemented as a chipset of chips that include separate and multiple analog and digital processors. For example, the processor 2852 may be a Complex Instruction Set Computers (CISC) processor, a Reduced Instruction Set Computer (RISC) processor, or a Minimal Instruction Set Computer (MISC) processor. The processor 2852 may provide, for example, for coordination of the other components of the mobile computing device 2850, such as control of user interfaces (UIs), applications run by the mobile computing device 2850, and/or wireless communication by the mobile computing device 2850.

The processor 2852 may communicate with a user through a control interface 2858 and a display interface 2856 coupled to the display 2854. The display 2854 may be, for example, a Thin-Film-Transistor Liquid Crystal Display (TFT) display, an Organic Light Emitting Diode (OLED) display, or other appropriate display technology. The display interface 2856 may include appropriate circuitry for driving the display 2854 to present graphical and other information to a user. The control interface 2858 may receive commands from a user and convert them for submission to the processor 2852. In addition, an external interface 2862 may provide communication with the processor 2852, so as to enable near area communication of the mobile computing device 2850 with other devices. The external interface 2862 may provide, for example, for wired communication in some implementations, or for wireless communication in other implementations, and multiple interfaces may also be used.

The memory 2864 stores information within the mobile computing device 2850. The memory 2864 can be implemented as one or more of a computer-readable medium or media, a volatile memory unit or units, or a non-volatile memory unit or units. An expansion memory 2874 may also be provided and connected to the mobile computing device 2850 through an expansion interface 2872, which may include, for example, a Single in Line Memory Module (SIMM) card interface. The expansion memory 2874 may provide extra storage space for the mobile computing device 2850, or may also store applications or other information for the mobile computing device 2850. Specifically, the expansion memory 2874 may include instructions to carry out or supplement the processes described above, and may include secure information also. Thus, for example, the expansion memory 2874 may be provided as a security module for the mobile computing device 2850, and may be programmed with instructions that permit secure use of the mobile computing device 2850. In addition, secure applications may be provided via the SIMM cards, along with additional information, such as placing identifying information on the SIMM card in a non-hackable manner.

The memory may include, for example, flash memory and/or non-volatile random access memory (NVRAM), as discussed below. In some implementations, instructions are stored in an information carrier. The instructions, when executed by one or more processing devices, such as processor 2852, perform one or more methods, such as those described above. The instructions can also be stored by one or more storage devices, such as one or more computer-readable or machine-readable mediums, such as the memory 2864, the expansion memory 2874, or memory on the processor 2852. In some implementations, the instructions can be received in a propagated signal, such as, over the transceiver 2868 or the external interface 2862.

The mobile computing device 2850 may communicate wirelessly through the communication interface 2866, which may include digital signal processing circuitry where necessary. The communication interface 2866 may provide for communications under various modes or protocols, such as Global System for Mobile communications (GSM) voice calls, Short Message Service (SMS), Enhanced Messaging Service (EMS), Multimedia Messaging Service (MMS) messaging, code division multiple access (CDMA), time division multiple access (TDMA), Personal Digital Cellular (PDC), Wideband Code Division Multiple Access (WCDMA), CDMA2000, General Packet Radio Service (GPRS). Such communication may occur, for example, through the transceiver 2868 using a radio frequency. In addition, short-range communication, such as using a Bluetooth or Wi-Fi, may occur. In addition, a Global Positioning System (GPS) receiver module 2870 may provide additional navigation- and location-related wireless data to the mobile computing device 2850, which may be used as appropriate by applications running on the mobile computing device 2850.

The mobile computing device 2850 may also communicate audibly using an audio codec 2860, which may receive spoken information from a user and convert it to usable digital information. The audio codec 2860 may likewise generate audible sound for a user, such as through a speaker, e.g., in a handset of the mobile computing device 2850. Such sound may include sound from voice telephone calls, may include recorded sound (e.g., voice messages, music files, etc.) and may also include sound generated by applications operating on the mobile computing device 2850.

The mobile computing device 2850 may be implemented in a number of different forms, as shown in FIG. 40. For example, it may be implemented a phone device 2880, a personal digital assistant 2882, and a tablet device (not shown). The mobile computing device 2850 may also be implemented as a component of a smart-phone, AR device, or other similar mobile device.

The computing device 2800 may be implemented as part of a microfluidic system such as the controller 2124 of the device 2100 described above with respect to FIG. 26A. The computing device 2800 may also be implemented in a remote computing device that communicates with the device 2100 to receive data transmitted from the device 2100 (e.g., captured images and estimated sizes of one or more droplets).

Computing device 2800 and/or 2850 can also include USB flash drives. The USB flash drives may store operating

LISTING OF EMBODIMENTS

Embodiment 1. A microfluidic apparatus including:
a microfluidic chip for generation of MicroOrgano-Spheres (MOS), in which a first microfluidic channel is defined in a surface of the microfluidic chip, the first microfluidic channel including:
  a droplet generation portion including an inlet portion, a junction between the inlet portion and an emulsifying fluid channel, and a chamber downstream of the junction, in which a cross-sectional area of the chamber is larger than a cross-sectional area of the inlet portion, and
  a polymerization portion downstream of the droplet generation portion, the polymerization portion having a serpentine configuration; and
a cartridge for MOS demulsification, the cartridge including:
  a collection container;
  a substrate disposed on the collection container, in which a second microfluidic channel is defined in a surface of the substrate that faces the collection container, and in which the second microfluidic channel is fluidically connected to an output of the polymerization portion of the first microfluidic channel; and
  a membrane disposed between the collection container and the surface of the substrate.

Embodiment 2. The microfluidic apparatus of embodiment 1, in which the droplet generation portion of the first microfluidic channel includes an outlet portion downstream of the chamber, in which a cross-sectional area of the chamber is larger than a cross-sectional area of the outlet portion.

Embodiment 3. The microfluidic apparatus of embodiment 2, in which at least some of the outlet portion extends in a direction parallel to the chamber.

Embodiment 4. The microfluidic apparatus of any of the preceding embodiments, in which the surface of the microfluidic chip is a first surface, and in which the polymerization portion of the microfluidic channel is defined on the first surface of the microfluidic chip and on a second surface of the microfluidic chip opposite the first surface.

Embodiment 5. The microfluidic apparatus of any of the preceding embodiments, in which the junction includes a junction with two hydrophobic fluid channels.

Embodiment 6. The microfluidic apparatus of embodiment 5, in which the junction is a right-angle junction.

Embodiment 7. The microfluidic apparatus of any of the preceding embodiments, in which the membrane includes a hydrophobic membrane.

Embodiment 8. The microfluidic apparatus of any of the preceding embodiments, in which the second microfluidic channel includes: an upstream section that has a simple serpentine configuration, and a downstream section that has a double serpentine configuration.

Embodiment 9. The microfluidic apparatus of any of the preceding embodiments, in which a cross-sectional area of the second microfluidic channel decreases from an input end of the second microfluidic channel to an output end of the second microfluidic channel.

Embodiment 10. The microfluidic apparatus of any of the preceding embodiments, in which the surface of the substrate is a first surface, and in which a media inlet channel is defined on a second surface of the substrate opposite the first surface of the substrate, the media inlet channel fluidically connected to an upstream section of the second microfluidic channel and configured to be connected to a media reservoir.

Embodiment 11. The microfluidic apparatus of embodiment 10, in which the demulsification cartridge includes the media reservoir.

Embodiment 12. The microfluidic apparatus of embodiment 11, in which the media inlet channel is fluidically connected to the media reservoir via a tube extending through the substrate and the collection container.

Embodiment 13. The microfluidic apparatus of embodiment 11 or 12, in which the collection container is disposed in a cavity defined in the media reservoir such that the collection container is positioned between the media reservoir and the substrate.

Embodiment 14. The microfluidic apparatus of any of embodiments 11 to 13, in which a bottom surface of the media reservoir is angled relative to a plane of the substrate.

Embodiment 15. The microfluidic apparatus of any of embodiments 11 to 14, in which the demulsification cartridge includes a duckbill valve extending through the substrate and the collection container, the duckbill valve configured to provide fluidic access to the media reservoir.

Embodiment 16. The microfluidic apparatus of any of the preceding embodiments, in which the demulsification cartridge includes a hydrophobic material disposed within the collection container.

Embodiment 17. The microfluidic apparatus of any of the preceding embodiments, in which a vacuum flow pathway is defined through a body of the collection container, the vacuum flow pathway configured to enable application of a vacuum to a surface of the membrane opposite the substrate.

Embodiment 18. The microfluidic apparatus of any of the preceding embodiments, including a reservoir fluidically connected to the first microfluidic channel via an input port defined at an input end of the first microfluidic channel.

Embodiment 19. The microfluidic apparatus of embodiment 18, in which the reservoir includes a base and a cover, the base and cover defining a cavity for a fluidic sample.

Embodiment 20. The microfluidic apparatus of embodiment 19, including an input port in the cover of the reservoir, the input port including a duckbill valve.

Embodiment 21. The microfluidic apparatus of embodiment 19 or 20, including an output port in the cover of the reservoir, the output port connected to a tube extending into the cavity of the reservoir.

Embodiment 22. The microfluidic apparatus of any of embodiments 19 to 21, in which a bottom surface of the base of the reservoir is angled relative to the cover.

Embodiment 23. The microfluidic apparatus of any of embodiments 18 to 22, including a reservoir holder configured to receive the reservoir, the reservoir holder including a cooling system configured to cool the reservoir.

Embodiment 24. The microfluidic apparatus of embodiment 23, in which the cooling system includes a thermoelectric cooling system.

Embodiment 25. The microfluidic apparatus of any of the preceding embodiments, in which one or more cutouts are defined in the microfluidic chip between the droplet generation portion and the polymerization portion.

Embodiment 26. The microfluidic apparatus of embodiment 25, in which edges of the one or more cutouts are angled relative to the surface of the microfluidic chip.

Embodiment 27. The microfluidic apparatus of embodiment 25 or 26, in which the one or more cutouts extend through an entire thickness of the microfluidic chip.

Embodiment 28. The microfluidic apparatus of any of the preceding embodiments, including a cover disposed on the surface of the microfluidic chip.

Embodiment 29. The microfluidic apparatus of embodiment 28, in which the cover includes an optically transparent cover.

Embodiment 30. The microfluidic apparatus of any of the preceding embodiments, in which multiple first microfluidic channel are defined in the surface of the microfluidic chip, and in which the apparatus includes multiple cartridges, in which the second microfluidic channel of each cartridge is fluidically connected to a corresponding one of the first microfluidic channel of the microfluidic chip.

Embodiment 31. The microfluidic apparatus of any of the preceding embodiments, in which the apparatus includes an output vial fluidically connected to the second microfluidic channel via an output port defined at the output end of the second microfluidic channel.

Embodiment 32. A system, combinable with any of embodiments 1-31, including: the microfluidic apparatus of any of the preceding embodiments; a housing, in which the microfluidic apparatus is disposed in the housing; and a polymerization block housed in the housing and positioned to apply a stimulus to the polymerization portion of the first microfluidic channel.

Embodiment 33. The system of embodiment 32, in which the polymerization block includes a thermal polymerization block configured to apply heat to the polymerization portion of the first microfluidic channel.

Embodiment 34. The system of embodiment 33, in which the thermal polymerization block includes a heater.

Embodiment 35. The system of embodiment 34, in which the thermal polymerization block includes a temperature sensor.

Embodiment 36. The system of embodiment 35, in which the temperature sensor includes one or more of a thermistor, a thermocouple, or a resistance temperature detector.

Embodiment 37. The system of embodiment 35 or 36, including a controller configured to control operation of the resistance heater responsive to temperature data received from the temperature sensor.

Embodiment 38. The system of any of embodiments 34 to 37, in which the heater includes a resistance heater.

Embodiment 39. The system of any of embodiments 34 to 38, in which the thermal polymerization block includes a thermally insulating cover, and in which the heater is disposed within a cavity defined within the thermally insulating cover.

Embodiment 40. The system of any of embodiments 32 to 39, in which the polymerization block includes a light polymerization block configured to illuminate the polymerization portion of the first microfluidic channel.

Embodiment 41. The system of embodiment 40, in which the light polymerization block includes a light emitting diode (LED).

Embodiment 42. The system of embodiment 41, in which the light polymerization block includes a photodetector.

Embodiment 43. The system of embodiment 42, including a controller configured to control operation of the LED responsive to light intensity data received from the photodetector.

Embodiment 44. The system of any of embodiments 41 to 43, in which the LED is disposed within a cavity defined in a housing of the light polymerization block.

Embodiment 45. The system of embodiment 44, in which a wall of the cavity is formed of a material that is capable of reflecting light at a wavelength of light output by the LED.

Embodiment 46. The system of any of embodiments 41 to 45, including a controller configured to control the LED to emit pulsed illumination.

Embodiment 47. The system of any of embodiments 32 to 46, in which the surface of the microfluidic chip is a first surface, and in which the polymerization block includes: a first block disposed adjacent the first surface of the microfluidic chip; and a second block disposed adjacent a second surface of the microfluidic chip, the second surface opposite the first surface.

Embodiment 48. The system of embodiment 47, in which the first and second blocks are secured against the microfluidic chip by one or more springs.

Embodiment 49. The system of embodiment 47 or 48, in which the first and second blocks are clamped to the microfluidic chip.

Embodiment 50. The system of any of embodiments 32 to 49, including a reservoir for emulsifying fluid, in which the emulsifying fluid channel of the microfluidic apparatus is fluidically connected to the reservoir.

Embodiment 51. The system of embodiment 50, in which the reservoir includes a reflective rib for fluid volume measurement disposed in a chamber of the reservoir.

Embodiment 52. The system of embodiment 50 or 51, including a pump disposed between the reservoir for emulsifying fluid and the emulsifying fluid channel.

Embodiment 53. The system of embodiment 52, including a controller configured to control operation of the pump.

Embodiment 54. The system of embodiment 53, in which the controller is configured to control operation of the pump to achieve a target fluid velocity in the second microfluidic channel.

Embodiment 55. The system of any of embodiments 32 to 54, including an imaging system positioned to capture images of at least a portion of the chamber.

Embodiment 56. The system of embodiment 55, including a controller configured to control a flow rate of fluid through the inlet portion of the microfluidic channel based on the images captured by the imaging system.

Embodiment 57. The system of embodiment 56, in which the controller is configured to control the flow rate of the fluid by controlling a pressure applied to a reservoir fluidically connected to the inlet portion of the microfluidic channel.

Embodiment 58. A microfluidic chip, combinable with any of embodiments 1-57, including:
multiple first microfluidic channels for generation of an emulsion of droplets of a first fluid in a second fluid, in which the first microfluidic channels are defined in a first surface of the microfluidic chip, in which each first microfluidic channel is fluidically independent from each other first microfluidic channel, and in which each first microfluidic channel includes:

an inlet portion configured to receive the first fluid from a respective source of the first fluid;

a junction between the inlet portion and a corresponding second fluid channel configured to carry the second fluid; and a chamber downstream of the junction, in which a cross-sectional area of the chamber is larger than a cross-sectional area of the inlet portion; and multiple second microfluidic channels for polymerization of the droplets of the emulsion to thereby generate MOSs, in which each second microfluidic channel is fluidically connected to an outlet of a corresponding one of the first microfluidic channels, in which each second microfluidic channel is a serpentine channel including a first portion defined on the first surface of the microfluidic chip and a second portion defined on a second surface of the microfluidic chip opposite the first surface.

Embodiment 59. The microfluidic chip of embodiment 58, in which each first microfluidic channel includes an outlet portion downstream of the chamber, in which the cross-sectional area of the chamber is larger than a cross-sectional area of the outlet portion.

Embodiment 60. The microfluidic chip of embodiment 59, in which a region of the outlet portion of each first microfluidic channel extends in a direction parallel to the respective chamber.

Embodiment 61. The microfluidic chip of any of embodiments 58 to 60, including a cover disposed on each of the first surface and the second surface of the microfluidic chip.

Embodiment 62. The microfluidic chip of embodiment 61, in which the cover includes an optically transparent cover.

Embodiment 63. The microfluidic chip of any of embodiments 58 to 62, in which the multiple first microfluidic channels are defined in a first region of the microfluidic chip, and in which the multiple second microfluidic channels are defined in a second region of the microfluidic chip distinct from the first region.

Embodiment 64. The microfluidic chip of embodiment 63, in which one or more cutouts are defined in the microfluidic chip between the first region and the second region.

Embodiment 65. The microfluidic chip of embodiment 64, in which edges of the one or more cutouts are angled relative to the first and second surfaces of the microfluidic chip.

Embodiment 66. The microfluidic chip of embodiment 64 or 65, in which the one or more cutouts extend through an entire thickness of the microfluidic chip.

Embodiment 67. The microfluidic chip of any of embodiments 58 to 66, in which each junction is a junction between the respective inlet portion and two corresponding second fluid channels.

Embodiment 68. The microfluidic chip of embodiment 67, in which the junction is a right-angle junction.

Embodiment 69. The microfluidic chip of any of embodiments 58 to 68, in which the microfluidic chip includes multiple inlet fingers, each inlet finger extending away from at least one other inlet finger and separated from each adjacent inlet finger by a gap, and in which at least some of the inlet portion of each first microfluidic channel is defined on a surface of a corresponding inlet finger.

Embodiment 70. The microfluidic chip of any of embodiments 58 to 69, in which the microfluidic chip includes multiple outlet fingers, each outlet finger extending away from at least one other outlet finger and separated from each adjacent outlet finger by a gap, and in which an outlet portion of each second microfluidic channel is defined on a surface of a corresponding outlet finger.

Embodiment 71. The microfluidic chip of any of embodiments 58 to 70, in which an output port of each second microfluidic channel is configured to be connected to a corresponding cartridge for demulsification of the emulsion.

Embodiment 72. An apparatus, combinable with any of embodiments 1-71, including:

a cartridge for transferring MOSs from an emulsion in a hydrophobic fluid into a suspension in aqueous fluid, the demulsification cartridge including:

a collection container defining a cavity for receiving the hydrophobic fluid;

a substrate disposed on the collection container, in which a microfluidic channel is defined in a first surface of the substrate that faces the collection container, and in which a media inlet channel for an aqueous fluid is fluidically connected to an upstream portion of the microfluidic channel; and a hydrophobic membrane disposed between the collection container and the surface of the substrate.

Embodiment 73. The apparatus of embodiment 72, including a media reservoir having a cavity configured to contain the aqueous fluid, in which the media inlet channel is fluidically connected to the media reservoir.

Embodiment 74. The apparatus of embodiment 73, including a tube extending through the substrate and the collection container, in which the media inlet channel is fluidically connected to the media reservoir via the tube.

Embodiment 75. The apparatus of embodiment 73 or 74, in which the collection container is disposed in the cavity of the media reservoir such that the collection container is positioned between the media reservoir and the substrate.

Embodiment 76. The apparatus of any of embodiments 73 to 75, in which a bottom surface of the media reservoir is angled relative to a plane of the substrate.

Embodiment 77. The apparatus of any of embodiments 73 to 76, including a duckbill valve disposed through an opening in the substrate and an opening in the collection container, the duckbill valve configured to allow aqueous fluid to be provided into the cavity of the media reservoir.

Embodiment 78. The apparatus of any of embodiments 72 to 77, in which the surface of the substrate is a first surface, and in which the media inlet channel is defined on a second surface of the substrate opposite the first surface.

Embodiment 79. The apparatus of any of embodiments 72 to 78, in which a cross-sectional area of the microfluidic channel is larger at an upstream end of the microfluidic channel than at a downstream end of the microfluidic channel.

Embodiment 80. The apparatus of embodiment 79, in which the upstream portion of the microfluidic channel has a simple serpentine configuration and in which the downstream portion of the microfluidic channel has a double serpentine configuration.

Embodiment 81. The apparatus of any of embodiments 72 to 80, including a hydrophobic absorbent material disposed in the cavity of the collection container.

Embodiment 82. A method, combinable with any of embodiments 1-81, including:
in a droplet generation portion of a first microfluidic channel defined in a surface of a microfluidic chip, generating droplets of a first fluid in the hydrophobic fluid, the first fluid including biological material and a matrix material, and
in a polymerization portion of the first microfluidic channel, applying a stimulus to the generated droplets to polymerize the matrix material, thereby forming MOSs emulsified in the hydrophobic fluid;
transferring the MOSs from the emulsion into a suspension in aqueous fluid, including:
flowing a mixture of aqueous fluid and the emulsion of MOSs in the hydrophobic fluid along a second microfluidic channel defined in a substrate;
as the mixture flows along the second microfluidic channel, transferring the hydrophobic fluid across a membrane forming a wall of the second microfluidic channel.

Embodiment 83. The method of embodiment 82, in which generating droplets of the first fluid includes generating the droplets at a junction between the first microfluidic channel and one or more channels carrying the hydrophobic fluid.

Embodiment 84. The method of embodiment 83, including controlling a flow rate of the hydrophobic fluid.

Embodiment 85. The method of any of embodiments 82 to 84, including controlling a flow rate of the first fluid based on a determined size of the generated droplets.

Embodiment 86. The method of embodiment 85, including determining the size of the generated droplets based on images of the droplets in the droplet generation portion of the first microfluidic channel.

Embodiment 87. The method of any of embodiments 82 to 86, in which applying a stimulus to the generated droplets includes heating the droplets.

Embodiment 88. The method of any of embodiments 82 to 87, in which applying a stimulus to the generated droplets includes illuminating the droplets with light having a wavelength configured to induce polymerization of the matrix material.

Embodiment 89. The method of embodiment 88, in which the surface of the microfluidic chip is a first surface, and in which the polymerization portion of the first microfluidic channel is defined on both the first surface and a second surface of the microfluidic chip, and in which illuminating the droplets includes illuminating the first and second surfaces of the microfluidic chip.

Embodiment 90. The method of embodiment 88 or 89, in which illuminating the droplets includes illuminating the droplets with pulsed illumination.

Embodiment 91. The method of any of embodiments 82 to 90, including receiving the transferred hydrophobic fluid into a collection container, in which the membrane is disposed between the collection container and the substrate.

Embodiment 92. The method of any of embodiments 82 to 91, in which transferring the hydrophobic fluid across the membrane including applying a vacuum to the membrane.

Embodiment 93. The method of any of embodiments 82 to 92, including providing the suspension of MOSs in aqueous fluid to an output vial.

Embodiment 94. The method of any of embodiments 82 to 93, including: generating droplets of each of multiple first fluids in each of multiple, fluidically independent first microfluidic channels defined in the surface of the microfluidic chip; and applying the stimulus to the generated droplets in each first microfluidic channel to form MOSs.

Embodiment 95. A method, combinable with any of embodiments 1-94, including:
flowing a first fluid through a first microfluidic channel of a microfluidic apparatus, in which the first fluid includes biological material and a matrix material;
flowing a second fluid through a second microfluidic channel of the microfluidic apparatus, in which the first fluid is immiscible with the second fluid;
combining the first fluid and the second fluid to form droplets of the first fluid dispersed in the second fluid in a third channel of a microfluidic apparatus;
by an imaging device, capturing multiple exposures of a droplet of the first fluid in the third microfluidic channel in a single image captured by the imaging device, the capturing of the multiple exposures including:
illuminating, by a light source, a region of the third microfluidic channel with multiple successive illumination pulses during a single frame of the imaging device;
determining a characteristic of the droplet based on an analysis of the captured exposures; and
based on the determined characteristic of the droplet, controlling the flow of the first fluid in the first microfluidic channel, the flow of the second fluid in the second microfluidic channel, or both.

Embodiment 96. The method of embodiment 95, in which flowing the second fluid through the second microfluidic channel includes flowing the second fluid through two second microfluidic channels, and in which combining the first fluid and the second fluid includes combining the first fluid and the second fluid at the junction between the first microfluidic channel and the two second microfluidic channels.

Embodiment 97. The method of embodiment 96, including identifying the droplet in each of the captured exposures.

Embodiment 98. The method of embodiment 97, including identifying a leading edge of the droplet in each of the captured exposures, a trailing edge of the droplet in each of the captured exposures, or both.

Embodiment 99. The method of embodiment 97, including identifying the droplet using frequency domain analysis or machine vision analysis or by creation of best fit circles.

Embodiment 100. The method of any of embodiments 96 to 99, in which determining a characteristic of the droplet based on an analysis of the captured exposures includes determining a distance traveled by the droplet between a time of a first one of the illumination pulses and a time of a second one of the illumination pulses.

Embodiment 101. The method of any of embodiments 96 to 100, in which determining a characteristic of the droplet based on an analysis of the captured exposures includes determining a velocity of the droplet in the third microfluidic channel.

Embodiment 102. The method of any of embodiments 96 to 101, in which determining a characteristic of the droplet based on an analysis of the captured exposures includes determining a size of the droplet.

Embodiment 103. The method of any of embodiments 96 to 102, in which determining a characteristic of the droplet based on an analysis of the captured exposures includes determining a distance between the droplet and an adjacent droplet in the third microfluidic channel.

Embodiment 104. The method of any of embodiments 96 to 103, including, based on the determined characteristic of the droplet, determining an estimated number of droplets formed by the combining of the first fluid and the second fluid.

Embodiment 105. The method of any of embodiments 96 to 104, including, based on the determined characteristic of the droplet, determining a droplet generation rate.

Embodiment 106. The method of any of embodiments 96 to 105, including controlling the flow of the first fluid in the first microfluidic channel to obtain droplets of a target size.

Embodiment 107. The method of any of embodiments 96 to 106, including controlling the flow of the second fluid in the second microfluidic channel to obtain droplets flowing in the third microfluidic channel at a target velocity.

Embodiment 108. The method of embodiment 107, in which controlling the flow of the first fluid in the first microfluidic channel includes controlling a pressure of a fluid reservoir fluidically coupled to the first microfluidic channel, the fluid reservoir containing the first fluid.

Embodiment 109. The method of embodiment 107 or 108, in which controlling the flow of the second fluid in the second microfluidic channel includes operating a pump with programmable flow rate to control a flow rate of the second fluid from a fluid reservoir fluidically coupled to the second microfluidic channel.

Embodiment 110. The method of any of embodiments 96 to 109, in which acquiring the multiple exposures includes synchronizing operation of a shutter of the imaging device with the light source of the imaging device.

Embodiment 111. The method of embodiment 110, in which synchronizing operation of the shutter of the imaging device with the light source of the imaging device includes controlling the shutter of the imaging device to remain open during the illumination of the region of the third microfluidic channel with the multiple successive illumination pulses.

Embodiment 112. The method of any of embodiments 96 to 111, in which illuminating the region of the third microfluidic channel with multiple successive illumination pulses includes controlling the light source to emit illumination pulses each having a duration of 5 microseconds (μsec) to 125 μsec, e.g., 25 to 50 μsec, and pulse separation of between about 1 millisecond (ms) and about 50 ms, e.g., 1-30 ms.

Embodiment 113. The method of any of embodiments 96 to 112, in which illuminating the region of the third microfluidic channel with multiple successive illumination pulses includes illuminating the region of the third microfluidic channel with a first illumination pulse of a first color and a second illumination pulse of a second color.

Embodiment 114. The method of any of embodiments 96 to 113, including illuminating the region of the third microfluidic channel with a collimated light source.

Embodiment 115. The method of any of embodiments 96 to 114, including exposing the droplets of the first fluid to a stimulus sufficient to polymerize the matrix material in the droplets, thereby forming polymerized droplets dispersed in the second fluid.

Embodiment 116. The method of embodiment 115, including using the polymerized droplets for assaying patient-specific therapies.

Embodiment 117. A system, combinable with any of embodiments 1-116, including:
a first microfluidic channel configured to be connected to a source of a first fluid;
a second microfluidic channel configured to be connected to a source of a second fluid, in which the first microfluidic channel and the second microfluidic channel intersect at a junction;
a first controller configured to control a flow regulator coupled to the source of the first fluid and to the source of the second fluid;
a third microfluidic channel downstream from the junction;
an imaging system including an imaging device and a light source;
a second controller configured to control the imaging system to capture multiple exposures of the at least a portion of the third microfluidic channel in a single image captured by the imaging device; and
a computing device including one or more processors coupled to a memory configured to cause the computing device to:
analyze the multiple exposures of the at least a portion of the third microfluidic channel to determine a characteristic of a droplet in each of the multiple captured exposures; and
cause the first controller to control the flow regulator based on the determined characteristic of the droplet.

Embodiment 118. The system of embodiment 117, in which the second controller is configured to: control a shutter of the imaging device to open; and control the light source to produce multiple successive illumination pulses while the shutter of the imaging device is open.

Embodiment 119. The system of embodiment 117 or 118, in which the one or more first controllers are configured to control: a valve or a pump for controlling a pressure of a first fluid reservoir fluidically coupled to the first microfluidic channel, the fluid reservoir containing the first fluid; and a pump with programmable flow rate for controlling a flow rate of the second fluid from a second fluid reservoir fluidically coupled to the second microfluidic channel.

Embodiment 120. The system of any of embodiments 117 to 119, in which the light source includes a light emitting diode.

Embodiment 121. The system of any of embodiments 117 to 120, in which the light source includes a collimated light source.

Embodiment 122. The system of any of embodiments 117 to 121, in which the light source includes multiple light sources, each light source configured to emit light of a different color.

Embodiment 123. The system of any of embodiments 117 to 122, in which the one or more processors and memory are configured to cause the computing device to identify the droplet in each of the captured exposures.

Embodiment 124. The system of embodiment 123, in which the one or more processors and memory are configured to cause the computing device to identify a leading edge of the droplet in each of the captured exposures, a trailing edge of the droplet in each of the captured exposures, a best fit circle, or a combination thereof.

Embodiment 125. The system of embodiment 124, in which the one or more processors and memory are configured to cause the computing device to identify the droplet using frequency domain analysis or machine vision analysis.

Embodiment 126. The system of any of embodiments 116 to 124, including multiple second microfluidic channels, in which the first microfluidic channel and the multiple second microfluidic channels intersect at the junction.

Embodiment 127. The system of any of embodiments 117 to 126, in which the one or more processors and memory are configured to cause the computing device to determine a velocity of the droplet in the third microfluidic channel.

Embodiment 128. The system of any of embodiments 117 to 127, in which the one or more processors and memory are configured to cause the computing device to determine a size of the droplet in the third microfluidic channel.

Embodiment 129. The system of any of embodiments 117 to 128, in which the system includes: a fourth microfluidic channel connected to the third microfluidic channel; and a heating element disposed adjacent the fourth microfluidic channel and configured to apply heat to at least a portion of the fourth microfluidic channel.

Embodiment 130. A system, combinable with any of embodiments 1-129, including:
a device configured to facilitate an interaction between a first fluid flow and a second fluid flow within a flow path of the device;
an optical sensor configured to obtain one or more images representing the flow path;
an image analysis module configured to:
  process the one or more images to identify at least one droplet generated in a flow path of the device by the interaction between the first fluid flow and the second fluid flow, and
  estimate a size of the at least one droplet; and
a control system configured to:
  determine that the size of the at least one droplet satisfies a threshold condition, and
  responsive to determining that the size of the at least one droplet satisfies the threshold condition, generate a signal that causes an adjustment to a flow rate of at least one of the first fluid flow or the second fluid flow.

Embodiment 131. The system of embodiment 130, wherein the device is a microfluidic device.

Embodiment 132. The system of embodiment 130 or 131, wherein the first fluid flow includes a flow of a hydrophilic solution.

Embodiment 133. They system of any of embodiments 130 to 130, wherein the first fluid flow includes a flow of a solution including an unpolymerized mixture including fluid matrix material and cells.

Embodiment 134. The system of any of embodiments 130 to 133, wherein the second fluid flow includes a flow a hydrophobic solution.

Embodiment 135. The system of any of embodiments 130 to 134, wherein the one or more images includes an image of the at least one droplet in an area of the device where the at least one droplet is not compressed by one or more walls of the device.

Embodiment 136. The system of any of embodiments 130 to 135, wherein processing the one or more images obtained by the optical sensor includes:
detecting edges of the at least one droplet in at least one of the one or more images;
identifying a first set of pixels corresponding to the detected edges of the at least one droplet;
identifying a circle corresponding to the at least one droplet based on the first set of pixels;
identifying a second set of pixels, wherein the second set of pixels includes a subset of the first set of pixels that are disposed within a threshold distance from a circumference of the identified circle; and
computing a metric that is representative of a distance of at least a portion of the second set of pixels from a predetermined location within the at least one droplet.

Embodiment 137. The system of embodiment 136, wherein processing the one or more images obtained by the optical sensor further includes: enhancing the at least one of the one or more images subsequent to detecting the edges of the at least one droplet.

Embodiment 138. The system of embodiment 136 or 137, wherein processing the one or more images obtained by the optical sensor further includes: downsizing the at least one of the one or more images prior to identifying the first set of pixels corresponding to the detected edges of the at least one droplet, and magnifying the at least one of the one or more images subsequent to identifying the first set of pixels corresponding to the detected edges of the at least one droplet.

Embodiment 139. The system of any of embodiment 135 to 138, wherein the image analysis module is configured to estimate the size of the at least one droplet based on the computed metric.

Embodiment 140. The system of embodiment 139, wherein the computed metric includes a weighted average of individual distances of the portion of the second set of pixels from the predetermined location within the at least one droplet, wherein one or more weight values of the weighted average are based on intensity values of the portion of the second set of pixels.

Embodiment 141. The system of any of embodiment 136 to 140, wherein processing the one or more images further includes excluding data corresponding to the detected edges of the at least one droplet if one or more filtering conditions is satisfied.

Embodiment 142. The system of embodiment 141, wherein the one or more filtering conditions includes an indication that the first set of pixels corresponds to the detected edges of a plurality of imaged droplets.

Embodiment 143. The system of embodiment 141 or 142, wherein the one or more filtering conditions includes an indication that the first set of pixels overlaps with at least one additional set of pixels.

Embodiment 144. The system of any of embodiment 141 to 143, wherein the one or more filtering conditions includes an indication of a detected signal that satisfies a threshold signal level condition, the detected signal originating from within a perimeter of the first set of pixels.

Embodiment 145. The system of any of embodiment 141 to 144, wherein the one or more filtering conditions includes a determination that the first set of pixels is less than a threshold proximity from an imaged wall of the device.

Embodiment 146. The system of any of embodiment 130 to 145, wherein the image analysis module is configured to estimate the size of the at least one droplet with sub-pixel radial resolution.

Embodiment 147. The system of any of embodiment 130 to 146, wherein the control system is configured to compare the size of the at least one droplet to a target size obtained via a user-input.

Embodiment 148. The system of any of embodiment 130 to 147, wherein the control system is configured to compare the size of the at least one droplet to a target size selected automatically by a computing device.

Embodiment 149. The system of any of embodiment 130 to 148, wherein the control system includes a feedback controller configured to generate the signal that causes the adjustment to the flow rate of at least one of the first fluid flow or the second fluid flow using proportional control, integral control, and/or derivative control.

Embodiment 150. The system of any of embodiment 130 to 149, wherein the control system is configured to generate the signal that causes the adjustment to the flow rate of at least one of the first fluid flow or the second fluid flow without feedback control when the image analysis module does not identify any droplets.

Embodiment 151. The system of any of embodiment 130 to 150, wherein the at least one droplet includes two or more droplets, and wherein the control system is configured to increase or decrease the flow rate of at least one of the first fluid flow or the second fluid flow without feedback control when a standard deviation of the size of the two or more droplets exceeds a threshold value.

Embodiment 152. The system of any of embodiment 130 to 151, wherein the image analysis module is further configured to process the one or more images to identify air bubbles in the flow path.

Embodiment 153. The system of any of embodiment 130 to 152, further including a storage device configured to store the one or more images and/or data representing the size of the at least one droplet.

Embodiment 154. The system of any of embodiment 130 to 153, further including a transmission module configured to transmit the one or more images and/or data representing the size of the at least one droplet to a remote computing device.

Embodiment 155. The system of any of embodiment 130 to 154, wherein the adjustment to the flow rate of the at least one of the first fluid flow or the second fluid flow includes an adjustment to a pressure applied to the first fluid or the second fluid.

Embodiment 156. A method, combinable with any of embodiments 1-155, including:
obtaining one or more images representing a flow path within a microfluidic system that facilitates an interaction between a first fluid flow and a second fluid flow;
processing the one or more images to identify at least one droplet generated in the flow path by the interaction between the first fluid flow and the second fluid flow;
estimating a size of the at least one droplet;
determining that the size of the at least one droplet satisfies a threshold condition; and
responsive to determining that the size of the at least one droplet satisfies the threshold condition, generating a signal that causes an adjustment to a flow rate of at least one of the first fluid flow or the second fluid flow.

Embodiment 157. The method of embodiment 156, wherein the signal is configured to increase or decrease the flow rate of at least one of the first fluid flow or the second fluid flow based on the size of the at least one droplet.

Embodiment 158. The method of embodiment 156 or 157, wherein the first fluid flow includes a flow of a hydrophilic solution and the second fluid flow includes a flow of a hydrophobic solution.

Embodiment 159. The method of embodiment 158, wherein the hydrophilic solution includes an unpolymerized mixture including fluid matrix material and cells.

Embodiment 160. The method of any of embodiment 156 to 159, wherein the one or more images includes an image of the at least one droplet in an area of a device where the at least one droplet is not compressed by one or more walls of the device.

Embodiment 161. The method of any of embodiment 156 to 160, wherein processing the one or more images includes:
detecting edges of the at least one droplet in at least one of the one or more images;
identifying a first set of pixels corresponding to the detected edges of the at least one droplet;
identifying a circle corresponding to the at least one droplet based on the first set of pixels;
identifying a second set of pixels, wherein the second set of pixels includes a subset of the first set of pixels that are disposed within a threshold distance from a circumference of the identified circle; and
computing a metric that is representative of at least a portion of the second set of pixels from a predetermined location within the at least one droplet.

Embodiment 162. The method of embodiment 161, wherein processing the one or more images further includes: enhancing the at least one of the one or more images subsequent to detecting the edges of the at least one droplet.

Embodiment 163. The method of embodiment 161 or 162, wherein processing the one or more images further includes: downsizing the at least one of the one or more images prior to identifying the first set of pixels corresponding to the detected edges of the at least one droplet, and magnifying the at least one of the one or more images subsequent to identifying the first set of pixels corresponding to the detected edges of the at least one droplet.

Embodiment 164. The method of any of embodiments 161 to 163, wherein estimating the size of the at least one droplet includes estimating the size based on the computed metric.

Embodiment 165. The method of embodiment 164, wherein the computed metric includes a weighted average of individual distances of the portion of the second set of pixels from the predetermined location within the at least one droplet, wherein one or more weight values of the weighted average are based on intensity values of the portion of the second set of pixels.

Embodiment 166. The method of any of embodiment 161 to 164, wherein processing the one or more images further includes excluding data corresponding to the detected edges of the at least one droplet if one or more filtering conditions is satisfied.

Embodiment 167. The method of embodiment 166, wherein the one or more filtering conditions includes an indication that the first set of pixels corresponds to the detected edges of a plurality of imaged droplets.

Embodiment 168. The method of embodiment 16 or 167, wherein the one or more filtering conditions includes an indication that the first set of pixels overlaps with at least one additional set of pixels.

Embodiment 169. The method of any of embodiments 166 to 168, wherein the one or more filtering conditions includes an indication of a detected signal that satisfies a threshold signal level condition, the detected signal originating from within a perimeter of the first set of pixels.

Embodiment 170. The method of any of embodiments 166 to 169, wherein the one or more filtering conditions includes a determination that the first set of pixels is less than a threshold proximity from an imaged wall of a device.

Embodiment 171. The method of any of embodiments 156 to 168, wherein estimating the size of the at least one droplet includes estimating the size with sub-pixel radial resolution.

Embodiment 172. The method of any of embodiments 156 to 171, wherein determining that the size of the at least one droplet satisfies the threshold condition includes: comparing the size of the at least one droplet to a target size obtained via a user-input.

Embodiment 173. The method of any of embodiments 156 to 172, wherein determining that the size of the at least one droplet satisfies the threshold condition includes: comparing the size of the at least one droplet to a target size selected automatically by a computing device.

Embodiment 174. The method of any of embodiments 156 to 173, wherein generating the signal that causes the adjustment to the flow rate of at least one of the first fluid flow or the second fluid flow includes: using a feedback controller to generate the signal using proportional control, integral control, and/or derivative control.

Embodiment 175. The method of any of embodiments 156 to 174, wherein generating the signal that causes the adjustment to the flow rate of at least one of the first fluid flow or the second fluid flow includes: generating the signal without feedback control when no droplets are identified in the one or more images.

Embodiment 176. The method of any of embodiments 156 to 175, wherein the at least one droplet includes two or more droplets, and wherein generating the signal that causes the adjustment to the flow rate of at least one of the first fluid flow or the second fluid flow includes: generating the signal without feedback control when a standard deviation of the size of the two or more droplets exceeds a threshold value.

Embodiment 177. The method of any of embodiments 156 to 176, further including processing the one or more images to identify air bubbles in the flow path.

Embodiment 178. The method of any of embodiments 156 to 177, further including storing, on a storage device, the one or more images and/or data representing the size of the at least one droplet.

Embodiment 179. The method of any of embodiments 156 to 178, further including transmitting, to a remote computing device, the one or more images and/or data representing the size of the at least one droplet.

Embodiment 180. The method of any of embodiments 156 to 179, wherein the adjustment to the flow rate of the at least one of the first fluid flow or the second fluid flow includes an adjustment to a pressure applied to the first fluid or the second fluid.

Embodiment 181. A non-transitory computer readable medium, combinable with any of embodiments 1-180, and storing instructions that are executable by a processing device, and upon such execution cause the processing device to perform operations including:
  obtaining one or more images representing a flow path within a microfluidic system that facilitates an interaction between a first fluid flow and a second fluid flow;
  processing the one or more images to identify at least one droplet generated in the flow path by the interaction between the first fluid flow and the second fluid flow;
  estimating a size of the at least one droplet;
  determining that the size of the at least one droplet satisfies a threshold condition; and
  responsive to determining that the size of the at least one droplet satisfies the threshold condition, generating a signal that causes an adjustment to a flow rate of at least one of the first fluid flow or the second fluid flow.

Embodiment 182. A method of liquid level sensing, combinable with any of embodiments 1-181, the method including:
  emitting light onto an external surface of a container containing a liquid, the container including at least one internal surface configured such that
    i) the light is totally internally reflected by the at least one internal surface if a level of the liquid in the container is lower than an incident position where the light is incident on the at least one internal surface, and
    ii) the light is transmitted through the at least one internal surface if the level of the liquid is higher than or identical to the incident position where the light is incident on the at least one internal surface;
  detecting the light from the container; and
  determining the level of the liquid in the container based on the detected light.

Embodiment 183. The method of embodiment 182, wherein the container includes a protrusion having the at least one internal surface.

Embodiment 184. The method of embodiment 183, wherein the container extends along a longitudinal direction, and the level of the liquid is defined from a bottom of the container along the longitudinal direction.

Embodiment 185. The method of embodiment 184, wherein the protrusion continuously extends along the longitudinal direction.

Embodiment 186. The method of any of embodiments 183 to 185, wherein the protrusion includes a first internal surface on a first side and a second internal surface on a second side, and wherein the light is totally internally reflected by the first internal surface and then by the second internal surface if the level of the liquid in the container is at or above the incident position along the longitudinal direction.

Embodiment 187. The method of embodiment 186, wherein an angle defined by the first internal surface and the second internal surface is substantially identical to 90 degrees.

Embodiment 188. The method of embodiment 186 or 187, wherein a first incident angle at which the light is incident on the first internal surface is substantially identical to a second incident angle at which the incident on the second internal surface.

Embodiment 189. The method of embodiment 188, wherein each of the first incident angle and the second incident angle is substantially identical to 45 degrees.

Embodiment 190. The method of any of embodiments 186 to 189, wherein the first side and the second side of the protrusion are connected together at an edge.

Embodiment 191. The method of any of embodiments 186 to 190, wherein the container includes a body for containing the liquid, and wherein the protrusion includes a third side that is part of the body of the container, the first side and the second side being externally connected to the body of the container.

Embodiment 192. The method of embodiment 191, wherein the protrusion has a triangle shape having the first side, the second side, and the third side.

Embodiment 193. The method of embodiment 191 or 192, wherein the body includes a first material, and the protrusion includes a second material.

Embodiment 194. The method of embodiment 193, wherein the second material is same as the first material, and the protrusion and the body are an integrated piece.

Embodiment 195. The method of embodiment 193, wherein the second material is different from the first material, and the protrusion and the body are attached together.

Embodiment 196. The method of any of embodiments 186 to 195, wherein the light is normally incident on the external surface of the container, and the light exits normally from the container.

Embodiment 197. The method of any of embodiments 186 to 196, wherein, if the level of the liquid in the container is below the incident position, the light propagates along a first direction to be incident on the first internal surface, and is reflected away from the second internal surface along a second direction that is substantially parallel but opposite to the first direction.

Embodiment 198. The method of embodiment 197, wherein the light is emitted from a light source, and the light is detected by a light detector, the light source and the light detector forming a pair, and wherein the incident position is predetermined based on a position of the light source.

Embodiment 199. The method of embodiment 198, wherein the light source and the light detector are arranged on a same side of the container, and wherein determining the level of the liquid in the container based on the detected light includes: in response to determining that a power of the detected light is greater than a predetermined threshold, determining that the level of the liquid is lower than the incident position, or in response to determining that a power of the detected light is smaller than or equal to the predetermined threshold, determining that the level of the liquid is higher than or identical to the incident position.

Embodiment 200. The method of embodiment 198, wherein the light source and the light detector are arranged on different sides of the container, and wherein determining the level of the liquid in the container based on the detected light includes: in response to determining that a power of the detected light is smaller than a predetermined threshold, determining that the level of the liquid is lower than the incident position, or in response to determining that a power of the detected light is greater than or equal to the predetermined threshold, determining that the level of the liquid is higher than or identical to the incident position.

Embodiment 201. The method of any of embodiments 198 to 200, including: gradually moving at least one of the container or the pair of the light source and the light detector along the longitudinal direction until a power of the detected light substantially changes across a predetermined threshold, and determining the level of the liquid based on a position of the light source when the power of the detected light substantially changes across the predetermined threshold.

Embodiment 202. The method of any of embodiments 198 to 5201, including: monitoring a power of the detected light while the level of the liquid in the container is increasing due to injection of the liquid into the container, wherein the incident position of the light corresponds to a predetermined level in the container; and in response to determining that the power of the detected light substantially changes across a predetermined threshold, controlling to stop the injection.

Embodiment 203. The method of any of embodiments 197 to 202, wherein the light is emitted from a plurality of light sources spaced along a longitudinal direction, and the light is detected by a plurality of light detectors spaced along the longitudinal direction.

Embodiment 204. The method of embodiment 203, wherein each light source of the plurality of light sources is associated with a respective light detector of the plurality of light detectors and configured to emit a corresponding portion of the light, and the respective light detector is configured to detect the corresponding portion of the light emitted from the light source.

Embodiment 205. The method of embodiment 204, wherein each light source of the plurality of light sources and the respective light detector are arranged in a plane that passes through the longitudinal axis of the container.

Embodiment 206. The method of embodiment 204, wherein each light source of the plurality of light sources and the respective light detector are arranged along the longitudinal direction.

Embodiment 207. The method of any of embodiments 204 to 206, wherein determining the level of the liquid in the container based on the detected light includes: determining the level of the liquid in the container based on detected corresponding portion of light by each of the plurality of light detectors.

Embodiment 208. The method of embodiment 207, wherein determining the level of the liquid in the container based on detected corresponding portion of light by each of the plurality of light detectors includes: determining that the level of the liquid in the container is higher than a first incident position at which a first corresponding portion of light from a first light source is incident on the first internal surface based on detected first corresponding portion of light by a first light detector, determining that the level of the liquid in the container is lower than a second incident position at which a second corresponding portion of light from a second light source is incident on the first internal surface based on detected second corresponding portion of light by a second light detector, and determining that the level of the liquid in the container is between the first incident position and the second incident position.

Embodiment 209. The method of embodiment 208, wherein the first incident position is predetermined based on a first position of the first light source, and the second incident position is predetermined based on a second position of the second light source.

Embodiment 210. The method of any one of embodiments 182 to 209, wherein the container is a tube, a vessel, or a tank.

Embodiment 211. A container for liquid level sensing, the container combinable with any of embodiments 1-210 and including:
a body defining a space configured to contain a liquid; and
a protrusion protruding from the body and including at least one internal surface configured such that
i) light is totally internally reflected by the at least one internal surface if the level of the liquid in the container is lower than an incident position where the light is incident on the at least one internal surface, and
ii) the light is transmitted through the at least one internal surface if the level of the liquid is higher than or identical to the incident position where the light is incident on the at least one internal surface.

Embodiment 212. The container of embodiment 211, wherein the container includes the container according to any of embodiments 182 to 195.

Embodiment 213. The container of embodiment 211 or 212, wherein the container is used to measure the level of the liquid according to the method of any of embodiments 182 to 210.

Embodiment 214. A method of forming a container for liquid level sensing, the method combinable with any of embodiments 1-213 and including:
forming a body of the container, the body defining a space configured to contain a liquid; and
forming a protrusion of the container, the protrusion including at least one internal surface configured such that
i) light is totally internally reflected by the at least one internal surface if the level of the liquid in the container is lower than an incident position where the light is incident on the at least one internal surface, and
ii) the light is transmitted through the at least one internal surface if the level of the liquid is higher than or identical to the incident position where the light is incident on the at least one internal surface.

Embodiment 215. The method of embodiment 214, wherein the container include a container according to any of embodiments 182 to 195.

Embodiment 216. The method of embodiment 214 or 215, wherein the protrusion protrudes from the body, and wherein forming the body of the container and forming the protrusion are performed together such that the body and the protrusion are formed as an integrated piece.

Embodiment 217. The method of embodiment 214 or 215, including: forming the container by attaching the protrusion onto the body of the container.

Embodiment 218. A liquid level sensor, combinable with any of embodiments 1-217 and including:
a container configured to contain a liquid;
a light source configured to emit light onto an external surface of the container; and
a light detector configured to detect the light from the container, wherein the container includes at least one internal surface configured such that
i) the light is totally internally reflected by the at least one internal surface if the level of the liquid in the container is lower than an incident position where the light is incident on the at least one internal surface, and
ii) the light is transmitted through the at least one internal surface if the level of the liquid is higher than or identical to the incident position where the light is incident on the at least one internal surface.

Embodiment 219. The liquid level sensor of embodiment 218, further including: at least one processor configured to determine the level of the liquid based on the detected light by the light detector.

Embodiment 220. The liquid level sensor of embodiment 218 or 219, wherein the container include a container according to any of embodiments 182 to 195.

Embodiment 221. The liquid level sensor of any of embodiments 218 to 221, wherein the liquid level sensor is configured to perform a method according to any of embodiments 182 to 210.

Embodiment 222. A liquid level sensing system, combinable with any of embodiments 1-221 and including:
a container configured to contain a liquid;
multiple optical sensors, each of the multiple optical sensors including:
a respective light source configured to emit a respective portion of light; and
a respective light detector configured to detect the respective portion of light from the container,
wherein the container includes at least one internal surface configured such that
i) the respective portion of light is totally internally reflected by the at least one internal surface if a level of the liquid in the container is lower than an incident position where the respective portion of light is incident on the at least one internal surface, and
ii) the respective portion of light is transmitted through the at least one internal surface if a level of the liquid is higher than or identical to the incident position where the respective portion of light is incident on the at least one internal surface; and
at least one processor configured to determine the level of liquid based on detected respective portions of light by the respective light detectors of the multiple optical sensors.

Embodiment 223. The liquid level sensing system of embodiment 222, configured to perform a method according to any of embodiments 182 to 210.

Embodiment 224. A fluidic system, combinable with any of embodiments 1-223 and including:
at least one input container configured to contain a liquid;
at least one fluidic channel configured to receive the liquid from the at least one input container and output the liquid from at least one output; and
at least one output container coupled to the at least one output and configured to receive the liquid through the at least one fluidic channel, wherein at least one container of the at least one input container or the at least one output container is configured for liquid level sensing, each container of the at least one container including at least one internal surface configured such that
  i) light is totally internally reflected by the at least one internal surface if a level of liquid in the container is lower than an incident position where the light is incident on the at least one internal surface, and
  ii) the light is transmitted through the at least one internal surface if the level of the liquid is higher than or identical to the incident position where the light is incident on the at least one internal surface.

Embodiment 225. The fluidic system of embodiment 224, further including at least one processor configured to: determine the level of the liquid in the container based on detected light from the container according to the method of any of embodiments 182 to 210.

Embodiment 226. The fluidic system of embodiment 225, wherein the at least one processor is configured to: determine a difference between a volume of the liquid in the at least one input container and a volume of the liquid in the at least one output container.

What is claimed is:

1. A microfluidic apparatus comprising:
a microfluidic chip for generation of droplets from sample material, in which a first microfluidic channel is defined in a surface of the microfluidic chip, the first microfluidic channel comprising:
  a droplet generation portion comprising:
    an inlet portion configured to be connected to a source of the sample material,
    a junction between the inlet portion and an emulsifying fluid channel, and
    a chamber downstream of the junction, in which a cross-sectional area of the chamber is larger than a cross-sectional area of the inlet portion, and
  a polymerization portion downstream of the droplet generation portion, the polymerization portion having a serpentine configuration; and
a cartridge for droplet demulsification, the cartridge comprising:
  a collection container defining a cavity;
  a substrate disposed on the collection container, in which a second microfluidic channel is defined in a surface of the substrate that faces the cavity of the collection container, and in which the second microfluidic channel is fluidically connected to an output of the polymerization portion of the first microfluidic channel and configured to be connected to an output vial; and
  a hydrophobic, oleophilic membrane disposed between the cavity of the collection container and the surface of the substrate,
  in which the second microfluidic channel comprises:
    an upstream section that has a simple serpentine configuration, and
    a downstream section that has a double serpentine configuration.

2. The microfluidic apparatus of claim 1, in which the surface of the microfluidic chip is a first surface, and in which the polymerization portion of the first microfluidic channel is defined on the first surface of the microfluidic chip and on a second surface of the microfluidic chip opposite the first surface.

3. The microfluidic apparatus of claim 1, in which the junction comprises a junction between the inlet portion and two emulsifying fluid channels.

4. The microfluidic apparatus of claim 1, in which the droplet generation portion of the first microfluidic channel comprises an outlet portion downstream of the chamber, in which a cross-sectional area of the chamber is larger than a cross-sectional area of the outlet portion.

5. A microfluidic apparatus comprising:
a microfluidic chip for generation of droplets from sample material, in which a first microfluidic channel is defined in a surface of the microfluidic chip, the first microfluidic channel comprising:
  a droplet generation portion comprising:
    an inlet portion configured to be connected to a source of the sample material,
    a junction between the inlet portion and an emulsifying fluid channel, and
    a chamber downstream of the junction, in which a cross-sectional area of the chamber is larger than a cross-sectional area of the inlet portion, and
  a polymerization portion downstream of the droplet generation portion, the polymerization portion having a serpentine configuration; and
a cartridge for droplet demulsification, the cartridge comprising:
  a collection container defining a cavity;
  a substrate disposed on the collection container, in which a second microfluidic channel is defined in a first surface of the substrate that faces the cavity of the collection container, and in which the second microfluidic channel is fluidically connected to an output of the polymerization portion of the first microfluidic channel and configured to be connected to an output vial, and
  in which a media inlet channel is defined on a second surface of the substrate opposite the first surface of the substrate, the media inlet channel fluidically connected to an upstream section of the second microfluidic channel and configured to be connected to a media reservoir; and
  a hydrophobic, oleophilic membrane disposed between the cavity of the collection container and the first surface of the substrate.

6. The microfluidic apparatus of claim 5, in which the media inlet channel is fluidically connected to the media reservoir via a tube extending through the substrate and the collection container.

7. The microfluidic apparatus of claim 5, in which the collection container is disposed in a cavity defined in the media reservoir such that the collection container is positioned between the media reservoir and the substrate.

8. The microfluidic apparatus of claim 5, in which a bottom surface of the media reservoir is angled relative to a plane of the substrate.

9. The microfluidic apparatus of claim 5, in which the demulsification cartridge comprises a duckbill valve extending through the substrate and the collection container, the duckbill valve configured to provide fluidic access to the media reservoir.

10. A microfluidic apparatus comprising:
a microfluidic chip for generation of droplets from sample material, in which a first microfluidic channel is defined in a surface of the microfluidic chip, the first microfluidic channel comprising:

a droplet generation portion comprising:
an inlet portion configured to be connected to a source of the sample material,
a junction between the inlet portion and an emulsifying fluid channel, and
a chamber downstream of the junction, in which a cross-sectional area of the chamber is larger than a cross-sectional area of the inlet portion, and
a polymerization portion downstream of the droplet generation portion, the polymerization portion having a serpentine configuration; and
a cartridge for droplet demulsification, the cartridge comprising:
a collection container defining a cavity;
a substrate disposed on the collection container, in which a second microfluidic channel is defined in a surface of the substrate that faces the cavity of the collection container, and in which the second microfluidic channel is fluidically connected to an output of the polymerization portion of the first microfluidic channel and configured to be connected to an output vial;
a hydrophobic material disposed within the collection container; and
a hydrophobic, oleophilic membrane disposed between the cavity of the collection container and the surface of the substrate.

11. The microfluidic apparatus of claim 1, comprising a reservoir fluidically connected to the first microfluidic channel via an input port defined at an input end of the first microfluidic channel.

12. The microfluidic apparatus of claim 11, comprising an input port in a cover of the reservoir, the input port comprising a duckbill valve.

13. The microfluidic apparatus of claim 11, comprising an output port in a cover of the reservoir, the output port connected to a tube extending into a cavity of the reservoir.

14. The microfluidic apparatus of claim 11, comprising a reservoir holder configured to receive the reservoir, the reservoir holder comprising a cooling system configured to cool the reservoir.

15. The microfluidic apparatus of claim 14, in which the cooling system comprises a thermoelectric cooling system.

16. A microfluidic apparatus comprising:
a microfluidic chip for generation of droplets from sample material, in which a first microfluidic channel is defined in a surface of the microfluidic chip, the first microfluidic channel comprising:
a droplet generation portion comprising:
an inlet portion configured to be connected to a source of the sample material,
a junction between the inlet portion and an emulsifying fluid channel, and
a chamber downstream of the junction, in which a cross-sectional area of the chamber is larger than a cross-sectional area of the inlet portion, and
a polymerization portion downstream of the droplet generation portion, the polymerization portion having a serpentine configuration,
in which one or more cutouts are defined in the microfluidic chip between the droplet generation portion and the polymerization portion; and
a cartridge for droplet demulsification, the cartridge comprising:
a collection container defining a cavity;
a substrate disposed on the collection container, in which a second microfluidic channel is defined in a surface of the substrate that faces the cavity of the collection container, and in which the second microfluidic channel is fluidically connected to an output of the polymerization portion of the first microfluidic channel and configured to be connected to an output vial; and
a hydrophobic, oleophilic membrane disposed between the cavity of the collection container and the surface of the substrate.

17. The microfluidic apparatus of claim 16, in which edges of the one or more cutouts are angled relative to the surface of the microfluidic chip.

18. The microfluidic apparatus of claim 16, in which the one or more cutouts extend through an entire thickness of the microfluidic chip.

19. The microfluidic apparatus of claim 1, in which multiple first microfluidic channels are defined in the surface of the microfluidic chip, in which the first microfluidic channel is among the multiple first microfluidic channels, and in which the apparatus comprises multiple cartridges, in which the cartridge is among the multiple cartridges, in which the second microfluidic channel of each cartridge is fluidically connected to a corresponding one of the first microfluidic channel of the microfluidic chip.

20. The microfluidic apparatus of claim 1, in which the apparatus comprises an output vial fluidically connected to the second microfluidic channel via an output port defined at an output end of the second microfluidic channel.

21. A system comprising:
a microfluidic apparatus comprising:
a microfluidic chip for generation of droplets from sample material, in which a first microfluidic channel is defined in a surface of the microfluidic chip, the first microfluidic channel comprising:
a droplet generation portion comprising:
an inlet portion configured to be connected to a source of the sample material,
a junction between the inlet portion and an emulsifying fluid channel, and
a chamber downstream of the junction, in which a cross-sectional area of the chamber is larger than a cross-sectional area of the inlet portion, and
a polymerization portion downstream of the droplet generation portion, the polymerization portion having a serpentine configuration;
a cartridge for droplet demulsification, the cartridge comprising:
a collection container defining a cavity;
a substrate disposed on the collection container, in which a second microfluidic channel is defined in a surface of the substrate that faces the cavity of the collection container, and in which the second microfluidic channel is fluidically connected to an output of the polymerization portion of the first microfluidic channel and configured to be connected to an output vial; and
a hydrophobic, oleophilic membrane disposed between the cavity of the collection container and the surface of the substrate;
a housing, in which the microfluidic apparatus is disposed in the housing; and
a polymerization block housed in the housing and positioned to apply a stimulus to the polymerization portion of the first microfluidic channel.

22. The system of claim 21, in which the polymerization block comprises a thermal polymerization block configured to apply heat to the polymerization portion of the first microfluidic channel.

23. The system of claim 21, in which the polymerization block comprises a light polymerization block configured to illuminate the polymerization portion of the first microfluidic channel.

24. The system of claim 21, in which the surface of the microfluidic chip is a first surface, and in which the polymerization block comprises:

a first block disposed adjacent the first surface of the microfluidic chip; and a second block disposed adjacent a second surface of the microfluidic chip, the second surface opposite the first surface.

25. The system of claim 21, comprising a reservoir for emulsifying fluid, in which the emulsifying fluid channel of the microfluidic apparatus is fluidically connected to the reservoir.

26. The system of claim 25, comprising a pump disposed between the reservoir for emulsifying fluid and the emulsifying fluid channel.

27. The system of claim 26, comprising a controller configured to control operation of the pump to achieve a target fluid velocity in the second microfluidic channel.

28. The system of claim 21, comprising an imaging system positioned to capture images of at least a portion of the chamber.

29. The system of claim 28, comprising a controller configured to control a flow rate of fluid through the inlet portion of the microfluidic channel based on the images captured by the imaging system.

* * * * *